(12) United States Patent
Abraham et al.

(10) Patent No.: US 7,537,911 B2
(45) Date of Patent: May 26, 2009

(54) ATM RELATED KINASE, ATX, NUCLEIC ACIDS ENCODING SAME AND METHODS OF USE

(75) Inventors: Robert T. Abraham, San Diego, CA (US); Diane M. Otterness, San Diego, CA (US)

(73) Assignees: Burnham Institute for Medical Research, La Jolla, CA (US); Duke University, Durham, NC (US)

( * ) Notice: Subject to any disclaimer, the term of this patent is extended or adjusted under 35 U.S.C. 154(b) by 15 days.

(21) Appl. No.: 11/788,003

(22) Filed: Apr. 17, 2007

(65) Prior Publication Data

US 2008/0166713 A1    Jul. 10, 2008

Related U.S. Application Data

(62) Division of application No. 11/643,551, filed on Dec. 20, 2006, now Pat. No. 7,217,551, which is a division of application No. 10/456,238, filed on Jun. 6, 2003, now Pat. No. 7,166,716.

(60) Provisional application No. 60/813,607, filed on Jun. 6, 2002.

(51) Int. Cl.
   *C12Q 1/48* (2006.01)
(52) U.S. Cl. ........................................ 435/15
(58) Field of Classification Search .................... 435/15
   See application file for complete search history.

(56) References Cited

U.S. PATENT DOCUMENTS

| | | | |
|---|---|---|---|
| 6,344,549 B1 | 2/2002 | Loughney et al. | |
| 6,348,311 B1 | 2/2002 | Kastan et al. | |
| 2005/0032725 A1 | 2/2005 | Rao et al. | |

OTHER PUBLICATIONS

Abraham, "Cell cycle checkpoint signaling through the ATM and ATR kinases," *Genes Dev.* 15(17):2177-2196 (2001).
Ahn et al., "Threonine 68 phosphorylation by ataxia telangiectasia mutated is required for efficient activation of Chk2 in response to ionizing radiation," *Cancer Res.* 60(21):5934-5936 (2000).
Andegeko et al., "Nuclear retention of ATM at sites of DNA double strand breaks," *J. Biol. Chem.* 276(41):38224-38230 (2001).
Banin et al., "Enhanced phosphorylation of p53 by ATM in response to DNA damage," *Science* 281 (5383):1674-1677 (1998).
Brumbaugh et al., GenEMbl Database, Accession No. AF395444, Jul. 2002.
Brummelkamp et al., "A system for stable expression of short interfering RNAs in mammalian cells," *Science* 296(5567):550-553 (2002).
Bunz et al., "Disruption of p53 in human cancer cells alters the response to therapeutic agents," *J. Clin Invest.* 104(3):263-269 (1999).
Cali et al., "mRNA surveillance mitigates genetic dominance in Caenorhabditis elegans," *Mol Gen Genet.* 260(2-3):176-184 (1998).

Canman et al., "Activation of the ATM kinase by ionizing radiation and phosphorylation of p53," *Science* 281 (5383):1677-1679 (1998).
Capecchi, "Altering the genome by homologous recombination," *Science* 244(4910):1288-1292 (1989).
Chen et al., "Identification of an 11-kDa FKBP12-rapamycin-binding domian within the 289-kDa FKBP 12-rapamycin-associated protein and characterization of a critical serine residue," *Proc. Natl. Acad. Sci. USA.* 92(11):4947-4951 (1995).
Cliby et al., "Overexpression of a kinase-inactive ATR protein causes sensitivity to DNA-damaging agents and defects in cell cycle checkpoints," *EMBO J.* 17(1):159-169 (1998).
Danenberg et al. "Thymidylate synthase inhibitors," *Semin Oncol.* 26(6):621-631 (1999).
Denning et al., "Cloning of a novel phosphatidylinositol kinase-related kinase: characterization of the human SMG-1 RNA surveillance protein," *J. Biol. Chem.*, 276:22709-22714 (2001).
Dias et al., *EST Database*, Accession No. AF395444, Jul. 1994.
Diaz-Meco et al. "Lamba-interacting protein, a novel protein that specifically interacts with the zinc finger domain of the atypical protein kinase C isotype lambda/iota and stimulates its kinase activity in vitro and in vivo," *Mol Cell Biol.* 16(1):105-114 (1996).
Dumaz et al., "Serine15 phosphorylation stimulated p53 transactivation but does not directly influence interaction with HDM2", *EMBO J.* 18(24):7002-7010 (1999).
Durocher and Jackson, "DNA-PK, ATM and ATR as sensors of DNA damage: variations on a theme?" *Curr. Opin. Cell Biol.*, 13:225-231 (2001).
Elbashir et al., "Duplexes of 21-nucleotide RNAs mediate RNA interference in cultured mammalian cells," *Nature* 411(6836):494-498 (2001).
Genbank Accession No. AB007881, May 2002.
Genbank Accession No. AB040413, Dec. 2000.
Genbank Accession No. D86974, Jan. 2004.
Genbank Accession No. U32581, Jul. 1999.

(Continued)

*Primary Examiner*—Maryam Monshipouri
(74) *Attorney, Agent, or Firm*—McDermott Will & Emery LLP

(57) ABSTRACT

The invention provides an isolated nucleic acid molecule having substantially the same nucleotide sequence as SEQ ID NO:1. Also provided is an isolated oligonucleotide having at least 15 contiguous nucleotides of a nucleotide sequence referenced as SEQ ID NO:11. An isolated polypeptide having substantially the same amino acid sequence as SEQ ID NO:2 is further provided as well as an antibody, or antigen binding fragment thereof, which specifically binds to an ATX polypeptide and has an amino acid sequence as referenced in SEQ ID NO:2. A method for identifying an ATX-modulatory compound is additionally provided. The method consists of measuring the level of an ATX polypeptide in the presence of a test compound, wherein a difference in the level of said ATX polypeptide in the presence of said test compound compared to in the absence of said test compound indicating that said test compound is an ATX-modulatory compound, and wherein said ATX-modulatory compound is not caffeine or wortmannin.

6 Claims, 19 Drawing Sheets

OTHER PUBLICATIONS

Giaccia et al., "The complexity of p53 modulation: emerging patterns from divergent signals," *Genes Dev.* 12(19):2973-2983 (1998).

Grem, "5-Fluorouracil: forty-plus and still ticking. A review of its preclinical and clinical development," *Invest New Drugs* 18(4):299-313 (2000).

Hodgkin et al., "A new kind of informational suppression in the Nematode Caenorhabditis elegans," *Genetics* 123:301-313 (1989).

Hunter, T., "When is a lipid kinase not a lipid kinase? When it is a protein kinase," *Cell*, 83:1-4 (1995).

Ishigaki et al., "Evidence for a pioneer round of mRNA translation: mRNAs subject to nonsense-mediated decay in mammalian cells are bound by CBP80 and CBP20," *Cell*, 106:607-617 (2001).

Karabinos et al., "Essential roles for four cytoplasmic intermediate filament proteins in Caenorhabditis elegans development," *Proc. Natl. Acad. Sci.*, 98:7863-7868 (2001).

Ko et al., "p53: puzzle and paradigm," *Genes Dev.* 10(9):1054-1072 (1996).

Lehmann and Carr, "The ataxia-telangiectasia gene: a link between checkpoint controls, neurodegeneration and cancer," *Trends in Genel.*, 11:375-377 (1995).

Melchionna et al., "Threonine 68 is required for radiation-induced phosphorylation and activation of Cds1," *Nat Cell Biol.*, 2(10):762-765 (2000).

North et al., "p53 and cell-cycle control: a finger in every pie," *Pathol. Biol.* 48(3):255-270 (2000).

O'Neill et al., "Utilization of oriented peptide libraries to identify substrate motifs selected by ATM," *J. Biol. Chem.* 275(30):22719-22727 (2000).

Page et al., "SMG-2 is a phosphorylated protein required for mRNA surveillance in Caenorhabditis elegans and related to Upf1P of yeast," *Mol. Cell Biol.* 19(9):5943-5951 (1999).

Pal et al., "Evidence that phosohorylation of human Upf1 protein varies with intracellular location and is mediated by a wortmannin-sensitive and rapamycin-sensitive P 3-kinase-related kinase signaling pathway," *RNA*, 7:5-15 (2001).

Powell et al., "Differential sensitivity of p53(−) and p53(+) cells to caffeine-induced radiosensitization and override of G2 delay," *Cancer Res.* 55(8):1643-1648 (1995).

Pulak et al., "mRNA surveillance by the Caenorhabditis elegans smg genes," *Genes Dev.* 7(10):1885-1897 (1993).

Rotman and Shiloh, "ATM: from gene to function," *Human Mol Gen.*, 7:1555-1563 (1998).

Rotman et al., "ATM: a mediator of multiple responses to genotoxic stress," *Oncogene* 18(45):6135-6144 (1999).

Russell et al., "Abrogation of the G2 checkpoint results in differential readiosensitization of G1 checkpoint-deficient and G1 checkpoint-component cells," *Cancer Res.* 55(8):1639-1642 (1995).

Ryan et al., "Regulation and function of the p53 tumor suppressor protein," *Curr. Opin. Cell Biol.* 13(3):332-337 (2001).

Sarkaria et al., "Inhibition of phosphoinositide 3-kinase related kinases by the radiosensitizing agent wortmannin," *Cancer Res.* 58(19):4375-4382 (1998).

Siliciano et al., "DNA damage induces phosphorylation of the amino terminus of p53," *Genes Dev.* 11(24):3471-3481 (1997).

Sun et al., "A mutated human homologue of yeast Upf1 protein has a dominant-negative effect on the decay of nonsense-containing mRNAs in mammalian cells," *Proc Natl. Acad. Sci. USA* 95(17):10009-10014 (1998).

Tibbetts et al., "A role for ATR in the DNA damage-induced phosphorylation of p53," *Genes Dev.* 13(2):152-157 (1999).

Tibbetts et al., "Functional interactions between BRCA1 and the checkpoint kinase ATR during genotoxic stress," *Genes Dev.* 14(23):2989-3002 (2000).

Vassilev et al., "The 400 kDa subunit of the PCAF histone acelytase complex belongs to the ATM superfamily," *Mol. Cell*, 2:869-875 (1998).

Waldman et al., "p21 is necessary for the p53-mediated G1 arrest in human cancer cells," *Cancer Res.* 55(22):5187-5190 (1995).

Walker et al., "Structural determinants of phosphoinositide 3-kinase inhibition by wortmannin, LY294002, quercetin, myricetin, and staurosporine," *Mol Cell.* 6(4):909-919 (2000).

Yamashita et al., "Human SMG-1, a novel phosphatidylinositol 3-kinase-related protein kinase, associates with components of the mRNA surveillance complex and is involved in the regulation of nonsense-mediated mRNA decay," *Genes Dev.*, 15(17):2215-2228 (2001).

Yao et al., "Selective radiosensitization of p53-deficient cells by caffeine-mediated activation of p34cdc2 kinase," *Nat Med.* 2(10):1140-1143 (1996).

Zamore, P., "RNA interference: listening to the sound of silence," *Nat. Struct. Biol.*, 8:746-750 (2001).

Zhang et al., "A p53 amino-terminal nuclear export signal inhibited by DNA damage-induced phosphorylation," *Science* 292(5523):1910-1915 (2001).

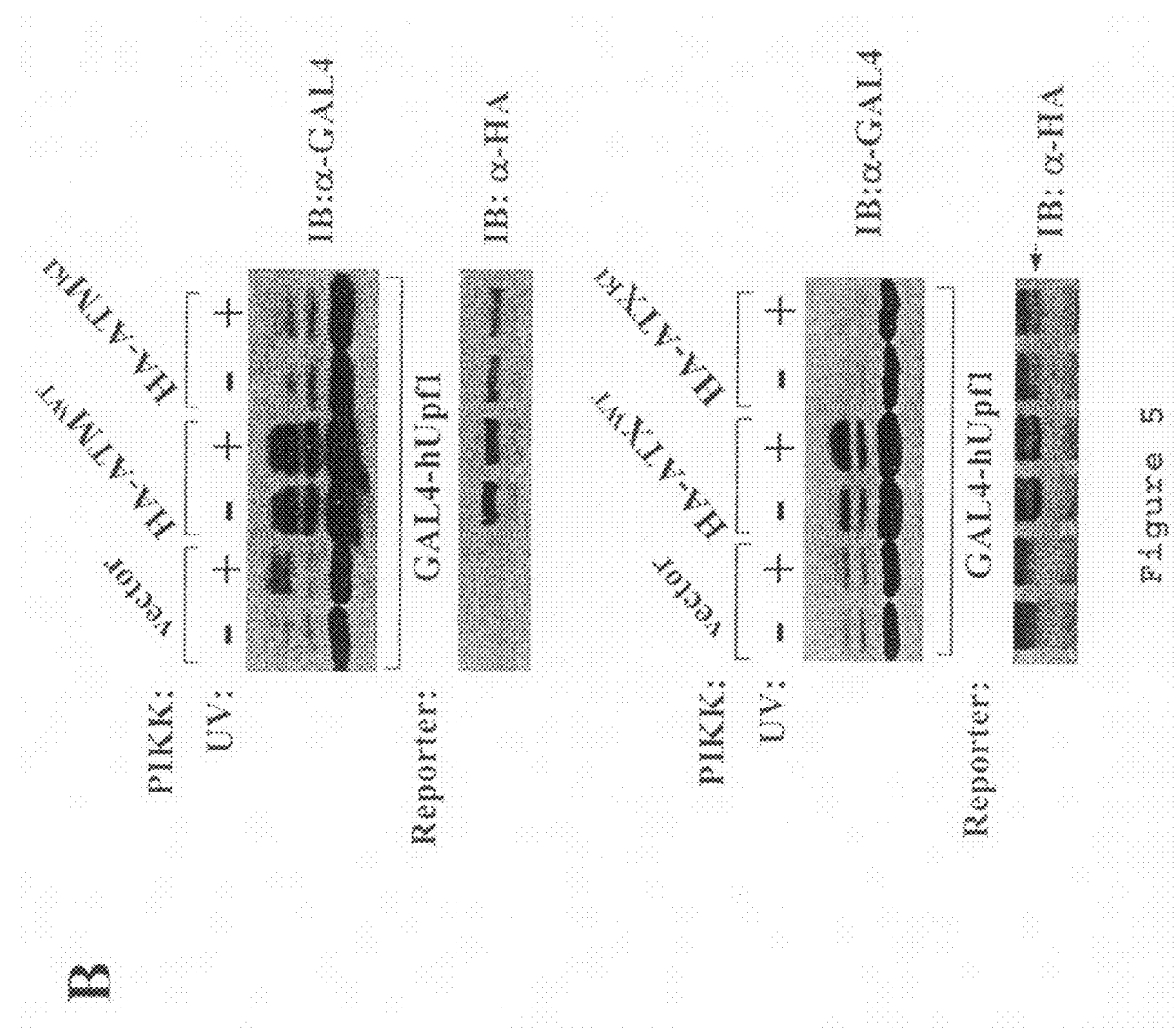

SEQUENCE LISTING

```
<160> NUMBER OF SEQ ID NOS: 11

<210> SEQ ID NO 1
<211> LENGTH: 12464
<212> TYPE: DNA
<213> ORGANISM: Homo sapiens
<220> FEATURE:
<221> NAME/KEY: CDS
<222> LOCATION: (91)...(10656)
```

<400> SEQUENCE: 1

```
caaccttcaa attcagctgt ggtgtctcgg caaaggcacg atgataccag agtccacgct    60
gacatacaga atgacgaaaa ggagagatcg atg tct tat tgt gat gag tct cga   114
                                  Met Ser Tyr Cys Asp Glu Ser Arg
                                    1               5 ctg tcg aat ctt ctt cgg agg atc acc cgg gaa gac gac aga gac cga   162
Leu Ser Asn Leu Leu Arg Arg Ile Thr Arg Glu Asp Asp Arg Asp Arg
         10                  15                  20 aga ttg gct act gta aag cag ttg aaa gaa ttt att cag caa cca gaa   210
Arg Leu Ala Thr Val Lys Gln Leu Lys Glu Phe Ile Gln Gln Pro Glu
 25                  30                  35                  40 aat aag ctg gta cta gtt aaa caa ttg gat aat atc ttg gct gct gta   258
Asn Lys Leu Val Leu Val Lys Gln Leu Asp Asn Ile Leu Ala Ala Val
                 45                  50                  55 cat gac gtg ctt aat gaa agt agc aaa ttg ctt cag gag ttg aga cag   306
His Asp Val Leu Asn Glu Ser Ser Lys Leu Leu Gln Glu Leu Arg Gln
             60                  65                  70 gag gga gct tgc tgt ctt ggc ctt ctt tgt gct tct ctg agc tat gag   354
Glu Gly Ala Cys Cys Leu Gly Leu Leu Cys Ala Ser Leu Ser Tyr Glu
         75                  80                  85 gct gag aag atc ttc aag tgg att ttt agc aaa ttt agc tca tct gca   402
Ala Glu Lys Ile Phe Lys Trp Ile Phe Ser Lys Phe Ser Ser Ser Ala
 90                  95                 100 aaa gat gaa gtt aaa ctc ctc tac tta tgt gcc acc tac aaa gca cta   450
Lys Asp Glu Val Lys Leu Leu Tyr Leu Cys Ala Thr Tyr Lys Ala Leu
105                 110                 115                 120 gag act gta gga gaa aag aaa gcc ttt tca tct gta atg cag ctt gta   498
Glu Thr Val Gly Glu Lys Lys Ala Phe Ser Ser Val Met Gln Leu Val
                125                 130                 135 atg acc agc ctg cag tct att ctt gaa aat gtg gat aca cca gaa ttg   546
Met Thr Ser Leu Gln Ser Ile Leu Glu Asn Val Asp Thr Pro Glu Leu
            140                 145                 150 ctt tgt aaa tgt gtt aag tgc att ctt ttg gtg gct cga tgt tac cct   594
Leu Cys Lys Cys Val Lys Cys Ile Leu Leu Val Ala Arg Cys Tyr Pro
        155                 160                 165 cat att ttc agc act aat ttt agg gat aca gtt gat ata tta gtt gga   642
His Ile Phe Ser Thr Asn Phe Arg Asp Thr Val Asp Ile Leu Val Gly
    170                 175                 180 tgg cat ata gat cat act cag aaa cct tcg ctc acg cag cag gta tct   690
Trp His Ile Asp His Thr Gln Lys Pro Ser Leu Thr Gln Gln Val Ser
185                 190                 195                 200 ggg tgg ttg cag agt ttg gag cca ttt tgg gta gct gat ctt gca ttt   738
Gly Trp Leu Gln Ser Leu Glu Pro Phe Trp Val Ala Asp Leu Ala Phe
                205                 210                 215 tct act act ctt ctt ggt cag ttt ctg gaa gac atg gaa gca tat gct   786
Ser Thr Thr Leu Leu Gly Gln Phe Leu Glu Asp Met Glu Ala Tyr Ala
            220                 225                 230 gag gac ctc agc cat gtg gcc tct ggg gaa tca gtg gat gaa gat gtc   834
Glu Asp Leu Ser His Val Ala Ser Gly Glu Ser Val Asp Glu Asp Val
        235                 240                 245 cct cct cca tca gtg tca tta cca aag ctg gct gca ctt ctc cgg gta   882
Pro Pro Pro Ser Val Ser Leu Pro Lys Leu Ala Ala Leu Leu Arg Val
    250                 255                 260 ttt agt act gtg gtg agg agc att ggg gaa cgc ttc agc cca att cgg   930
Phe Ser Thr Val Val Arg Ser Ile Gly Glu Arg Phe Ser Pro Ile Arg
265                 270                 275                 280
```

|  |  |
|---|---|
| ggt cct cca att act gag gca tat gta aca gat gtt ctg tac aga gta<br>Gly Pro Pro Ile Thr Glu Ala Tyr Val Thr Asp Val Leu Tyr Arg Val<br>285 290 295 | 978 |
| atg aga tgt gtg acg gct gca aac cag gtg ttt ttt tct gag gct gtg<br>Met Arg Cys Val Thr Ala Ala Asn Gln Val Phe Phe Ser Glu Ala Val<br>300 305 310 | 1026 |
| ttg aca gct gct aat gag tgt gtt ggt gtt ttg ctc ggc agc ttg gat<br>Leu Thr Ala Ala Asn Glu Cys Val Gly Val Leu Leu Gly Ser Leu Asp<br>315 320 325 | 1074 |
| cct agc atg act ata cat tgt gac atg gtc att aca tat gga tta gac<br>Pro Ser Met Thr Ile His Cys Asp Met Val Ile Thr Tyr Gly Leu Asp<br>330 335 340 | 1122 |
| caa ctg gag aat tgc cag act tgt ggt acc gat tat atc atc tca gtc<br>Gln Leu Glu Asn Cys Gln Thr Cys Gly Thr Asp Tyr Ile Ile Ser Val<br>345 350 355 360 | 1170 |
| ttg aat tta ctc acg ctg att gtt gaa cag ata aat acg aaa ctg cca<br>Leu Asn Leu Leu Thr Leu Ile Val Glu Gln Ile Asn Thr Lys Leu Pro<br>365 370 375 | 1218 |
| tca tca ttt gta gaa aaa ctg ttt ata cca tca tct aaa cta cta ttc<br>Ser Ser Phe Val Glu Lys Leu Phe Ile Pro Ser Ser Lys Leu Leu Phe<br>380 385 390 | 1266 |
| ttg cgt tat cat aaa gaa aaa gag gtt gtt gct gta gcc cat gct gtt<br>Leu Arg Tyr His Lys Glu Lys Glu Val Val Ala Val Ala His Ala Val<br>395 400 405 | 1314 |
| tat caa gca gtg ctc agc ttg aag aat att cct gtt ttg gag act gcc<br>Tyr Gln Ala Val Leu Ser Leu Lys Asn Ile Pro Val Leu Glu Thr Ala<br>410 415 420 | 1362 |
| tat aag tta ata ttg gga gaa atg act tgt gcc cta aac aac ctc cta<br>Tyr Lys Leu Ile Leu Gly Glu Met Thr Cys Ala Leu Asn Asn Leu Leu<br>425 430 435 440 | 1410 |
| cac agt cta caa ctt cct gag gcc tgt tct gaa ata aaa cat gag gct<br>His Ser Leu Gln Leu Pro Glu Ala Cys Ser Glu Ile Lys His Glu Ala<br>445 450 455 | 1458 |
| ttt aag aat cat gtg ttc aat gta gac aat gca aaa ttt gta gtt ata<br>Phe Lys Asn His Val Phe Asn Val Asp Asn Ala Lys Phe Val Val Ile<br>460 465 470 | 1506 |
| ttt gac ctc agt gcc ctg act aca att gga aat gcc aaa aac tca cta<br>Phe Asp Leu Ser Ala Leu Thr Thr Ile Gly Asn Ala Lys Asn Ser Leu<br>475 480 485 | 1554 |
| ata ggg atg tgg gcg cta tct cca act gtc ttt gca ctt ctg agt aag<br>Ile Gly Met Trp Ala Leu Ser Pro Thr Val Phe Ala Leu Leu Ser Lys<br>490 495 500 | 1602 |
| aat ctg atg att gtg cac agt gac ctg gct gtt cac ttc cct gcc att<br>Asn Leu Met Ile Val His Ser Asp Leu Ala Val His Phe Pro Ala Ile<br>505 510 515 520 | 1650 |
| cag tat gct gtg ctc tac aca ttg tat tct cat tgt acc agg cat gat<br>Gln Tyr Ala Val Leu Tyr Thr Leu Tyr Ser His Cys Thr Arg His Asp<br>525 530 535 | 1698 |
| cac ttt atc tct agt agc ctc agt tct tcc tct cct tct ttg ttt gat<br>His Phe Ile Ser Ser Ser Leu Ser Ser Ser Pro Ser Leu Phe Asp<br>540 545 550 | 1746 |
| gga gct gtg att agc act gta act acg gct aca aag aaa cat ttc tca<br>Gly Ala Val Ile Ser Thr Val Thr Thr Ala Thr Lys Lys His Phe Ser<br>555 560 565 | 1794 |
| att ata tta aat ctt ctg gga ata tta ctt aag aaa gat aac ctt aac<br>Ile Ile Leu Asn Leu Leu Gly Ile Leu Leu Lys Lys Asp Asn Leu Asn<br>570 575 580 | 1842 |
| cag gac acg agg aaa ctg tta atg act tgg gct ttg gaa gca gct gtt<br>Gln Asp Thr Arg Lys Leu Leu Met Thr Trp Ala Leu Glu Ala Ala Val<br>585 590 595 600 | 1890 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tta | atg | aag | aag | tct | gaa | aca | tac | gca | cct | tta | ttc | tct | ctt | ccg | tct | 1938 |
| Leu | Met | Lys | Lys | Ser | Glu | Thr | Tyr | Ala | Pro | Leu | Phe | Ser | Leu | Pro | Ser |      |
|     |     |     |     | 605 |     |     |     |     | 610 |     |     |     |     | 615 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttc | cat | aaa | ttt | tgc | aaa | ggc | ctt | tta | gcc | aac | act | ctc | gtt | gaa | gat | 1986 |
| Phe | His | Lys | Phe | Cys | Lys | Gly | Leu | Leu | Ala | Asn | Thr | Leu | Val | Glu | Asp |      |
|     |     | 620 |     |     |     |     | 625 |     |     |     |     | 630 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | aat | atc | tgt | ctg | cag | gca | tgc | agc | agt | cta | cat | gct | ctg | tcc | tct | 2034 |
| Val | Asn | Ile | Cys | Leu | Gln | Ala | Cys | Ser | Ser | Leu | His | Ala | Leu | Ser | Ser |      |
|     |     | 635 |     |     |     |     | 640 |     |     |     |     | 645 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | ttg | cca | gat | gat | ctt | tta | cag | aga | tgt | gtc | gat | gtt | tgc | cgt | gtt | 2082 |
| Ser | Leu | Pro | Asp | Asp | Leu | Leu | Gln | Arg | Cys | Val | Asp | Val | Cys | Arg | Val |      |
| 650 |     |     |     |     | 655 |     |     |     |     | 660 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| caa | cta | gtg | cac | agt | gga | act | cgt | att | cga | caa | gca | ttt | gga | aaa | ctg | 2130 |
| Gln | Leu | Val | His | Ser | Gly | Thr | Arg | Ile | Arg | Gln | Ala | Phe | Gly | Lys | Leu |      |
| 665 |     |     |     |     | 670 |     |     |     |     | 675 |     |     |     |     | 680 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttg | aaa | tca | att | cct | tta | gat | gtt | gtc | cta | agc | aat | aac | aat | cac | aca | 2178 |
| Leu | Lys | Ser | Ile | Pro | Leu | Asp | Val | Val | Leu | Ser | Asn | Asn | Asn | His | Thr |      |
|     |     |     |     | 685 |     |     |     |     | 690 |     |     |     |     | 695 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaa | att | caa | gaa | att | tct | tta | gca | tta | aga | agt | cac | atg | agt | aaa | gca | 2226 |
| Glu | Ile | Gln | Glu | Ile | Ser | Leu | Ala | Leu | Arg | Ser | His | Met | Ser | Lys | Ala |      |
|     |     |     |     | 700 |     |     |     |     | 705 |     |     |     |     | 710 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | agt | aat | aca | ttc | cac | ccc | caa | gat | ttc | tct | gat | gtt | att | agt | ttt | 2274 |
| Pro | Ser | Asn | Thr | Phe | His | Pro | Gln | Asp | Phe | Ser | Asp | Val | Ile | Ser | Phe |      |
|     |     |     |     | 715 |     |     |     |     | 720 |     |     |     |     | 725 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| att | ttg | tat | ggg | aac | tct | cat | aga | aca | ggg | aag | gac | aat | tgg | ttg | gaa | 2322 |
| Ile | Leu | Tyr | Gly | Asn | Ser | His | Arg | Thr | Gly | Lys | Asp | Asn | Trp | Leu | Glu |      |
|     |     | 730 |     |     |     |     | 735 |     |     |     |     | 740 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aga | ctg | ttc | tat | agc | tgc | cag | aga | ctg | gat | aag | cgt | gac | cag | tca | aca | 2370 |
| Arg | Leu | Phe | Tyr | Ser | Cys | Gln | Arg | Leu | Asp | Lys | Arg | Asp | Gln | Ser | Thr |      |
| 745 |     |     |     |     | 750 |     |     |     |     | 755 |     |     |     |     | 760 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| att | cca | cgc | aat | ctc | ctg | aag | aca | gat | gct | gtc | ctt | tgg | cag | tgg | gcc | 2418 |
| Ile | Pro | Arg | Asn | Leu | Leu | Lys | Thr | Asp | Ala | Val | Leu | Trp | Gln | Trp | Ala |      |
|     |     |     |     | 765 |     |     |     |     | 770 |     |     |     |     | 775 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ata | tgg | gaa | gct | gca | caa | ttc | act | gtt | ctt | tct | aag | ctg | aga | acc | cca | 2466 |
| Ile | Trp | Glu | Ala | Ala | Gln | Phe | Thr | Val | Leu | Ser | Lys | Leu | Arg | Thr | Pro |      |
|     |     |     |     | 780 |     |     |     |     | 785 |     |     |     |     | 790 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | ggc | aga | gct | caa | gac | acc | ttc | cag | aca | att | gaa | ggt | atc | att | cga | 2514 |
| Leu | Gly | Arg | Ala | Gln | Asp | Thr | Phe | Gln | Thr | Ile | Glu | Gly | Ile | Ile | Arg |      |
|     |     | 795 |     |     |     |     | 800 |     |     |     |     | 805 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agt | ctc | gca | gct | cac | aca | tta | aac | cct | gat | cag | gat | gtt | agt | cag | tgg | 2562 |
| Ser | Leu | Ala | Ala | His | Thr | Leu | Asn | Pro | Asp | Gln | Asp | Val | Ser | Gln | Trp |      |
|     | 810 |     |     |     |     | 815 |     |     |     |     | 820 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aca | act | gca | gac | aat | gat | gaa | ggc | cat | ggt | aac | aac | caa | ctt | aga | ctt | 2610 |
| Thr | Thr | Ala | Asp | Asn | Asp | Glu | Gly | His | Gly | Asn | Asn | Gln | Leu | Arg | Leu |      |
| 825 |     |     |     |     | 830 |     |     |     |     | 835 |     |     |     |     | 840 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtt | ctt | ctt | ctg | cag | tat | ctg | gaa | aat | ctg | gag | aaa | tta | atg | tat | aat | 2658 |
| Val | Leu | Leu | Leu | Gln | Tyr | Leu | Glu | Asn | Leu | Glu | Lys | Leu | Met | Tyr | Asn |      |
|     |     |     |     | 845 |     |     |     |     | 850 |     |     |     |     | 855 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gca | tac | gag | gga | tgt | gct | aat | gca | tta | act | tca | cct | ccc | aag | gtc | att | 2706 |
| Ala | Tyr | Glu | Gly | Cys | Ala | Asn | Ala | Leu | Thr | Ser | Pro | Pro | Lys | Val | Ile |      |
|     |     |     | 860 |     |     |     |     | 865 |     |     |     |     | 870 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aga | act | ttt | ttc | tat | acc | aat | cgc | caa | act | tgt | cag | gac | tgg | cta | acg | 2754 |
| Arg | Thr | Phe | Phe | Tyr | Thr | Asn | Arg | Gln | Thr | Cys | Gln | Asp | Trp | Leu | Thr |      |
|     |     |     | 875 |     |     |     |     | 880 |     |     |     |     | 885 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cgg | att | cga | ctc | tcc | atc | atg | agg | gta | gga | ttg | ttg | gca | ggc | cag | cct | 2802 |
| Arg | Ile | Arg | Leu | Ser | Ile | Met | Arg | Val | Gly | Leu | Leu | Ala | Gly | Gln | Pro |      |
|     |     | 890 |     |     |     |     | 895 |     |     |     |     | 900 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gca | gtg | aca | gtg | aga | cat | ggc | ttt | gac | ttg | ctt | aca | gag | atg | aaa | aca | 2850 |
| Ala | Val | Thr | Val | Arg | His | Gly | Phe | Asp | Leu | Leu | Thr | Glu | Met | Lys | Thr |      |
| 905 |     |     |     |     | 910 |     |     |     |     | 915 |     |     |     |     | 920 |      |

-continued

| | |
|---|---|
| acc agc cta tct cag ggg aat gaa ttg gaa gta acc att atg atg gtg<br>Thr Ser Leu Ser Gln Gly Asn Glu Leu Glu Val Thr Ile Met Met Val<br>                    925                    930                935 | 2898 |
| gta gaa gca tta tgt gaa ctt cat tgt cct gaa gct ata cag gga att<br>Val Glu Ala Leu Cys Glu Leu His Cys Pro Glu Ala Ile Gln Gly Ile<br>                    940                    945                950 | 2946 |
| gct gtc tgg tca tca tct att gtt gga aaa aat ctt ctg tgg att aac<br>Ala Val Trp Ser Ser Ser Ile Val Gly Lys Asn Leu Leu Trp Ile Asn<br>                    955                    960                965 | 2994 |
| tca gtg gct caa cag gct gaa ggg agg ttt gaa aag gcc tct gtg gag<br>Ser Val Ala Gln Gln Ala Glu Gly Arg Phe Glu Lys Ala Ser Val Glu<br>           970                    975                980 | 3042 |
| tac cag gaa cac ctg tgt gcc atg aca ggt gtt gat tgc tgc atc tcc<br>Tyr Gln Glu His Leu Cys Ala Met Thr Gly Val Asp Cys Cys Ile Ser<br>985                    990                    995              1000 | 3090 |
| agc ttt gac aaa tcg gtg ctc acc tta gcc aat gct ggg cgt aac agt<br>Ser Phe Asp Lys Ser Val Leu Thr Leu Ala Asn Ala Gly Arg Asn Ser<br>                    1005                1010              1015 | 3138 |
| gcc agc ccg aaa cat tct ctg aat ggt gaa tcc aga aaa act gtg ctg<br>Ala Ser Pro Lys His Ser Leu Asn Gly Glu Ser Arg Lys Thr Val Leu<br>                    1020                1025              1030 | 3186 |
| tcc aaa ccg act gac tct tcc cct gag gtt ata aat tat tta gga aat<br>Ser Lys Pro Thr Asp Ser Ser Pro Glu Val Ile Asn Tyr Leu Gly Asn<br>                    1035                1040              1045 | 3234 |
| aaa gca tgt gag tgc tac atc tca att gcc gat tgg gct gct gtg cag<br>Lys Ala Cys Glu Cys Tyr Ile Ser Ile Ala Asp Trp Ala Ala Val Gln<br>1050                1055              1060 | 3282 |
| gaa tgg cag aac gct atc cat gac ttg aaa aag agt acc agt agc act<br>Glu Trp Gln Asn Ala Ile His Asp Leu Lys Lys Ser Thr Ser Ser Thr<br>1065                1070              1075              1080 | 3330 |
| tcc ctc aac ctg aaa gct gac ttc aac tat ata aaa tca tta agc agc<br>Ser Leu Asn Leu Lys Ala Asp Phe Asn Tyr Ile Lys Ser Leu Ser Ser<br>                    1085                1090              1095 | 3378 |
| ttt gag tct gga aaa ttt gtt gaa tgt acc gag caa tta gaa ttg tta<br>Phe Glu Ser Gly Lys Phe Val Glu Cys Thr Glu Gln Leu Glu Leu Leu<br>                    1100                1105              1110 | 3426 |
| cca gga gaa aat atc aat cta ctt gct gga gga tca aaa gaa aaa ata<br>Pro Gly Glu Asn Ile Asn Leu Leu Ala Gly Gly Ser Lys Glu Lys Ile<br>                    1115                1120              1125 | 3474 |
| gac atg aaa aaa ctg ctt cct aac atg tta agt ccg gat ccg agg gaa<br>Asp Met Lys Lys Leu Leu Pro Asn Met Leu Ser Pro Asp Pro Arg Glu<br>          1130                1135                1140 | 3522 |
| ctt cag aaa tcc att gaa gtt caa ttg tta aga agt tct gtt tgt ttg<br>Leu Gln Lys Ser Ile Glu Val Gln Leu Leu Arg Ser Ser Val Cys Leu<br>1145                1150              1155              1160 | 3570 |
| gca act gct tta aac ccg ata gaa caa gat cag aag tgg cag tct ata<br>Ala Thr Ala Leu Asn Pro Ile Glu Gln Asp Gln Lys Trp Gln Ser Ile<br>                    1165                1170              1175 | 3618 |
| act gaa aat gtg gta aag tac ttg aag caa aca tcc cgc atc gct att<br>Thr Glu Asn Val Val Lys Tyr Leu Lys Gln Thr Ser Arg Ile Ala Ile<br>                    1180                1185              1190 | 3666 |
| gga cct ctg aga ctt tct act tta aca gtt tca cag tct ttg cca gtt<br>Gly Pro Leu Arg Leu Ser Thr Leu Thr Val Ser Gln Ser Leu Pro Val<br>                    1195                1200              1205 | 3714 |
| cta agt acc ttg cag ctg tat tgc tca tct gct ttg gag aac aca gtt<br>Leu Ser Thr Leu Gln Leu Tyr Cys Ser Ser Ala Leu Glu Asn Thr Val<br>                    1210                1215              1220 | 3762 |
| tct aac aga ctt tca aca gag gac tgt ctt att cca ctc ttc agt gaa<br>Ser Asn Arg Leu Ser Thr Glu Asp Cys Leu Ile Pro Leu Phe Ser Glu<br>1225                1230              1235              1240 | 3810 |

```
gct tta cgt tca tgt aaa cag cat gac gtg agg cca tgg atg cag gca    3858
Ala Leu Arg Ser Cys Lys Gln His Asp Val Arg Pro Trp Met Gln Ala
            1245                1250                1255 tta agg tat act atg tac cag aat cag ttg ttg gag aaa att aaa gaa    3906
Leu Arg Tyr Thr Met Tyr Gln Asn Gln Leu Leu Glu Lys Ile Lys Glu
        1260                1265                1270 caa aca gtc cca att aga agc cat ctc atg gaa tta ggt cta aca gca    3954
Gln Thr Val Pro Ile Arg Ser His Leu Met Glu Leu Gly Leu Thr Ala
    1275                1280                1285 gca aaa ttt gct aga aaa cga ggg aat gtg tcc ctt gca aca aga ctg    4002
Ala Lys Phe Ala Arg Lys Arg Gly Asn Val Ser Leu Ala Thr Arg Leu
1290                1295                1300 ctg gca cag tgc agt gaa gtt cag ctg gga aag acc act gca cag        4050
Leu Ala Gln Cys Ser Glu Val Gln Leu Gly Lys Thr Thr Ala Gln
1305                1310                1315                1320 gat tta gtc caa cat ttt aaa aaa cta tca acc caa ggt caa gtg gat    4098
Asp Leu Val Gln His Phe Lys Lys Leu Ser Thr Gln Gly Gln Val Asp
                1325                1330                1335 gaa aaa tgg ggg ccc gaa ctt gat att gaa aaa acc aaa ttg ctt tat    4146
Glu Lys Trp Gly Pro Glu Leu Asp Ile Glu Lys Thr Lys Leu Leu Tyr
            1340                1345                1350 aca gca ggc cag tca aca cat gca atg gaa atg ttg agt tct tgt gcc    4194
Thr Ala Gly Gln Ser Thr His Ala Met Glu Met Leu Ser Ser Cys Ala
        1355                1360                1365 ata tct ttc tgc aag tct gtg aaa gct gaa tat gca gtt gct aaa tca    4242
Ile Ser Phe Cys Lys Ser Val Lys Ala Glu Tyr Ala Val Ala Lys Ser
    1370                1375                1380 att ctg aca ctg gct aaa tgg atc cag gca gaa tgg aaa gag att tca    4290
Ile Leu Thr Leu Ala Lys Trp Ile Gln Ala Glu Trp Lys Glu Ile Ser
1385                1390                1395                1400 gga cag ctg aaa cag gtt tac aga gct cag cac caa cag aac ttc aca    4338
Gly Gln Leu Lys Gln Val Tyr Arg Ala Gln His Gln Gln Asn Phe Thr
                1405                1410                1415 ggt ctt tct act ttg tct aaa aac ata ctc act cta ata gaa ctg cca    4386
Gly Leu Ser Thr Leu Ser Lys Asn Ile Leu Thr Leu Ile Glu Leu Pro
            1420                1425                1430 tct gtt aat acg atg gaa gaa gag tat cct cgg atc gag agt gaa tct    4434
Ser Val Asn Thr Met Glu Glu Glu Tyr Pro Arg Ile Glu Ser Glu Ser
        1435                1440                1445 aca gtg cat att gga gtt gga gaa cct gac ttc att ttg gga cag ttg    4482
Thr Val His Ile Gly Val Gly Glu Pro Asp Phe Ile Leu Gly Gln Leu
    1450                1455                1460 tat cac ctg tct tca gta cag gca cct gaa gta gcc aaa tct tgg gca    4530
Tyr His Leu Ser Ser Val Gln Ala Pro Glu Val Ala Lys Ser Trp Ala
1465                1470                1475                1480 gcg ttg gcc agc tgg gct tat agg tgg ggc aga aag gtg gtt gac aat    4578
Ala Leu Ala Ser Trp Ala Tyr Arg Trp Gly Arg Lys Val Val Asp Asn
                1485                1490                1495 gcc agt cag gga gaa ggt gtt cgt ctg ctg cct aga gaa aaa tct gaa    4626
Ala Ser Gln Gly Glu Gly Val Arg Leu Leu Pro Arg Glu Lys Ser Glu
            1500                1505                1510 gtt cag aat cta ctt cca gac act ata act gag gaa gag aaa gag aga    4674
Val Gln Asn Leu Leu Pro Asp Thr Ile Thr Glu Glu Glu Lys Glu Arg
        1515                1520                1525 ata tat ggt att ctt gga cag gct gtg tgt cgg ccg gcg ggg att cag    4722
Ile Tyr Gly Ile Leu Gly Gln Ala Val Cys Arg Pro Ala Gly Ile Gln
    1530                1535                1540 gat gaa gat ata aca ctt cag ata act gag agt gaa gac aac gaa gaa    4770
Asp Glu Asp Ile Thr Leu Gln Ile Thr Glu Ser Glu Asp Asn Glu Glu
1545                1550                1555                1560
```

-continued

```
gat gac atg gtt gat gtt atc tgg cgt cag ttg ata tca agc tgc cca    4818
Asp Asp Met Val Asp Val Ile Trp Arg Gln Leu Ile Ser Ser Cys Pro
            1565                1570                1575 tgg ctt tca gaa ctt gat gaa agt gca act gaa gga gtt att aaa gtg    4866
Trp Leu Ser Glu Leu Asp Glu Ser Ala Thr Glu Gly Val Ile Lys Val
        1580                1585                1590 tgg agg aaa gtt gta gat aga ata ttc agc ctg tac aaa ctc tct tgc    4914
Trp Arg Lys Val Val Asp Arg Ile Phe Ser Leu Tyr Lys Leu Ser Cys
    1595                1600                1605 agt gca tac ttt act ttc ctt aaa ctc aac gct ggt caa att cct tta    4962
Ser Ala Tyr Phe Thr Phe Leu Lys Leu Asn Ala Gly Gln Ile Pro Leu
1610                1615                1620 gat gag gat gac cct agg ctg cat tta agt cac aga gtg gaa cag agc    5010
Asp Glu Asp Asp Pro Arg Leu His Leu Ser His Arg Val Glu Gln Ser
1625                1630                1635                1640 act gat gac atg att gtg atg gcc aca ttg cgc ctg ctg cgg ttg ctc    5058
Thr Asp Asp Met Ile Val Met Ala Thr Leu Arg Leu Leu Arg Leu Leu
            1645                1650                1655 gtg aag cat gct ggt gag ctt cgg cag tat ctg gag cac ggc ttg gag    5106
Val Lys His Ala Gly Glu Leu Arg Gln Tyr Leu Glu His Gly Leu Glu
        1660                1665                1670 aca aca ccc act gca cca tgg aga gga att att ccg caa ctt ttc tca    5154
Thr Thr Pro Thr Ala Pro Trp Arg Gly Ile Ile Pro Gln Leu Phe Ser
    1675                1680                1685 cgc tta aac cac cct gaa gtg tat gtg cgc caa agt att tgt aac ctt    5202
Arg Leu Asn His Pro Glu Val Tyr Val Arg Gln Ser Ile Cys Asn Leu
1690                1695                1700 ctc tgc cgt gtg gct caa gat tcc cca cat ctc ata ttg tat cct gca    5250
Leu Cys Arg Val Ala Gln Asp Ser Pro His Leu Ile Leu Tyr Pro Ala
1705                1710                1715                1720 ata gtg ggt acc ata tcg ctt agt agt gaa tcc cag gct tca gga aat    5298
Ile Val Gly Thr Ile Ser Leu Ser Ser Glu Ser Gln Ala Ser Gly Asn
            1725                1730                1735 aaa ttt tcc act gca att cca act tta ctt ggc aat att caa gga gaa    5346
Lys Phe Ser Thr Ala Ile Pro Thr Leu Leu Gly Asn Ile Gln Gly Glu
        1740                1745                1750 gaa ttg ctg gtt tct gaa tgt gag gga gga agt cct cct gca tct cag    5394
Glu Leu Leu Val Ser Glu Cys Glu Gly Gly Ser Pro Pro Ala Ser Gln
    1755                1760                1765 gat agc aat aag gat gaa cct aaa agt gga tta aat gaa gac caa gcc    5442
Asp Ser Asn Lys Asp Glu Pro Lys Ser Gly Leu Asn Glu Asp Gln Ala
1770                1775                1780 atg atg cag gat tgt tac agc aaa att gta gat aag ctg tcc tct gca    5490
Met Met Gln Asp Cys Tyr Ser Lys Ile Val Asp Lys Leu Ser Ser Ala
1785                1790                1795                1800 aac ccc acc atg gta tta cag gtt cag atg ctc gtg gct gaa ctg cgc    5538
Asn Pro Thr Met Val Leu Gln Val Gln Met Leu Val Ala Glu Leu Arg
            1805                1810                1815 agg gtc act gtg ctc tgg gat gag ctc tgg ctg gga gtt ttg ctg caa    5586
Arg Val Thr Val Leu Trp Asp Glu Leu Trp Leu Gly Val Leu Leu Gln
        1820                1825                1830 caa cac atg tat gtc ctg aga cga att cag cag ctt gaa gat gag gtg    5634
Gln His Met Tyr Val Leu Arg Arg Ile Gln Gln Leu Glu Asp Glu Val
    1835                1840                1845 aag aga gtc cag aac aac aac acc tta cgc aaa gaa gag aaa att gca    5682
Lys Arg Val Gln Asn Asn Asn Thr Leu Arg Lys Glu Glu Lys Ile Ala
1850                1855                1860 atc atg agg gag aag cac aca gct ttg atg aag ccc atc gta ttt gct    5730
Ile Met Arg Glu Lys His Thr Ala Leu Met Lys Pro Ile Val Phe Ala
1865                1870                1875                1880
```

```
ttg gag cat gtg agg agt atc aca gcg gct cct gca gaa aca cct cat      5778
Leu Glu His Val Arg Ser Ile Thr Ala Ala Pro Ala Glu Thr Pro His
                1885                1890                1895 gaa aaa tgg ttt cag gat aac tat ggt gat gcc att gaa aat gcc cta      5826
Glu Lys Trp Phe Gln Asp Asn Tyr Gly Asp Ala Ile Glu Asn Ala Leu
            1900                1905                1910 gaa aaa ctg aag act cca ttg aac cct gca aag cct ggg agc agc tgg      5874
Glu Lys Leu Lys Thr Pro Leu Asn Pro Ala Lys Pro Gly Ser Ser Trp
        1915                1920                1925 att cca ttt aaa gag ata atg cta agt ttg caa cag aga gca cag aaa      5922
Ile Pro Phe Lys Glu Ile Met Leu Ser Leu Gln Gln Arg Ala Gln Lys
    1930                1935                1940 cgt gca agt tac atc ttg cgt ctt gaa gaa atc agt cca tgg ttg gct      5970
Arg Ala Ser Tyr Ile Leu Arg Leu Glu Glu Ile Ser Pro Trp Leu Ala
1945                1950                1955                1960 gcc atg act aac act gaa att gct ctt cct ggg gaa gtc tca gcc aga      6018
Ala Met Thr Asn Thr Glu Ile Ala Leu Pro Gly Glu Val Ser Ala Arg
                1965                1970                1975 gac act gtc aca atc cat agt gtg ggc gga acc atc aca atc tta ccg      6066
Asp Thr Val Thr Ile His Ser Val Gly Gly Thr Ile Thr Ile Leu Pro
            1980                1985                1990 act aaa acc aag cca aag aaa ctt ctc ttt ctt gga tca gat ggg aag      6114
Thr Lys Thr Lys Pro Lys Lys Leu Leu Phe Leu Gly Ser Asp Gly Lys
        1995                2000                2005 agc tat cct tat ctt ttc aaa gga ctg gag gat tta cat ctg gat gag      6162
Ser Tyr Pro Tyr Leu Phe Lys Gly Leu Glu Asp Leu His Leu Asp Glu
    2010                2015                2020 aga ata atg cag ttc cta tct att gtg aat acc atg ttt gct aca att      6210
Arg Ile Met Gln Phe Leu Ser Ile Val Asn Thr Met Phe Ala Thr Ile
2025                2030                2035                2040 aat cgc caa gaa aca ccc cgg ttc cat gct cga cac tat tct gta aca      6258
Asn Arg Gln Glu Thr Pro Arg Phe His Ala Arg His Tyr Ser Val Thr
                2045                2050                2055 cca cta gga aca aga tca gga cta atc cag tgg gta gat gga gcc aca      6306
Pro Leu Gly Thr Arg Ser Gly Leu Ile Gln Trp Val Asp Gly Ala Thr
            2060                2065                2070 ccc tta ttt ggt ctt tac aaa cga tgg caa caa cgg gaa gct gcc tta      6354
Pro Leu Phe Gly Leu Tyr Lys Arg Trp Gln Gln Arg Glu Ala Ala Leu
        2075                2080                2085 caa gca caa aag gcc caa gat tcc tac caa act cct cag aat cct gga      6402
Gln Ala Gln Lys Ala Gln Asp Ser Tyr Gln Thr Pro Gln Asn Pro Gly
    2090                2095                2100 att gta ccc cgt cct agt gaa ctt tat tac agt aaa att ggc cct gct      6450
Ile Val Pro Arg Pro Ser Glu Leu Tyr Tyr Ser Lys Ile Gly Pro Ala
2105                2110                2115                2120 ttg aaa aca gtt ggg ctt agc ctg gat gtg tcc cgt cgg gat tgg cct      6498
Leu Lys Thr Val Gly Leu Ser Leu Asp Val Ser Arg Arg Asp Trp Pro
                2125                2130                2135 ctt cat gta atg aag gca gta ttg gaa gag tta atg gag gcc aca ccc      6546
Leu His Val Met Lys Ala Val Leu Glu Glu Leu Met Glu Ala Thr Pro
            2140                2145                2150 ccg aat ctc ctt gcc aaa gag ctc tgg tca tct tgc aca aca cct gat      6594
Pro Asn Leu Leu Ala Lys Glu Leu Trp Ser Ser Cys Thr Thr Pro Asp
        2155                2160                2165 gaa tgg tgg aga gtt acg cag tct tat gca aga tct act gca gtc atg      6642
Glu Trp Trp Arg Val Thr Gln Ser Tyr Ala Arg Ser Thr Ala Val Met
    2170                2175                2180 tct atg gtt gga tac ata att ggc ctt gga gac aga cat ctg gat aat      6690
Ser Met Val Gly Tyr Ile Ile Gly Leu Gly Asp Arg His Leu Asp Asn
2185                2190                2195                2200
```

```
gtt ctt ata gat atg acg act gga gaa gtt gtt cac ata gat tac aat    6738
Val Leu Ile Asp Met Thr Thr Gly Glu Val Val His Ile Asp Tyr Asn
            2205                2210                2215 gtt tgc ttt gaa aaa ggt aaa agc ctt aga gtt cct gag aaa gta cct    6786
Val Cys Phe Glu Lys Gly Lys Ser Leu Arg Val Pro Glu Lys Val Pro
        2220                2225                2230 ttt cga atg aca caa aac att gaa aca gca ctg ggt gta act gga gta    6834
Phe Arg Met Thr Gln Asn Ile Glu Thr Ala Leu Gly Val Thr Gly Val
    2235                2240                2245 gaa ggt gta ttt agg ctt tca tgt gag cag gtt tta cac att atg cgg    6882
Glu Gly Val Phe Arg Leu Ser Cys Glu Gln Val Leu His Ile Met Arg
2250                2255                2260 cgt ggc aga gag acc ctg ctg acg ctg ctg gag gcc ttt gtg tac gac    6930
Arg Gly Arg Glu Thr Leu Leu Thr Leu Leu Glu Ala Phe Val Tyr Asp
2265                2270                2275                2280 cct ctg gtg gac tgg aca gca gga ggc gag gct ggg ttt gct ggt gct    6978
Pro Leu Val Asp Trp Thr Ala Gly Gly Glu Ala Gly Phe Ala Gly Ala
                2285                2290                2295 gtc tat ggt gga ggt ggc cag cag gcc gag agc aag cag agc aag aga    7026
Val Tyr Gly Gly Gly Gly Gln Gln Ala Glu Ser Lys Gln Ser Lys Arg
            2300                2305                2310 gag atg gag cga gag atc acc cgc agc ctg ttt tct tct aga gta gct    7074
Glu Met Glu Arg Glu Ile Thr Arg Ser Leu Phe Ser Ser Arg Val Ala
        2315                2320                2325 gag att aag gtg aac tgg ttt aag aat aga gat gag atg ctg gtt gtg    7122
Glu Ile Lys Val Asn Trp Phe Lys Asn Arg Asp Glu Met Leu Val Val
    2330                2335                2340 ctt ccc aag ttg gac ggt agc tta gat gaa tac cta agc ttg caa gag    7170
Leu Pro Lys Leu Asp Gly Ser Leu Asp Glu Tyr Leu Ser Leu Gln Glu
2345                2350                2355                2360 caa ctg aca gat gtg gaa aaa ctg cag ggc aaa cta ctg gag gaa ata    7218
Gln Leu Thr Asp Val Glu Lys Leu Gln Gly Lys Leu Leu Glu Glu Ile
                2365                2370                2375 gag ttt cta gaa gga gct gaa ggg gtg gat cat cct tct cat act ctg    7266
Glu Phe Leu Glu Gly Ala Glu Gly Val Asp His Pro Ser His Thr Leu
            2380                2385                2390 caa cac agg tat tct gag cac acc caa cta cag act cag caa aga gct    7314
Gln His Arg Tyr Ser Glu His Thr Gln Leu Gln Thr Gln Gln Arg Ala
        2395                2400                2405 gtt cag gaa gca atc cag gtg aag ctg aat gaa ttt gaa caa tgg ata    7362
Val Gln Glu Ala Ile Gln Val Lys Leu Asn Glu Phe Glu Gln Trp Ile
    2410                2415                2420 aca cat tat cag gct gca ttc aat aat tta gaa gca aca cag ctt gca    7410
Thr His Tyr Gln Ala Ala Phe Asn Asn Leu Glu Ala Thr Gln Leu Ala
2425                2430                2435                2440 agc ttg ctt caa gag ata agc aca caa atg gac ctt ggt cct cca agt    7458
Ser Leu Leu Gln Glu Ile Ser Thr Gln Met Asp Leu Gly Pro Pro Ser
                2445                2450                2455 tac gtg cca gca aca gcc ttt ctg cag aat gct ggt cag gcc cac ttg    7506
Tyr Val Pro Ala Thr Ala Phe Leu Gln Asn Ala Gly Gln Ala His Leu
            2460                2465                2470 att agc cag tgc gag cag ctg gag ggg gag gtt ggt gct ctc ctg cag    7554
Ile Ser Gln Cys Glu Gln Leu Glu Gly Glu Val Gly Ala Leu Leu Gln
        2475                2480                2485 cag agg cgc tcc gtg ctc cgt ggc tgt ctg gag caa ctg cat cac tat    7602
Gln Arg Arg Ser Val Leu Arg Gly Cys Leu Glu Gln Leu His His Tyr
    2490                2495                2500 gca acc gtg gcc ctg cag tat ccg aag gcc ata ttt cag aaa cat cga    7650
Ala Thr Val Ala Leu Gln Tyr Pro Lys Ala Ile Phe Gln Lys His Arg
2505                2510                2515                2520
```

```
att gaa cag tgg aag acc tgg atg gaa gag ctc atc tgt aac acc aca     7698
Ile Glu Gln Trp Lys Thr Trp Met Glu Glu Leu Ile Cys Asn Thr Thr
            2525                2530                2535 gta gag cgt tgt caa gag ctc tat agg aaa tat gaa atg caa tat gct     7746
Val Glu Arg Cys Gln Glu Leu Tyr Arg Lys Tyr Glu Met Gln Tyr Ala
        2540                2545                2550 ccc cag cca ccc cca aca gtg tgt cag ttc atc act gcc act gaa atg     7794
Pro Gln Pro Pro Pro Thr Val Cys Gln Phe Ile Thr Ala Thr Glu Met
    2555                2560                2565 acc ctg cag cga tac gca gca gac atc aac agc aga ctt att aga caa     7842
Thr Leu Gln Arg Tyr Ala Ala Asp Ile Asn Ser Arg Leu Ile Arg Gln
2570                2575                2580 gtg gaa cgc ttg aaa cag gaa gct gtc act gtg cca gtt tgt gaa gat     7890
Val Glu Arg Leu Lys Gln Glu Ala Val Thr Val Pro Val Cys Glu Asp
2585                2590                2595                2600 cag ttg aaa gaa att gaa cgt tgc att aaa gtt ttc ctt cat gag aat     7938
Gln Leu Lys Glu Ile Glu Arg Cys Ile Lys Val Phe Leu His Glu Asn
            2605                2610                2615 gga gaa gaa gga tct ttg agt cta gca agt gtt att att tct gcc ctt     7986
Gly Glu Glu Gly Ser Leu Ser Leu Ala Ser Val Ile Ile Ser Ala Leu
        2620                2625                2630 tgt acc ctt aca agg cgt aac ctg atg atg gaa ggt gca gcg tca agt     8034
Cys Thr Leu Thr Arg Arg Asn Leu Met Met Glu Gly Ala Ala Ser Ser
    2635                2640                2645 gct gga gaa cag ctg gtt gat ctg act tct cgg gat gga gcc tgg ttc     8082
Ala Gly Glu Gln Leu Val Asp Leu Thr Ser Arg Asp Gly Ala Trp Phe
2650                2655                2660 ttg gag gaa ctc tgc agt atg agc gga aac gtc acc tgc ttg gtt cag     8130
Leu Glu Glu Leu Cys Ser Met Ser Gly Asn Val Thr Cys Leu Val Gln
2665                2670                2675                2680 tta ctg aag cag tgc cac ctg gtg cca cag gac tta gat atc ccg aac     8178
Leu Leu Lys Gln Cys His Leu Val Pro Gln Asp Leu Asp Ile Pro Asn
            2685                2690                2695 ccc atg gaa gcg tct gag aca gtt cac tta gcc aat gga gtg tat acc     8226
Pro Met Glu Ala Ser Glu Thr Val His Leu Ala Asn Gly Val Tyr Thr
        2700                2705                2710 tca ctt cag gaa ttg aat tcg aat ttc cgg caa atc ata ttt cca gaa     8274
Ser Leu Gln Glu Leu Asn Ser Asn Phe Arg Gln Ile Ile Phe Pro Glu
    2715                2720                2725 gca ctt cga tgt tta atg aaa ggg gaa tac acg tta gaa agt atg ctg     8322
Ala Leu Arg Cys Leu Met Lys Gly Glu Tyr Thr Leu Glu Ser Met Leu
2730                2735                2740 cat gaa ctg gac ggt ctt att gag cag acc acc gat ggc gtt ccc ctg     8370
His Glu Leu Asp Gly Leu Ile Glu Gln Thr Thr Asp Gly Val Pro Leu
2745                2750                2755                2760 cag act cta gtg gaa tct ctt cag gcc tac tta aga aac gca gct atg     8418
Gln Thr Leu Val Glu Ser Leu Gln Ala Tyr Leu Arg Asn Ala Ala Met
            2765                2770                2775 gga ctg gaa gaa gaa aca cat gct cat tac atc gat gtt gcc aga cta     8466
Gly Leu Glu Glu Glu Thr His Ala His Tyr Ile Asp Val Ala Arg Leu
        2780                2785                2790 cta cat gct cag tac ggt gaa tta atc caa ccg aga aat ggt tca gtt     8514
Leu His Ala Gln Tyr Gly Glu Leu Ile Gln Pro Arg Asn Gly Ser Val
    2795                2800                2805 gat gaa aca ccc aaa atg tca gct ggc cag atg ctt ttg gta gca ttc     8562
Asp Glu Thr Pro Lys Met Ser Ala Gly Gln Met Leu Leu Val Ala Phe
2810                2815                2820 gat ggc atg ttt gct caa gtt gaa act gct ttc agc tta tta gtt gaa     8610
Asp Gly Met Phe Ala Gln Val Glu Thr Ala Phe Ser Leu Leu Val Glu
2825                2830                2835                2840
```

```
aag ttg aac aag atg gaa att ccc ata gct tgg cga aag att gac atc      8658
Lys Leu Asn Lys Met Glu Ile Pro Ile Ala Trp Arg Lys Ile Asp Ile
                2845                2850                2855 ata agg gaa gcc agg agt act caa gtt aat ttt ttt gat gat gat aat      8706
Ile Arg Glu Ala Arg Ser Thr Gln Val Asn Phe Phe Asp Asp Asp Asn
                2860                2865                2870 cac cgg cag gtg cta gaa gag att ttc ttt cta aaa aga cta cag act      8754
His Arg Gln Val Leu Glu Glu Ile Phe Phe Leu Lys Arg Leu Gln Thr
                2875                2880                2885 att aag gag ttc ttc agg ctc tgt ggt acc ttt tct aaa aca ttg tca      8802
Ile Lys Glu Phe Phe Arg Leu Cys Gly Thr Phe Ser Lys Thr Leu Ser
                2890                2895                2900 gga tca agt tca ctt gaa gat cag aat act gtg aat ggg cct gta cag      8850
Gly Ser Ser Ser Leu Glu Asp Gln Asn Thr Val Asn Gly Pro Val Gln
2905                2910                2915                2920 att gtc aat gtg aaa acc ctt ttt aga aac tct tgt ttc agt gaa gac      8898
Ile Val Asn Val Lys Thr Leu Phe Arg Asn Ser Cys Phe Ser Glu Asp
                2925                2930                2935 caa atg gcc aaa cct atc aag gca ttc aca gct gac ttt gtg agg cag      8946
Gln Met Ala Lys Pro Ile Lys Ala Phe Thr Ala Asp Phe Val Arg Gln
                2940                2945                2950 ctc ttg ata ggg cta ccc aac caa gcc ctc gga ctc aca ctg tgc agt      8994
Leu Leu Ile Gly Leu Pro Asn Gln Ala Leu Gly Leu Thr Leu Cys Ser
                2955                2960                2965 ttt atc agt gct ctg ggt gta gac atc att gct caa gta gag gca aag      9042
Phe Ile Ser Ala Leu Gly Val Asp Ile Ile Ala Gln Val Glu Ala Lys
                2970                2975                2980 gac ttt ggt gcc gaa agc aaa gtt tct gtt gat gat ctc tgt aag aaa      9090
Asp Phe Gly Ala Glu Ser Lys Val Ser Val Asp Asp Leu Cys Lys Lys
2985                2990                2995                3000 gcg gtg gaa cat aac atc cag ata ggg aag ttc tct cag ctg gtt atg      9138
Ala Val Glu His Asn Ile Gln Ile Gly Lys Phe Ser Gln Leu Val Met
                3005                3010                3015 aac agg gca act gtg tta gca agt tct tac gac act gcc tgg aag aag      9186
Asn Arg Ala Thr Val Leu Ala Ser Ser Tyr Asp Thr Ala Trp Lys Lys
                3020                3025                3030 cat gac ttg gtg cga agg cta gaa acc agt att tct tct tgt aag aca      9234
His Asp Leu Val Arg Arg Leu Glu Thr Ser Ile Ser Ser Cys Lys Thr
                3035                3040                3045 agc ctg cag cgg gtt cag ctg cat att gcc atg ttt cag tgg caa cat      9282
Ser Leu Gln Arg Val Gln Leu His Ile Ala Met Phe Gln Trp Gln His
                3050                3055                3060 gaa gat cta ctt atc aat aga cca caa gcc atg tca gtc aca cct ccc      9330
Glu Asp Leu Leu Ile Asn Arg Pro Gln Ala Met Ser Val Thr Pro Pro
3065                3070                3075                3080 cca cgg tct gct atc cta acc agc atg aaa aag aag ctg cat acc ctg      9378
Pro Arg Ser Ala Ile Leu Thr Ser Met Lys Lys Lys Leu His Thr Leu
                3085                3090                3095 agc cag att gaa act tct att gca aca gtt cag gag aag cta gct gca      9426
Ser Gln Ile Glu Thr Ser Ile Ala Thr Val Gln Glu Lys Leu Ala Ala
                3100                3105                3110 ctt gaa tca agt att gaa cag cga ctc aag tgg gca ggt ggt gcc aac      9474
Leu Glu Ser Ser Ile Glu Gln Arg Leu Lys Trp Ala Gly Gly Ala Asn
                3115                3120                3125 cct gca ttg gcc cct gta cta caa gat ttt gaa gca acg ata gct gaa      9522
Pro Ala Leu Ala Pro Val Leu Gln Asp Phe Glu Ala Thr Ile Ala Glu
                3130                3135                3140 aga aga aat ctt gtc ctt aaa gag agc caa aga gca agt cag gtc aca      9570
Arg Arg Asn Leu Val Leu Lys Glu Ser Gln Arg Ala Ser Gln Val Thr
3145                3150                3155                3160
```

```
                                              -continued
ttt ctc tgc agc aat atc att cat ttt gaa agt tta cga aca aga act      9618
Phe Leu Cys Ser Asn Ile Ile His Phe Glu Ser Leu Arg Thr Arg Thr
            3165                3170                3175 gca gaa gcc tta aac ctg gat gcg gcg tta ttt gaa cta atc aag cga      9666
Ala Glu Ala Leu Asn Leu Asp Ala Ala Leu Phe Glu Leu Ile Lys Arg
        3180                3185                3190 tgt cag cag atg tgt tcg ttt gca tca cag ttt aac agt tca gtg tct      9714
Cys Gln Gln Met Cys Ser Phe Ala Ser Gln Phe Asn Ser Ser Val Ser
    3195                3200                3205 gag tta gag ctt cgt tta tta cag aga gtg gac act ggt ctt gaa cat      9762
Glu Leu Glu Leu Arg Leu Leu Gln Arg Val Asp Thr Gly Leu Glu His
3210                3215                3220 cct att ggc agc tct gaa tgg ctt ttg tca gca cac aaa cag ttg acc      9810
Pro Ile Gly Ser Ser Glu Trp Leu Leu Ser Ala His Lys Gln Leu Thr
3225                3230                3235                3240 cag gat atg tct act cag agg gca att cag aca gag aaa gag cag cag      9858
Gln Asp Met Ser Thr Gln Arg Ala Ile Gln Thr Glu Lys Glu Gln Gln
            3245                3250                3255 ata gaa acg gtc tgt gaa aca att cag aat ctg gtt gat aat ata aag      9906
Ile Glu Thr Val Cys Glu Thr Ile Gln Asn Leu Val Asp Asn Ile Lys
        3260                3265                3270 act gtg ctc act ggt cat aac cga cag ctt gga gat gtc aaa cat ctc      9954
Thr Val Leu Thr Gly His Asn Arg Gln Leu Gly Asp Val Lys His Leu
    3275                3280                3285 ttg aaa gct atg gct aag gat gaa gaa gct gct ctg gca gat ggt gaa     10002
Leu Lys Ala Met Ala Lys Asp Glu Glu Ala Ala Leu Ala Asp Gly Glu
3290                3295                3300 gat gtt ccc tat gag aac agt gtt agg cag ttt ttg ggt gaa tat aaa     10050
Asp Val Pro Tyr Glu Asn Ser Val Arg Gln Phe Leu Gly Glu Tyr Lys
3305                3310                3315                3320 tca tgg caa gac aac att caa aca gtt cta ttt aca tta gtc cag gct     10098
Ser Trp Gln Asp Asn Ile Gln Thr Val Leu Phe Thr Leu Val Gln Ala
            3325                3330                3335 atg ggt cag gtt cga agt caa gaa cac gtt gaa atg ctc cag gaa atc     10146
Met Gly Gln Val Arg Ser Gln Glu His Val Glu Met Leu Gln Glu Ile
        3340                3345                3350 act ccc acc ttg aaa gaa ctg aaa aca caa agt cag agt atc tat aat     10194
Thr Pro Thr Leu Lys Glu Leu Lys Thr Gln Ser Gln Ser Ile Tyr Asn
    3355                3360                3365 aat tta gtg agt ttt gca tca ccc tta gtc acc gat gca aca aat gaa     10242
Asn Leu Val Ser Phe Ala Ser Pro Leu Val Thr Asp Ala Thr Asn Glu
3370                3375                3380 tgt tcg agt cca acg tca tct gct act tat cag cca tcc ttc gct gca     10290
Cys Ser Ser Pro Thr Ser Ser Ala Thr Tyr Gln Pro Ser Phe Ala Ala
3385                3390                3395                3400 gca gtc cgg agt aac act ggc cag aag act cag cct gat gtc atg tca     10338
Ala Val Arg Ser Asn Thr Gly Gln Lys Thr Gln Pro Asp Val Met Ser
            3405                3410                3415 cag aat gct aga aag ctg atc cag aaa aat ctt gct aca tca gct gat     10386
Gln Asn Ala Arg Lys Leu Ile Gln Lys Asn Leu Ala Thr Ser Ala Asp
        3420                3425                3430 act cca cca agc acc gtt cca gga act ggc aag agt gtt gct tgt agt     10434
Thr Pro Pro Ser Thr Val Pro Gly Thr Gly Lys Ser Val Ala Cys Ser
    3435                3440                3445 cct aaa aag gca gtc aga gac cct aaa act ggg aaa gcg gtg caa gag     10482
Pro Lys Lys Ala Val Arg Asp Pro Lys Thr Gly Lys Ala Val Gln Glu
3450                3455                3460 aga aac tcc tat gca gtg agt gtg tgg aag aga gtg aaa gcc aag tta     10530
Arg Asn Ser Tyr Ala Val Ser Val Trp Lys Arg Val Lys Ala Lys Leu
3465                3470                3475                3480
```

-continued

| | |
|---|---|
| gag ggc cga gat gtt gat ccg aat agg agg atg tca gtt gct gaa cag<br>Glu Gly Arg Asp Val Asp Pro Asn Arg Arg Met Ser Val Ala Glu Gln<br>                    3485                     3490                  3495 | 10578 |
| gtt gac tat gtc att aag gaa gca act aat cta gat aac ttg gct cag<br>Val Asp Tyr Val Ile Lys Glu Ala Thr Asn Leu Asp Asn Leu Ala Gln<br>            3500                     3505                     3510 | 10626 |
| ctg tat gaa ggt tgg aca gcc tgg gtg tga atggcaagac agtagatgag<br>Leu Tyr Glu Gly Trp Thr Ala Trp Val *<br>            3515                     3520 | 10676 |
| tctggttaag cgaggtcaga catccaccag aatcaactca gcctcaggca tccaaagcca | 10736 |
| caccacagtc ggtggtgatg caactggggg cttactctga ggaaacctag gaaatctcgg | 10796 |
| tgcactagga agtgaatccc gcaggacagc tgcactcagg gatacgccca acaccatggc | 10856 |
| ctgcaacccc agggtcaagg gtgaaggaaa gcaagctcac cgcctgaaca cggagattgt | 10916 |
| ctttctgcca cagaacagca gcagacgtgt cgggaggtta gctgcggaaa gaaatcggga | 10976 |
| tgccgcggag cacagagtga tttgaactc cattccacct gaccctgtgt gtacaatcca | 11036 |
| ggaaaaaaac aaaccccact cagaaacaga gaaaactggg gtcgcgaaga aatcacagcc | 11096 |
| aaggaagatt tgatgcattc agattctcgt gtaacacttg ttgcttggca acagtactgg | 11156 |
| ttgggttgac cagtaagtag aaaaaggcta aaggctatgc gatatgaatt cagaaatgg | 11216 |
| actgaaaatg gagagctatg taacagatac actacagtag aagaacttac ttctgaaatg | 11276 |
| aagggaaaaa aaccaccccca tcgttcccta ctcctcccca ccacttaccc gttccccctt | 11336 |
| tacctaatct agtagattag ccatctttca aattcacttt tatttcagtc cttatatttc | 11396 |
| atatacttcc gtctcgatgc tgttaacaac ttctgataac atggaaaatt caaggattgt | 11456 |
| ttaaaggtct gatgatcaca cacaaaatgt aattccggtt attaagtca tttctgtgat | 11516 |
| tctatcatgt acagtttcca gaattgtcac tgtgcattca aaagtaatga atctaacaga | 11576 |
| catttgattt aatgtacact ccctttttgct tatagtgtgc attttttttg gaggtcattc | 11636 |
| aaattttccc tcttctgtga tagctgtagt ttctttcata gaaagtagct aatccagtgt | 11696 |
| aatcttttac cttttaaaa accaagatag agtatctatt agagttttac attgttgatg | 11756 |
| atagattaac aataaagtga tgttctggtg gaggtagact gaaattttt taattcatgt | 11816 |
| ttttcatttg atacttttaa tttacactta gtaaattaaa agttgtttaa tttacttggc | 11876 |
| attttaggac atgtacatga aacagtgaaa atgagatcca ccaacatctt ttattaagtt | 11936 |
| cagttattag tctgtgaagt gctttacttt ttgcacaatt ttaatagctt gctattcagt | 11996 |
| aatacattat agtgaattca tgatcaaggt ttccttaaat ttagcattgc atttcagtac | 12056 |
| tgactgtgta agctaaattg ctgatccaaa ataaaaaccc agactagaat agggttctta | 12116 |
| aaatcaagta tcaatacaaa atagaacaca attaaaatct taattgttgg ctgggcacag | 12176 |
| tggctcacgc ctgtaatccc agcactttgg gaggccgagg cgggcggatc atgaggttag | 12236 |
| gagagcgaga ccatcctggc taacacggtg aaaccccgtc tttactaaaa tacaaaaaaa | 12296 |
| attagccggg tgtggtggcg ggcgcctgta gtcccagcta ctcgggaggc tgaggcagga | 12356 |
| gaatggcgtg aacccaggag gcggagcttg cagtgagccg agattgtgcc actgcactcc | 12416 |
| agcctgggca acagagctag actctgtgtc aaaaataaat gactagat | 12464 |

<210> SEQ ID NO 2
<211> LENGTH: 3521
<212> TYPE: PRT
<213> ORGANISM: Homo sapiens

<400> SEQUENCE: 2

```
Met Ser Tyr Cys Asp Glu Ser Arg Leu Ser Asn Leu Leu Arg Arg Ile
1               5                   10                  15

Thr Arg Glu Asp Asp Arg Asp Arg Arg Leu Ala Thr Val Lys Gln Leu
            20                  25                  30

Lys Glu Phe Ile Gln Gln Pro Glu Asn Lys Leu Val Leu Val Lys Gln
                35                  40                  45

Leu Asp Asn Ile Leu Ala Ala Val His Asp Val Leu Asn Glu Ser Ser
        50                  55                  60

Lys Leu Leu Gln Glu Leu Arg Gln Glu Gly Ala Cys Cys Leu Gly Leu
65                  70                  75                  80

Leu Cys Ala Ser Leu Ser Tyr Glu Ala Glu Lys Ile Phe Lys Trp Ile
                85                  90                  95

Phe Ser Lys Phe Ser Ser Ser Ala Lys Asp Glu Val Lys Leu Leu Tyr
                100                 105                 110

Leu Cys Ala Thr Tyr Lys Ala Leu Glu Thr Val Gly Glu Lys Lys Ala
            115                 120                 125

Phe Ser Ser Val Met Gln Leu Val Met Thr Ser Leu Gln Ser Ile Leu
130                 135                 140

Glu Asn Val Asp Thr Pro Glu Leu Leu Cys Lys Cys Val Lys Cys Ile
145                 150                 155                 160

Leu Leu Val Ala Arg Cys Tyr Pro His Ile Phe Ser Thr Asn Phe Arg
                165                 170                 175

Asp Thr Val Asp Ile Leu Val Gly Trp His Ile Asp His Thr Gln Lys
            180                 185                 190

Pro Ser Leu Thr Gln Gln Val Ser Gly Trp Leu Gln Ser Leu Glu Pro
                195                 200                 205

Phe Trp Val Ala Asp Leu Ala Phe Ser Thr Thr Leu Gly Gln Phe
        210                 215                 220

Leu Glu Asp Met Glu Ala Tyr Ala Glu Asp Leu Ser His Val Ala Ser
225                 230                 235                 240

Gly Glu Ser Val Asp Glu Asp Val Pro Pro Ser Val Ser Leu Pro
                245                 250                 255

Lys Leu Ala Ala Leu Leu Arg Val Phe Ser Thr Val Val Arg Ser Ile
            260                 265                 270

Gly Glu Arg Phe Ser Pro Ile Arg Gly Pro Pro Ile Thr Glu Ala Tyr
                275                 280                 285

Val Thr Asp Val Leu Tyr Arg Val Met Arg Cys Val Thr Ala Ala Asn
        290                 295                 300

Gln Val Phe Phe Ser Glu Ala Val Leu Thr Ala Ala Asn Glu Cys Val
305                 310                 315                 320

Gly Val Leu Leu Gly Ser Leu Asp Pro Ser Met Thr Ile His Cys Asp
                325                 330                 335

Met Val Ile Thr Tyr Gly Leu Asp Gln Leu Glu Asn Cys Gln Thr Cys
            340                 345                 350

Gly Thr Asp Tyr Ile Ile Ser Val Leu Asn Leu Leu Thr Leu Ile Val
            355                 360                 365

Glu Gln Ile Asn Thr Lys Leu Pro Ser Ser Phe Val Glu Lys Leu Phe
        370                 375                 380

Ile Pro Ser Ser Lys Leu Leu Phe Leu Arg Tyr His Lys Glu Lys Glu
385                 390                 395                 400

Val Val Ala Val Ala His Ala Val Tyr Gln Ala Val Leu Ser Leu Lys
                405                 410                 415
```

-continued

```
Asn Ile Pro Val Leu Glu Thr Ala Tyr Lys Leu Ile Leu Gly Glu Met
            420                 425                 430

Thr Cys Ala Leu Asn Asn Leu Leu His Ser Leu Gln Leu Pro Glu Ala
        435                 440                 445

Cys Ser Glu Ile Lys His Glu Ala Phe Lys Asn His Val Phe Asn Val
    450                 455                 460

Asp Asn Ala Lys Phe Val Val Ile Phe Asp Leu Ser Ala Leu Thr Thr
465                 470                 475                 480

Ile Gly Asn Ala Lys Asn Ser Leu Ile Gly Met Trp Ala Leu Ser Pro
                485                 490                 495

Thr Val Phe Ala Leu Leu Ser Lys Asn Leu Met Ile Val His Ser Asp
            500                 505                 510

Leu Ala Val His Phe Pro Ala Ile Gln Tyr Ala Val Leu Tyr Thr Leu
        515                 520                 525

Tyr Ser His Cys Thr Arg His Asp His Phe Ile Ser Ser Ser Leu Ser
    530                 535                 540

Ser Ser Ser Pro Ser Leu Phe Asp Gly Ala Val Ile Ser Thr Val Thr
545                 550                 555                 560

Thr Ala Thr Lys Lys His Phe Ser Ile Ile Leu Asn Leu Leu Gly Ile
                565                 570                 575

Leu Leu Lys Lys Asp Asn Leu Asn Gln Asp Thr Arg Lys Leu Leu Met
            580                 585                 590

Thr Trp Ala Leu Glu Ala Ala Val Leu Met Lys Lys Ser Glu Thr Tyr
        595                 600                 605

Ala Pro Leu Phe Ser Leu Pro Ser Phe His Lys Phe Cys Lys Gly Leu
    610                 615                 620

Leu Ala Asn Thr Leu Val Glu Asp Val Asn Ile Cys Leu Gln Ala Cys
625                 630                 635                 640

Ser Ser Leu His Ala Leu Ser Ser Ser Leu Pro Asp Asp Leu Leu Gln
                645                 650                 655

Arg Cys Val Asp Val Cys Arg Val Gln Leu Val His Ser Gly Thr Arg
            660                 665                 670

Ile Arg Gln Ala Phe Gly Lys Leu Leu Lys Ser Ile Pro Leu Asp Val
        675                 680                 685

Val Leu Ser Asn Asn Asn His Thr Glu Ile Gln Glu Ile Ser Leu Ala
    690                 695                 700

Leu Arg Ser His Met Ser Lys Ala Pro Ser Asn Thr Phe His Pro Gln
705                 710                 715                 720

Asp Phe Ser Asp Val Ile Ser Phe Ile Leu Tyr Gly Asn Ser His Arg
                725                 730                 735

Thr Gly Lys Asp Asn Trp Leu Glu Arg Leu Phe Tyr Ser Cys Gln Arg
            740                 745                 750

Leu Asp Lys Arg Asp Gln Ser Thr Ile Pro Arg Asn Leu Leu Lys Thr
        755                 760                 765

Asp Ala Val Leu Trp Gln Trp Ala Ile Trp Glu Ala Ala Gln Phe Thr
    770                 775                 780

Val Leu Ser Lys Leu Arg Thr Pro Leu Gly Arg Ala Gln Asp Thr Phe
785                 790                 795                 800

Gln Thr Ile Glu Gly Ile Ile Arg Ser Leu Ala Ala His Thr Leu Asn
                805                 810                 815

Pro Asp Gln Asp Val Ser Gln Trp Thr Thr Ala Asp Asn Asp Glu Gly
            820                 825                 830
```

```
His Gly Asn Asn Gln Leu Arg Leu Val Leu Leu Gln Tyr Leu Glu
    835                 840                 845

Asn Leu Glu Lys Leu Met Tyr Asn Ala Tyr Glu Gly Cys Ala Asn Ala
850                 855                 860

Leu Thr Ser Pro Pro Lys Val Ile Arg Thr Phe Phe Tyr Thr Asn Arg
865                 870                 875                 880

Gln Thr Cys Gln Asp Trp Leu Thr Arg Ile Arg Leu Ser Ile Met Arg
                885                 890                 895

Val Gly Leu Leu Ala Gly Gln Pro Ala Val Thr Val Arg His Gly Phe
            900                 905                 910

Asp Leu Leu Thr Glu Met Lys Thr Thr Ser Leu Ser Gln Gly Asn Glu
            915                 920                 925

Leu Glu Val Thr Ile Met Met Val Val Glu Ala Leu Cys Glu Leu His
        930                 935                 940

Cys Pro Glu Ala Ile Gln Gly Ile Ala Val Trp Ser Ser Ile Val
945                 950                 955                 960

Gly Lys Asn Leu Leu Trp Ile Asn Ser Val Ala Gln Gln Ala Glu Gly
                965                 970                 975

Arg Phe Glu Lys Ala Ser Val Glu Tyr Gln Glu His Leu Cys Ala Met
            980                 985                 990

Thr Gly Val Asp Cys Cys Ile Ser Ser Phe Asp Lys Ser Val Leu Thr
    995                 1000                1005

Leu Ala Asn Ala Gly Arg Asn Ser Ala Ser Pro Lys His Ser Leu Asn
    1010                1015                1020

Gly Glu Ser Arg Lys Thr Val Leu Ser Lys Pro Thr Asp Ser Ser Pro
1025                1030                1035                1040

Glu Val Ile Asn Tyr Leu Gly Asn Lys Ala Cys Glu Cys Tyr Ile Ser
                1045                1050                1055

Ile Ala Asp Trp Ala Ala Val Gln Glu Trp Gln Asn Ala Ile His Asp
                1060                1065                1070

Leu Lys Lys Ser Thr Ser Ser Thr Ser Leu Asn Leu Lys Ala Asp Phe
            1075                1080                1085

Asn Tyr Ile Lys Ser Leu Ser Ser Phe Glu Ser Gly Lys Phe Val Glu
            1090                1095                1100

Cys Thr Glu Gln Leu Glu Leu Pro Gly Glu Asn Ile Asn Leu Leu
1105                1110                1115                1120

Ala Gly Gly Ser Lys Glu Lys Ile Asp Met Lys Lys Leu Leu Pro Asn
                1125                1130                1135

Met Leu Ser Pro Asp Pro Arg Glu Leu Gln Lys Ser Ile Glu Val Gln
            1140                1145                1150

Leu Leu Arg Ser Ser Val Cys Leu Ala Thr Ala Leu Asn Pro Ile Glu
            1155                1160                1165

Gln Asp Gln Lys Trp Gln Ser Ile Thr Glu Asn Val Val Lys Tyr Leu
            1170                1175                1180

Lys Gln Thr Ser Arg Ile Ala Ile Gly Pro Leu Arg Leu Ser Thr Leu
1185                1190                1195                1200

Thr Val Ser Gln Ser Leu Pro Val Leu Ser Thr Leu Gln Leu Tyr Cys
                1205                1210                1215

Ser Ser Ala Leu Glu Asn Thr Val Ser Asn Arg Leu Ser Thr Glu Asp
                1220                1225                1230

Cys Leu Ile Pro Leu Phe Ser Glu Ala Leu Arg Ser Cys Lys Gln His
            1235                1240                1245
```

-continued

Asp Val Arg Pro Trp Met Gln Ala Leu Arg Tyr Thr Met Tyr Gln Asn
1250                 1255                1260

Gln Leu Leu Glu Lys Ile Lys Glu Gln Thr Val Pro Ile Arg Ser His
1265                1270                1275                1280

Leu Met Glu Leu Gly Leu Thr Ala Ala Lys Phe Ala Arg Lys Arg Gly
            1285                1290                1295

Asn Val Ser Leu Ala Thr Arg Leu Leu Ala Gln Cys Ser Glu Val Gln
            1300                1305                1310

Leu Gly Lys Thr Thr Thr Ala Gln Asp Leu Val Gln His Phe Lys Lys
            1315                1320                1325

Leu Ser Thr Gln Gly Gln Val Asp Glu Lys Trp Gly Pro Glu Leu Asp
1330                1335                1340

Ile Glu Lys Thr Lys Leu Leu Tyr Thr Ala Gly Gln Ser Thr His Ala
1345                1350                1355                1360

Met Glu Met Leu Ser Ser Cys Ala Ile Ser Phe Cys Lys Ser Val Lys
            1365                1370                1375

Ala Glu Tyr Ala Val Ala Lys Ser Ile Leu Thr Leu Ala Lys Trp Ile
            1380                1385                1390

Gln Ala Glu Trp Lys Glu Ile Ser Gly Gln Leu Lys Gln Val Tyr Arg
    1395                1400                1405

Ala Gln His Gln Gln Asn Phe Thr Gly Leu Ser Thr Leu Ser Lys Asn
    1410                1415                1420

Ile Leu Thr Leu Ile Glu Leu Pro Ser Val Asn Thr Met Glu Glu Glu
1425                1430                1435                1440

Tyr Pro Arg Ile Glu Ser Glu Ser Thr Val His Ile Gly Val Gly Glu
            1445                1450                1455

Pro Asp Phe Ile Leu Gly Gln Leu Tyr His Leu Ser Ser Val Gln Ala
            1460                1465                1470

Pro Glu Val Ala Lys Ser Trp Ala Ala Leu Ala Ser Trp Ala Tyr Arg
            1475                1480                1485

Trp Gly Arg Lys Val Val Asp Asn Ala Ser Gln Gly Glu Gly Val Arg
            1490                1495                1500

Leu Leu Pro Arg Glu Lys Ser Glu Val Gln Asn Leu Leu Pro Asp Thr
1505                1510                1515                1520

Ile Thr Glu Glu Glu Lys Glu Arg Ile Tyr Gly Ile Leu Gly Gln Ala
            1525                1530                1535

Val Cys Arg Pro Ala Gly Ile Gln Asp Glu Asp Ile Thr Leu Gln Ile
            1540                1545                1550

Thr Glu Ser Glu Asp Asn Glu Glu Asp Met Val Asp Val Ile Trp
            1555                1560                1565

Arg Gln Leu Ile Ser Ser Cys Pro Trp Leu Ser Glu Leu Asp Glu Ser
    1570                1575                1580

Ala Thr Glu Gly Val Ile Lys Val Trp Arg Lys Val Val Asp Arg Ile
1585                1590                1595                1600

Phe Ser Leu Tyr Lys Leu Ser Cys Ser Ala Tyr Phe Thr Phe Leu Lys
            1605                1610                1615

Leu Asn Ala Gly Gln Ile Pro Leu Asp Glu Asp Pro Arg Leu His
            1620                1625                1630

Leu Ser His Arg Val Glu Gln Ser Thr Asp Asp Met Ile Val Met Ala
            1635                1640                1645

Thr Leu Arg Leu Leu Arg Leu Leu Val Lys His Ala Gly Glu Leu Arg
            1650                1655                1660

-continued

```
Gln Tyr Leu Glu His Gly Leu Glu Thr Thr Pro Thr Ala Pro Trp Arg
1665                1670                1675                1680

Gly Ile Ile Pro Gln Leu Phe Ser Arg Leu Asn His Pro Glu Val Tyr
            1685                1690                1695

Val Arg Gln Ser Ile Cys Asn Leu Leu Cys Arg Val Ala Gln Asp Ser
        1700                1705                1710

Pro His Leu Ile Leu Tyr Pro Ala Ile Val Gly Thr Ile Ser Leu Ser
    1715                1720                1725

Ser Glu Ser Gln Ala Ser Gly Asn Lys Phe Ser Thr Ala Ile Pro Thr
1730                1735                1740

Leu Leu Gly Asn Ile Gln Gly Glu Glu Leu Leu Val Ser Glu Cys Glu
1745                1750                1755                1760

Gly Gly Ser Pro Pro Ala Ser Gln Asp Ser Asn Lys Asp Glu Pro Lys
            1765                1770                1775

Ser Gly Leu Asn Glu Asp Gln Ala Met Met Gln Asp Cys Tyr Ser Lys
        1780                1785                1790

Ile Val Asp Lys Leu Ser Ser Ala Asn Pro Thr Met Val Leu Gln Val
    1795                1800                1805

Gln Met Leu Val Ala Glu Leu Arg Arg Val Thr Val Leu Trp Asp Glu
1810                1815                1820

Leu Trp Leu Gly Val Leu Leu Gln Gln His Met Tyr Val Leu Arg Arg
1825                1830                1835                1840

Ile Gln Gln Leu Glu Asp Glu Val Lys Arg Val Gln Asn Asn Asn Thr
            1845                1850                1855

Leu Arg Lys Glu Glu Lys Ile Ala Ile Met Arg Glu Lys His Thr Ala
        1860                1865                1870

Leu Met Lys Pro Ile Val Phe Ala Leu Glu His Val Arg Ser Ile Thr
    1875                1880                1885

Ala Ala Pro Ala Glu Thr Pro His Glu Lys Trp Phe Gln Asp Asn Tyr
1890                1895                1900

Gly Asp Ala Ile Glu Asn Ala Leu Glu Lys Leu Lys Thr Pro Leu Asn
1905                1910                1915                1920

Pro Ala Lys Pro Gly Ser Ser Trp Ile Pro Phe Lys Glu Ile Met Leu
            1925                1930                1935

Ser Leu Gln Gln Arg Ala Gln Lys Arg Ala Ser Tyr Ile Leu Arg Leu
        1940                1945                1950

Glu Glu Ile Ser Pro Trp Leu Ala Ala Met Thr Asn Thr Glu Ile Ala
    1955                1960                1965

Leu Pro Gly Glu Val Ser Ala Arg Asp Thr Val Thr Ile His Ser Val
1970                1975                1980

Gly Gly Thr Ile Thr Ile Leu Pro Thr Lys Thr Lys Pro Lys Lys Leu
1985                1990                1995                2000

Leu Phe Leu Gly Ser Asp Gly Lys Ser Tyr Pro Tyr Leu Phe Lys Gly
            2005                2010                2015

Leu Glu Asp Leu His Leu Asp Glu Arg Ile Met Gln Phe Leu Ser Ile
        2020                2025                2030

Val Asn Thr Met Phe Ala Thr Ile Asn Arg Gln Glu Thr Pro Arg Phe
    2035                2040                2045

His Ala Arg His Tyr Ser Val Thr Pro Leu Gly Thr Arg Ser Gly Leu
2050                2055                2060

Ile Gln Trp Val Asp Gly Ala Thr Pro Leu Phe Gly Leu Tyr Lys Arg
2065                2070                2075                2080
```

```
Trp Gln Gln Arg Glu Ala Ala Leu Gln Ala Gln Lys Ala Gln Asp Ser
            2085                2090                2095

Tyr Gln Thr Pro Gln Asn Pro Gly Ile Val Pro Arg Pro Ser Glu Leu
        2100                2105                2110

Tyr Tyr Ser Lys Ile Gly Pro Ala Leu Lys Thr Val Gly Leu Ser Leu
    2115                2120                2125

Asp Val Ser Arg Arg Asp Trp Pro Leu His Val Met Lys Ala Val Leu
2130                2135                2140

Glu Glu Leu Met Glu Ala Thr Pro Pro Asn Leu Leu Ala Lys Glu Leu
2145                2150                2155                2160

Trp Ser Ser Cys Thr Thr Pro Asp Glu Trp Trp Val Thr Gln Ser
            2165                2170                2175

Tyr Ala Arg Ser Thr Ala Val Met Ser Met Val Gly Tyr Ile Ile Gly
        2180                2185                2190

Leu Gly Asp Arg His Leu Asp Asn Val Leu Ile Asp Met Thr Thr Gly
    2195                2200                2205

Glu Val Val His Ile Asp Tyr Asn Val Cys Phe Glu Lys Gly Lys Ser
2210                2215                2220

Leu Arg Val Pro Glu Lys Val Pro Phe Arg Met Thr Gln Asn Ile Glu
2225                2230                2235                2240

Thr Ala Leu Gly Val Thr Gly Val Glu Gly Val Phe Arg Leu Ser Cys
        2245                2250                2255

Glu Gln Val Leu His Ile Met Arg Arg Gly Arg Glu Thr Leu Leu Thr
            2260                2265                2270

Leu Leu Glu Ala Phe Val Tyr Asp Pro Leu Val Asp Trp Thr Ala Gly
        2275                2280                2285

Gly Glu Ala Gly Phe Ala Gly Ala Val Tyr Gly Gly Gly Gln Gln
    2290                2295                2300

Ala Glu Ser Lys Gln Ser Lys Arg Glu Met Glu Arg Glu Ile Thr Arg
2305                2310                2315                2320

Ser Leu Phe Ser Ser Arg Val Ala Glu Ile Lys Val Asn Trp Phe Lys
        2325                2330                2335

Asn Arg Asp Glu Met Leu Val Val Leu Pro Lys Leu Asp Gly Ser Leu
            2340                2345                2350

Asp Glu Tyr Leu Ser Leu Gln Glu Gln Leu Thr Asp Val Glu Lys Leu
        2355                2360                2365

Gln Gly Lys Leu Leu Glu Glu Ile Glu Phe Leu Glu Gly Ala Glu Gly
    2370                2375                2380

Val Asp His Pro Ser His Thr Leu Gln His Arg Tyr Ser Glu His Thr
2385                2390                2395                2400

Gln Leu Gln Thr Gln Gln Arg Ala Val Gln Glu Ala Ile Gln Val Lys
        2405                2410                2415

Leu Asn Glu Phe Glu Gln Trp Ile Thr His Tyr Gln Ala Ala Phe Asn
            2420                2425                2430

Asn Leu Glu Ala Thr Gln Leu Ala Ser Leu Leu Gln Glu Ile Ser Thr
        2435                2440                2445

Gln Met Asp Leu Gly Pro Pro Ser Tyr Val Pro Ala Thr Ala Phe Leu
    2450                2455                2460

Gln Asn Ala Gly Gln Ala His Leu Ile Ser Gln Cys Glu Gln Leu Glu
2465                2470                2475                2480

Gly Glu Val Gly Ala Leu Leu Gln Gln Arg Arg Ser Val Leu Arg Gly
        2485                2490                2495
```

```
Cys Leu Glu Gln Leu His His Tyr Ala Thr Val Ala Leu Gln Tyr Pro
                2500                2505                2510
Lys Ala Ile Phe Gln Lys His Arg Ile Glu Gln Trp Lys Thr Trp Met
            2515                2520                2525
Glu Glu Leu Ile Cys Asn Thr Thr Val Glu Arg Cys Gln Glu Leu Tyr
        2530                2535                2540
Arg Lys Tyr Glu Met Gln Tyr Ala Pro Gln Pro Pro Thr Val Cys
2545                2550                2555                2560
Gln Phe Ile Thr Ala Thr Glu Met Thr Leu Gln Arg Tyr Ala Ala Asp
                2565                2570                2575
Ile Asn Ser Arg Leu Ile Arg Gln Val Glu Arg Leu Lys Gln Glu Ala
            2580                2585                2590
Val Thr Val Pro Val Cys Glu Asp Gln Leu Lys Glu Ile Glu Arg Cys
        2595                2600                2605
Ile Lys Val Phe Leu His Glu Asn Gly Glu Glu Gly Ser Leu Ser Leu
    2610                2615                2620
Ala Ser Val Ile Ile Ser Ala Leu Cys Thr Leu Thr Arg Arg Asn Leu
2625                2630                2635                2640
Met Met Glu Gly Ala Ala Ser Ser Ala Gly Glu Gln Leu Val Asp Leu
                2645                2650                2655
Thr Ser Arg Asp Gly Ala Trp Phe Leu Glu Glu Leu Cys Ser Met Ser
            2660                2665                2670
Gly Asn Val Thr Cys Leu Val Gln Leu Leu Lys Gln Cys His Leu Val
        2675                2680                2685
Pro Gln Asp Leu Asp Ile Pro Asn Pro Met Glu Ala Ser Glu Thr Val
    2690                2695                2700
His Leu Ala Asn Gly Val Tyr Thr Ser Leu Gln Glu Leu Asn Ser Asn
2705                2710                2715                2720
Phe Arg Gln Ile Ile Phe Pro Glu Ala Leu Arg Cys Leu Met Lys Gly
                2725                2730                2735
Glu Tyr Thr Leu Glu Ser Met Leu His Glu Leu Asp Gly Leu Ile Glu
            2740                2745                2750
Gln Thr Thr Asp Gly Val Pro Leu Gln Thr Leu Val Glu Ser Leu Gln
        2755                2760                2765
Ala Tyr Leu Arg Asn Ala Ala Met Gly Leu Glu Glu Glu Thr His Ala
    2770                2775                2780
His Tyr Ile Asp Val Ala Arg Leu Leu His Ala Gln Tyr Gly Glu Leu
2785                2790                2795                2800
Ile Gln Pro Arg Asn Gly Ser Val Asp Glu Thr Pro Lys Met Ser Ala
                2805                2810                2815
Gly Gln Met Leu Leu Val Ala Phe Asp Gly Met Phe Ala Gln Val Glu
            2820                2825                2830
Thr Ala Phe Ser Leu Leu Val Glu Lys Leu Asn Lys Met Glu Ile Pro
        2835                2840                2845
Ile Ala Trp Arg Lys Ile Asp Ile Ile Arg Glu Ala Arg Ser Thr Gln
    2850                2855                2860
Val Asn Phe Phe Asp Asp Asp Asn His Arg Gln Val Leu Glu Glu Ile
2865                2870                2875                2880
Phe Phe Leu Lys Arg Leu Gln Thr Ile Lys Glu Phe Phe Arg Leu Cys
                2885                2890                2895
Gly Thr Phe Ser Lys Thr Leu Ser Gly Ser Ser Ser Leu Glu Asp Gln
            2900                2905                2910
```

-continued

Asn Thr Val Asn Gly Pro Val Gln Ile Val Asn Val Lys Thr Leu Phe
            2915                2920                2925

Arg Asn Ser Cys Phe Ser Glu Asp Gln Met Ala Lys Pro Ile Lys Ala
    2930                2935                2940

Phe Thr Ala Asp Phe Val Arg Gln Leu Leu Ile Gly Leu Pro Asn Gln
2945                2950                2955                2960

Ala Leu Gly Leu Thr Leu Cys Ser Phe Ile Ser Ala Leu Gly Val Asp
            2965                2970                2975

Ile Ile Ala Gln Val Glu Ala Lys Asp Phe Gly Ala Glu Ser Lys Val
            2980                2985                2990

Ser Val Asp Asp Leu Cys Lys Lys Ala Val Glu His Asn Ile Gln Ile
            2995                3000                3005

Gly Lys Phe Ser Gln Leu Val Met Asn Arg Ala Thr Val Leu Ala Ser
            3010                3015                3020

Ser Tyr Asp Thr Ala Trp Lys Lys His Asp Leu Val Arg Arg Leu Glu
3025                3030                3035                3040

Thr Ser Ile Ser Ser Cys Lys Thr Ser Leu Gln Arg Val Gln Leu His
            3045                3050                3055

Ile Ala Met Phe Gln Trp Gln His Glu Asp Leu Leu Ile Asn Arg Pro
            3060                3065                3070

Gln Ala Met Ser Val Thr Pro Pro Arg Ser Ala Ile Leu Thr Ser
            3075                3080                3085

Met Lys Lys Lys Leu His Thr Leu Ser Gln Ile Glu Thr Ser Ile Ala
            3090                3095                3100

Thr Val Gln Glu Lys Leu Ala Ala Leu Glu Ser Ser Ile Glu Gln Arg
3105                3110                3115                3120

Leu Lys Trp Ala Gly Gly Ala Asn Pro Ala Leu Ala Pro Val Leu Gln
            3125                3130                3135

Asp Phe Glu Ala Thr Ile Ala Glu Arg Arg Asn Leu Val Leu Lys Glu
            3140                3145                3150

Ser Gln Arg Ala Ser Gln Val Thr Phe Leu Cys Ser Asn Ile Ile His
            3155                3160                3165

Phe Glu Ser Leu Arg Thr Arg Thr Ala Glu Ala Leu Asn Leu Asp Ala
            3170                3175                3180

Ala Leu Phe Glu Leu Ile Lys Arg Cys Gln Gln Met Cys Ser Phe Ala
3185                3190                3195                3200

Ser Gln Phe Asn Ser Ser Val Ser Glu Leu Glu Leu Arg Leu Leu Gln
            3205                3210                3215

Arg Val Asp Thr Gly Leu Glu His Pro Ile Gly Ser Ser Glu Trp Leu
            3220                3225                3230

Leu Ser Ala His Lys Gln Leu Thr Gln Asp Met Ser Thr Gln Arg Ala
            3235                3240                3245

Ile Gln Thr Glu Lys Glu Gln Gln Ile Glu Thr Val Cys Glu Thr Ile
            3250                3255                3260

Gln Asn Leu Val Asp Asn Ile Lys Thr Val Leu Thr Gly His Asn Arg
3265                3270                3275                3280

Gln Leu Gly Asp Val Lys His Leu Leu Lys Ala Met Ala Lys Asp Glu
            3285                3290                3295

Glu Ala Ala Leu Ala Asp Gly Glu Asp Val Pro Tyr Glu Asn Ser Val
            3300                3305                3310

Arg Gln Phe Leu Gly Glu Tyr Lys Ser Trp Gln Asp Asn Ile Gln Thr
            3315                3320                3325

-continued

Val Leu Phe Thr Leu Val Gln Ala Met Gly Gln Val Arg Ser Gln Glu
    3330                3335                3340

His Val Glu Met Leu Gln Glu Ile Thr Pro Thr Leu Lys Glu Leu Lys
3345                3350                3355                3360

Thr Gln Ser Gln Ser Ile Tyr Asn Asn Leu Val Ser Phe Ala Ser Pro
            3365                3370                3375

Leu Val Thr Asp Ala Thr Asn Glu Cys Ser Ser Pro Thr Ser Ser Ala
        3380                3385                3390

Thr Tyr Gln Pro Ser Phe Ala Ala Val Arg Ser Asn Thr Gly Gln
        3395                3400                3405

Lys Thr Gln Pro Asp Val Met Ser Gln Asn Ala Arg Lys Leu Ile Gln
    3410                3415                3420

Lys Asn Leu Ala Thr Ser Ala Asp Thr Pro Ser Thr Val Pro Gly
3425                3430                3435                3440

Thr Gly Lys Ser Val Ala Cys Ser Pro Lys Lys Ala Val Arg Asp Pro
            3445                3450                3455

Lys Thr Gly Lys Ala Val Gln Glu Arg Asn Ser Tyr Ala Val Ser Val
        3460                3465                3470

Trp Lys Arg Val Lys Ala Lys Leu Glu Gly Arg Asp Val Asp Pro Asn
    3475                3480                3485

Arg Arg Met Ser Val Ala Glu Gln Val Asp Tyr Val Ile Lys Glu Ala
    3490                3495                3500

Thr Asn Leu Asp Asn Leu Ala Gln Leu Tyr Glu Gly Trp Thr Ala Trp
3505                3510                3515                3520

Val

<210> SEQ ID NO 3
<211> LENGTH: 2629
<212> TYPE: DNA
<213> ORGANISM: Homo sapiens
<220> FEATURE:
<221> NAME/KEY: CDS
<222> LOCATION: (252)...(1433)

<400> SEQUENCE: 3
acttgtcatg gcgactgtcc agctttgtgc caggagcctc gcaggggttg atgggattgg      60
ggttttcccc tcccatgtgc tcaagactgg cgctaaaagt tttgagcttc tcaaagtct      120 agagccaccg tccagggagc aggtagctgc tgggctccgg ggacactttg cgttcgggct      180
gggagcgtgc tttccacgac ggtgacacgc ttccctggat tggcagccag actgccttcc      240
gggtcactgc c atg gag gag ccg cag tca gat cct agc gtc gag ccc cct      290
              Met Glu Glu Pro Gln Ser Asp Pro Ser Val Glu Pro Pro
                1               5                   10 ctg agt cag gaa aca ttt tca gac cta tgg aaa cta ctt cct gaa aac      338
Leu Ser Gln Glu Thr Phe Ser Asp Leu Trp Lys Leu Leu Pro Glu Asn
 15                  20                  25 aac gtt ctg tcc ccc ttg ccg tcc caa gca atg gat gat ttg atg ctg      386
Asn Val Leu Ser Pro Leu Pro Ser Gln Ala Met Asp Asp Leu Met Leu
 30                  35                  40                  45 tcc ccg gac gat att gaa caa tgg ttc act gaa gac cca ggt cca gat      434
Ser Pro Asp Asp Ile Glu Gln Trp Phe Thr Glu Asp Pro Gly Pro Asp
                 50                  55                  60 gaa gct ccc aga atg cca gag gct gct ccc cgc gtg gcc cct gca cca      482
Glu Ala Pro Arg Met Pro Glu Ala Ala Pro Arg Val Ala Pro Ala Pro
         65                  70                  75

```
gca gct cct aca ccg gcg gcc cct gca cca gcc ccc tcc tgg ccc ctg      530
Ala Ala Pro Thr Pro Ala Ala Pro Ala Pro Ala Pro Ser Trp Pro Leu
            80                  85                  90 tca tct tct gtc cct tcc cag aaa acc tac cag ggc agc tac ggt ttc      578
Ser Ser Ser Val Pro Ser Gln Lys Thr Tyr Gln Gly Ser Tyr Gly Phe
 95                 100                 105 cgt ctg ggc ttc ttg cat tct ggg aca gcc aag tct gtg act tgc acg      626
Arg Leu Gly Phe Leu His Ser Gly Thr Ala Lys Ser Val Thr Cys Thr
110                 115                 120                 125 tac tcc cct gcc ctc aac aag atg ttt tgc caa ctg gcc aag acc tgc      674
Tyr Ser Pro Ala Leu Asn Lys Met Phe Cys Gln Leu Ala Lys Thr Cys
                130                 135                 140 cct gtg cag ctg tgg gtt gat tcc aca ccc ccg ccc ggc acc cgc gtc      722
Pro Val Gln Leu Trp Val Asp Ser Thr Pro Pro Pro Gly Thr Arg Val
            145                 150                 155 cgc gcc atg gcc atc tac aag cag tca cag cac atg acg gag gtt gtg      770
Arg Ala Met Ala Ile Tyr Lys Gln Ser Gln His Met Thr Glu Val Val
        160                 165                 170 agg cgc tgc ccc cac cat gag cgc tgc tca gat agc gat ggt ctg gcc      818
Arg Arg Cys Pro His His Glu Arg Cys Ser Asp Ser Asp Gly Leu Ala
    175                 180                 185 cct cct cag cat ctt atc cga gtg gaa gga aat ttg cgt gtg gag tat      866
Pro Pro Gln His Leu Ile Arg Val Glu Gly Asn Leu Arg Val Glu Tyr
190                 195                 200                 205 ttg gat gac aga aac act ttt cga cat agt gtg gtg gtg ccc tat gag      914
Leu Asp Asp Arg Asn Thr Phe Arg His Ser Val Val Val Pro Tyr Glu
                210                 215                 220 ccg cct gag gtt ggc tct gac tgt acc acc atc cac tac aac tac atg      962
Pro Pro Glu Val Gly Ser Asp Cys Thr Thr Ile His Tyr Asn Tyr Met
            225                 230                 235 tgt aac agt tcc tgc atg ggc ggc atg aac cgg agg ccc atc ctc acc     1010
Cys Asn Ser Ser Cys Met Gly Gly Met Asn Arg Arg Pro Ile Leu Thr
        240                 245                 250 atc atc aca ctg gaa gac tcc agt ggt aat cta ctg gga cgg aac agc     1058
Ile Ile Thr Leu Glu Asp Ser Ser Gly Asn Leu Leu Gly Arg Asn Ser
    255                 260                 265 ttt gag gtg cgt gtt tgt gcc tgt cct ggg aga gac cgg cgc aca gag     1106
Phe Glu Val Arg Val Cys Ala Cys Pro Gly Arg Asp Arg Arg Thr Glu
270                 275                 280                 285 gaa gag aat ctc cgc aag aaa ggg gag cct cac cac gag ctg ccc cca     1154
Glu Glu Asn Leu Arg Lys Lys Gly Glu Pro His His Glu Leu Pro Pro
                290                 295                 300 ggg agc act aag cga gca ctg ccc aac aac acc agc tcc tct ccc cag     1202
Gly Ser Thr Lys Arg Ala Leu Pro Asn Asn Thr Ser Ser Ser Pro Gln
            305                 310                 315 cca aag aag aaa cca ctg gat gga gaa tat ttc acc ctt cag atc cgt     1250
Pro Lys Lys Lys Pro Leu Asp Gly Glu Tyr Phe Thr Leu Gln Ile Arg
        320                 325                 330 ggg cgt gag cgc ttc gag atg ttc cga gag ctg aat gag gcc ttg gaa     1298
Gly Arg Glu Arg Phe Glu Met Phe Arg Glu Leu Asn Glu Ala Leu Glu
    335                 340                 345 ctc aag gat gcc cag gct ggg aag gag cca ggg ggg agc agg gct cac     1346
Leu Lys Asp Ala Gln Ala Gly Lys Glu Pro Gly Gly Ser Arg Ala His
350                 355                 360                 365 tcc agc cac ctg aag tcc aaa aag ggt cag tct acc tcc cgc cat aaa     1394
Ser Ser His Leu Lys Ser Lys Lys Gly Gln Ser Thr Ser Arg His Lys
                370                 375                 380 aaa ctc atg ttc aag aca gaa ggg cct gac tca gac tga cattctccac     1443
Lys Leu Met Phe Lys Thr Glu Gly Pro Asp Ser Asp  *
            385                 390
```

-continued

```
ttcttgttcc ccactgacag cctcccaccc ccatctctcc ctcccctgcc attttgggtt      1503
ttgggtcttt gaacccttgc ttgcaatagg tgtgcgtcag aagcacccag gacttccatt      1563
tgctttgtcc cggggctcca ctgaacaagt tggcctgcac tggtgttttg ttgtggggag      1623
gaggatgggg agtaggacat accagcttag attttaaggt ttttactgtg agggatgttt      1683
gggagatgta agaaatgttc ttgcagttaa gggttagttt acaatcagcc acattctagg      1743
taggtagggg cccacttcac cgtactaacc agggaagctg tccctcatgt tgaattttct      1803
ctaacttcaa ggcccatatc tgtgaaatgc tggcatttgc acctacctca cagagtgcat      1863
tgtgagggtt aatgaaataa tgtacatctg gccttgaaac cacctttat tacatggggt       1923
ctaaaacttg accccttga gggtgcctgt tccctctccc tctccctgtt ggctggtggg       1983
ttggtagttt ctacagttgg gcagctggtt aggtagaggg agttgtcaag tcttgctggc      2043
ccagccaaac cctgtctgac aacctcttgg tcgaccttag tacctaaaag gaaatctcac      2103
cccatcccac accctggagg atttcatctc ttgtatatga tgatctggat ccaccaagac      2163
ttgttttatg ctcagggtca atttcttttt tcttttttt ttttttttt cttttcttt         2223
gagactgggt ctcgctttgt tgcccaggct ggagtggagt ggcgtgatct tggcttactg      2283
cagcctttgc ctccccggct cgagcagtcc tgcctcagcc tccggagtag ctgggaccac      2343
aggttcatgc caccatggcc agccaacttt tgcatgtttt gtagagatgg ggtctcacag      2403
tgttgcccag gctggtctca aactcctggg ctcaggcgat ccacctgtct cagcctccca      2463
gagtgctggg attacaattg tgagccacca cgtggagctg gaagggtcaa catcttttac      2523
attctgcaag cacatctgca ttttcacccc acccttcccc tccttctccc tttttatatc      2583
ccatttttat atcgatctct tattttacaa taaaactttg ctgcca                    2629
```

<210> SEQ ID NO 4
<211> LENGTH: 393
<212> TYPE: PRT
<213> ORGANISM: Homo sapiens

<400> SEQUENCE: 4

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160
```

```
Ala Ile Tyr Lys Gln Ser Gln His Met Thr Glu Val Val Arg Arg Cys
            165                 170                 175
Pro His His Glu Arg Cys Ser Asp Ser Asp Gly Leu Ala Pro Pro Gln
        180                 185                 190
His Leu Ile Arg Val Glu Gly Asn Leu Arg Val Glu Tyr Leu Asp Asp
    195                 200                 205
Arg Asn Thr Phe Arg His Ser Val Val Pro Tyr Glu Pro Pro Glu
210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
            245                 250                 255
Leu Glu Asp Ser Ser Gly Asn Leu Leu Gly Arg Asn Ser Phe Glu Val
        260                 265                 270
Arg Val Cys Ala Cys Pro Gly Arg Asp Arg Arg Thr Glu Glu Glu Asn
    275                 280                 285
Leu Arg Lys Lys Gly Glu Pro His His Glu Leu Pro Pro Gly Ser Thr
290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Leu Gln Ile Arg Gly Arg Glu
            325                 330                 335
Arg Phe Glu Met Phe Arg Glu Leu Asn Glu Ala Leu Glu Leu Lys Asp
        340                 345                 350
Ala Gln Ala Gly Lys Glu Pro Gly Gly Ser Arg Ala His Ser Ser His
    355                 360                 365
Leu Lys Ser Lys Lys Gly Gln Ser Thr Ser Arg His Lys Lys Leu Met
370                 375                 380
Phe Lys Thr Glu Gly Pro Asp Ser Asp
385                 390

<210> SEQ ID NO 5
<211> LENGTH: 12606
<212> TYPE: DNA
<213> ORGANISM: Homo sapiens
<220> FEATURE:
<221> NAME/KEY: CDS
<222> LOCATION: (1703)...(10798)

<400> SEQUENCE: 5
attgacttga tgcacaacat cacaaaggcg attttgaga  actgatagtg catcagccga      60
cccaggtaat ttaaaatatt cttcatccag agatagaggt ggttcttcct cttacggact    120
gcaaccttca aattcagctg tggtgtctcg caaaggcac gatgatacca gagtccacgc    180
tgacatacag aatgacgaaa aggagagatc gatgtcttat tgtgatgagt ctcgactgtc    240
gaatcttctt cggaggatca cccgggaaga cgacagagac cgaagattgg ctactgtaaa    300
gcagttgaaa gaatttattc agcaaccaga aataagctg gtactagtta acaattgga     360 taatatcttg gctgctgtac atgacgtgct taatgaaagt agcaaattgc ttcaggagtt    420
gagacaggag ggagcttgct gtcttggcct tctttgtgct tctctgagct atgaggctga    480
gaagatcttc aagtggattt ttagcaaatt tagctcatct gcaaagatg aagttaaact     540 cctctactta tgtgccacct acaaagcact agagactgta ggagaaaaga aagccttttc    600
atctgtaatg cagcttgtaa tgaccagcct gcagtctatt cttgaaaatg tggatacacc    660
agaattgctt tgtaaatgtg ttaagtgcat tcttttggtg gctcgatgtt accctcatat    720
```

```
tttcagcact aattttaggg atacagttga tatattagtt ggatggcata tagatcatac      780
tcagaaacct tcgctcacgc agcaggtatc tgggtggttg cagagtttgg agccattttg      840
ggtagctgat cttgcatttt ctactactct tcttggtcag tttctggaag acatggaagc      900
atatgctgag gacctcagcc atgtggcctc tggggaatca gtggatgaag atgtccctcc      960
tccatcagtg tcattaccaa agctggctgc acttctccgg gtatttagta ctgtggtgag     1020
gagcattggg gaacgcttca gcccaattcg ggtcctccca attactgagg catatgtaac     1080
agatgttctg tacagagtaa tgagatgtgt gacggctgca aaccaggtgt ttttttctga     1140
ggctgtgttg acagctgcta atgagtgtgt tggtgttttg ctcggcagct tggatcctag     1200
catgactata cattgtgaca tggtcattac atatggatta gaccaactgg agaattgcca     1260
gacttgtggt accgattata tcatctcagt cttgaattta ctcacgctga ttgttgaaca     1320
gataaatacg aaactgccat catcatttgt agaaaaactg tttataccat catctaaact     1380
actattcttg cgttatcata agaaaaaga ggttgttgct gtagcccatg ctgtttatca     1440
agcagtgctc agcttgaaga atattcctgt tttggagact gcctataagt taatattggg     1500
agaaatgact tgtgccctaa acaacctcct acacagtcta caacttcctg aggcctgttc     1560
tgaaataaaa catgaggctt ttaagaatca tgtgttcaat gtagacaatg caaaatttgt     1620
agttatattt gacctcaatt gactacaaaa tttgtagtta aatttgacta caattggaaa     1680
tgccaaaaac tcactaatag gg atg tgg gcg cta tct cca act gtc ttt gca     1732
                         Met Trp Ala Leu Ser Pro Thr Val Phe Ala
                          1               5                  10 ctt ctg agt aag aat ctg atg att gtg cac agt gac ctg gct gtt cac     1780
Leu Leu Ser Lys Asn Leu Met Ile Val His Ser Asp Leu Ala Val His
            15                  20                  25 ttc cct gcc att cag tat gct gtg ctc tac aca ttg tat tct cat tgt     1828
Phe Pro Ala Ile Gln Tyr Ala Val Leu Tyr Thr Leu Tyr Ser His Cys
        30                  35                  40 acc agg cat gat cac ttt atc tct agt agc ctc agt tct tcc tct cct     1876
Thr Arg His Asp His Phe Ile Ser Ser Ser Leu Ser Ser Ser Ser Pro
    45                  50                  55 tct ttg ttt gat gga gct gtg att agc act gta act acg gct aca aag     1924
Ser Leu Phe Asp Gly Ala Val Ile Ser Thr Val Thr Thr Ala Thr Lys
60                  65                  70 aaa cat ttc tca att ata tta aat ctt ctg gga ata tta ctt aag aaa     1972
Lys His Phe Ser Ile Ile Leu Asn Leu Leu Gly Ile Leu Leu Lys Lys
    75                  80                  85                  90 gat aac ctt aac cag gac acg agg aaa ctg tta atg act tgg gct ttg     2020
Asp Asn Leu Asn Gln Asp Thr Arg Lys Leu Leu Met Thr Trp Ala Leu
                95                  100                 105 gaa gca gct gtt tta atg aag aag tct gaa aca tac gca cct tta ttc     2068
Glu Ala Ala Val Leu Met Lys Lys Ser Glu Thr Tyr Ala Pro Leu Phe
            110                 115                 120 tct ctt ccg tct ttc cat aaa ttt tgc aaa ggc ctt tta gcc aac act     2116
Ser Leu Pro Ser Phe His Lys Phe Cys Lys Gly Leu Leu Ala Asn Thr
        125                 130                 135 ctc gtt gaa gat gtg aat atc tgt ctg cag gca tgc agc agt cta cat     2164
Leu Val Glu Asp Val Asn Ile Cys Leu Gln Ala Cys Ser Ser Leu His
    140                 145                 150 gct ctg tcc tct tcc ttg cca gat gat ctt tta cag aga tgt gtc gat     2212
Ala Leu Ser Ser Ser Leu Pro Asp Asp Leu Leu Gln Arg Cys Val Asp
155                 160                 165                 170
```

```
gtt tgc cgt gtt caa cta gtg cac agt gga act cgt att cga caa gca         2260
Val Cys Arg Val Gln Leu Val His Ser Gly Thr Arg Ile Arg Gln Ala
            175                 180                 185 ttt gga aaa ctg ttg aaa tca att cct tta gat gtt gtc cta agc aat         2308
Phe Gly Lys Leu Leu Lys Ser Ile Pro Leu Asp Val Val Leu Ser Asn
        190                 195                 200 aac aat cac aca gaa att caa gaa att tct tta gca tta aga agt cac         2356
Asn Asn His Thr Glu Ile Gln Glu Ile Ser Leu Ala Leu Arg Ser His
    205                 210                 215 atg agt aaa gca cca agt aat aca ttc cac ccc caa gat ttc tct gat         2404
Met Ser Lys Ala Pro Ser Asn Thr Phe His Pro Gln Asp Phe Ser Asp
220                 225                 230 gtt att agt ttt att ttg tat ggg aac tct cat aga aca ggg aag gac         2452
Val Ile Ser Phe Ile Leu Tyr Gly Asn Ser His Arg Thr Gly Lys Asp
235                 240                 245                 250 aat tgg ttg gaa aga ctg ttc tat agc tgc cag aga ctg gat aag cgt         2500
Asn Trp Leu Glu Arg Leu Phe Tyr Ser Cys Gln Arg Leu Asp Lys Arg
                255                 260                 265 gac cag tca aca att cca cgc aat ctc ctg aag aca gat gct gtc ctt         2548
Asp Gln Ser Thr Ile Pro Arg Asn Leu Leu Lys Thr Asp Ala Val Leu
            270                 275                 280 tgg cag tgg gcc ata tgg gaa gct gca caa ttc act gtt ctt tct aag         2596
Trp Gln Trp Ala Ile Trp Glu Ala Ala Gln Phe Thr Val Leu Ser Lys
        285                 290                 295 ctg aga acc cca ctg ggc aga gct caa gac acc ttc cag aca att gaa         2644
Leu Arg Thr Pro Leu Gly Arg Ala Gln Asp Thr Phe Gln Thr Ile Glu
    300                 305                 310 ggt atc att cga agt ctc gca gct cac aca tta aac cct gat cag gat         2692
Gly Ile Ile Arg Ser Leu Ala Ala His Thr Leu Asn Pro Asp Gln Asp
315                 320                 325                 330 gtt agt cag tgg aca act gca gac aat gat gaa ggc cat ggt aac aac         2740
Val Ser Gln Trp Thr Thr Ala Asp Asn Asp Glu Gly His Gly Asn Asn
                335                 340                 345 caa ctt aga ctt gtt ctt ctt ctg cag tat ctg gaa aat ctg gag aaa         2788
Gln Leu Arg Leu Val Leu Leu Leu Gln Tyr Leu Glu Asn Leu Glu Lys
            350                 355                 360 tta atg tat aat gca tac gag gga tgt gct aat gca tta act tca cct         2836
Leu Met Tyr Asn Ala Tyr Glu Gly Cys Ala Asn Ala Leu Thr Ser Pro
        365                 370                 375 ccc aag gtc att aga act ttt ttc tat acc aat cgc caa act tgt cag         2884
Pro Lys Val Ile Arg Thr Phe Phe Tyr Thr Asn Arg Gln Thr Cys Gln
    380                 385                 390 gac tgg cta acg cgg att cga ctc tcc atc atg agg gta gga ttg ttg         2932
Asp Trp Leu Thr Arg Ile Arg Leu Ser Ile Met Arg Val Gly Leu Leu
395                 400                 405                 410 gca ggc cag cct gca gtg aca gtg aga cat ggc ttt gac ttg ctt aca         2980
Ala Gly Gln Pro Ala Val Thr Val Arg His Gly Phe Asp Leu Leu Thr
                415                 420                 425 gag atg aaa aca acc agc cta tct cag ggg aat gaa ttg gaa gta acc         3028
Glu Met Lys Thr Thr Ser Leu Ser Gln Gly Asn Glu Leu Glu Val Thr
            430                 435                 440 att atg atg gtg gta gaa gca tta tgt gaa ctt cat tgt cct gaa gct         3076
Ile Met Met Val Val Glu Ala Leu Cys Glu Leu His Cys Pro Glu Ala
        445                 450                 455 ata cag gga att gct gtc tgg tca tca tct att gtt gga aaa aat ctt         3124
Ile Gln Gly Ile Ala Val Trp Ser Ser Ser Ile Val Gly Lys Asn Leu
    460                 465                 470 ctg tgg att aac tca gtg gct caa cag gct gaa ggg agg ttt gaa aag         3172
Leu Trp Ile Asn Ser Val Ala Gln Gln Ala Glu Gly Arg Phe Glu Lys
475                 480                 485                 490
```

-continued

| | |
|---|---|
| gcc tct gtg gag tac cag gaa cac ctg tgt gcc atg aca ggt gtt gat<br>Ala Ser Val Glu Tyr Gln Glu His Leu Cys Ala Met Thr Gly Val Asp<br>           495                  500               505 | 3220 |
| tgc tgc atc tcc agc ttt gac aaa tcg gtg ctc acc tta gcc aat gct<br>Cys Cys Ile Ser Ser Phe Asp Lys Ser Val Leu Thr Leu Ala Asn Ala<br>          510                  515               520 | 3268 |
| ggg cgt aac agt gcc agc ccg aaa cat tct ctg aat ggt gaa tcc aga<br>Gly Arg Asn Ser Ala Ser Pro Lys His Ser Leu Asn Gly Glu Ser Arg<br>525                  530               535 | 3316 |
| aaa act gtg ctg tcc aaa ccg act gac tct tcc cct gag gtt ata aat<br>Lys Thr Val Leu Ser Lys Pro Thr Asp Ser Ser Pro Glu Val Ile Asn<br>540                  545              550 | 3364 |
| tat tta gga aat aaa gca tgt gag tgc tac atc tca att gcc gat tgg<br>Tyr Leu Gly Asn Lys Ala Cys Glu Cys Tyr Ile Ser Ile Ala Asp Trp<br>555                560               565              570 | 3412 |
| gct gct gtg cag gaa tgg cag aac gct atc cat gac ttg aaa aag agt<br>Ala Ala Val Gln Glu Trp Gln Asn Ala Ile His Asp Leu Lys Lys Ser<br>                575               580              585 | 3460 |
| acc agt agc act tcc ctc aac ctg aaa gct gac ttc aac tat ata aaa<br>Thr Ser Ser Thr Ser Leu Asn Leu Lys Ala Asp Phe Asn Tyr Ile Lys<br>          590                  595               600 | 3508 |
| tca tta agc agc ttt gag tct gga aaa ttt gtt gaa tgt acc gag caa<br>Ser Leu Ser Ser Phe Glu Ser Gly Lys Phe Val Glu Cys Thr Glu Gln<br>                605               610              615 | 3556 |
| tta gaa ttg tta cca gga gaa aat atc aat cta ctt gct gga gga tca<br>Leu Glu Leu Leu Pro Gly Glu Asn Ile Asn Leu Leu Ala Gly Gly Ser<br>         620                  625               630 | 3604 |
| aaa gaa aaa ata gac atg aaa aaa ctg ctt cct aac atg tta agt ccg<br>Lys Glu Lys Ile Asp Met Lys Lys Leu Leu Pro Asn Met Leu Ser Pro<br>635                  640               645              650 | 3652 |
| gat ccg agg gaa ctt cag aaa tcc att gaa gtt caa ttg tta aga agt<br>Asp Pro Arg Glu Leu Gln Lys Ser Ile Glu Val Gln Leu Leu Arg Ser<br>                655               660              665 | 3700 |
| tct gtt tgt ttg gca act gct tta aac ccg ata gaa caa gat cag aag<br>Ser Val Cys Leu Ala Thr Ala Leu Asn Pro Ile Glu Gln Asp Gln Lys<br>         670                  675               680 | 3748 |
| tgg cag tct ata act gaa aat gtg gta aag tac ttg aag caa aca tcc<br>Trp Gln Ser Ile Thr Glu Asn Val Val Lys Tyr Leu Lys Gln Thr Ser<br>685                  690               695 | 3796 |
| cgc atc gct att gga cct ctg aga ctt tct act tta aca gtt tca cag<br>Arg Ile Ala Ile Gly Pro Leu Arg Leu Ser Thr Leu Thr Val Ser Gln<br>         700                  705               710 | 3844 |
| tct ttg cca gtt cta agt acc ttg cag ctg tat tgc tca tct gct ttg<br>Ser Leu Pro Val Leu Ser Thr Leu Gln Leu Tyr Cys Ser Ser Ala Leu<br>715                  720               725              730 | 3892 |
| gag aac aca gtt tct aac aga ctt tca aca gag gac tgt ctt att cca<br>Glu Asn Thr Val Ser Asn Arg Leu Ser Thr Glu Asp Cys Leu Ile Pro<br>                735               740              745 | 3940 |
| ctc ttc agt gaa gct tta cgt tca tgt aaa cag cat gac gtg agg cca<br>Leu Phe Ser Glu Ala Leu Arg Ser Cys Lys Gln His Asp Val Arg Pro<br>         750                  755               760 | 3988 |
| tgg atg cag gca tta agg tat act atg tac cag aat cag ttg ttg gag<br>Trp Met Gln Ala Leu Arg Tyr Thr Met Tyr Gln Asn Gln Leu Leu Glu<br>765                  770               775 | 4036 |
| aaa att aaa gaa caa aca gtc cca att aga agc cat ctc atg gaa tta<br>Lys Ile Lys Glu Gln Thr Val Pro Ile Arg Ser His Leu Met Glu Leu<br>                780               785              790 | 4084 |
| ggt cta aca gca gca aaa ttt gct aga aaa cga ggg aat gtg tcc ctt<br>Gly Leu Thr Ala Ala Lys Phe Ala Arg Lys Arg Gly Asn Val Ser Leu<br>795                  800               805              810 | 4132 |

-continued

```
gca aca aga ctg ctg gca cag tgc agt gaa gtt cag ctg gga aag acc      4180
Ala Thr Arg Leu Leu Ala Gln Cys Ser Glu Val Gln Leu Gly Lys Thr
            815             820             825 acc act gca cag gat tta gtc caa cat ttt aaa aaa cta tca acc caa      4228
Thr Thr Ala Gln Asp Leu Val Gln His Phe Lys Lys Leu Ser Thr Gln
        830             835             840 ggt caa gtg gat gaa aaa tgg ggg ccc gaa ctt gat att gaa aaa acc      4276
Gly Gln Val Asp Glu Lys Trp Gly Pro Glu Leu Asp Ile Glu Lys Thr
    845             850             855 aaa ttg ctt tat aca gca ggc cag tca aca cat gca atg gaa atg ttg      4324
Lys Leu Leu Tyr Thr Ala Gly Gln Ser Thr His Ala Met Glu Met Leu
860             865             870 agt tct tgt gcc ata tct ttc tgc aag tct gtg aaa gct gaa tat gca      4372
Ser Ser Cys Ala Ile Ser Phe Cys Lys Ser Val Lys Ala Glu Tyr Ala
875             880             885             890 gtt gct aaa tca att ctg aca ctg gct aaa tgg atc cag gca gaa tgg      4420
Val Ala Lys Ser Ile Leu Thr Leu Ala Lys Trp Ile Gln Ala Glu Trp
            895             900             905 aaa gag att tca gga cag ctg aaa cag gtt tac aga gct cag cac caa      4468
Lys Glu Ile Ser Gly Gln Leu Lys Gln Val Tyr Arg Ala Gln His Gln
        910             915             920 cag aac ttc aca ggt ctt tct act ttg tct aaa aac ata ctc act cta      4516
Gln Asn Phe Thr Gly Leu Ser Thr Leu Ser Lys Asn Ile Leu Thr Leu
    925             930             935 ata gaa ctg cca tct gtt aat acg atg gaa gaa gag tat cct cgg atc      4564
Ile Glu Leu Pro Ser Val Asn Thr Met Glu Glu Glu Tyr Pro Arg Ile
940             945             950 gag agt gaa tct aca gtg cat att gga gtt gga gaa cct gac ttc att      4612
Glu Ser Glu Ser Thr Val His Ile Gly Val Gly Glu Pro Asp Phe Ile
955             960             965             970 ttg gga cag ttg tat cac ctg tct tca gta cag gca cct gaa gta gcc      4660
Leu Gly Gln Leu Tyr His Leu Ser Ser Val Gln Ala Pro Glu Val Ala
            975             980             985 aaa tct tgg gca gcg ttg gcc agc tgg gct tat agg tgg ggc aga aag      4708
Lys Ser Trp Ala Ala Leu Ala Ser Trp Ala Tyr Arg Trp Gly Arg Lys
        990             995             1000 gtg gtt gac aat gcc agt cag gga gaa ggt gtt cgt ctg ctg cct aga      4756
Val Val Asp Asn Ala Ser Gln Gly Glu Gly Val Arg Leu Leu Pro Arg
    1005            1010            1015 gaa aaa tct gaa gtt cag aat cta ctt cca gac act ata act gag gaa      4804
Glu Lys Ser Glu Val Gln Asn Leu Leu Pro Asp Thr Ile Thr Glu Glu
1020            1025            1030 gag aaa gag aga ata tat ggt att ctt gga cag gct gtg tgt cgg ccg      4852
Glu Lys Glu Arg Ile Tyr Gly Ile Leu Gly Gln Ala Val Cys Arg Pro
1035            1040            1045            1050 gcg ggg att cag gat gaa gat ata aca ctt cag ata act gag agt gaa      4900
Ala Gly Ile Gln Asp Glu Asp Ile Thr Leu Gln Ile Thr Glu Ser Glu
            1055            1060            1065 gac aac gaa gaa gat gac atg gtt gat gtt atc tgg cgt cag ttg ata      4948
Asp Asn Glu Glu Asp Asp Met Val Asp Val Ile Trp Arg Gln Leu Ile
        1070            1075            1080 tca agc tgc cca tgg ctt tca gaa ctt gat gaa agt gca act gaa gga      4996
Ser Ser Cys Pro Trp Leu Ser Glu Leu Asp Glu Ser Ala Thr Glu Gly
    1085            1090            1095 gtt att aaa gtg tgg agg aaa gtt gta gat aga ata ttc agc ctg tac      5044
Val Ile Lys Val Trp Arg Lys Val Val Asp Arg Ile Phe Ser Leu Tyr
1100            1105            1110 aaa ctc tct tgc agt gca tac ttt act ttc ctt aaa ctc aac gct ggt      5092
Lys Leu Ser Cys Ser Ala Tyr Phe Thr Phe Leu Lys Leu Asn Ala Gly
1115            1120            1125            1130
```

```
caa att cct tta gat gag gat gac cct agg ctg cat tta agt cac aga      5140
Gln Ile Pro Leu Asp Glu Asp Asp Pro Arg Leu His Leu Ser His Arg
            1135                1140                1145 gtg gaa cag agc act gat gac atg att gtg atg gcc aca ttg cgc ctg      5188
Val Glu Gln Ser Thr Asp Asp Met Ile Val Met Ala Thr Leu Arg Leu
        1150                1155                1160 ctg cgg ttg ctc gtg aag cat gct ggt gag ctt cgg cag tat ctg gag      5236
Leu Arg Leu Leu Val Lys His Ala Gly Glu Leu Arg Gln Tyr Leu Glu
    1165                1170                1175 cac ggc ttg gag aca aca ccc act gca cca tgg aga gga att att ccg      5284
His Gly Leu Glu Thr Thr Pro Thr Ala Pro Trp Arg Gly Ile Ile Pro
1180                1185                1190 caa ctt ttc tca cgc tta aac cac cct gaa gtg tat gtg cgc caa agt      5332
Gln Leu Phe Ser Arg Leu Asn His Pro Glu Val Tyr Val Arg Gln Ser
1195                1200                1205                1210 att tgt aac ctt ctc tgc cgt gtg gct caa gat tcc cca cat ctc ata      5380
Ile Cys Asn Leu Leu Cys Arg Val Ala Gln Asp Ser Pro His Leu Ile
            1215                1220                1225 ttg tat cct gca ata gtg ggt acc ata tcg ctt agt agt gaa tcc cag      5428
Leu Tyr Pro Ala Ile Val Gly Thr Ile Ser Leu Ser Ser Glu Ser Gln
        1230                1235                1240 gct tca gga aat aaa ttt tcc act gca att cca act tta ctt ggc aat      5476
Ala Ser Gly Asn Lys Phe Ser Thr Ala Ile Pro Thr Leu Leu Gly Asn
    1245                1250                1255 att caa gga gaa gaa ttg ctg gtt tct gaa tgt gag gga gga agt cct      5524
Ile Gln Gly Glu Glu Leu Leu Val Ser Glu Cys Glu Gly Gly Ser Pro
1260                1265                1270 cct gca tct cag gat agc aat aag gat gaa cct aaa agt gga tta aat      5572
Pro Ala Ser Gln Asp Ser Asn Lys Asp Glu Pro Lys Ser Gly Leu Asn
1275                1280                1285                1290 gaa gac caa gcc atg atg cag gat tgt tac agc aaa att gta gat aag      5620
Glu Asp Gln Ala Met Met Gln Asp Cys Tyr Ser Lys Ile Val Asp Lys
            1295                1300                1305 ctg tcc tct gca aac ccc acc atg gta tta cag gtt cag atg ctc gtg      5668
Leu Ser Ser Ala Asn Pro Thr Met Val Leu Gln Val Gln Met Leu Val
        1310                1315                1320 gct gaa ctg cgc agg gtc act gtg ctc tgg gat gag ctc tgg ctg gga      5716
Ala Glu Leu Arg Arg Val Thr Val Leu Trp Asp Glu Leu Trp Leu Gly
    1325                1330                1335 gtt ttg ctg caa caa cac atg tat gtc ctg aga cga att cag cag ctt      5764
Val Leu Leu Gln Gln His Met Tyr Val Leu Arg Arg Ile Gln Gln Leu
    1340                1345                1350 gaa gat gag gtg aag aga gtc cag aac aac aac acc tta cgc aaa gaa      5812
Glu Asp Glu Val Lys Arg Val Gln Asn Asn Asn Thr Leu Arg Lys Glu
1355                1360                1365                1370 gag aaa att gca atc atg agg gag aag cac aca gct ttg atg aag ccc      5860
Glu Lys Ile Ala Ile Met Arg Glu Lys His Thr Ala Leu Met Lys Pro
            1375                1380                1385 atc gta ttt gct ttg gag cat gtg agg agt atc aca gcg gct cct gca      5908
Ile Val Phe Ala Leu Glu His Val Arg Ser Ile Thr Ala Ala Pro Ala
        1390                1395                1400 gaa aca cct cat gaa aaa tgg ttt cag gat aac tat ggt gat gcc att      5956
Glu Thr Pro His Glu Lys Trp Phe Gln Asp Asn Tyr Gly Asp Ala Ile
    1405                1410                1415 gaa aat gcc cta gaa aaa ctg aag act cca ttg aac cct gca aag cct      6004
Glu Asn Ala Leu Glu Lys Leu Lys Thr Pro Leu Asn Pro Ala Lys Pro
1420                1425                1430 ggg agc agc tgg att cca ttt aaa gag ata atg cta agt ttg caa cag      6052
Gly Ser Ser Trp Ile Pro Phe Lys Glu Ile Met Leu Ser Leu Gln Gln
1435                1440                1445                1450
```

| | |
|---|---|
| aga gca cag aaa cgt gca agt tac atc ttg cgt ctt gaa gaa atc agt<br>Arg Ala Gln Lys Arg Ala Ser Tyr Ile Leu Arg Leu Glu Glu Ile Ser<br>                1455                      1460                   1465 | 6100 |
| cca tgg ttg gct gcc atg act aac act gaa att gct ctt cct ggg aa<br>Pro Trp Leu Ala Ala Met Thr Asn Thr Glu Ile Ala Leu Pro Gly Glu<br>1470                       1475                    1480 | 6148 |
| gtc tca gcc aga gac act gtc aca atc cat agt gtg ggc gga acc atc<br>Val Ser Ala Arg Asp Thr Val Thr Ile His Ser Val Gly Gly Thr Ile<br>                1485                      1490                   1495 | 6196 |
| aca atc tta ccg act aaa acc aag cca aag aaa ctt ctc ttt ctt gga<br>Thr Ile Leu Pro Thr Lys Thr Lys Pro Lys Lys Leu Leu Phe Leu Gly<br>1500                       1505                    1510 | 6244 |
| tca gat ggg aag agc tat cct tat ctt ttc aaa gga ctg gag gat tta<br>Ser Asp Gly Lys Ser Tyr Pro Tyr Leu Phe Lys Gly Leu Glu Asp Leu<br>1515                       1520                    1525                   1530 | 6292 |
| cat ctg gat gag aga ata atg cag ttc cta tct att gtg aat acc atg<br>His Leu Asp Glu Arg Ile Met Gln Phe Leu Ser Ile Val Asn Thr Met<br>                1535                      1540                   1545 | 6340 |
| ttt gct aca att aat cgc caa gaa aca ccc cgg ttc cat gct cga cac<br>Phe Ala Thr Ile Asn Arg Gln Glu Thr Pro Arg Phe His Ala Arg His<br>                1550                      1555                   1560 | 6388 |
| tat tct gta aca cca cta gga aca aga tca gga cta atc cag tgg gta<br>Tyr Ser Val Thr Pro Leu Gly Thr Arg Ser Gly Leu Ile Gln Trp Val<br>                1565                      1570                   1575 | 6436 |
| gat gga gcc aca ccc tta ttt ggt ctt tac aaa cga tgg caa caa cgg<br>Asp Gly Ala Thr Pro Leu Phe Gly Leu Tyr Lys Arg Trp Gln Gln Arg<br>1580                       1585                    1590 | 6484 |
| gaa gct gcc tta caa gca caa aag gcc caa gat tcc tac caa act cct<br>Glu Ala Ala Leu Gln Ala Gln Lys Ala Gln Asp Ser Tyr Gln Thr Pro<br>1595                       1600                    1605                   1610 | 6532 |
| cag aat cct gga att gta ccc cgt cct agt gaa ctt tat tac agt aaa<br>Gln Asn Pro Gly Ile Val Pro Arg Pro Ser Glu Leu Tyr Tyr Ser Lys<br>                1615                      1620                   1625 | 6580 |
| att ggc cct gct ttg aaa aca gtt ggg ctt agc ctg gat gtg tcc cgt<br>Ile Gly Pro Ala Leu Lys Thr Val Gly Leu Ser Leu Asp Val Ser Arg<br>                1630                      1635                   1640 | 6628 |
| cgg gat tgg cct ctt cat gta atg aag gca gta ttg gaa gag tta atg<br>Arg Asp Trp Pro Leu His Val Met Lys Ala Val Leu Glu Glu Leu Met<br>                1645                      1650                   1655 | 6676 |
| gag gcc aca ccc ccg aat ctc ctt gcc aaa gag ctc tgg tca tct tgc<br>Glu Ala Thr Pro Pro Asn Leu Leu Ala Lys Glu Leu Trp Ser Ser Cys<br>1660                       1665                    1670 | 6724 |
| aca aca cct gat gaa tgg tgg aga gtt acg cag tct tat gca aga tct<br>Thr Thr Pro Asp Glu Trp Trp Arg Val Thr Gln Ser Tyr Ala Arg Ser<br>1675                       1680                    1685                   1690 | 6772 |
| act gca gtc atg tct atg gtt gga tac ata att ggc ttg gga gac aga<br>Thr Ala Val Met Ser Met Val Gly Tyr Ile Ile Gly Leu Gly Asp Arg<br>                1695                      1700                   1705 | 6820 |
| cat ctg gat aat gtt ctt ata gat atg acg act gga gaa gtt gtt cac<br>His Leu Asp Asn Val Leu Ile Asp Met Thr Thr Gly Glu Val Val His<br>                1710                      1715                   1720 | 6868 |
| ata gat tac aat gtt tgc ttt gaa aaa ggt aaa agc ctt aga gtt cct<br>Ile Asp Tyr Asn Val Cys Phe Glu Lys Gly Lys Ser Leu Arg Val Pro<br>                1725                      1730                   1735 | 6916 |
| gag aaa gta cct ttt cga atg aca caa aac att gaa aca gca ctg ggt<br>Glu Lys Val Pro Phe Arg Met Thr Gln Asn Ile Glu Thr Ala Leu Gly<br>1740                       1745                    1750 | 6964 |
| gta act gga gta gaa ggt gta ttt agg ctt tca tgt gag cag gtt tta<br>Val Thr Gly Val Glu Gly Val Phe Arg Leu Ser Cys Glu Gln Val Leu<br>1755                       1760                    1765                   1770 | 7012 |

```
cac att atg cgg cgt ggc aga gag acc ctg ctg acg ctg ctg gag gcc      7060
His Ile Met Arg Arg Gly Arg Glu Thr Leu Leu Thr Leu Leu Glu Ala
            1775                1780                1785 ttt gtg tac gac cct ctg gtg gac tgg aca gca gga ggc gag gct ggg      7108
Phe Val Tyr Asp Pro Leu Val Asp Trp Thr Ala Gly Gly Glu Ala Gly
            1790                1795                1800 ttt gct ggt gct gtc tat ggt gga ggt ggc cag cag gcc gag agc aag      7156
Phe Ala Gly Ala Val Tyr Gly Gly Gly Gly Gln Gln Ala Glu Ser Lys
            1805                1810                1815 cag agc aag aga gag atg gag cga gag atc acc cgc agc ctg ttt tct      7204
Gln Ser Lys Arg Glu Met Glu Arg Glu Ile Thr Arg Ser Leu Phe Ser
            1820                1825                1830 tct aga gta gct gag att aag gtg aac tgg ttt aag aat aga gat gag      7252
Ser Arg Val Ala Glu Ile Lys Val Asn Trp Phe Lys Asn Arg Asp Glu
1835                1840                1845                1850 atg ctg gtt gtg ctt ccc aag ttg gac ggt agc tta gat gaa tac cta      7300
Met Leu Val Val Leu Pro Lys Leu Asp Gly Ser Leu Asp Glu Tyr Leu
            1855                1860                1865 agc ttg caa gag caa ctg aca gat gtg gaa aaa ctg cag ggc aaa cta      7348
Ser Leu Gln Glu Gln Leu Thr Asp Val Glu Lys Leu Gln Gly Lys Leu
            1870                1875                1880 ctg gag gaa ata gag ttt cta gaa gga gct gaa ggg gtg gat cat cct      7396
Leu Glu Glu Ile Glu Phe Leu Glu Gly Ala Glu Gly Val Asp His Pro
            1885                1890                1895 tct cat act ctg caa cac agg tat tct gag cac acc caa cta cag act      7444
Ser His Thr Leu Gln His Arg Tyr Ser Glu His Thr Gln Leu Gln Thr
            1900                1905                1910 cag caa aga gct gtt cag gaa gca atc cag gtg aag ctg aat gaa ttt      7492
Gln Gln Arg Ala Val Gln Glu Ala Ile Gln Val Lys Leu Asn Glu Phe
1915                1920                1925                1930 gaa caa tgg ata aca cat tat cag gct gca ttc aat aat tta gaa gca      7540
Glu Gln Trp Ile Thr His Tyr Gln Ala Ala Phe Asn Asn Leu Glu Ala
            1935                1940                1945 aca cag ctt gca agc ttg ctt caa gag ata agc aca caa atg gac ctt      7588
Thr Gln Leu Ala Ser Leu Leu Gln Glu Ile Ser Thr Gln Met Asp Leu
            1950                1955                1960 ggt cct cca agt tac gtg cca gca aca gcc ttt ctg cag aat gct ggt      7636
Gly Pro Pro Ser Tyr Val Pro Ala Thr Ala Phe Leu Gln Asn Ala Gly
            1965                1970                1975 cag gcc cac ttg att agc cag tgc gag cag ctg gag ggg gag gtt ggt      7684
Gln Ala His Leu Ile Ser Gln Cys Glu Gln Leu Glu Gly Glu Val Gly
            1980                1985                1990 gct ctc ctg cag cag agg cgc tcc gtg ctc cgt ggc tgt ctg gag caa      7732
Ala Leu Leu Gln Gln Arg Arg Ser Val Leu Arg Gly Cys Leu Glu Gln
1995                2000                2005                2010 ctg cat cac tat gca acc gtg gcc ctg cag tat ccg aag gcc ata ttt      7780
Leu His His Tyr Ala Thr Val Ala Leu Gln Tyr Pro Lys Ala Ile Phe
            2015                2020                2025 cag aaa cat cga att gaa cag tgg aag acc tgg atg gaa gag ctc atc      7828
Gln Lys His Arg Ile Glu Gln Trp Lys Thr Trp Met Glu Glu Leu Ile
            2030                2035                2040 tgt aac acc aca gta gag cgt tgt caa gag ctc tat agg aaa tat gaa      7876
Cys Asn Thr Thr Val Glu Arg Cys Gln Glu Leu Tyr Arg Lys Tyr Glu
            2045                2050                2055 atg caa tat gct ccc cag cca ccc cca aca gtg tgt cag ttc atc act      7924
Met Gln Tyr Ala Pro Gln Pro Pro Pro Thr Val Cys Gln Phe Ile Thr
            2060                2065                2070 gcc act gaa atg acc ctg cag cga tac gca gca gac atc aac agc aga      7972
Ala Thr Glu Met Thr Leu Gln Arg Tyr Ala Ala Asp Ile Asn Ser Arg
2075                2080                2085                2090
```

```
                                                        -continued ctt att aga caa gtg gaa cgc ttg aaa cag gaa gct gtc act gtg cca         8020
Leu Ile Arg Gln Val Glu Arg Leu Lys Gln Glu Ala Val Thr Val Pro
            2095                2100                2105 gtt tgt gaa gat cag ttg aaa gaa att gaa cgt tgc att aaa gtt ttc         8068
Val Cys Glu Asp Gln Leu Lys Glu Ile Glu Arg Cys Ile Lys Val Phe
            2110                2115                2120 ctt cat gag aat gga gaa gaa gga tct ttg agt cta gca agt gtt att         8116
Leu His Glu Asn Gly Glu Glu Gly Ser Leu Ser Leu Ala Ser Val Ile
            2125                2130                2135 att tct gcc ctt tgt acc ctt aca agg cgt aac ctg atg atg gaa ggt         8164
Ile Ser Ala Leu Cys Thr Leu Thr Arg Arg Asn Leu Met Met Glu Gly
            2140                2145                2150 gca gcg tca agt gct gga gaa cag ctg gtt gat ctg act tct cgg gat         8212
Ala Ala Ser Ser Ala Gly Glu Gln Leu Val Asp Leu Thr Ser Arg Asp
2155                2160                2165                2170 gga gcc tgg ttc ttg gag gaa ctc tgc agt atg agc gga aac gtc acc         8260
Gly Ala Trp Phe Leu Glu Glu Leu Cys Ser Met Ser Gly Asn Val Thr
            2175                2180                2185 tgc ttg gtt cag tta ctg aag cag tgc cac ctg gtg cca cag gac tta         8308
Cys Leu Val Gln Leu Leu Lys Gln Cys His Leu Val Pro Gln Asp Leu
            2190                2195                2200 gat atc ccg aac ccc atg gaa gcg tct gag aca gtt cac tta gcc aat         8356
Asp Ile Pro Asn Pro Met Glu Ala Ser Glu Thr Val His Leu Ala Asn
            2205                2210                2215 gga gtg tat acc tca ctt cag gaa ttg aat tcg aat ttc cgg caa atc         8404
Gly Val Tyr Thr Ser Leu Gln Glu Leu Asn Ser Asn Phe Arg Gln Ile
            2220                2225                2230 ata ttt cca gaa gca ctt cga tgt tta atg aaa ggg gaa tac acg tta         8452
Ile Phe Pro Glu Ala Leu Arg Cys Leu Met Lys Gly Glu Tyr Thr Leu
2235                2240                2245                2250 gaa agt atg ctg cat gaa ctg gac ggt ctt att gag cag acc acc gat         8500
Glu Ser Met Leu His Glu Leu Asp Gly Leu Ile Glu Gln Thr Thr Asp
            2255                2260                2265 ggc gtt ccc ctg cag act cta gtg gaa tct ctt cag gcc tac tta aga         8548
Gly Val Pro Leu Gln Thr Leu Val Glu Ser Leu Gln Ala Tyr Leu Arg
            2270                2275                2280 aac gca gct atg gga ctg gaa gaa gaa aca cat gct cat tac atc gat         8596
Asn Ala Ala Met Gly Leu Glu Glu Glu Thr His Ala His Tyr Ile Asp
            2285                2290                2295 gtt gcc aga cta cta cat gct cag tac ggt gaa tta atc caa ccg aga         8644
Val Ala Arg Leu Leu His Ala Gln Tyr Gly Glu Leu Ile Gln Pro Arg
            2300                2305                2310 aat ggt tca gtt gat gaa aca ccc aaa atg tca gct ggc cag atg ctt         8692
Asn Gly Ser Val Asp Glu Thr Pro Lys Met Ser Ala Gly Gln Met Leu
2315                2320                2325                2330 ttg gta gca ttc gat ggc atg ttt gct caa gtt gaa act gct ttc agc         8740
Leu Val Ala Phe Asp Gly Met Phe Ala Gln Val Glu Thr Ala Phe Ser
            2335                2340                2345 tta tta gtt gaa aag ttg aac aag atg gaa att ccc ata gct tgg cga         8788
Leu Leu Val Glu Lys Leu Asn Lys Met Glu Ile Pro Ile Ala Trp Arg
            2350                2355                2360 aag att gac atc ata agg gaa gcc agg agt act caa gtt aat ttt ttt         8836
Lys Ile Asp Ile Ile Arg Glu Ala Arg Ser Thr Gln Val Asn Phe Phe
            2365                2370                2375 gat gat gat aat cac cgg cag gtg cta gaa gag att ttc ttt cta aaa         8884
Asp Asp Asp Asn His Arg Gln Val Leu Glu Glu Ile Phe Phe Leu Lys
            2380                2385                2390 aga cta cag act att aag gag ttc ttc agg ctc tgt ggt acc ttt tct         8932
Arg Leu Gln Thr Ile Lys Glu Phe Phe Arg Leu Cys Gly Thr Phe Ser
2395                2400                2405                2410
```

```
aaa aca ttg tca gga tca agt tca ctt gaa gat cag aat act gtg aat    8980
Lys Thr Leu Ser Gly Ser Ser Ser Leu Glu Asp Gln Asn Thr Val Asn
            2415                2420                2425 ggg cct gta cag att gtc aat gtg aaa acc ctt ttt aga aac tct tgt    9028
Gly Pro Val Gln Ile Val Asn Val Lys Thr Leu Phe Arg Asn Ser Cys
        2430                2435                2440 ttc agt gaa gac caa atg gcc aaa cct atc aag gca ttc aca gct gac    9076
Phe Ser Glu Asp Gln Met Ala Lys Pro Ile Lys Ala Phe Thr Ala Asp
    2445                2450                2455 ttt gtg agg cag ctc ttg ata ggg cta ccc aac caa gcc ctc gga ctc    9124
Phe Val Arg Gln Leu Leu Ile Gly Leu Pro Asn Gln Ala Leu Gly Leu
2460                2465                2470 aca ctg tgc agt ttt atc agt gct ctg ggt gta gac atc att gct caa    9172
Thr Leu Cys Ser Phe Ile Ser Ala Leu Gly Val Asp Ile Ile Ala Gln
2475                2480                2485                2490 gta gag gca aag gac ttt ggt gcc gaa agc aaa gtt tct gtt gat gat    9220
Val Glu Ala Lys Asp Phe Gly Ala Glu Ser Lys Val Ser Val Asp Asp
            2495                2500                2505 ctc tgt aag aaa gcg gtg gaa cat aac atc cag ata ggg aag ttc tct    9268
Leu Cys Lys Lys Ala Val Glu His Asn Ile Gln Ile Gly Lys Phe Ser
        2510                2515                2520 cag ctg gtt atg aac agg gca act gtg tta gca agt tct tac gac act    9316
Gln Leu Val Met Asn Arg Ala Thr Val Leu Ala Ser Ser Tyr Asp Thr
    2525                2530                2535 gcc tgg aag aag cat gac ttg gtg cga agg cta gaa acc agt att tct    9364
Ala Trp Lys Lys His Asp Leu Val Arg Arg Leu Glu Thr Ser Ile Ser
2540                2545                2550 tct tgt aag aca agc ctg cag cgg gtt cag ctg cat att gcc atg ttt    9412
Ser Cys Lys Thr Ser Leu Gln Arg Val Gln Leu His Ile Ala Met Phe
2555                2560                2565                2570 cag tgg caa cat gaa gat cta ctt atc aat aga cca caa gcc atg tca    9460
Gln Trp Gln His Glu Asp Leu Leu Ile Asn Arg Pro Gln Ala Met Ser
            2575                2580                2585 gtc aca cct ccc cca cgg tct gct atc cta acc agc atg aaa aag aag    9508
Val Thr Pro Pro Pro Arg Ser Ala Ile Leu Thr Ser Met Lys Lys Lys
        2590                2595                2600 ctg cat acc ctg agc cag att gaa act tct att gca aca gtt cag gag    9556
Leu His Thr Leu Ser Gln Ile Glu Thr Ser Ile Ala Thr Val Gln Glu
    2605                2610                2615 aag cta gct gca ctt gaa tca agt att gaa cag cga ctc aag tgg gca    9604
Lys Leu Ala Ala Leu Glu Ser Ser Ile Glu Gln Arg Leu Lys Trp Ala
2620                2625                2630 ggt ggt gcc aac cct gca ttg gcc cct gta cta caa gat ttt gaa gca    9652
Gly Gly Ala Asn Pro Ala Leu Ala Pro Val Leu Gln Asp Phe Glu Ala
2635                2640                2645                2650 acg ata gct gaa aga aga aat ctt gtc ctt aaa gag agc caa aga gca    9700
Thr Ile Ala Glu Arg Arg Asn Leu Val Leu Lys Glu Ser Gln Arg Ala
            2655                2660                2665 agt cag gtc aca ttt ctc tgc agc aat atc att cat ttt gaa agt tta    9748
Ser Gln Val Thr Phe Leu Cys Ser Asn Ile Ile His Phe Glu Ser Leu
        2670                2675                2680 cga aca aga act gca gaa gcc tta aac ctg gat gcg gcg tta ttt gaa    9796
Arg Thr Arg Thr Ala Glu Ala Leu Asn Leu Asp Ala Ala Leu Phe Glu
    2685                2690                2695 cta atc aag cga tgt cag cag atg tgt tcg ttt gca tca cag ttt aac    9844
Leu Ile Lys Arg Cys Gln Gln Met Cys Ser Phe Ala Ser Gln Phe Asn
2700                2705                2710 agt tca gtg tct gag tta gag ctt cgt tta tta cag aga gtg gac act    9892
Ser Ser Val Ser Glu Leu Glu Leu Arg Leu Leu Gln Arg Val Asp Thr
2715                2720                2725                2730
```

```
ggt ctt gaa cat cct att ggc agc tct gaa tgg ctt ttg tca gca cac     9940
Gly Leu Glu His Pro Ile Gly Ser Ser Glu Trp Leu Leu Ser Ala His
            2735                2740                2745 aaa cag ttg acc cag gat atg tct act cag agg gca att cag aca gag     9988
Lys Gln Leu Thr Gln Asp Met Ser Thr Gln Arg Ala Ile Gln Thr Glu
        2750                2755                2760 aaa gag cag cag ata gaa acg gtc tgt gaa aca att cag aat ctg gtt    10036
Lys Glu Gln Gln Ile Glu Thr Val Cys Glu Thr Ile Gln Asn Leu Val
            2765                2770                2775 gat aat ata aag act gtg ctc act ggt cat aac cga cag ctt gga gat    10084
Asp Asn Ile Lys Thr Val Leu Thr Gly His Asn Arg Gln Leu Gly Asp
        2780                2785                2790 gtc aaa cat ctc ttg aaa gct atg gct aag gat gaa gaa gct gct ctg    10132
Val Lys His Leu Leu Lys Ala Met Ala Lys Asp Glu Glu Ala Ala Leu
2795                2800                2805                2810 gca gat ggt gaa gat gtt ccc tat gag aac agt gtt agg cag ttt ttg    10180
Ala Asp Gly Glu Asp Val Pro Tyr Glu Asn Ser Val Arg Gln Phe Leu
            2815                2820                2825 ggt gaa tat aaa tca tgg caa gac aac att caa aca gtt cta ttt aca    10228
Gly Glu Tyr Lys Ser Trp Gln Asp Asn Ile Gln Thr Val Leu Phe Thr
        2830                2835                2840 tta gtc cag gct atg ggt cag gtt cga agt caa gaa cac gtt gaa atg    10276
Leu Val Gln Ala Met Gly Gln Val Arg Ser Gln Glu His Val Glu Met
        2845                2850                2855 ctc cag gaa atc act ccc acc ttg aaa gaa ctg aaa aca caa agt cag    10324
Leu Gln Glu Ile Thr Pro Thr Leu Lys Glu Leu Lys Thr Gln Ser Gln
        2860                2865                2870 agt atc tat aat aat tta gtg agt ttt gca tca ccc tta gtc acc gat    10372
Ser Ile Tyr Asn Asn Leu Val Ser Phe Ala Ser Pro Leu Val Thr Asp
2875                2880                2885                2890 gca aca aat gaa tgt tcg agt cca acg tca tct gct act tat cag cca    10420
Ala Thr Asn Glu Cys Ser Ser Pro Thr Ser Ser Ala Thr Tyr Gln Pro
            2895                2900                2905 tcc ttc gct gca gca gtc cgg agt aac act ggc cag aag act cag cct    10468
Ser Phe Ala Ala Ala Val Arg Ser Asn Thr Gly Gln Lys Thr Gln Pro
        2910                2915                2920 gat gtc atg tca cag aat gct aga aag ctg atc cag aaa aat ctt gct    10516
Asp Val Met Ser Gln Asn Ala Arg Lys Leu Ile Gln Lys Asn Leu Ala
        2925                2930                2935 aca tca gct gat act cca cca agc acc gtt cca gga act ggc aag agt    10564
Thr Ser Ala Asp Thr Pro Pro Ser Thr Val Pro Gly Thr Gly Lys Ser
2940                2945                2950 gtt gct tgt agt cct aaa aag gca gtc aga gac cct aaa act ggg aaa    10612
Val Ala Cys Ser Pro Lys Lys Ala Val Arg Asp Pro Lys Thr Gly Lys
2955                2960                2965                2970 gcg gtg caa gag aga aac tcc tat gca gtg agt gtg tgg aag aga gtg    10660
Ala Val Gln Glu Arg Asn Ser Tyr Ala Val Ser Val Trp Lys Arg Val
            2975                2980                2985 aaa gcc aag tta gag ggc cga gat gtt gat ccg aat agg agg atg tca    10708
Lys Ala Lys Leu Glu Gly Arg Asp Val Asp Pro Asn Arg Arg Met Ser
        2990                2995                3000 gtt gct gaa cag gtt gac tat gtc att aag gaa gca act aat cta gat    10756
Val Ala Glu Gln Val Asp Tyr Val Ile Lys Glu Ala Thr Asn Leu Asp
        3005                3010                3015 aac ttg gct cag ctg tat gaa ggt tgg aca gcc tgg gtg tga             10798
Asn Leu Ala Gln Leu Tyr Glu Gly Trp Thr Ala Trp Val  *
            3020                3025                3030 atggcaagac agtagatgag tctggttaag cgaggtcaga catccaccag aatcaactca    10858
gcctcaggca tccaaagcca caccacagtc ggtggtgatg caactggggg cttactctga    10918
```

-continued

```
ggaaacctag gaaatctcgg tgcactagga agtgaatccc gcaggacagc tgcactcagg    10978
gatacgccca acaccatggc ctgcaacccc agggtcaagg gtgaaggaaa gcaagctcac    11038
cgcctgaaca cggagattgt ctttctgcca cagaacagca gcagacgtgt cgggaggtta    11098
gctgcggaaa gaaatcggga tgccgcggag cacagagtga tttggaactc cattccacct    11158
gaccctgtgt gtacaatcca ggaaaaaaac aaacccccact cagaaacaga gaaaactggg   11218
gtcgcgaaga aatcacagcc aaggaagatt tgatgcattc agattctcgt gtaacacttg    11278
ttgcttggca acagtactgg ttgggttgac cagtaagtag aaaaaggcta aaggctatgc    11338
gatatgaatt tcagaaatgg actgaaaatg gagagctatg taacagatac actacagtag    11398
aagaacttac ttctgaaatg aagggaaaaa aaccaccccca tcgttcccta ctcctcccca   11458
ccacttaccc gttcccccctt tacctaatct agtagattag ccatctttca aattcacttt   11518
tatttcagtc cttatatttc atatacttcc gtctcgatgc tgttaacaac ttctgataac    11578
atggaaaatt caaggattgt ttaaaggtct gatgatcaca cacaaaatgt aattccggtt    11638
atttaagtca tttctgtgat tctatcatgt acagttttcca gaattgtcac tgtgcattca   11698
aaagtaatga atctaacaga catttgattt aatgtacact ccctttttgct tatagtgtgc   11758
atttttttttg gaggtcattc aaattttccc tcttctgtga tagctgtagt ttctttcata   11818
gaaagtagct aatccagtgt aatcttttac cttttttaaaa accaagatag agtatctatt   11878
agagttttac attgttgatg atagattaac aataaagtga tgttctggtg gaggtagact    11938
gaaattttttt taattcatgt ttttcatttg atacttttaa tttacactta gtaaattaaa   11998
agttgtttaa tttacttggc attttaggac atgtacatga aacagtgaaa atgagatcca    12058
ccaacatctt ttattaagtt cagttattag tctgtgaagt gctttacttt ttgcacaatt    12118
ttaatagctt gctattcagt aatacattat agtgaattca tgatcaaggt ttccttaaat    12178
ttagcattgc atttcagtac tgactgtgta agctaaattg ctgatccaaa ataaaaaccc    12238
agactagaat agggttctta aaatcaagta tcaatacaaa atagaacaca attaaaatct    12298
taattgttgg ctgggcacag tggctcacgc ctgtaatccc agcactttgg gaggccgagg    12358
cgggcggatc atgaggttag gagagcgaga ccatcctggc taacacggtg aaaccccgtc    12418
tttactaaaa tacaaaaaaa attagccggg tgtggtggcg ggcgcctgta gtcccagcta    12478
ctcgggaggc tgaggcagga gaatggcgtg aacccaggag gcggagcttg cagtgagccg    12538
agattgtgcc actgcactcc agcctgggca acagagctag actctgtgtc aaaaataaat    12598
gactagat                                                             12606
```

<210> SEQ ID NO 6
<211> LENGTH: 3031
<212> TYPE: PRT
<213> ORGANISM: Homo sapiens

<400> SEQUENCE: 6

```
Met Trp Ala Leu Ser Pro Thr Val Phe Ala Leu Leu Ser Lys Asn Leu
1               5                   10                  15

Met Ile Val His Ser Asp Leu Ala Val His Phe Pro Ala Ile Gln Tyr
            20                  25                  30

Ala Val Leu Tyr Thr Leu Tyr Ser His Cys Thr Arg His Asp His Phe
        35                  40                  45

Ile Ser Ser Ser Leu Ser Ser Ser Pro Ser Leu Phe Asp Gly Ala
    50                  55                  60
```

-continued

```
Val Ile Ser Thr Val Thr Ala Thr Lys Lys His Phe Ser Ile Ile
 65                  70                  75                  80

Leu Asn Leu Leu Gly Ile Leu Lys Lys Asp Asn Leu Asn Gln Asp
                 85                  90                  95

Thr Arg Lys Leu Leu Met Thr Trp Ala Leu Glu Ala Ala Val Leu Met
            100                 105                 110

Lys Lys Ser Glu Thr Tyr Ala Pro Leu Phe Ser Leu Pro Ser Phe His
            115                 120                 125

Lys Phe Cys Lys Gly Leu Leu Ala Asn Thr Leu Val Glu Asp Val Asn
            130                 135                 140

Ile Cys Leu Gln Ala Cys Ser Ser Leu His Ala Leu Ser Ser Ser Leu
145                 150                 155                 160

Pro Asp Asp Leu Leu Gln Arg Cys Val Asp Val Cys Arg Val Gln Leu
                165                 170                 175

Val His Ser Gly Thr Arg Ile Arg Gln Ala Phe Gly Lys Leu Leu Lys
                180                 185                 190

Ser Ile Pro Leu Asp Val Val Leu Ser Asn Asn Asn His Thr Glu Ile
                195                 200                 205

Gln Glu Ile Ser Leu Ala Leu Arg Ser His Met Ser Lys Ala Pro Ser
210                 215                 220

Asn Thr Phe His Pro Gln Asp Phe Ser Asp Val Ile Ser Phe Ile Leu
225                 230                 235                 240

Tyr Gly Asn Ser His Arg Thr Gly Lys Asp Asn Trp Leu Glu Arg Leu
                245                 250                 255

Phe Tyr Ser Cys Gln Arg Leu Asp Lys Arg Asp Gln Ser Thr Ile Pro
                260                 265                 270

Arg Asn Leu Leu Lys Thr Asp Ala Val Leu Trp Gln Trp Ala Ile Trp
                275                 280                 285

Glu Ala Ala Gln Phe Thr Val Leu Ser Lys Leu Arg Thr Pro Leu Gly
290                 295                 300

Arg Ala Gln Asp Thr Phe Gln Thr Ile Glu Gly Ile Ile Arg Ser Leu
305                 310                 315                 320

Ala Ala His Thr Leu Asn Pro Asp Gln Asp Val Ser Gln Trp Thr Thr
                325                 330                 335

Ala Asp Asn Asp Glu Gly His Gly Asn Asn Gln Leu Arg Leu Val Leu
                340                 345                 350

Leu Leu Gln Tyr Leu Glu Asn Leu Glu Lys Leu Met Tyr Asn Ala Tyr
                355                 360                 365

Glu Gly Cys Ala Asn Ala Leu Thr Ser Pro Pro Lys Val Ile Arg Thr
370                 375                 380

Phe Phe Tyr Thr Asn Arg Gln Thr Cys Gln Asp Trp Leu Thr Arg Ile
385                 390                 395                 400

Arg Leu Ser Ile Met Arg Val Gly Leu Leu Ala Gly Gln Pro Ala Val
                405                 410                 415

Thr Val Arg His Gly Phe Asp Leu Leu Thr Glu Met Lys Thr Thr Ser
                420                 425                 430

Leu Ser Gln Gly Asn Glu Leu Glu Val Thr Ile Met Met Val Val Glu
            435                 440                 445

Ala Leu Cys Glu Leu His Cys Pro Glu Ala Ile Gln Gly Ile Ala Val
            450                 455                 460

Trp Ser Ser Ser Ile Val Gly Lys Asn Leu Leu Trp Ile Asn Ser Val
465                 470                 475                 480
```

-continued

```
Ala Gln Gln Ala Glu Gly Arg Phe Glu Lys Ala Ser Val Glu Tyr Gln
                485                 490                 495

Glu His Leu Cys Ala Met Thr Gly Val Asp Cys Cys Ile Ser Ser Phe
            500                 505                 510

Asp Lys Ser Val Leu Thr Leu Ala Asn Ala Gly Arg Asn Ser Ala Ser
        515                 520                 525

Pro Lys His Ser Leu Asn Gly Glu Ser Arg Lys Thr Val Leu Ser Lys
    530                 535                 540

Pro Thr Asp Ser Ser Pro Glu Val Ile Asn Tyr Leu Gly Asn Lys Ala
545                 550                 555                 560

Cys Glu Cys Tyr Ile Ser Ile Ala Asp Trp Ala Val Gln Glu Trp
                565                 570                 575

Gln Asn Ala Ile His Asp Leu Lys Lys Ser Thr Ser Ser Thr Ser Leu
            580                 585                 590

Asn Leu Lys Ala Asp Phe Asn Tyr Ile Lys Ser Leu Ser Ser Phe Glu
        595                 600                 605

Ser Gly Lys Phe Val Glu Cys Thr Glu Gln Leu Glu Leu Leu Pro Gly
    610                 615                 620

Glu Asn Ile Asn Leu Leu Ala Gly Gly Ser Lys Glu Lys Ile Asp Met
625                 630                 635                 640

Lys Lys Leu Leu Pro Asn Met Leu Ser Pro Asp Pro Arg Glu Leu Gln
                645                 650                 655

Lys Ser Ile Glu Val Gln Leu Leu Arg Ser Ser Val Cys Leu Ala Thr
            660                 665                 670

Ala Leu Asn Pro Ile Glu Gln Asp Gln Lys Trp Gln Ser Ile Thr Glu
        675                 680                 685

Asn Val Val Lys Tyr Leu Lys Gln Thr Ser Arg Ile Ala Ile Gly Pro
    690                 695                 700

Leu Arg Leu Ser Thr Leu Thr Val Ser Gln Ser Leu Pro Val Leu Ser
705                 710                 715                 720

Thr Leu Gln Leu Tyr Cys Ser Ser Ala Leu Glu Asn Thr Val Ser Asn
                725                 730                 735

Arg Leu Ser Thr Glu Asp Cys Leu Ile Pro Leu Phe Ser Glu Ala Leu
            740                 745                 750

Arg Ser Cys Lys Gln His Asp Val Arg Pro Trp Met Gln Ala Leu Arg
        755                 760                 765

Tyr Thr Met Tyr Gln Asn Gln Leu Leu Glu Lys Ile Lys Glu Gln Thr
    770                 775                 780

Val Pro Ile Arg Ser His Leu Met Glu Leu Gly Leu Thr Ala Ala Lys
785                 790                 795                 800

Phe Ala Arg Lys Arg Gly Asn Val Ser Leu Ala Thr Arg Leu Leu Ala
                805                 810                 815

Gln Cys Ser Glu Val Gln Leu Gly Lys Thr Thr Thr Ala Gln Asp Leu
            820                 825                 830

Val Gln His Phe Lys Lys Leu Ser Thr Gln Gly Gln Val Asp Glu Lys
        835                 840                 845

Trp Gly Pro Glu Leu Asp Ile Glu Lys Thr Lys Leu Leu Tyr Thr Ala
    850                 855                 860

Gly Gln Ser Thr His Ala Met Glu Met Leu Ser Ser Cys Ala Ile Ser
865                 870                 875                 880

Phe Cys Lys Ser Val Lys Ala Glu Tyr Ala Val Ala Lys Ser Ile Leu
                885                 890                 895
```

-continued

Thr Leu Ala Lys Trp Ile Gln Ala Glu Trp Lys Glu Ile Ser Gly Gln
              900             905             910

Leu Lys Gln Val Tyr Arg Ala Gln His Gln Gln Asn Phe Thr Gly Leu
              915             920             925

Ser Thr Leu Ser Lys Asn Ile Leu Thr Leu Ile Glu Leu Pro Ser Val
              930             935             940

Asn Thr Met Glu Glu Glu Tyr Pro Arg Ile Glu Ser Glu Ser Thr Val
945             950             955             960

His Ile Gly Val Gly Glu Pro Asp Phe Ile Leu Gly Gln Leu Tyr His
              965             970             975

Leu Ser Ser Val Gln Ala Pro Glu Val Ala Lys Ser Trp Ala Ala Leu
              980             985             990

Ala Ser Trp Ala Tyr Arg Trp Gly Arg Lys Val Val Asp Asn Ala Ser
              995             1000            1005

Gln Gly Glu Gly Val Arg Leu Leu Pro Arg Glu Lys Ser Glu Val Gln
              1010            1015            1020

Asn Leu Leu Pro Asp Thr Ile Thr Glu Glu Lys Glu Arg Ile Tyr
1025            1030            1035            1040

Gly Ile Leu Gly Gln Ala Val Cys Arg Pro Ala Gly Ile Gln Asp Glu
              1045            1050            1055

Asp Ile Thr Leu Gln Ile Thr Glu Ser Glu Asp Asn Glu Glu Asp Asp
              1060            1065            1070

Met Val Asp Val Ile Trp Arg Gln Leu Ile Ser Ser Cys Pro Trp Leu
              1075            1080            1085

Ser Glu Leu Asp Glu Ser Ala Thr Glu Gly Val Ile Lys Val Trp Arg
              1090            1095            1100

Lys Val Val Asp Arg Ile Phe Ser Leu Tyr Lys Leu Ser Cys Ser Ala
1105            1110            1115            1120

Tyr Phe Thr Phe Leu Lys Leu Asn Ala Gly Gln Ile Pro Leu Asp Glu
              1125            1130            1135

Asp Asp Pro Arg Leu His Leu Ser His Arg Val Glu Gln Ser Thr Asp
              1140            1145            1150

Asp Met Ile Val Met Ala Thr Leu Arg Leu Leu Arg Leu Leu Val Lys
              1155            1160            1165

His Ala Gly Glu Leu Arg Gln Tyr Leu Glu His Gly Leu Glu Thr Thr
              1170            1175            1180

Pro Thr Ala Pro Trp Arg Gly Ile Ile Pro Gln Leu Phe Ser Arg Leu
1185            1190            1195            1200

Asn His Pro Glu Val Tyr Val Arg Gln Ser Ile Cys Asn Leu Leu Cys
              1205            1210            1215

Arg Val Ala Gln Asp Ser Pro His Leu Ile Leu Tyr Pro Ala Ile Val
              1220            1225            1230

Gly Thr Ile Ser Leu Ser Ser Glu Ser Gln Ala Ser Gly Asn Lys Phe
              1235            1240            1245

Ser Thr Ala Ile Pro Thr Leu Leu Gly Asn Ile Gln Gly Glu Glu Leu
              1250            1255            1260

Leu Val Ser Glu Cys Glu Gly Gly Ser Pro Ala Ser Gln Asp Ser
1265            1270            1275            1280

Asn Lys Asp Glu Pro Lys Ser Gly Leu Asn Glu Asp Gln Ala Met Met
              1285            1290            1295

Gln Asp Cys Tyr Ser Lys Ile Val Asp Lys Leu Ser Ser Ala Asn Pro
              1300            1305            1310

-continued

```
Thr Met Val Leu Gln Val Gln Met Leu Val Ala Glu Leu Arg Arg Val
        1315                1320                1325

Thr Val Leu Trp Asp Glu Leu Trp Leu Gly Val Leu Gln Gln His
    1330                1335                1340

Met Tyr Val Leu Arg Arg Ile Gln Gln Leu Glu Asp Glu Val Lys Arg
1345                1350                1355                1360

Val Gln Asn Asn Asn Thr Leu Arg Lys Glu Glu Lys Ile Ala Ile Met
                1365                1370                1375

Arg Glu Lys His Thr Ala Leu Met Lys Pro Ile Val Phe Ala Leu Glu
            1380                1385                1390

His Val Arg Ser Ile Thr Ala Ala Pro Ala Glu Thr Pro His Glu Lys
        1395                1400                1405

Trp Phe Gln Asp Asn Tyr Gly Asp Ala Ile Glu Asn Ala Leu Glu Lys
    1410                1415                1420

Leu Lys Thr Pro Leu Asn Pro Ala Lys Pro Gly Ser Ser Trp Ile Pro
1425                1430                1435                1440

Phe Lys Glu Ile Met Leu Ser Leu Gln Gln Arg Ala Gln Lys Arg Ala
                1445                1450                1455

Ser Tyr Ile Leu Arg Leu Glu Glu Ile Ser Pro Trp Leu Ala Ala Met
            1460                1465                1470

Thr Asn Thr Glu Ile Ala Leu Pro Gly Glu Val Ser Ala Arg Asp Thr
        1475                1480                1485

Val Thr Ile His Ser Val Gly Gly Thr Ile Thr Ile Leu Pro Thr Lys
    1490                1495                1500

Thr Lys Pro Lys Lys Leu Leu Phe Leu Gly Ser Asp Gly Lys Ser Tyr
1505                1510                1515                1520

Pro Tyr Leu Phe Lys Gly Leu Glu Asp Leu His Leu Asp Glu Arg Ile
                1525                1530                1535

Met Gln Phe Leu Ser Ile Val Asn Thr Met Phe Ala Thr Ile Asn Arg
            1540                1545                1550

Gln Glu Thr Pro Arg Phe His Ala Arg His Tyr Ser Val Thr Pro Leu
        1555                1560                1565

Gly Thr Arg Ser Gly Leu Ile Gln Trp Val Asp Gly Ala Thr Pro Leu
    1570                1575                1580

Phe Gly Leu Tyr Lys Arg Trp Gln Gln Arg Glu Ala Ala Leu Gln Ala
1585                1590                1595                1600

Gln Lys Ala Gln Asp Ser Tyr Gln Thr Pro Gln Asn Pro Gly Ile Val
                1605                1610                1615

Pro Arg Pro Ser Glu Leu Tyr Tyr Ser Lys Ile Gly Pro Ala Leu Lys
            1620                1625                1630

Thr Val Gly Leu Ser Leu Asp Val Ser Arg Arg Asp Trp Pro Leu His
        1635                1640                1645

Val Met Lys Ala Val Leu Glu Glu Leu Met Gly Ala Thr Pro Pro Asn
    1650                1655                1660

Leu Leu Ala Lys Glu Leu Trp Ser Ser Cys Thr Thr Pro Asp Glu Trp
1665                1670                1675                1680

Trp Arg Val Thr Gln Ser Tyr Ala Arg Ser Thr Ala Val Met Ser Met
                1685                1690                1695

Val Gly Tyr Ile Ile Gly Leu Gly Asp Arg His Leu Asp Asn Val Leu
            1700                1705                1710

Ile Asp Met Thr Thr Gly Glu Val Val His Ile Asp Tyr Asn Val Cys
        1715                1720                1725
```

-continued

```
Phe Glu Lys Gly Lys Ser Leu Arg Val Pro Glu Lys Val Pro Phe Arg
    1730                1735                1740

Met Thr Gln Asn Ile Glu Thr Ala Leu Gly Val Thr Gly Val Glu Gly
1745                1750                1755                1760

Val Phe Arg Leu Ser Cys Glu Gln Val Leu His Ile Met Arg Arg Gly
                1765                1770                1775

Arg Glu Thr Leu Leu Thr Leu Leu Glu Ala Phe Val Tyr Asp Pro Leu
            1780                1785                1790

Val Asp Trp Thr Ala Gly Gly Glu Ala Gly Phe Ala Gly Ala Val Tyr
        1795                1800                1805

Gly Gly Gly Gly Gln Gln Ala Glu Ser Lys Gln Ser Lys Arg Glu Met
    1810                1815                1820

Glu Arg Glu Ile Thr Arg Ser Leu Phe Ser Ser Arg Val Ala Glu Ile
1825                1830                1835                1840

Lys Val Asn Trp Phe Lys Asn Arg Asp Glu Met Leu Val Val Leu Pro
                1845                1850                1855

Lys Leu Asp Gly Ser Leu Asp Glu Tyr Leu Ser Leu Gln Glu Gln Leu
            1860                1865                1870

Thr Asp Val Glu Lys Leu Gln Gly Lys Leu Leu Glu Glu Ile Glu Phe
        1875                1880                1885

Leu Glu Gly Ala Glu Gly Val Asp His Pro Ser His Thr Leu Gln His
    1890                1895                1900

Arg Tyr Ser Glu His Thr Gln Leu Gln Thr Gln Gln Arg Ala Val Gln
1905                1910                1915                1920

Glu Ala Ile Gln Val Lys Leu Asn Glu Phe Glu Gln Trp Ile Thr His
                1925                1930                1935

Tyr Gln Ala Ala Phe Asn Asn Leu Glu Ala Thr Gln Leu Ala Ser Leu
            1940                1945                1950

Leu Gln Glu Ile Ser Thr Gln Met Asp Leu Gly Pro Pro Ser Tyr Val
        1955                1960                1965

Pro Ala Thr Ala Phe Leu Gln Asn Ala Gly Gln Ala His Leu Ile Ser
    1970                1975                1980

Gln Cys Glu Gln Leu Glu Gly Glu Val Gly Ala Leu Leu Gln Gln Arg
1985                1990                1995                2000

Arg Ser Val Leu Arg Gly Cys Leu Glu Gln Leu His His Tyr Ala Thr
                2005                2010                2015

Val Ala Leu Gln Tyr Pro Lys Ala Ile Phe Gln Lys His Arg Ile Glu
            2020                2025                2030

Gln Trp Lys Thr Trp Met Glu Glu Leu Ile Cys Asn Thr Thr Val Glu
        2035                2040                2045

Arg Cys Gln Glu Leu Tyr Arg Lys Tyr Glu Met Gln Tyr Ala Pro Gln
    2050                2055                2060

Pro Pro Pro Thr Val Cys Gln Phe Ile Thr Ala Thr Glu Met Thr Leu
2065                2070                2075                2080

Gln Arg Tyr Ala Ala Asp Ile Asn Ser Arg Leu Ile Arg Gln Val Glu
                2085                2090                2095

Arg Leu Lys Gln Glu Ala Val Thr Val Pro Val Cys Glu Asp Gln Leu
            2100                2105                2110

Lys Glu Ile Glu Arg Cys Ile Lys Val Phe Leu His Glu Asn Gly Glu
        2115                2120                2125

Glu Gly Ser Leu Ser Leu Ala Ser Val Ile Ile Ser Ala Leu Cys Thr
    2130                2135                2140
```

-continued

Leu Thr Arg Arg Asn Leu Met Met Glu Gly Ala Ala Ser Ser Ala Gly
2145                2150                2155                2160

Glu Gln Leu Val Asp Leu Thr Ser Arg Asp Gly Ala Trp Phe Leu Glu
            2165                2170                2175

Glu Leu Cys Ser Met Ser Gly Asn Val Thr Cys Leu Val Gln Leu Leu
        2180                2185                2190

Lys Gln Cys His Leu Val Pro Gln Asp Leu Asp Ile Pro Asn Pro Met
    2195                2200                2205

Glu Ala Ser Glu Thr Val His Leu Ala Asn Gly Val Tyr Thr Ser Leu
2210                2215                2220

Gln Glu Leu Asn Ser Asn Phe Arg Gln Ile Ile Phe Pro Glu Ala Leu
2225                2230                2235                2240

Arg Cys Leu Met Lys Gly Glu Tyr Thr Leu Glu Ser Met Leu His Glu
            2245                2250                2255

Leu Asp Gly Leu Ile Glu Gln Thr Thr Asp Gly Val Pro Leu Gln Thr
        2260                2265                2270

Leu Val Glu Ser Leu Gln Ala Tyr Leu Arg Asn Ala Ala Met Gly Leu
    2275                2280                2285

Glu Glu Glu Thr His Ala His Tyr Ile Asp Val Ala Arg Leu Leu His
2290                2295                2300

Ala Gln Tyr Gly Glu Leu Ile Gln Pro Arg Asn Gly Ser Val Asp Glu
2305                2310                2315                2320

Thr Pro Lys Met Ser Ala Gly Gln Met Leu Leu Val Ala Phe Asp Gly
            2325                2330                2335

Met Phe Ala Gln Val Glu Thr Ala Phe Ser Leu Leu Val Glu Lys Leu
        2340                2345                2350

Asn Lys Met Glu Ile Pro Ile Ala Trp Arg Lys Ile Asp Ile Ile Arg
    2355                2360                2365

Glu Ala Arg Ser Thr Gln Val Asn Phe Phe Asp Asp Asp Asn His Arg
2370                2375                2380

Gln Val Leu Glu Glu Ile Phe Phe Leu Lys Arg Leu Gln Thr Ile Lys
2385                2390                2395                2400

Glu Phe Phe Arg Leu Cys Gly Thr Phe Ser Lys Thr Leu Ser Gly Ser
            2405                2410                2415

Ser Ser Leu Glu Asp Gln Asn Thr Val Asn Gly Pro Val Gln Ile Val
        2420                2425                2430

Asn Val Lys Thr Leu Phe Arg Asn Ser Cys Phe Ser Glu Asp Gln Met
    2435                2440                2445

Ala Lys Pro Ile Lys Ala Phe Thr Ala Asp Phe Val Arg Gln Leu Leu
2450                2455                2460

Ile Gly Leu Pro Asn Gln Ala Leu Gly Leu Thr Leu Cys Ser Phe Ile
2465                2470                2475                2480

Ser Ala Leu Gly Val Asp Ile Ile Ala Gln Val Glu Ala Lys Asp Phe
            2485                2490                2495

Gly Ala Glu Ser Lys Val Ser Val Asp Asp Leu Cys Lys Lys Ala Val
        2500                2505                2510

Glu His Asn Ile Gln Ile Gly Lys Phe Ser Gln Leu Val Met Asn Arg
    2515                2520                2525

Ala Thr Val Leu Ala Ser Ser Tyr Asp Thr Ala Trp Lys Lys His Asp
2530                2535                2540

Leu Val Arg Arg Leu Glu Thr Ser Ile Ser Ser Cys Lys Thr Ser Leu
2545                2550                2555                2560

-continued

```
Gln Arg Val Gln Leu His Ile Ala Met Phe Gln Trp Gln His Glu Asp
                2565                2570                2575

Leu Leu Ile Asn Arg Pro Gln Ala Met Ser Val Thr Pro Pro Pro Arg
            2580                2585                2590

Ser Ala Ile Leu Thr Ser Met Lys Lys Lys Leu His Thr Leu Ser Gln
        2595                2600                2605

Ile Glu Thr Ser Ile Ala Thr Val Gln Glu Lys Leu Ala Ala Leu Glu
    2610                2615                2620

Ser Ser Ile Glu Gln Arg Leu Lys Trp Ala Gly Gly Ala Asn Pro Ala
2625                2630                2635                2640

Leu Ala Pro Val Leu Gln Asp Phe Glu Ala Thr Ile Ala Glu Arg Arg
            2645                2650                2655

Asn Leu Val Leu Lys Glu Ser Gln Arg Ala Ser Gln Val Thr Phe Leu
        2660                2665                2670

Cys Ser Asn Ile Ile His Phe Glu Ser Leu Arg Thr Arg Thr Ala Glu
    2675                2680                2685

Ala Leu Asn Leu Asp Ala Ala Leu Phe Glu Leu Ile Lys Arg Cys Gln
    2690                2695                2700

Gln Met Cys Ser Phe Ala Ser Gln Phe Asn Ser Ser Val Ser Glu Leu
2705                2710                2715                2720

Glu Leu Arg Leu Leu Gln Arg Val Asp Thr Gly Leu Glu His Pro Ile
            2725                2730                2735

Gly Ser Ser Glu Trp Leu Leu Ser Ala His Lys Gln Leu Thr Gln Asp
        2740                2745                2750

Met Ser Thr Gln Arg Ala Ile Gln Thr Glu Lys Glu Gln Gln Ile Glu
    2755                2760                2765

Thr Val Cys Glu Thr Ile Gln Asn Leu Val Asp Asn Ile Lys Thr Val
    2770                2775                2780

Leu Thr Gly His Asn Arg Gln Leu Gly Asp Val Lys His Leu Leu Lys
2785                2790                2795                2800

Ala Met Ala Lys Asp Glu Glu Ala Ala Leu Ala Asp Gly Glu Asp Val
            2805                2810                2815

Pro Tyr Glu Asn Ser Val Arg Gln Phe Leu Gly Glu Tyr Lys Ser Trp
        2820                2825                2830

Gln Asp Asn Ile Gln Thr Val Leu Phe Thr Leu Val Gln Ala Met Gly
    2835                2840                2845

Gln Val Arg Ser Gln Glu His Val Glu Met Leu Gln Glu Ile Thr Pro
    2850                2855                2860

Thr Leu Lys Glu Leu Lys Thr Gln Ser Gln Ser Ile Tyr Asn Asn Leu
2865                2870                2875                2880

Val Ser Phe Ala Ser Pro Leu Val Thr Asp Ala Thr Asn Glu Cys Ser
            2885                2890                2895

Ser Pro Thr Ser Ser Ala Thr Tyr Gln Pro Ser Phe Ala Ala Ala Val
        2900                2905                2910

Arg Ser Asn Thr Gly Gln Lys Thr Gln Pro Asp Val Met Ser Gln Asn
        2915                2920                2925

Ala Arg Lys Leu Ile Gln Lys Asn Leu Ala Thr Ser Ala Asp Thr Pro
        2930                2935                2940

Pro Ser Thr Val Pro Gly Thr Gly Lys Ser Val Ala Cys Ser Pro Lys
2945                2950                2955                2960

Lys Ala Val Arg Asp Pro Lys Thr Gly Lys Ala Val Gln Glu Arg Asn
            2965                2970                2975
```

```
Ser Tyr Ala Val Ser Val Trp Lys Arg Val Lys Ala Lys Leu Glu Gly
            2980                2985                2990

Arg Asp Val Asp Pro Asn Arg Arg Met Ser Val Ala Glu Gln Val Asp
            2995                3000                3005

Tyr Val Ile Lys Glu Ala Thr Asn Leu Asp Asn Leu Ala Gln Leu Tyr
            3010                3015                3020

Glu Gly Trp Thr Ala Trp Val
3025                3030

<210> SEQ ID NO 7
<211> LENGTH: 12539
<212> TYPE: DNA
<213> ORGANISM: Homo sapiens
<220> FEATURE:
<221> NAME/KEY: CDS
<222> LOCATION: (141)...(10730)

<400> SEQUENCE: 7
gtggctacag tgtcaatgga ggatctgggg aaaatactta tggtcggaag tcgttggggc      60
aagagctgag ggttaacaat gtgaccagcc ctgagttcac cagtgttcag catggcagtc     120
gtgctttagc caccaaagac atg agg aaa tca cag gag aga tcg atg tct tat    173
                        Met Arg Lys Ser Gln Glu Arg Ser Met Ser Tyr
                          1               5                  10 tct gat gag tct cga ctg tcg aat ctt ctt cgg agg atc acc cgg gaa       221
Ser Asp Glu Ser Arg Leu Ser Asn Leu Leu Arg Arg Ile Thr Arg Glu
            15                  20                  25 gac gac aga gac cga aga ttg gct act gta aag cag ttg aaa gaa ttt       269
Asp Asp Arg Asp Arg Arg Leu Ala Thr Val Lys Gln Leu Lys Glu Phe
        30                  35                  40 att cag caa cca gaa aat aag ctg gta cta gtt aaa caa ttg gat aat       317
Ile Gln Gln Pro Glu Asn Lys Leu Val Leu Val Lys Gln Leu Asp Asn
    45                  50                  55 atc ttg gct gct gta cat gac gtg ctt aat gaa agt agc aaa ttg ctt       365
Ile Leu Ala Ala Val His Asp Val Leu Asn Glu Ser Ser Lys Leu Leu
60                  65                  70                  75 cag gag ttg aga cag gag gga gct tgc tgt ctt ggc ctt ctt tgt gct       413
Gln Glu Leu Arg Gln Glu Gly Ala Cys Cys Leu Gly Leu Leu Cys Ala
                80                  85                  90 tct ctg agc tat gag gct gag aag atc ttc aag tgg att ttt agc aaa       461
Ser Leu Ser Tyr Glu Ala Glu Lys Ile Phe Lys Trp Ile Phe Ser Lys
            95                 100                 105 ttt agc tca tct gca aaa gat gaa gtt aaa ctc ctc tac tta tgt gcc       509
Phe Ser Ser Ser Ala Lys Asp Glu Val Lys Leu Leu Tyr Leu Cys Ala
        110                 115                 120 acc tac aaa gca cta gag act gta gga gaa aag aaa gcc ttt tca tct       557
Thr Tyr Lys Ala Leu Glu Thr Val Gly Glu Lys Lys Ala Phe Ser Ser
    125                 130                 135 gta atg cag ctt gta atg acc agc ctg cag tct att ctt gaa aat gtg       605
Val Met Gln Leu Val Met Thr Ser Leu Gln Ser Ile Leu Glu Asn Val
140                 145                 150                 155 gat aca cca gaa ttg ctt tgt aaa tgt gtt aag tgc att ctt ttg gtg       653
Asp Thr Pro Glu Leu Leu Cys Lys Cys Val Lys Cys Ile Leu Leu Val
                160                 165                 170 gct cga tgt tac cct cat att ttc agc act aat ttt agg gat aca gtt       701
Ala Arg Cys Tyr Pro His Ile Phe Ser Thr Asn Phe Arg Asp Thr Val
            175                 180                 185 gat ata tta gtt gga tgg cat ata gat cat act cag aaa cct tcg ctc       749
Asp Ile Leu Val Gly Trp His Ile Asp His Thr Gln Lys Pro Ser Leu
        190                 195                 200
```

```
acg cag cag gta tct ggg tgg ttg cag agt ttg gag cca ttt tgg gta    797
Thr Gln Gln Val Ser Gly Trp Leu Gln Ser Leu Glu Pro Phe Trp Val
    205                 210                 215 gct gat ctt gca ttt tct act act ctt ctt ggt cag ttt ctg gaa gac    845
Ala Asp Leu Ala Phe Ser Thr Thr Leu Leu Gly Gln Phe Leu Glu Asp
220                 225                 230                 235 atg gaa gca tat gct gag gac ctc agc cat gtg gcc tct ggg gaa tca    893
Met Glu Ala Tyr Ala Glu Asp Leu Ser His Val Ala Ser Gly Glu Ser
                    240                 245                 250 gtg gat gaa gat gtc cct cct cca tca gtg tca tta cca aag ctg gct    941
Val Asp Glu Asp Val Pro Pro Pro Ser Val Ser Leu Pro Lys Leu Ala
                255                 260                 265 gca ctt ctc cgg gta ttt agt act gtg gtg agg agc att ggg gaa cgc    989
Ala Leu Leu Arg Val Phe Ser Thr Val Val Arg Ser Ile Gly Glu Arg
            270                 275                 280 ttc agc cca att cgg ggt cct cca att act gag gca tat gta aca gat   1037
Phe Ser Pro Ile Arg Gly Pro Pro Ile Thr Glu Ala Tyr Val Thr Asp
        285                 290                 295 gtt ctg tac aga gta atg aga tgt gtg acg gct gca aac cag gtg ttt   1085
Val Leu Tyr Arg Val Met Arg Cys Val Thr Ala Ala Asn Gln Val Phe
300                 305                 310                 315 ttt tct gag gct gtg ttg aca gct gct aat gag tgt gtt ggt gtt ttg   1133
Phe Ser Glu Ala Val Leu Thr Ala Ala Asn Glu Cys Val Gly Val Leu
                    320                 325                 330 ctc ggc agc ttg gat cct agc atg act ata cat tgt gac atg gtc att   1181
Leu Gly Ser Leu Asp Pro Ser Met Thr Ile His Cys Asp Met Val Ile
                335                 340                 345 aca tat gga tta gac caa ctg gag aat tgc cag act tgt ggt acc gat   1229
Thr Tyr Gly Leu Asp Gln Leu Glu Asn Cys Gln Thr Cys Gly Thr Asp
            350                 355                 360 tat atc atc tca gtc ttg aat tta ctc acg ctg att gtt gaa cag ata   1277
Tyr Ile Ile Ser Val Leu Asn Leu Leu Thr Leu Ile Val Glu Gln Ile
        365                 370                 375 aat acg aaa ctg cca tca tca ttt gta gaa aaa ctg ttt ata cca tca   1325
Asn Thr Lys Leu Pro Ser Ser Phe Val Glu Lys Leu Phe Ile Pro Ser
380                 385                 390                 395 tct aaa cta cta ttc ttg cgt tat cat aaa gaa aaa gag gtt gtt gct   1373
Ser Lys Leu Leu Phe Leu Arg Tyr His Lys Glu Lys Glu Val Val Ala
                    400                 405                 410 gta gcc cat gct gtt tat caa gca gtg ctc agc ttg aag aat att cct   1421
Val Ala His Ala Val Tyr Gln Ala Val Leu Ser Leu Lys Asn Ile Pro
                415                 420                 425 gtt ttg gag act gcc tat aag tta ata ttg gga gaa atg act tgt gcc   1469
Val Leu Glu Thr Ala Tyr Lys Leu Ile Leu Gly Glu Met Thr Cys Ala
            430                 435                 440 cta aac aac ctc cta cac agt cta caa ctt cct gag gcc tgt tct gaa   1517
Leu Asn Asn Leu Leu His Ser Leu Gln Leu Pro Glu Ala Cys Ser Glu
        445                 450                 455 ata aaa cat gag gct ttt aag aat cat gtg ttc aat gta gac aat gca   1565
Ile Lys His Glu Ala Phe Lys Asn His Val Phe Asn Val Asp Asn Ala
460                 465                 470                 475 aaa ttt gta gtt aaa ttt gac ctc agt gcc ctg act aca att gga aat   1613
Lys Phe Val Val Lys Phe Asp Leu Ser Ala Leu Thr Thr Ile Gly Asn
                    480                 485                 490 gcc aaa aac tca cta ata ggg atg tgg gcg cta tct cca act gtc ttt   1661
Ala Lys Asn Ser Leu Ile Gly Met Trp Ala Leu Ser Pro Thr Val Phe
                495                 500                 505 gca ctt ctg agt aag aat ctg atg att gtg cac agt gac ctg gct gtt   1709
Ala Leu Leu Ser Lys Asn Leu Met Ile Val His Ser Asp Leu Ala Val
            510                 515                 520
```

```
cac ttc cct gcc att cag tat gct gtg ctc tac aca ttg tat tct cat    1757
His Phe Pro Ala Ile Gln Tyr Ala Val Leu Tyr Thr Leu Tyr Ser His
    525                 530                 535 tgt acc agg cat gat cac ttt atc tct agt agc ctc agt tct gcc tct    1805
Cys Thr Arg His Asp His Phe Ile Ser Ser Ser Leu Ser Ser Ala Ser
540                 545                 550                 555 cct tct ttg ttt gat gga gct gtg att agc act gta act acg gct aca    1853
Pro Ser Leu Phe Asp Gly Ala Val Ile Ser Thr Val Thr Thr Ala Thr
                560                 565                 570 aag aaa cat ttc tca att ata tta aat ctt ctg gga ata tta ctt aag    1901
Lys Lys His Phe Ser Ile Ile Leu Asn Leu Leu Gly Ile Leu Leu Lys
            575                 580                 585 aaa gat aac ctt aac cag gac acg agg aaa ctg tta atg act tgg gct    1949
Lys Asp Asn Leu Asn Gln Asp Thr Arg Lys Leu Leu Met Thr Trp Ala
        590                 595                 600 ttg gaa gca gct gtt tta atg agg aag tct gaa aca tac gca cct tta    1997
Leu Glu Ala Ala Val Leu Met Arg Lys Ser Glu Thr Tyr Ala Pro Leu
605                 610                 615 ttc tct ctt ccg tct ttc cat aaa ttt tgc aaa ggc ctt tta gcc aac    2045
Phe Ser Leu Pro Ser Phe His Lys Phe Cys Lys Gly Leu Leu Ala Asn
620                 625                 630                 635 act ctc gtt gaa gat gtg aat atc tgt ctg cag gca tgc agc agt cta    2093
Thr Leu Val Glu Asp Val Asn Ile Cys Leu Gln Ala Cys Ser Ser Leu
                640                 645                 650 cat gct ctg tcc tct tcc ttg cca gat gat ctt tta cag aga tgt gtc    2141
His Ala Leu Ser Ser Ser Leu Pro Asp Asp Leu Leu Gln Arg Cys Val
            655                 660                 665 gat gtt tgc cgt gtt caa cta gtg cac agt gga act cgt att cga caa    2189
Asp Val Cys Arg Val Gln Leu Val His Ser Gly Thr Arg Ile Arg Gln
        670                 675                 680 gca ttt gga aaa ctg ttg aaa tca att cct tta gat gtt gtc cta agc    2237
Ala Phe Gly Lys Leu Leu Lys Ser Ile Pro Leu Asp Val Val Leu Ser
685                 690                 695 aat aac aat cac aca gaa att caa gaa att tct tta gca tta aga agt    2285
Asn Asn Asn His Thr Glu Ile Gln Glu Ile Ser Leu Ala Leu Arg Ser
700                 705                 710                 715 cac atg agt aaa gca cca agt aat aca ttc cac ccc caa gat ttc tct    2333
His Met Ser Lys Ala Pro Ser Asn Thr Phe His Pro Gln Asp Phe Ser
                720                 725                 730 gat gtt att agt ttt att ttg tat ggg aac tct cat aga aca ggg aag    2381
Asp Val Ile Ser Phe Ile Leu Tyr Gly Asn Ser His Arg Thr Gly Lys
            735                 740                 745 gac aat tgg ttg gaa aga ctg ttc tat agc tgc cag aga ctg gat aag    2429
Asp Asn Trp Leu Glu Arg Leu Phe Tyr Ser Cys Gln Arg Leu Asp Lys
        750                 755                 760 cgt gac cag tca aca att cca cgc aat ctc ctg aag aca gat gct gtc    2477
Arg Asp Gln Ser Thr Ile Pro Arg Asn Leu Leu Lys Thr Asp Ala Val
765                 770                 775 ctt tgg cag tgg gcc ata tgg gaa gct gca caa ttc act gtt ctt tct    2525
Leu Trp Gln Trp Ala Ile Trp Glu Ala Ala Gln Phe Thr Val Leu Ser
                780                 785                 790 aag ctg aga acc cca ctg ggc aga gct caa gac acc ttc cag aca att    2573
Lys Leu Arg Thr Pro Leu Gly Arg Ala Gln Asp Thr Phe Gln Thr Ile
            800                 805                 810 gaa ggt atc att cga agt ctc gca gct cac aca tta aac cct gat cag    2621
Glu Gly Ile Ile Arg Ser Leu Ala Ala His Thr Leu Asn Pro Asp Gln
        815                 820                 825 gat gtt agt cag tgg aca act gca gac aat gat gaa ggc cat ggt aac    2669
Asp Val Ser Gln Trp Thr Thr Ala Asp Asn Asp Glu Gly His Gly Asn
830                 835                 840
```

```
aac caa ctt aga ctt gtt ctt ctt ctg cag tat ctg gaa aat ctg gag    2717
Asn Gln Leu Arg Leu Val Leu Leu Leu Gln Tyr Leu Glu Asn Leu Glu
    845                 850                 855 aaa tta atg tat aat gca tac gag gga tgt gct aat gca tta act tca    2765
Lys Leu Met Tyr Asn Ala Tyr Glu Gly Cys Ala Asn Ala Leu Thr Ser
860                 865                 870                 875 cct ccc aag gtc att aga act ttt ttc tat acc aat cgc caa act tgt    2813
Pro Pro Lys Val Ile Arg Thr Phe Phe Tyr Thr Asn Arg Gln Thr Cys
                    880                 885                 890 cag gac tgg cta acg cgg att cga ctc tcc atc atg agg gta gga ttg    2861
Gln Asp Trp Leu Thr Arg Ile Arg Leu Ser Ile Met Arg Val Gly Leu
            895                 900                 905 ttg gca ggc cag cct gca gtg aca gtg aga cat ggc ttt gac ttg ctt    2909
Leu Ala Gly Gln Pro Ala Val Thr Val Arg His Gly Phe Asp Leu Leu
        910                 915                 920 aca gag atg aaa aca acc agc cta tct cag ggg aat gaa ttg gaa gta    2957
Thr Glu Met Lys Thr Thr Ser Leu Ser Gln Gly Asn Glu Leu Glu Val
925                 930                 935 acc att atg atg gtg gta gaa gca tta tgt gaa ctt cat tgt cct gaa    3005
Thr Ile Met Met Val Val Glu Ala Leu Cys Glu Leu His Cys Pro Glu
940                 945                 950                 955 gct ata cag gga att gct gtc tgg tca tca tct att gtt gga aaa aat    3053
Ala Ile Gln Gly Ile Ala Val Trp Ser Ser Ser Ile Val Gly Lys Asn
                    960                 965                 970 ctt ctg tgg att aac tca gtg gct caa cag gct gaa ggg agg ttt gaa    3101
Leu Leu Trp Ile Asn Ser Val Ala Gln Gln Ala Glu Gly Arg Phe Glu
            975                 980                 985 aag gcc tct gtg gag tac cag gaa cac ctg tgt gcc atg aca ggt gtt    3149
Lys Ala Ser Val Glu Tyr Gln Glu His Leu Cys Ala Met Thr Gly Val
        990                 995                 1000 gat tgc tgc atc tcc agc ttt gac aaa tcg gtg ctc acc tta gcc aat    3197
Asp Cys Cys Ile Ser Ser Phe Asp Lys Ser Val Leu Thr Leu Ala Asn
    1005                1010                1015 gct ggg cgt aac agt gcc agc ccg aaa cat tct ctg aat ggt gaa tcc    3245
Ala Gly Arg Asn Ser Ala Ser Pro Lys His Ser Leu Asn Gly Glu Ser
1020                1025                1030                1035 aga aaa act gtg ctg tcc aaa ccg act gac tct tcc cct gag gtt ata    3293
Arg Lys Thr Val Leu Ser Lys Pro Thr Asp Ser Ser Pro Glu Val Ile
                    1040                1045                1050 aat tat tta gga aat aaa gca tgt gag ttc tac atc tca att gcc gat    3341
Asn Tyr Leu Gly Asn Lys Ala Cys Glu Phe Tyr Ile Ser Ile Ala Asp
            1055                1060                1065 tgg gct gct gtg cag gaa tgg cag aac gct atc cat gac ttg aaa aag    3389
Trp Ala Ala Val Gln Glu Trp Gln Asn Ala Ile His Asp Leu Lys Lys
        1070                1075                1080 agt acc agt agc act tcc ctc aac ctg aaa gct gac ttc aac tat ata    3437
Ser Thr Ser Ser Thr Ser Leu Asn Leu Lys Ala Asp Phe Asn Tyr Ile
1085                1090                1095 aaa tca tta agc agc ttt gag tct gga aaa ttt gtt gaa tgt acc gag    3485
Lys Ser Leu Ser Ser Phe Glu Ser Gly Lys Phe Val Glu Cys Thr Glu
1100                1105                1110                1115 cag tta gaa ttg tta cca gga gaa aat atc aat cta ctt gct gga gga    3533
Gln Leu Glu Leu Leu Pro Gly Glu Asn Ile Asn Leu Leu Ala Gly Gly
                    1120                1125                1130 tca aaa gaa aaa ata gac atg aaa aaa ctg ctt cct aac atg tta agt    3581
Ser Lys Glu Lys Ile Asp Met Lys Lys Leu Leu Pro Asn Met Leu Ser
            1135                1140                1145 ccg gat ccg agg gaa ctt cag aaa tcc att gaa gtt caa ttg tta aga    3629
Pro Asp Pro Arg Glu Leu Gln Lys Ser Ile Glu Val Gln Leu Leu Arg
        1150                1155                1160
```

```
agt tct gtt tgt ttg gca act gct tta aac ccg ata gaa caa gat cag    3677
Ser Ser Val Cys Leu Ala Thr Ala Leu Asn Pro Ile Glu Gln Asp Gln
        1165                1170                1175 aag tgg cag tct ata act gaa aat gtg gta aag tac ttg aag caa aca    3725
Lys Trp Gln Ser Ile Thr Glu Asn Val Val Lys Tyr Leu Lys Gln Thr
1180                1185                1190                1195 tcc cgc atc gct att gga cct ctg aga ctt tct act tta aca gtt tca    3773
Ser Arg Ile Ala Ile Gly Pro Leu Arg Leu Ser Thr Leu Thr Val Ser
                1200                1205                1210 cag tct ttg cca gtt cta agt acc ttg cag ctg tat tgc tca tct gct    3821
Gln Ser Leu Pro Val Leu Ser Thr Leu Gln Leu Tyr Cys Ser Ser Ala
        1215                1220                1225 ttg gag aac aca gtt tct aac aga ctt tca aca gag gac tgt ctt att    3869
Leu Glu Asn Thr Val Ser Asn Arg Leu Ser Thr Glu Asp Cys Leu Ile
        1230                1235                1240 cca ctc ttc agt gaa gct tta cgt tca tgt aaa cag cat gac gtg agg    3917
Pro Leu Phe Ser Glu Ala Leu Arg Ser Cys Lys Gln His Asp Val Arg
1245                1250                1255 cca tgg atg cag gca tta agg tat act atg tac cag aat cag ttg ttg    3965
Pro Trp Met Gln Ala Leu Arg Tyr Thr Met Tyr Gln Asn Gln Leu Leu
1260                1265                1270                1275 gag aaa att aaa gaa caa aca gtc cca att aga agc cat ctc atg gaa    4013
Glu Lys Ile Lys Glu Gln Thr Val Pro Ile Arg Ser His Leu Met Glu
                1280                1285                1290 tta ggt cta aca gca gca aaa ttt gct aga aaa cga ggg aat gtg tcc    4061
Leu Gly Leu Thr Ala Ala Lys Phe Ala Arg Lys Arg Gly Asn Val Ser
        1295                1300                1305 ctt gca aca aga ctg ctg gca cag tgc agt gaa gtt cag ctg gga aag    4109
Leu Ala Thr Arg Leu Leu Ala Gln Cys Ser Glu Val Gln Leu Gly Lys
        1310                1315                1320 acc acc act gca cag gat tta gtc caa cat ttt aaa aaa cta tca acc    4157
Thr Thr Thr Ala Gln Asp Leu Val Gln His Phe Lys Lys Leu Ser Thr
1325                1330                1335 caa ggt caa gtg gat gaa aaa tgg ggg ccc gaa ctt gat att gaa aaa    4205
Gln Gly Gln Val Asp Glu Lys Trp Gly Pro Glu Leu Asp Ile Glu Lys
1340                1345                1350                1355 acc aaa ttg ctt tat aca gca ggc cag tca aca cat gca atg gaa atg    4253
Thr Lys Leu Leu Tyr Thr Ala Gly Gln Ser Thr His Ala Met Glu Met
                1360                1365                1370 ttg agt tct tgt gcc ata tct ttc tgc aag tct gtg aaa gct gaa tat    4301
Leu Ser Ser Cys Ala Ile Ser Phe Cys Lys Ser Val Lys Ala Glu Tyr
        1375                1380                1385 gca gtt gct aaa tca att ctg aca ctg gct aaa tgg atc cag gca gaa    4349
Ala Val Ala Lys Ser Ile Leu Thr Leu Ala Lys Trp Ile Gln Ala Glu
        1390                1395                1400 tgg aaa gag att tca gga cag ctg aaa cag gtt tac aga gct cag cac    4397
Trp Lys Glu Ile Ser Gly Gln Leu Lys Gln Val Tyr Arg Ala Gln His
1405                1410                1415 caa cag aac ttc aca ggt ctt tct act ttg tct aaa aac ata ctc act    4445
Gln Gln Asn Phe Thr Gly Leu Ser Thr Leu Ser Lys Asn Ile Leu Thr
1420                1425                1430                1435 cta ata gaa ctg cca tct gtt aat acg atg gaa gaa gag tat cct cgg    4493
Leu Ile Glu Leu Pro Ser Val Asn Thr Met Glu Glu Glu Tyr Pro Arg
                1440                1445                1450 atc gag agt gaa tct aca gtg cat att gga gtt gga gaa cct gac ttc    4541
Ile Glu Ser Glu Ser Thr Val His Ile Gly Val Gly Glu Pro Asp Phe
        1455                1460                1465 att ttg gga cag ttg tat cac ctg tct tca gta cag gca cct gaa gta    4589
Ile Leu Gly Gln Leu Tyr His Leu Ser Ser Val Gln Ala Pro Glu Val
        1470                1475                1480
```

-continued

| | |
|---|---|
| gcc aaa tct tgg gca gcg ttg gcc agc tgg gct tat agg tgg ggc aga<br>Ala Lys Ser Trp Ala Ala Leu Ala Ser Trp Ala Tyr Arg Trp Gly Arg<br>1485                     1490                     1495 | 4637 |
| aag gtg gtt gac aat gcc agt cag gga gaa ggt gtt cgt ctg ctg cct<br>Lys Val Val Asp Asn Ala Ser Gln Gly Glu Gly Val Arg Leu Leu Pro<br>1500                     1505                     1510                     1515 | 4685 |
| aga gaa aaa tct gaa gtt cag aat cta ctt cca gac act ata act gag<br>Arg Glu Lys Ser Glu Val Gln Asn Leu Leu Pro Asp Thr Ile Thr Glu<br>1520                     1525                     1530 | 4733 |
| gaa gag aaa gag aga ata tat ggt att ctt gga cag gct gtg tgt cgg<br>Glu Glu Lys Glu Arg Ile Tyr Gly Ile Leu Gly Gln Ala Val Cys Arg<br>1535                     1540                     1545 | 4781 |
| ccg gcg ggg att cag gat gaa gat ata aca ctt cag ata act gag agt<br>Pro Ala Gly Ile Gln Asp Glu Asp Ile Thr Leu Gln Ile Thr Glu Ser<br>1550                     1555                     1560 | 4829 |
| gaa gac aac gaa gaa gat gac atg gtt gat gtt atc tgg cgt cag ttg<br>Glu Asp Asn Glu Glu Asp Asp Met Val Asp Val Ile Trp Arg Gln Leu<br>1565                     1570                     1575 | 4877 |
| ata tca agc tgc cca tgg ctt tca gaa ctt gat gaa agt gca act gaa<br>Ile Ser Ser Cys Pro Trp Leu Ser Glu Leu Asp Glu Ser Ala Thr Glu<br>1580                     1585                     1590                     1595 | 4925 |
| gga gtt att aaa gtg tgg agg aaa gtt gta gat aga ata ttc agc ctg<br>Gly Val Ile Lys Val Trp Arg Lys Val Val Asp Arg Ile Phe Ser Leu<br>1600                     1605                     1610 | 4973 |
| tac aaa ctc tct tgc agt gca tac ttt act ttc ctt aaa ctc aac gct<br>Tyr Lys Leu Ser Cys Ser Ala Tyr Phe Thr Phe Leu Lys Leu Asn Ala<br>1615                     1620                     1625 | 5021 |
| ggt caa att cct tta gat gag gat gac cct agg ctg cat tta agt cac<br>Gly Gln Ile Pro Leu Asp Glu Asp Asp Pro Arg Leu His Leu Ser His<br>1630                     1635                     1640 | 5069 |
| aga gtg gaa cag agc act gat gac atg att gtg atg gcc aca ttg cgc<br>Arg Val Glu Gln Ser Thr Asp Asp Met Ile Val Met Ala Thr Leu Arg<br>1645                     1650                     1655 | 5117 |
| ctg ctg cgg ttg ctc gtg aag cat gct ggt gag ctt cgg cag tat ctg<br>Leu Leu Arg Leu Leu Val Lys His Ala Gly Glu Leu Arg Gln Tyr Leu<br>1660                     1665                     1670                     1675 | 5165 |
| gag cac ggc ttg gag aca aca ccc act gca cca tgg agg gga att att<br>Glu His Gly Leu Glu Thr Thr Pro Thr Ala Pro Trp Arg Gly Ile Ile<br>1680                     1685                     1690 | 5213 |
| ccg caa ctt ttc tca cgc tta aac cac cct gaa gtg tat gtg cgc caa<br>Pro Gln Leu Phe Ser Arg Leu Asn His Pro Glu Val Tyr Val Arg Gln<br>1695                     1700                     1705 | 5261 |
| agt att tgt aac ctt ctc tgc cgt gtg gct caa gat tcc cca cat ctc<br>Ser Ile Cys Asn Leu Leu Cys Arg Val Ala Gln Asp Ser Pro His Leu<br>1710                     1715                     1720 | 5309 |
| ata ttg tat cct gca ata gtg ggt acc ata tcg ctt agt agt gaa tcc<br>Ile Leu Tyr Pro Ala Ile Val Gly Thr Ile Ser Leu Ser Ser Glu Ser<br>1725                     1730                     1735 | 5357 |
| cag gct tca gga aat aaa ttt tcc act gca att cca act tta ctt ggc<br>Gln Ala Ser Gly Asn Lys Phe Ser Thr Ala Ile Pro Thr Leu Leu Gly<br>1740                     1745                     1750                     1755 | 5405 |
| aat att caa gga gaa gaa ttg ctg gtt tct gaa tgt gag gga gga agt<br>Asn Ile Gln Gly Glu Glu Leu Leu Val Ser Glu Cys Glu Gly Gly Ser<br>1760                     1765                     1770 | 5453 |
| cct cct gca tct cag gat agc aat aag gat gaa cct aaa agt gga tta<br>Pro Pro Ala Ser Gln Asp Ser Asn Lys Asp Glu Pro Lys Ser Gly Leu<br>1775                     1780                     1785 | 5501 |
| aat gaa gac caa gcc atg atg cag gat tgt tac agc aaa att gta gat<br>Asn Glu Asp Gln Ala Met Met Gln Asp Cys Tyr Ser Lys Ile Val Asp<br>1790                     1795                     1800 | 5549 |

```
aag ctg tcc tct gca aac ccc acc atg gta tta cag gtt cag atg ctc    5597
Lys Leu Ser Ser Ala Asn Pro Thr Met Val Leu Gln Val Gln Met Leu
    1805                1810                1815 gtg gct gaa ctg cgc agg gtc act gtg ctc tgg gat gag ctc tgg ctg    5645
Val Ala Glu Leu Arg Arg Val Thr Val Leu Trp Asp Glu Leu Trp Leu
1820                1825                1830                1835 gga gtt ttg ctg caa caa cac atg tat gtc ctg aga cga att cag cag    5693
Gly Val Leu Leu Gln Gln His Met Tyr Val Leu Arg Arg Ile Gln Gln
        1840                1845                1850 ctt gaa gat gag gtg aag aga gtc cag aac aac aac acc tta cgc aaa    5741
Leu Glu Asp Glu Val Lys Arg Val Gln Asn Asn Asn Thr Leu Arg Lys
            1855                1860                1865 gaa gag aaa att gca atc atg agg gag agg cac aca gct ttg atg aag    5789
Glu Glu Lys Ile Ala Ile Met Arg Glu Arg His Thr Ala Leu Met Lys
                1870                1875                1880 ccc atc gta ttt gct ttg gag cat gtg agg agt atc aca gcg gct cct    5837
Pro Ile Val Phe Ala Leu Glu His Val Arg Ser Ile Thr Ala Ala Pro
    1885                1890                1895 gca gaa aca cct cat gaa aaa tgg ttt cag gat aac tat ggt gat gcc    5885
Ala Glu Thr Pro His Glu Lys Trp Phe Gln Asp Asn Tyr Gly Asp Ala
1900                1905                1910                1915 att gaa aat gcc cta gaa aaa ctg aag act cca ttg aac cct gca aag    5933
Ile Glu Asn Ala Leu Glu Lys Leu Lys Thr Pro Leu Asn Pro Ala Lys
        1920                1925                1930 cct ggg agc agc tgg att cca ttt aaa gag ata atg cta agt ttg caa    5981
Pro Gly Ser Ser Trp Ile Pro Phe Lys Glu Ile Met Leu Ser Leu Gln
            1935                1940                1945 cag aga gca cag aaa cgt gca agt tac atc ttg cgt ctt gaa gaa atc    6029
Gln Arg Ala Gln Lys Arg Ala Ser Tyr Ile Leu Arg Leu Glu Glu Ile
                1950                1955                1960 agt cca tgg ttg gct gcc atg act aac act gaa att gct ctt cct ggg    6077
Ser Pro Trp Leu Ala Ala Met Thr Asn Thr Glu Ile Ala Leu Pro Gly
    1965                1970                1975 gaa gtc tca gcc aga gac act gtc aca atc cat agt gtg ggc gga acc    6125
Glu Val Ser Ala Arg Asp Thr Val Thr Ile His Ser Val Gly Gly Thr
1980                1985                1990                1995 atc aca atc tta ccg act aaa acc aag cca aag aaa ctt ctc ttt ctt    6173
Ile Thr Ile Leu Pro Thr Lys Thr Lys Pro Lys Lys Leu Leu Phe Leu
        2000                2005                2010 gga tca gat ggg aag agc tat cct tat ctt ttc aaa gga ctg gag gat    6221
Gly Ser Asp Gly Lys Ser Tyr Pro Tyr Leu Phe Lys Gly Leu Glu Asp
            2015                2020                2025 tta cat ctg gat gag aga ata atg cag ttc cta tct att gtg aat acc    6269
Leu His Leu Asp Glu Arg Ile Met Gln Phe Leu Ser Ile Val Asn Thr
                2030                2035                2040 atg ttt gct aca att aat cgc caa gaa aca ccc cgg ttc cat gct cga    6317
Met Phe Ala Thr Ile Asn Arg Gln Glu Thr Pro Arg Phe His Ala Arg
    2045                2050                2055 cac tat tct gta aca cca cta gga aca aga tca gga cta atc cag tgg    6365
His Tyr Ser Val Thr Pro Leu Gly Thr Arg Ser Gly Leu Ile Gln Trp
2060                2065                2070                2075 gta gat gga gcc aca ccc tta ttt ggt ctt tac aaa cga tgg caa caa    6413
Val Asp Gly Ala Thr Pro Leu Phe Gly Leu Tyr Lys Arg Trp Gln Gln
        2080                2085                2090 cgg gaa gct gcc tta caa gca caa aag gcc caa gat tcc tac caa act    6461
Arg Glu Ala Ala Leu Gln Ala Gln Lys Ala Gln Asp Ser Tyr Gln Thr
            2095                2100                2105 cct cag aat cct gga att gta ccc cgt cct agt gaa ctt tat tac agt    6509
Pro Gln Asn Pro Gly Ile Val Pro Arg Pro Ser Glu Leu Tyr Tyr Ser
                2110                2115                2120
```

```
aaa att ggc cct gct ttg aaa aca gtt ggg ctt agc ctg gat gtg tcc        6557
Lys Ile Gly Pro Ala Leu Lys Thr Val Gly Leu Ser Leu Asp Val Ser
    2125                2130                2135 cgt cgg gat tgg cct ctt cat gta atg aag gca gta ttg gaa gag tta        6605
Arg Arg Asp Trp Pro Leu His Val Met Lys Ala Val Leu Glu Glu Leu
2140                2145                2150                2155 atg gag gcc aca ccc ccg aat ctc ctt gcc aaa gag ctc tgg tca tct        6653
Met Glu Ala Thr Pro Pro Asn Leu Leu Ala Lys Glu Leu Trp Ser Ser
                2160                2165                2170 tgc aca aca cct gat gaa tgg tgg aga gtt acg cag tct tat gca aga        6701
Cys Thr Thr Pro Asp Glu Trp Trp Arg Val Thr Gln Ser Tyr Ala Arg
            2175                2180                2185 tct act gca gtc atg tct atg gtt gga tac ata att ggc ctt gga gac        6749
Ser Thr Ala Val Met Ser Met Val Gly Tyr Ile Ile Gly Leu Gly Asp
        2190                2195                2200 aga cat ctg gat aat gtt ctt ata gat atg acg act gga gaa gtt gtt        6797
Arg His Leu Asp Asn Val Leu Ile Asp Met Thr Thr Gly Glu Val Val
    2205                2210                2215 cac ata gat tac aat gtt tgc ttt gaa aaa ggt aaa agc ctt aga gtt        6845
His Ile Asp Tyr Asn Val Cys Phe Glu Lys Gly Lys Ser Leu Arg Val
2220                2225                2230                2235 cct gag aaa gta cct ttt cga atg aca caa aac att gaa aca gca ctg        6893
Pro Glu Lys Val Pro Phe Arg Met Thr Gln Asn Ile Glu Thr Ala Leu
                2240                2245                2250 ggt gta act gga gta gaa ggt gta ttt agg ctt tca tgt gag cag gtt        6941
Gly Val Thr Gly Val Glu Gly Val Phe Arg Leu Ser Cys Glu Gln Val
            2255                2260                2265 tta cac att atg cgg cgt ggc aga gag acc ctg ctg acg ctg ctg gag        6989
Leu His Ile Met Arg Arg Gly Arg Glu Thr Leu Leu Thr Leu Leu Glu
        2270                2275                2280 gcc ttt gtg tac gac cct ctg gtg gac tgg aca gca gga ggc gag gct        7037
Ala Phe Val Tyr Asp Pro Leu Val Asp Trp Thr Ala Gly Gly Glu Ala
    2285                2290                2295 ggg ttt gct ggt gct gtc tat ggt gga ggt ggc cag cag gcc gag agc        7085
Gly Phe Ala Gly Ala Val Tyr Gly Gly Gly Gly Gln Gln Ala Glu Ser
2300                2305                2310                2315 aag cag agc aag aga gag atg gag cga gag atc acc cgc agc ctg ttt        7133
Lys Gln Ser Lys Arg Glu Met Glu Arg Glu Ile Thr Arg Ser Leu Phe
                2320                2325                2330 tct tct aga gta gct gag att aag gtg aac tgg ttt aag aat aga gat        7181
Ser Ser Arg Val Ala Glu Ile Lys Val Asn Trp Phe Lys Asn Arg Asp
            2335                2340                2345 gag atg ctg gtt gtg ctt ccc aag ttg gac ggt agc tta gat gaa tac        7229
Glu Met Leu Val Val Leu Pro Lys Leu Asp Gly Ser Leu Asp Glu Tyr
        2350                2355                2360 cta agc ttg caa gag caa ctg aca gat gtg gaa aaa ctg cag ggc aaa        7277
Leu Ser Leu Gln Glu Gln Leu Thr Asp Val Glu Lys Leu Gln Gly Lys
    2365                2370                2375 cta ctg gag gaa ata gag ttt cta gaa gga gct gaa ggg gtg gat cat        7325
Leu Leu Glu Glu Ile Glu Phe Leu Glu Gly Ala Glu Gly Val Asp His
2380                2385                2390                2395 cct tct cat act ctg caa cac agg tat tct gag cac acc caa cta cag        7373
Pro Ser His Thr Leu Gln His Arg Tyr Ser Glu His Thr Gln Leu Gln
                2400                2405                2410 act cag caa aga gct gtt cag gaa gca atc cag gtg aag ctg aat gaa        7421
Thr Gln Gln Arg Ala Val Gln Glu Ala Ile Gln Val Lys Leu Asn Glu
            2415                2420                2425 ttt gaa caa tgg ata aca cat tat cag gct gca ttc aat aat tta gaa        7469
Phe Glu Gln Trp Ile Thr His Tyr Gln Ala Ala Phe Asn Asn Leu Glu
        2430                2435                2440
```

```
gca aca cag ctt gca agc ttg ctt caa gag ata agc aca caa atg gac      7517
Ala Thr Gln Leu Ala Ser Leu Leu Gln Glu Ile Ser Thr Gln Met Asp
    2445             2450             2455 ctt ggt cct cca agt tac gtg cca gca aca gcc ttt ctg cag aat gct      7565
Leu Gly Pro Pro Ser Tyr Val Pro Ala Thr Ala Phe Leu Gln Asn Ala
2460             2465             2470             2475 ggt cag gcc cac ttg att agc cag tgc gag cag ctg gag ggg gag gtt      7613
Gly Gln Ala His Leu Ile Ser Gln Cys Glu Gln Leu Glu Gly Glu Val
            2480             2485             2490 ggt gct ctc ctg cag cag agg cgc tcc gtg ctc cgt ggc tgt ctg gag      7661
Gly Ala Leu Leu Gln Gln Arg Arg Ser Val Leu Arg Gly Cys Leu Glu
        2495             2500             2505 caa ctg cat cac tat gca acc gtg gcc ctg cag tat ccg aag gcc ata      7709
Gln Leu His His Tyr Ala Thr Val Ala Leu Gln Tyr Pro Lys Ala Ile
    2510             2515             2520 ttt cag aaa cat cga att gaa cag tgg aag acc tgg atg gaa gag ctc      7757
Phe Gln Lys His Arg Ile Glu Gln Trp Lys Thr Trp Met Glu Glu Leu
2525             2530             2535 atc tgt aac acc aca gta gag cgt tgt caa gag ctc tat agg aaa tat      7805
Ile Cys Asn Thr Thr Val Glu Arg Cys Gln Glu Leu Tyr Arg Lys Tyr
2540             2545             2550             2555 gaa atg caa tat gct ccc cag cca ccc cca aca gtg tgt cag ttc atc      7853
Glu Met Gln Tyr Ala Pro Gln Pro Pro Pro Thr Val Cys Gln Phe Ile
            2560             2565             2570 act gcc act gaa atg acc ctg cag cga tac gca gca gac atc aac agc      7901
Thr Ala Thr Glu Met Thr Leu Gln Arg Tyr Ala Ala Asp Ile Asn Ser
            2575             2580             2585 aga ctt att aga caa gtg gaa cgc ttg aaa cag gaa gct gtc act gtg      7949
Arg Leu Ile Arg Gln Val Glu Arg Leu Lys Gln Glu Ala Val Thr Val
        2590             2595             2600 cca gtt tgt gaa gat cag ttg aaa gaa att gaa cgt tgc att aaa gtt      7997
Pro Val Cys Glu Asp Gln Leu Lys Glu Ile Glu Arg Cys Ile Lys Val
        2605             2610             2615 ttc ctt cat gag aat gga gaa gaa gga tct ttg agt cta gca agt gtt      8045
Phe Leu His Glu Asn Gly Glu Glu Gly Ser Leu Ser Leu Ala Ser Val
2620             2625             2630             2635 att att tct gcc ctt tgt acc ctt aca agg cgt aac ctg atg atg gaa      8093
Ile Ile Ser Ala Leu Cys Thr Leu Thr Arg Arg Asn Leu Met Met Glu
            2640             2645             2650 ggt gca gcg tca agt gct gga gaa cag ctg gtt gat ctg act tct cgg      8141
Gly Ala Ala Ser Ser Ala Gly Glu Gln Leu Val Asp Leu Thr Ser Arg
            2655             2660             2665 gat gga gcc tgg ttc ttg gag gaa ctc tgc agt atg agc gga aac gtc      8189
Asp Gly Ala Trp Phe Leu Glu Glu Leu Cys Ser Met Ser Gly Asn Val
        2670             2675             2680 acc tgc ttg gtt cag tta ctg aag cag tgc cac ctg gtg cca cag gac      8237
Thr Cys Leu Val Gln Leu Leu Lys Gln Cys His Leu Val Pro Gln Asp
        2685             2690             2695 tta gat atc ccg aac ccc atg gaa gcg tct gag aca gtt cac tta gcc      8285
Leu Asp Ile Pro Asn Pro Met Glu Ala Ser Glu Thr Val His Leu Ala
2700             2705             2710             2715 aat gga gtg tat acc tca ctt cag gaa ttg aat tcg aat ttc cgg caa      8333
Asn Gly Val Tyr Thr Ser Leu Gln Glu Leu Asn Ser Asn Phe Arg Gln
            2720             2725             2730 atc ata ttt cca gaa gca ctt cga tgt tta atg aaa ggg gaa tac acg      8381
Ile Ile Phe Pro Glu Ala Leu Arg Cys Leu Met Lys Gly Glu Tyr Thr
            2735             2740             2745 tta gaa agt atg ctg cat gaa ctg gac ggt ctt att gag cag acc acc      8429
Leu Glu Ser Met Leu His Glu Leu Asp Gly Leu Ile Glu Gln Thr Thr
        2750             2755             2760
```

```
gat ggc gtt ccc ctg cag act cta gtg gaa tct ctt cag gcc tac tta    8477
Asp Gly Val Pro Leu Gln Thr Leu Val Glu Ser Leu Gln Ala Tyr Leu
    2765                2770                2775 aga aac gca gct atg gga ctg gaa gaa gaa aca cat gct cat tac atc    8525
Arg Asn Ala Ala Met Gly Leu Glu Glu Glu Thr His Ala His Tyr Ile
2780                2785                2790                2795 gat gtt gcc aga cta cta cat gct cag tac ggt gaa tta atc caa ccg    8573
Asp Val Ala Arg Leu Leu His Ala Gln Tyr Gly Glu Leu Ile Gln Pro
                2800                2805                2810 aga aat ggt tca gtt gat gaa aca ccc aaa atg tca gct ggc cag atg    8621
Arg Asn Gly Ser Val Asp Glu Thr Pro Lys Met Ser Ala Gly Gln Met
            2815                2820                2825 ctt ttg gta gca ttc gat ggc atg ttt gct caa gtt gaa act gct ttc    8669
Leu Leu Val Ala Phe Asp Gly Met Phe Ala Gln Val Glu Thr Ala Phe
        2830                2835                2840 agc tta tta gtt gaa aag ttg aac aag atg gaa att ccc ata gct tgg    8717
Ser Leu Leu Val Glu Lys Leu Asn Lys Met Glu Ile Pro Ile Ala Trp
    2845                2850                2855 cga aag att gac atc ata agg gaa gcc agg agt act caa gtt aat ttt    8765
Arg Lys Ile Asp Ile Ile Arg Glu Ala Arg Ser Thr Gln Val Asn Phe
2860                2865                2870                2875 ttt gat gat gat aat cac cgg cag gtg cta gaa gag att ttc ttt cta    8813
Phe Asp Asp Asp Asn His Arg Gln Val Leu Glu Glu Ile Phe Phe Leu
                2880                2885                2890 aaa aga cta cag act att aag gag ttc ttc agg ctc tgt ggt acc ttt    8861
Lys Arg Leu Gln Thr Ile Lys Glu Phe Phe Arg Leu Cys Gly Thr Phe
            2895                2900                2905 tct aaa aca ttg tca gga tca agt tca ctt gaa gat cag aat act gtg    8909
Ser Lys Thr Leu Ser Gly Ser Ser Ser Leu Glu Asp Gln Asn Thr Val
        2910                2915                2920 aat ggg cct gta cag att gtc aat gtg aaa acc ctt ttt aga aac tct    8957
Asn Gly Pro Val Gln Ile Val Asn Val Lys Thr Leu Phe Arg Asn Ser
    2925                2930                2935 tgt ttc agt gaa gac caa atg gcc aaa cct atc aag gca ttc aca gct    9005
Cys Phe Ser Glu Asp Gln Met Ala Lys Pro Ile Lys Ala Phe Thr Ala
2940                2945                2950                2955 gac ttt gtg agg cag ctc ttg ata ggg cta ccc aac caa gcc ctc gga    9053
Asp Phe Val Arg Gln Leu Leu Ile Gly Leu Pro Asn Gln Ala Leu Gly
                2960                2965                2970 ctc aca ctg tgc agt ttt atc agt gct ctg ggt gta gac atc att gct    9101
Leu Thr Leu Cys Ser Phe Ile Ser Ala Leu Gly Val Asp Ile Ile Ala
            2975                2980                2985 caa gta gag gca aag gac ttt ggt gcc gaa agc aaa gtt tct gtt gat    9149
Gln Val Glu Ala Lys Asp Phe Gly Ala Glu Ser Lys Val Ser Val Asp
        2990                2995                3000 gat ctc tgt aag aaa gcg gtg gaa cat aac atc cag ata ggg aag ttc    9197
Asp Leu Cys Lys Lys Ala Val Glu His Asn Ile Gln Ile Gly Lys Phe
    3005                3010                3015 tct cag ctg gtt atg aac agg gca act gtg tta gca agt ctc tac gac    9245
Ser Gln Leu Val Met Asn Arg Ala Thr Val Leu Ala Ser Ser Tyr Asp
3020                3025                3030                3035 act gcc tgg aag aag cat gac ttg gtg cga agg cta gaa acc agt att    9293
Thr Ala Trp Lys Lys His Asp Leu Val Arg Arg Leu Glu Thr Ser Ile
                3040                3045                3050 tct tct tgt aag aca agc ctg cag cgg gtt cag ctg cat att gcc atg    9341
Ser Ser Cys Lys Thr Ser Leu Gln Arg Val Gln Leu His Ile Ala Met
            3055                3060                3065 ttt cag tgg caa cat gaa gat cta ctt atc aat aga cca caa gcc atg    9389
Phe Gln Trp Gln His Glu Asp Leu Leu Ile Asn Arg Pro Gln Ala Met
        3070                3075                3080
```

-continued

```
tca gtc aca cct ccc cca cgg tct gct atc cta acc agc atg aaa aag      9437
Ser Val Thr Pro Pro Pro Arg Ser Ala Ile Leu Thr Ser Met Lys Lys
    3085             3090                 3095 aag ctg cat acc ctg agc cag att gaa act tct att gcg aca gtt cag      9485
Lys Leu His Thr Leu Ser Gln Ile Glu Thr Ser Ile Ala Thr Val Gln
3100             3105                 3110                 3115 gag aag cta gct gca ctt gaa tca agt att gaa cag cga ctc aag tgg      9533
Glu Lys Leu Ala Ala Leu Glu Ser Ser Ile Glu Gln Arg Leu Lys Trp
             3120                 3125                 3130 gca ggt ggt gcc aac cct gca ttg gcc cct gta cta caa gat ttt gaa      9581
Ala Gly Gly Ala Asn Pro Ala Leu Ala Pro Val Leu Gln Asp Phe Glu
         3135                 3140                 3145 gca acg ata gct gaa aga aga aat ctt gtc ctt aaa gag agc caa aga      9629
Ala Thr Ile Ala Glu Arg Arg Asn Leu Val Leu Lys Glu Ser Gln Arg
     3150                 3155                 3160 gca agt cag gtc aca ttt ctc tgc agc aat atc att cat ttt gaa agt      9677
Ala Ser Gln Val Thr Phe Leu Cys Ser Asn Ile Ile His Phe Glu Ser
 3165                 3170                 3175 tta cga aca aga act gca gaa gcc tta aac ctg gat gcg gcg tta ttt      9725
Leu Arg Thr Arg Thr Ala Glu Ala Leu Asn Leu Asp Ala Ala Leu Phe
3180             3185                 3190                 3195 gaa cta atc aag cga tgt cag cag atg tgt tcg ttt gca tca cag ttt      9773
Glu Leu Ile Lys Arg Cys Gln Gln Met Cys Ser Phe Ala Ser Gln Phe
             3200                 3205                 3210 aac agt tca gtg tct gag tta gag ctt cgt tta tta cag aga gtg gac      9821
Asn Ser Ser Val Ser Glu Leu Glu Leu Arg Leu Leu Gln Arg Val Asp
         3215                 3220                 3225 act ggt ctt gaa cat cct att ggc agc tct gaa tgg ctt ttg tca gca      9869
Thr Gly Leu Glu His Pro Ile Gly Ser Ser Glu Trp Leu Leu Ser Ala
     3230                 3235                 3240 cac aaa cag ttg acc cag gat atg tct act cag agg gca att cag aca      9917
His Lys Gln Leu Thr Gln Asp Met Ser Thr Gln Arg Ala Ile Gln Thr
 3245                 3250                 3255 gag aaa gag cag cag ata gaa acg gtc tgt gaa aca att cag aat ctg      9965
Glu Lys Glu Gln Gln Ile Glu Thr Val Cys Glu Thr Ile Gln Asn Leu
3260             3265                 3270                 3275 gtt gat aat ata aag act gtg ctc act ggt cat aac cga cag ctt gga     10013
Val Asp Asn Ile Lys Thr Val Leu Thr Gly His Asn Arg Gln Leu Gly
             3280                 3285                 3290 gat gtc aaa cat ctc ttg aaa gct atg gct aag gat gaa gaa gct gct     10061
Asp Val Lys His Leu Leu Lys Ala Met Ala Lys Asp Glu Glu Ala Ala
         3295                 3300                 3305 ctg gca gat ggt gaa gat gtt ccc tat gag aac agt gtt agg cag ttt     10109
Leu Ala Asp Gly Glu Asp Val Pro Tyr Glu Asn Ser Val Arg Gln Phe
     3310                 3315                 3320 ttg ggt gaa tat aaa tca tgg caa gac aac att caa aca gtt cta ttt     10157
Leu Gly Glu Tyr Lys Ser Trp Gln Asp Asn Ile Gln Thr Val Leu Phe
 3325                 3330                 3335 aca tta gtc cag gct atg ggt cag gtt cga agt caa gaa cac gtt gaa     10205
Thr Leu Val Gln Ala Met Gly Gln Val Arg Ser Gln Glu His Val Glu
3340             3345                 3350                 3355 atg ctc cag gaa atc act ccc acc ttg aaa gaa ctg aaa aca caa agt     10253
Met Leu Gln Glu Ile Thr Pro Thr Leu Lys Glu Leu Lys Thr Gln Ser
             3360                 3365                 3370 cag agt atc tat aat aat tta gtg agt ttt gca tca ccc tta gtc acc     10301
Gln Ser Ile Tyr Asn Asn Leu Val Ser Phe Ala Ser Pro Leu Val Thr
         3375                 3380                 3385 gat gca aca aat gaa tgt tcg agt cca acg tca tct gct act tat cag     10349
Asp Ala Thr Asn Glu Cys Ser Ser Pro Thr Ser Ser Ala Thr Tyr Gln
     3390                 3395                 3400
```

```
cca tcc ttc gct gca gca gtc cgg agt aac act ggc cag aag act cag        10397
Pro Ser Phe Ala Ala Ala Val Arg Ser Asn Thr Gly Gln Lys Thr Gln
    3405                3410                3415 cct gat gtc atg tca cag aat gct aga aag ctg atc cag aaa aat ctt        10445
Pro Asp Val Met Ser Gln Asn Ala Arg Lys Leu Ile Gln Lys Asn Leu
3420                3425                3430                3435 gct aca tca gct gat act cca cca agc acc gtt cca gga act ggc aag        10493
Ala Thr Ser Ala Asp Thr Pro Pro Ser Thr Val Pro Gly Thr Gly Lys
            3440                3445                3450 agt gtt gct tgt agt cct aaa aag gca gtc aga gac cct aaa act ggg        10541
Ser Val Ala Cys Ser Pro Lys Lys Ala Val Arg Asp Pro Lys Thr Gly
                3455                3460                3465 aaa gcg gtg caa gag aga aac tcc tat gca gtg agt gtg tgg aag aga        10589
Lys Ala Val Gln Glu Arg Asn Ser Tyr Ala Val Ser Val Trp Lys Arg
                    3470                3475                3480 gtg aaa gcc aag tta gag ggc cga gat gtt gat ccg aat agg agg atg        10637
Val Lys Ala Lys Leu Glu Gly Arg Asp Val Asp Pro Asn Arg Arg Met
3485                3490                3495 tca gtt gct gaa cag gtt gac tat gtc att aag gaa gca act aat cta        10685
Ser Val Ala Glu Gln Val Asp Tyr Val Ile Lys Glu Ala Thr Asn Leu
3500                3505                3510                3515 gat aac ttg gct cag ctg tat gaa ggt tgg aca gcc tgg gtg tga            10730
Asp Asn Leu Ala Gln Leu Tyr Glu Gly Trp Thr Ala Trp Val  *
            3520                3525 atggcaagac agtagatgag tctggttaag cgaggtcaga catccaccag aatcaactca      10790
gcctcaggca tccaaagcca caccacagtc ggtggtgatg caactggggg cttactctga      10850
ggaaacctag gaaatctcgg tgcactagga agtgaatccc gcaggacagc tgcactcagg      10910
gatacgccca acaccatggc ctgcaacccc agggtcaagg gtgaaggaaa gcaaagctca      10970
ccgcctgaac acggagattg tctttctgcc acagaacagc agcagacgtg tcgggaggtt      11030
agctgcggaa agaaatcggg atgccgcgga gcacagagtg atttggaact ccattccacc      11090
tgaccctgtg tgtacaatcc aggaaaaaaa caaaccccac tcagaaacag agaaaactgg      11150
ggtcgcgaag aaatcacagc caaggaagat ttgatgcatt cagattctcg tgtaacactt      11210
gttgcttggc aacagtactg gttgggttga ccagtaagta gaaaaaggct aaaggctatg      11270
cgatatgaat ttcagaaatg gactgaaaat ggagagctat gtaacagata cactacagta      11330
gaagaactta cttctgaaat gaagggaaaa aaaccacccc atcgttccct actcctcccc      11390
accacttacc cgttcccect ttacctaatc tagtagatta gccatctttc aaattcactt      11450
ttatttcagt ccttatattt catatacttc cgtctcgatg ctgttaacaa cttctgataa      11510
catggaaaat tcaaggattg tttaaaggtc tgatgatcac acacaaaatg taattccggt      11570
tatttaagtc atttctgtga ttctatcatg tacagtttcc agaattgtca ctgtgcattc      11630
aaaagtaatg aatctaacag acatttgatt taatgtacac tcccttttgc ttatagtgtg      11690
catttttttt ggaggtcatt caaatttttcc ctcttctgtg atagctgtag tttctttcat      11750
agaaagtagc taatccagtg taatctttta ccttttttaaa aaccaagata gagtatctat      11810
tagagtttta cattgttgat gatagattaa caataaagtg atgttctggt ggaggtagac      11870
tgaaattttt ttaattcatg tttttcattt gatactttta atttacactt agtaaattaa      11930
aagttgttta atttacttgg catttagga catgtacatg aaacagtgaa atgagatcc        11990 accaacatct tttattaagt tcagttatta gtctgtgaag tgctttactt tttgcacaat      12050
tttaatagct tgctattcag taatacatta tagtgaattc atgatcaagg tttccttaaa      12110
tttagcattg catttcagta ctgactgtgt aagctaaatt gctgatccaa aataaaaaacc    12170
```

```
cagactagaa tagggttctt aaaatcaagt atcaatacaa aatagaacac aattaaaatc    12230
ttaattgttg gctgggcaca gtggctcacg cctgtaatcc cagcactttg ggaggccgag    12290
gcgggcggat catgaggtta ggagagcgag accatcctgg ctaacacggt gaaacccgt     12350 ctttactaaa atacaaaaaa aattagccgg gtgtggtggc gggcgcctgt agtcccagct    12410
actcgggagg ctgaggcagg agaatggcgt gaacccagga ggcggagctt gcagtgagcc    12470
gagattgtgc cactgcactc cagcctgggc aacagagcta gactctgtgt caaaataaa     12530 tgactagat                                                           12539
```

<210> SEQ ID NO 8
<211> LENGTH: 3529
<212> TYPE: PRT
<213> ORGANISM: Homo sapiens

<400> SEQUENCE: 8

```
Met Arg Lys Ser Gln Glu Arg Ser Met Ser Tyr Ser Asp Glu Ser Arg
  1               5                  10                  15

Leu Ser Asn Leu Leu Arg Arg Ile Thr Arg Glu Asp Asp Arg Asp Arg
             20                  25                  30

Arg Leu Ala Thr Val Lys Gln Leu Lys Glu Phe Ile Gln Gln Pro Glu
         35                  40                  45

Asn Lys Leu Val Leu Val Lys Gln Leu Asp Asn Ile Leu Ala Ala Val
     50                  55                  60

His Asp Val Leu Asn Glu Ser Ser Lys Leu Leu Gln Glu Leu Arg Gln
 65                  70                  75                  80

Glu Gly Ala Cys Cys Leu Gly Leu Leu Cys Ala Ser Leu Ser Tyr Glu
                 85                  90                  95

Ala Glu Lys Ile Phe Lys Trp Ile Phe Ser Lys Phe Ser Ser Ser Ala
            100                 105                 110

Lys Asp Glu Val Lys Leu Leu Tyr Leu Cys Ala Thr Tyr Lys Ala Leu
        115                 120                 125

Glu Thr Val Gly Glu Lys Lys Ala Phe Ser Ser Val Met Gln Leu Val
    130                 135                 140

Met Thr Ser Leu Gln Ser Ile Leu Glu Asn Val Asp Thr Pro Glu Leu
145                 150                 155                 160

Leu Cys Lys Cys Val Lys Cys Ile Leu Leu Val Ala Arg Cys Tyr Pro
                165                 170                 175

His Ile Phe Ser Thr Asn Phe Arg Asp Thr Val Asp Ile Leu Val Gly
            180                 185                 190

Trp His Ile Asp His Thr Gln Lys Pro Ser Leu Thr Gln Gln Val Ser
        195                 200                 205

Gly Trp Leu Gln Ser Leu Glu Pro Phe Trp Val Ala Asp Leu Ala Phe
    210                 215                 220

Ser Thr Thr Leu Leu Gly Gln Phe Leu Glu Asp Met Glu Ala Tyr Ala
225                 230                 235                 240

Glu Asp Leu Ser His Val Ala Ser Gly Glu Ser Val Asp Glu Asp Val
                245                 250                 255

Pro Pro Pro Ser Val Ser Leu Pro Lys Leu Ala Ala Leu Leu Arg Val
            260                 265                 270

Phe Ser Thr Val Val Arg Ser Ile Gly Glu Arg Phe Ser Pro Ile Arg
        275                 280                 285

Gly Pro Pro Ile Thr Glu Ala Tyr Val Thr Asp Val Leu Tyr Arg Val
    290                 295                 300
```

```
Met Arg Cys Val Thr Ala Ala Asn Gln Val Phe Phe Ser Glu Ala Val
305                 310                 315                 320

Leu Thr Ala Ala Asn Glu Cys Val Gly Val Leu Leu Gly Ser Leu Asp
                325                 330                 335

Pro Ser Met Thr Ile His Cys Asp Met Val Ile Thr Tyr Gly Leu Asp
            340                 345                 350

Gln Leu Glu Asn Cys Gln Thr Cys Gly Thr Asp Tyr Ile Ile Ser Val
        355                 360                 365

Leu Asn Leu Leu Thr Leu Ile Val Glu Gln Ile Asn Thr Lys Leu Pro
    370                 375                 380

Ser Ser Phe Val Glu Lys Leu Phe Ile Pro Ser Ser Lys Leu Leu Phe
385                 390                 395                 400

Leu Arg Tyr His Lys Glu Lys Val Val Ala Val His Ala Val
                405                 410                 415

Tyr Gln Ala Val Leu Ser Leu Lys Asn Ile Pro Val Leu Glu Thr Ala
                420                 425                 430

Tyr Lys Leu Ile Leu Gly Glu Met Thr Cys Ala Leu Asn Asn Leu Leu
        435                 440                 445

His Ser Leu Gln Leu Pro Glu Ala Cys Ser Glu Ile Lys His Glu Ala
    450                 455                 460

Phe Lys Asn His Val Phe Asn Val Asp Asn Ala Lys Phe Val Val Lys
465                 470                 475                 480

Phe Asp Leu Ser Ala Leu Thr Thr Ile Gly Asn Ala Lys Asn Ser Leu
                485                 490                 495

Ile Gly Met Trp Ala Leu Ser Pro Thr Val Phe Ala Leu Leu Ser Lys
            500                 505                 510

Asn Leu Met Ile Val His Ser Asp Leu Ala Val His Phe Pro Ala Ile
        515                 520                 525

Gln Tyr Ala Val Leu Tyr Thr Leu Tyr Ser His Cys Thr Arg His Asp
    530                 535                 540

His Phe Ile Ser Ser Ser Leu Ser Ser Ala Ser Pro Ser Leu Phe Asp
545                 550                 555                 560

Gly Ala Val Ile Ser Thr Val Thr Thr Ala Thr Lys Lys His Phe Ser
                565                 570                 575

Ile Ile Leu Asn Leu Leu Gly Ile Leu Leu Lys Lys Asp Asn Leu Asn
            580                 585                 590

Gln Asp Thr Arg Lys Leu Leu Met Thr Trp Ala Leu Glu Ala Ala Val
        595                 600                 605

Leu Met Arg Lys Ser Glu Thr Tyr Ala Pro Leu Phe Ser Leu Pro Ser
    610                 615                 620

Phe His Lys Phe Cys Lys Gly Leu Leu Ala Asn Thr Leu Val Glu Asp
625                 630                 635                 640

Val Asn Ile Cys Leu Gln Ala Cys Ser Ser Leu His Ala Leu Ser Ser
                645                 650                 655

Ser Leu Pro Asp Asp Leu Leu Gln Arg Cys Val Asp Val Cys Arg Val
            660                 665                 670

Gln Leu Val His Ser Gly Thr Arg Ile Arg Gln Ala Phe Gly Lys Leu
        675                 680                 685

Leu Lys Ser Ile Pro Leu Asp Val Val Leu Ser Asn Asn Asn His Thr
    690                 695                 700

Glu Ile Gln Glu Ile Ser Leu Ala Leu Arg Ser His Met Ser Lys Ala
705                 710                 715                 720
```

-continued

```
Pro Ser Asn Thr Phe His Pro Gln Asp Phe Ser Asp Val Ile Ser Phe
            725                 730                 735

Ile Leu Tyr Gly Asn Ser His Arg Thr Gly Lys Asp Asn Trp Leu Glu
            740                 745                 750

Arg Leu Phe Tyr Ser Cys Gln Arg Leu Asp Lys Arg Asp Gln Ser Thr
            755                 760                 765

Ile Pro Arg Asn Leu Leu Lys Thr Asp Ala Val Leu Trp Gln Trp Ala
770                 775                 780

Ile Trp Glu Ala Ala Gln Phe Thr Val Leu Ser Lys Leu Arg Thr Pro
785                 790                 795                 800

Leu Gly Arg Ala Gln Asp Thr Phe Gln Thr Ile Glu Gly Ile Ile Arg
            805                 810                 815

Ser Leu Ala Ala His Thr Leu Asn Pro Asp Gln Asp Val Ser Gln Trp
            820                 825                 830

Thr Thr Ala Asp Asn Asp Glu Gly His Gly Asn Asn Gln Leu Arg Leu
            835                 840                 845

Val Leu Leu Gln Tyr Leu Glu Asn Leu Glu Lys Leu Met Tyr Asn
850                 855                 860

Ala Tyr Glu Gly Cys Ala Asn Ala Leu Thr Ser Pro Lys Val Ile
865                 870                 875                 880

Arg Thr Phe Phe Tyr Thr Asn Arg Gln Thr Cys Gln Asp Trp Leu Thr
            885                 890                 895

Arg Ile Arg Leu Ser Ile Met Arg Val Gly Leu Leu Ala Gly Gln Pro
            900                 905                 910

Ala Val Thr Val Arg His Gly Phe Asp Leu Leu Thr Glu Met Lys Thr
            915                 920                 925

Thr Ser Leu Ser Gln Gly Asn Glu Leu Glu Val Thr Ile Met Met Val
            930                 935                 940

Val Glu Ala Leu Cys Glu Leu His Cys Pro Glu Ala Ile Gln Gly Ile
945                 950                 955                 960

Ala Val Trp Ser Ser Ser Ile Val Gly Lys Asn Leu Leu Trp Ile Asn
            965                 970                 975

Ser Val Ala Gln Gln Ala Glu Gly Arg Phe Glu Lys Ala Ser Val Glu
            980                 985                 990

Tyr Gln Glu His Leu Cys Ala Met Thr Gly Val Asp Cys Cys Ile Ser
            995                 1000                1005

Ser Phe Asp Lys Ser Val Leu Thr Leu Ala Asn Ala Gly Arg Asn Ser
            1010                1015                1020

Ala Ser Pro Lys His Ser Leu Asn Gly Glu Ser Arg Lys Thr Val Leu
1025                1030                1035                1040

Ser Lys Pro Thr Asp Ser Ser Pro Glu Val Ile Asn Tyr Leu Gly Asn
            1045                1050                1055

Lys Ala Cys Glu Phe Tyr Ile Ser Ile Ala Asp Trp Ala Ala Val Gln
            1060                1065                1070

Glu Trp Gln Asn Ala Ile His Asp Leu Lys Lys Ser Thr Ser Ser Thr
            1075                1080                1085

Ser Leu Asn Leu Lys Ala Asp Phe Asn Tyr Ile Lys Ser Leu Ser Ser
            1090                1095                1100

Phe Glu Ser Gly Lys Phe Val Glu Cys Thr Glu Gln Leu Glu Leu Leu
1105                1110                1115                1120

Pro Gly Glu Asn Ile Asn Leu Leu Ala Gly Gly Ser Lys Glu Lys Ile
            1125                1130                1135
```

```
Asp Met Lys Lys Leu Leu Pro Asn Met Leu Ser Pro Asp Pro Arg Glu
        1140                1145                1150

Leu Gln Lys Ser Ile Glu Val Gln Leu Leu Arg Ser Ser Val Cys Leu
        1155                1160                1165

Ala Thr Ala Leu Asn Pro Ile Glu Gln Asp Gln Lys Trp Gln Ser Ile
        1170                1175                1180

Thr Glu Asn Val Val Lys Tyr Leu Lys Gln Thr Ser Arg Ile Ala Ile
1185                1190                1195                1200

Gly Pro Leu Arg Leu Ser Thr Leu Thr Val Ser Gln Ser Leu Pro Val
            1205                1210                1215

Leu Ser Thr Leu Gln Leu Tyr Cys Ser Ser Ala Leu Glu Asn Thr Val
        1220                1225                1230

Ser Asn Arg Leu Ser Thr Glu Asp Cys Leu Ile Pro Leu Phe Ser Glu
        1235                1240                1245

Ala Leu Arg Ser Cys Lys Gln His Asp Val Arg Pro Trp Met Gln Ala
        1250                1255                1260

Leu Arg Tyr Thr Met Tyr Gln Asn Gln Leu Leu Glu Lys Ile Lys Glu
1265                1270                1275                1280

Gln Thr Val Pro Ile Arg Ser His Leu Met Glu Leu Gly Leu Thr Ala
            1285                1290                1295

Ala Lys Phe Ala Arg Lys Arg Gly Asn Val Ser Leu Ala Thr Arg Leu
        1300                1305                1310

Leu Ala Gln Cys Ser Glu Val Gln Leu Gly Lys Thr Thr Thr Ala Gln
        1315                1320                1325

Asp Leu Val Gln His Phe Lys Lys Leu Ser Thr Gln Gly Gln Val Asp
        1330                1335                1340

Glu Lys Trp Gly Pro Glu Leu Asp Ile Glu Lys Thr Lys Leu Leu Tyr
1345                1350                1355                1360

Thr Ala Gly Gln Ser Thr His Ala Met Glu Met Leu Ser Ser Cys Ala
            1365                1370                1375

Ile Ser Phe Cys Lys Ser Val Lys Ala Glu Tyr Ala Val Ala Lys Ser
        1380                1385                1390

Ile Leu Thr Leu Ala Lys Trp Ile Gln Ala Glu Trp Lys Glu Ile Ser
        1395                1400                1405

Gly Gln Leu Lys Gln Val Tyr Arg Ala Gln His Gln Gln Asn Phe Thr
        1410                1415                1420

Gly Leu Ser Thr Leu Ser Lys Asn Ile Leu Thr Leu Ile Glu Leu Pro
1425                1430                1435                1440

Ser Val Asn Thr Met Glu Glu Glu Tyr Pro Arg Ile Glu Ser Glu Ser
            1445                1450                1455

Thr Val His Ile Gly Val Gly Glu Pro Asp Phe Ile Leu Gly Gln Leu
            1460                1465                1470

Tyr His Leu Ser Ser Val Gln Ala Pro Glu Val Ala Lys Ser Trp Ala
        1475                1480                1485

Ala Leu Ala Ser Trp Ala Tyr Arg Trp Gly Arg Lys Val Val Asp Asn
        1490                1495                1500

Ala Ser Gln Gly Glu Gly Val Arg Leu Leu Pro Arg Glu Lys Ser Glu
1505                1510                1515                1520

Val Gln Asn Leu Leu Pro Asp Thr Ile Thr Glu Glu Lys Glu Arg
            1525                1530                1535

Ile Tyr Gly Ile Leu Gly Gln Ala Val Cys Arg Pro Ala Gly Ile Gln
        1540                1545                1550
```

-continued

```
Asp Glu Asp Ile Thr Leu Gln Ile Thr Glu Ser Glu Asp Asn Glu Glu
    1555                1560                1565

Asp Asp Met Val Asp Val Ile Trp Arg Gln Leu Ile Ser Ser Cys Pro
    1570                1575                1580

Trp Leu Ser Glu Leu Asp Glu Ser Ala Thr Glu Gly Val Ile Lys Val
1585                1590                1595                1600

Trp Arg Lys Val Val Asp Arg Ile Phe Ser Leu Tyr Lys Leu Ser Cys
            1605                1610                1615

Ser Ala Tyr Phe Thr Phe Leu Lys Leu Asn Ala Gly Gln Ile Pro Leu
            1620                1625                1630

Asp Glu Asp Asp Pro Arg Leu His Leu Ser His Arg Val Glu Gln Ser
            1635                1640                1645

Thr Asp Asp Met Ile Val Met Ala Thr Leu Arg Leu Leu Arg Leu Leu
            1650                1655                1660

Val Lys His Ala Gly Glu Leu Arg Gln Tyr Leu Glu His Gly Leu Glu
1665                1670                1675                1680

Thr Thr Pro Thr Ala Pro Trp Arg Gly Ile Ile Pro Gln Leu Phe Ser
            1685                1690                1695

Arg Leu Asn His Pro Glu Val Tyr Val Arg Gln Ser Ile Cys Asn Leu
            1700                1705                1710

Leu Cys Arg Val Ala Gln Asp Ser Pro His Leu Ile Leu Tyr Pro Ala
            1715                1720                1725

Ile Val Gly Thr Ile Ser Leu Ser Ser Glu Ser Gln Ala Ser Gly Asn
            1730                1735                1740

Lys Phe Ser Thr Ala Ile Pro Thr Leu Leu Gly Asn Ile Gln Gly Glu
1745                1750                1755                1760

Glu Leu Leu Val Ser Glu Cys Glu Gly Gly Ser Pro Pro Ala Ser Gln
            1765                1770                1775

Asp Ser Asn Lys Asp Glu Pro Lys Ser Gly Leu Asn Glu Asp Gln Ala
            1780                1785                1790

Met Met Gln Asp Cys Tyr Ser Lys Ile Val Asp Lys Leu Ser Ser Ala
            1795                1800                1805

Asn Pro Thr Met Val Leu Gln Val Gln Met Leu Val Ala Glu Leu Arg
            1810                1815                1820

Arg Val Thr Val Leu Trp Asp Glu Leu Trp Leu Gly Val Leu Leu Gln
1825                1830                1835                1840

Gln His Met Tyr Val Leu Arg Arg Ile Gln Gln Leu Glu Asp Glu Val
            1845                1850                1855

Lys Arg Val Gln Asn Asn Asn Thr Leu Arg Lys Glu Glu Lys Ile Ala
            1860                1865                1870

Ile Met Arg Glu Arg His Thr Ala Leu Met Lys Pro Ile Val Phe Ala
            1875                1880                1885

Leu Glu His Val Arg Ser Ile Thr Ala Ala Pro Ala Glu Thr Pro His
            1890                1895                1900

Glu Lys Trp Phe Gln Asp Asn Tyr Gly Asp Ala Ile Glu Asn Ala Leu
1905                1910                1915                1920

Glu Lys Leu Lys Thr Pro Leu Asn Pro Ala Lys Pro Gly Ser Ser Trp
            1925                1930                1935

Ile Pro Phe Lys Glu Ile Met Leu Ser Leu Gln Gln Arg Ala Gln Lys
            1940                1945                1950

Arg Ala Ser Tyr Ile Leu Arg Leu Glu Glu Ile Ser Pro Trp Leu Ala
            1955                1960                1965
```

-continued

```
Ala Met Thr Asn Thr Glu Ile Ala Leu Pro Gly Val Ser Ala Arg
    1970                1975                1980

Asp Thr Val Thr Ile His Ser Val Gly Gly Thr Ile Thr Ile Leu Pro
1985                1990                1995                2000

Thr Lys Thr Lys Pro Lys Lys Leu Leu Phe Leu Gly Ser Asp Gly Lys
                2005                2010                2015

Ser Tyr Pro Tyr Leu Phe Lys Gly Leu Glu Asp Leu His Leu Asp Glu
                2020                2025                2030

Arg Ile Met Gln Phe Leu Ser Ile Val Asn Thr Met Phe Ala Thr Ile
            2035                2040                2045

Asn Arg Gln Glu Thr Pro Arg Phe His Ala Arg His Tyr Ser Val Thr
    2050                2055                2060

Pro Leu Gly Thr Arg Ser Gly Leu Ile Gln Trp Val Asp Gly Ala Thr
2065                2070                2075                2080

Pro Leu Phe Gly Leu Tyr Lys Arg Trp Gln Gln Arg Glu Ala Ala Leu
                2085                2090                2095

Gln Ala Gln Lys Ala Gln Asp Ser Tyr Gln Thr Pro Gln Asn Pro Gly
            2100                2105                2110

Ile Val Pro Arg Pro Ser Glu Leu Tyr Tyr Ser Lys Ile Gly Pro Ala
            2115                2120                2125

Leu Lys Thr Val Gly Leu Ser Leu Asp Val Ser Arg Arg Asp Trp Pro
    2130                2135                2140

Leu His Val Met Lys Ala Val Leu Glu Glu Leu Met Glu Ala Thr Pro
2145                2150                2155                2160

Pro Asn Leu Leu Ala Lys Glu Leu Trp Ser Ser Cys Thr Thr Pro Asp
                2165                2170                2175

Glu Trp Trp Arg Val Thr Gln Ser Tyr Ala Arg Ser Thr Ala Val Met
            2180                2185                2190

Ser Met Val Gly Tyr Ile Ile Gly Leu Gly Asp Arg His Leu Asp Asn
            2195                2200                2205

Val Leu Ile Asp Met Thr Thr Gly Glu Val Val His Ile Asp Tyr Asn
    2210                2215                2220

Val Cys Phe Glu Lys Gly Lys Ser Leu Arg Val Pro Glu Lys Val Pro
2225                2230                2235                2240

Phe Arg Met Thr Gln Asn Ile Glu Thr Ala Leu Gly Val Thr Gly Val
                2245                2250                2255

Glu Gly Val Phe Arg Leu Ser Cys Glu Gln Val Leu His Ile Met Arg
            2260                2265                2270

Arg Gly Arg Glu Thr Leu Leu Thr Leu Leu Glu Ala Phe Val Tyr Asp
        2275                2280                2285

Pro Leu Val Asp Trp Thr Ala Gly Gly Glu Ala Gly Phe Ala Gly Ala
    2290                2295                2300

Val Tyr Gly Gly Gly Gln Gln Ala Glu Ser Lys Gln Ser Lys Arg
2305                2310                2315                2320

Glu Met Glu Arg Glu Ile Thr Arg Ser Leu Phe Ser Ser Arg Val Ala
                2325                2330                2335

Glu Ile Lys Val Asn Trp Phe Lys Asn Arg Asp Glu Met Leu Val Val
            2340                2345                2350

Leu Pro Lys Leu Asp Gly Ser Leu Asp Glu Tyr Leu Ser Leu Gln Glu
        2355                2360                2365

Gln Leu Thr Asp Val Glu Lys Leu Gln Gly Lys Leu Leu Glu Glu Ile
    2370                2375                2380
```

-continued

Glu Phe Leu Glu Gly Ala Glu Gly Val Asp His Pro Ser His Thr Leu
2385                2390                2395                2400

Gln His Arg Tyr Ser Glu His Thr Gln Leu Gln Thr Gln Gln Arg Ala
            2405                2410                2415

Val Gln Glu Ala Ile Gln Val Lys Leu Asn Glu Phe Glu Gln Trp Ile
        2420                2425                2430

Thr His Tyr Gln Ala Ala Phe Asn Asn Leu Glu Ala Thr Gln Leu Ala
            2435                2440                2445

Ser Leu Leu Gln Glu Ile Ser Thr Gln Met Asp Leu Gly Pro Pro Ser
    2450                2455                2460

Tyr Val Pro Ala Thr Ala Phe Leu Gln Asn Ala Gly Gln Ala His Leu
2465                2470                2475                2480

Ile Ser Gln Cys Glu Gln Leu Glu Gly Glu Val Gly Ala Leu Leu Gln
            2485                2490                2495

Gln Arg Arg Ser Val Leu Arg Gly Cys Leu Glu Gln Leu His His Tyr
        2500                2505                2510

Ala Thr Val Ala Leu Gln Tyr Pro Lys Ala Ile Phe Gln Lys His Arg
            2515                2520                2525

Ile Glu Gln Trp Lys Thr Trp Met Glu Glu Leu Ile Cys Asn Thr Thr
    2530                2535                2540

Val Glu Arg Cys Gln Glu Leu Tyr Arg Lys Tyr Glu Met Gln Tyr Ala
2545                2550                2555                2560

Pro Gln Pro Pro Pro Thr Val Cys Gln Phe Ile Thr Ala Thr Glu Met
            2565                2570                2575

Thr Leu Gln Arg Tyr Ala Ala Asp Ile Asn Ser Arg Leu Ile Arg Gln
        2580                2585                2590

Val Glu Arg Leu Lys Gln Glu Ala Val Thr Val Pro Val Cys Glu Asp
            2595                2600                2605

Gln Leu Lys Glu Ile Glu Arg Cys Ile Lys Val Phe Leu His Glu Asn
    2610                2615                2620

Gly Glu Glu Gly Ser Leu Ser Leu Ala Ser Val Ile Ile Ser Ala Leu
2625                2630                2635                2640

Cys Thr Leu Thr Arg Arg Asn Leu Met Met Glu Gly Ala Ala Ser Ser
            2645                2650                2655

Ala Gly Glu Gln Leu Val Asp Leu Thr Ser Arg Asp Gly Ala Trp Phe
        2660                2665                2670

Leu Glu Glu Leu Cys Ser Met Ser Gly Asn Val Thr Cys Leu Val Gln
    2675                2680                2685

Leu Leu Lys Gln Cys His Leu Val Pro Gln Asp Leu Asp Ile Pro Asn
    2690                2695                2700

Pro Met Glu Ala Ser Glu Thr Val His Leu Ala Asn Gly Val Tyr Thr
2705                2710                2715                2720

Ser Leu Gln Glu Leu Asn Ser Asn Phe Arg Gln Ile Ile Phe Pro Glu
            2725                2730                2735

Ala Leu Arg Cys Leu Met Lys Gly Glu Tyr Thr Leu Glu Ser Met Leu
        2740                2745                2750

His Glu Leu Asp Gly Leu Ile Glu Gln Thr Thr Asp Gly Val Pro Leu
            2755                2760                2765

Gln Thr Leu Val Glu Ser Leu Gln Ala Tyr Leu Arg Asn Ala Ala Met
    2770                2775                2780

Gly Leu Glu Glu Glu Thr His Ala His Tyr Ile Asp Val Ala Arg Leu
2785                2790                2795                2800

-continued

```
Leu His Ala Gln Tyr Gly Glu Leu Ile Gln Pro Arg Asn Gly Ser Val
                2805                2810                2815
Asp Glu Thr Pro Lys Met Ser Ala Gly Gln Met Leu Leu Val Ala Phe
                2820                2825                2830
Asp Gly Met Phe Ala Gln Val Glu Thr Ala Phe Ser Leu Leu Val Glu
                2835                2840                2845
Lys Leu Asn Lys Met Glu Ile Pro Ile Ala Trp Arg Lys Ile Asp Ile
                2850                2855                2860
Ile Arg Glu Ala Arg Ser Thr Gln Val Asn Phe Phe Asp Asp Asn
2865            2870                2875                2880
His Arg Gln Val Leu Glu Glu Ile Phe Phe Leu Lys Arg Leu Gln Thr
                2885                2890                2895
Ile Lys Glu Phe Phe Arg Leu Cys Gly Thr Phe Ser Lys Thr Leu Ser
                2900                2905                2910
Gly Ser Ser Ser Leu Glu Asp Gln Asn Thr Val Asn Gly Pro Val Gln
                2915                2920                2925
Ile Val Asn Val Lys Thr Leu Phe Arg Asn Ser Cys Phe Ser Glu Asp
                2930                2935                2940
Gln Met Ala Lys Pro Ile Lys Ala Phe Thr Ala Asp Phe Val Arg Gln
2945            2950                2955                2960
Leu Leu Ile Gly Leu Pro Asn Gln Ala Leu Gly Leu Thr Leu Cys Ser
                2965                2970                2975
Phe Ile Ser Ala Leu Gly Val Asp Ile Ile Ala Gln Val Glu Ala Lys
                2980                2985                2990
Asp Phe Gly Ala Glu Ser Lys Val Ser Val Asp Asp Leu Cys Lys Lys
                2995                3000                3005
Ala Val Glu His Asn Ile Gln Ile Gly Lys Phe Ser Gln Leu Val Met
                3010                3015                3020
Asn Arg Ala Thr Val Leu Ala Ser Ser Tyr Asp Thr Ala Trp Lys Lys
3025            3030                3035                3040
His Asp Leu Val Arg Arg Leu Glu Thr Ser Ile Ser Ser Cys Lys Thr
                3045                3050                3055
Ser Leu Gln Arg Val Gln Leu His Ile Ala Met Phe Gly Trp Gln His
                3060                3065                3070
Glu Asp Leu Leu Ile Asn Arg Pro Gln Ala Met Ser Val Thr Pro Pro
                3075                3080                3085
Pro Arg Ser Ala Ile Leu Thr Ser Met Lys Lys Lys Leu His Thr Leu
                3090                3095                3100
Ser Gln Ile Glu Thr Ser Ile Ala Thr Val Gln Glu Lys Leu Ala Ala
3105            3110                3115                3120
Leu Glu Ser Ser Ile Glu Gln Arg Leu Lys Trp Ala Gly Gly Ala Asn
                3125                3130                3135
Pro Ala Leu Ala Pro Val Leu Gln Asp Phe Glu Ala Thr Ile Ala Glu
                3140                3145                3150
Arg Arg Asn Leu Val Leu Lys Glu Ser Gln Arg Ala Ser Gln Val Thr
                3155                3160                3165
Phe Leu Cys Ser Asn Ile Ile His Phe Glu Ser Leu Arg Thr Arg Thr
                3170                3175                3180
Ala Glu Ala Leu Asn Leu Asp Ala Ala Leu Phe Glu Leu Ile Lys Arg
3185            3190                3195                3200
Cys Gln Gln Met Cys Ser Phe Ala Ser Gln Phe Asn Ser Ser Val Ser
                3205                3210                3215
```

```
Glu Leu Glu Leu Arg Leu Leu Gln Arg Val Asp Thr Gly Leu Glu His
        3220                3225                3230

Pro Ile Gly Ser Ser Glu Trp Leu Leu Ser Ala His Lys Gln Leu Thr
        3235                3240                3245

Gln Asp Met Ser Thr Gln Arg Ala Ile Gln Thr Glu Lys Glu Gln Gln
        3250                3255                3260

Ile Glu Thr Val Cys Glu Thr Ile Gln Asn Leu Val Asp Asn Ile Lys
3265                3270                3275                3280

Thr Val Leu Thr Gly His Asn Arg Gln Leu Gly Asp Val Lys His Leu
            3285                3290                3295

Leu Lys Ala Met Ala Lys Asp Glu Glu Ala Ala Leu Ala Asp Gly Glu
        3300                3305                3310

Asp Val Pro Tyr Glu Asn Ser Val Arg Gln Phe Leu Gly Glu Tyr Lys
        3315                3320                3325

Ser Trp Gln Asp Asn Ile Gln Thr Val Leu Phe Thr Leu Val Gln Ala
        3330                3335                3340

Met Gly Gln Val Arg Ser Gln Glu His Val Glu Met Leu Gln Glu Ile
3345                3350                3355                3360

Thr Pro Thr Leu Lys Glu Leu Lys Thr Gln Ser Gln Ser Ile Tyr Asn
            3365                3370                3375

Asn Leu Val Ser Phe Ala Ser Pro Leu Val Thr Asp Ala Thr Asn Glu
        3380                3385                3390

Cys Ser Ser Pro Thr Ser Ser Ala Thr Tyr Gln Pro Ser Phe Ala Ala
        3395                3400                3405

Ala Val Arg Ser Asn Thr Gly Gln Lys Thr Gln Pro Asp Val Met Ser
        3410                3415                3420

Gln Asn Ala Arg Lys Leu Ile Gln Lys Asn Leu Ala Thr Ser Ala Asp
3425                3430                3435                3440

Thr Pro Pro Ser Thr Val Pro Gly Thr Gly Lys Ser Val Ala Cys Ser
            3445                3450                3455

Pro Lys Lys Ala Val Arg Asp Pro Lys Thr Gly Lys Ala Val Gln Glu
        3460                3465                3470

Arg Asn Ser Tyr Ala Val Ser Val Trp Lys Arg Val Lys Ala Lys Leu
        3475                3480                3485

Glu Gly Arg Asp Val Asp Pro Asn Arg Arg Met Ser Val Ala Glu Gln
        3490                3495                3500

Val Asp Tyr Val Ile Lys Glu Ala Thr Asn Leu Asp Asn Leu Ala Gln
3505                3510                3515                3520

Leu Tyr Glu Gly Trp Thr Ala Trp Val
            3525

<210> SEQ ID NO 9
<211> LENGTH: 13110
<212> TYPE: DNA
<213> ORGANISM: Homo sapiens
<220> FEATURE:
<221> NAME/KEY: CDS
<222> LOCATION: (328)...(11298)

<400> SEQUENCE: 9
ggggaagcag tggccgtgtg agcgtgagga gctgccgcca ccgcctgctc ctcgtcctcc      60
tcgtcctccg ggcccccagc gtcgtgggcc gcgcacggcc ctggaagaga cgtcgcctcg     120
ccttcatccg cctctctcac cgcgccgctc cctcgtcctg ccctgcgggc tcaggcggaa     180
cccggaacgg ccgtcctctt cccccgccct ccgccgccgc ctcctcctcc tccttctcgg     240
```

```
cttcctcctc agccccgggc cggagcgggg tgtcggcggc ggccggttcg ggcggcggcg        300
cttggccatg tcgtgtcggg aaggta atg agc cgc aga gcc ccg ggg tct cgg        354
                             Met Ser Arg Arg Ala Pro Gly Ser Arg
                              1               5 ctg agc agc ggc ggc acc aac tat tcg cgg agc tgg aat gac tgg caa        402
Leu Ser Ser Gly Gly Thr Asn Tyr Ser Arg Ser Trp Asn Asp Trp Gln
 10              15                  20                  25 ccc aga act gat agt gca tca gct gac cca ggt aat tta aaa tat tct        450
Pro Arg Thr Asp Ser Ala Ser Ala Asp Pro Gly Asn Leu Lys Tyr Ser
             30                  35                  40 tca tcc aga gat aga ggt ggt tct tcc tct tac gga ctg caa cct tca        498
Ser Ser Arg Asp Arg Gly Gly Ser Ser Ser Tyr Gly Leu Gln Pro Ser
             45                  50                  55 aat tca gct gtg gtg tct cgg caa agg cac gat gat acc aga gtc cac        546
Asn Ser Ala Val Val Ser Arg Gln Arg His Asp Asp Thr Arg Val His
             60                  65                  70 gct gac ata cag aat gac gaa aag ggt ggc tac agt gtc aat gga gga        594
Ala Asp Ile Gln Asn Asp Glu Lys Gly Gly Tyr Ser Val Asn Gly Gly
         75                  80                  85 tct ggg gaa aat act tat ggt cgg aag tcg ttg ggg caa gag ctg agg        642
Ser Gly Glu Asn Thr Tyr Gly Arg Lys Ser Leu Gly Gln Glu Leu Arg
 90              95                 100                 105 gtt aac aat gtg acc agc cct gag ttc acc agt gtt cag cat ggc agt        690
Val Asn Asn Val Thr Ser Pro Glu Phe Thr Ser Val Gln His Gly Ser
                110                 115                 120 cgt gct tta gcc acc aaa gac atg agg aaa tca cag gag aga tcg atg        738
Arg Ala Leu Ala Thr Lys Asp Met Arg Lys Ser Gln Glu Arg Ser Met
            125                 130                 135 tct tat tct gat gag tct cga ctg tcg aat ctt ctt cgg agg atc acc        786
Ser Tyr Ser Asp Glu Ser Arg Leu Ser Asn Leu Leu Arg Arg Ile Thr
            140                 145                 150 cgg gaa gac gac aga gac cga aga ttg gct act gta aag cag ttg aaa        834
Arg Glu Asp Asp Arg Asp Arg Arg Leu Ala Thr Val Lys Gln Leu Lys
155                 160                 165 gaa ttt att cag caa cca gaa aat aag ctg gta cta gtt aaa caa ttg        882
Glu Phe Ile Gln Gln Pro Glu Asn Lys Leu Val Leu Val Lys Gln Leu
170                 175                 180                 185 gat aat atc ttg gct gct gta cat gac gtg ctt aat gaa agt agc aaa        930
Asp Asn Ile Leu Ala Ala Val His Asp Val Leu Asn Glu Ser Ser Lys
                190                 195                 200 ttg ctt cag gag ttg aga cag gag gga gct tgc tgt ctt ggc ctt ctt        978
Leu Leu Gln Glu Leu Arg Gln Glu Gly Ala Cys Cys Leu Gly Leu Leu
            205                 210                 215 tgt gct tct ctg agc tat gag gct gag aag atc ttc aag tgg att ttt       1026
Cys Ala Ser Leu Ser Tyr Glu Ala Glu Lys Ile Phe Lys Trp Ile Phe
            220                 225                 230 agc aaa ttt agc tca tct gca aaa gat gaa gtt aaa ctc ctc tac tta       1074
Ser Lys Phe Ser Ser Ser Ala Lys Asp Glu Val Lys Leu Leu Tyr Leu
            235                 240                 245 tgt gcc acc tac aaa gca cta gag act gta gga gaa aag aaa gcc ttt       1122
Cys Ala Thr Tyr Lys Ala Leu Glu Thr Val Gly Glu Lys Lys Ala Phe
250                 255                 260                 265 tca tct gta atg cag ctt gta atg acc agc ctg cag tct att ctt gaa       1170
Ser Ser Val Met Gln Leu Val Met Thr Ser Leu Gln Ser Ile Leu Glu
                270                 275                 280 aat gtg gat aca cca gaa ttg ctt tgt aaa tgt gtt aag tgc att ctt       1218
Asn Val Asp Thr Pro Glu Leu Leu Cys Lys Cys Val Lys Cys Ile Leu
            285                 290                 295
```

```
ttg gtg gct cga tgt tac cct cat att ttc agc act aat ttt agg gat    1266
Leu Val Ala Arg Cys Tyr Pro His Ile Phe Ser Thr Asn Phe Arg Asp
    300                 305                 310 aca gtt gat ata tta gtt gga tgg cat ata gat cat act cag aaa cct    1314
Thr Val Asp Ile Leu Val Gly Trp His Ile Asp His Thr Gln Lys Pro
315                 320                 325 tcg ctc acg cag cag gta tct ggg tgg ttg cag agt ttg gag cca ttt    1362
Ser Leu Thr Gln Gln Val Ser Gly Trp Leu Gln Ser Leu Glu Pro Phe
330                 335                 340                 345 tgg gta gct gat ctt gca ttt tct act act ctt ctt ggt cag ttt ctg    1410
Trp Val Ala Asp Leu Ala Phe Ser Thr Thr Leu Leu Gly Gln Phe Leu
                350                 355                 360 gaa gac atg gaa gca tat gct gag gac ctc agc cat gtg gcc tct ggg    1458
Glu Asp Met Glu Ala Tyr Ala Glu Asp Leu Ser His Val Ala Ser Gly
            365                 370                 375 gaa tca gtg gat gaa gat gtc cct cct cca tca gtc tta cca aag        1506
Glu Ser Val Asp Glu Asp Val Pro Pro Pro Ser Val Ser Leu Pro Lys
        380                 385                 390 ctg gct gca ctt ctc cgg gta ttt agt act gtg gtg agg agc att ggg    1554
Leu Ala Ala Leu Leu Arg Val Phe Ser Thr Val Val Arg Ser Ile Gly
    395                 400                 405 gaa cgc ttc agc cca att cgg ggt cct cca att act gag gca tat gta    1602
Glu Arg Phe Ser Pro Ile Arg Gly Pro Pro Ile Thr Glu Ala Tyr Val
410                 415                 420                 425 aca gat gtt ctg tac aga gta atg aga tgt gtg acg gct gca aac cag    1650
Thr Asp Val Leu Tyr Arg Val Met Arg Cys Val Thr Ala Ala Asn Gln
                430                 435                 440 gtg ttt ttt tct gag gct gtg ttg aca gct gct aat gag tgt gtt ggt    1698
Val Phe Phe Ser Glu Ala Val Leu Thr Ala Ala Asn Glu Cys Val Gly
            445                 450                 455 gtt ttg ctc ggc agc ttg gat cct agc atg act ata cat tgt gac atg    1746
Val Leu Leu Gly Ser Leu Asp Pro Ser Met Thr Ile His Cys Asp Met
        460                 465                 470 gtc att aca tat gga tta gac caa ctg gag aat tgc cag act tgt ggt    1794
Val Ile Thr Tyr Gly Leu Asp Gln Leu Glu Asn Cys Gln Thr Cys Gly
    475                 480                 485 acc gat tat atc atc tca gtc ttg aat tta ctc acg ctg att gtt gaa    1842
Thr Asp Tyr Ile Ile Ser Val Leu Asn Leu Leu Thr Leu Ile Val Glu
490                 495                 500                 505 cag ata aat acg aaa ctg cca tca tca ttt gta gaa aaa ctg ttt ata    1890
Gln Ile Asn Thr Lys Leu Pro Ser Ser Phe Val Glu Lys Leu Phe Ile
                510                 515                 520 cca tca tct aaa cta cta ttc ttg cgt tat cat aaa gaa aaa gag gtt    1938
Pro Ser Ser Lys Leu Leu Phe Leu Arg Tyr His Lys Glu Lys Glu Val
            525                 530                 535 gtt gct gta gcc cat gct gtt tat caa gca gtg ctc agc ttg aag aat    1986
Val Ala Val Ala His Ala Val Tyr Gln Ala Val Leu Ser Leu Lys Asn
        540                 545                 550 att cct gtt ttg gag act gcc tat aag tta ata ttg gga gaa atg act    2034
Ile Pro Val Leu Glu Thr Ala Tyr Lys Leu Ile Leu Gly Glu Met Thr
    555                 560                 565 tgt gcc cta aac aac ctc cta cac agt cta caa ctt cct gag gcc tgt    2082
Cys Ala Leu Asn Asn Leu Leu His Ser Leu Gln Leu Pro Glu Ala Cys
570                 575                 580                 585 tct gaa ata aaa cat gag gct ttt aag aat cat gtg ttc aat gta gac    2130
Ser Glu Ile Lys His Glu Ala Phe Lys Asn His Val Phe Asn Val Asp
                590                 595                 600 aat gca aaa ttt gta gtt aaa ttt gac ctc agt gcc ctg act aca att    2178
Asn Ala Lys Phe Val Val Lys Phe Asp Leu Ser Ala Leu Thr Thr Ile
            605                 610                 615
```

-continued

| | | |
|---|---|---|
| gga aat gcc aaa aac tca cta ata ggg atg tgg gcg cta tct cca act<br>Gly Asn Ala Lys Asn Ser Leu Ile Gly Met Trp Ala Leu Ser Pro Thr<br>620                       625                     630 | 2226 |
| gtc ttt gca ctt ctg agt aag aat ctg atg att gtg cac agt gac ctg<br>Val Phe Ala Leu Leu Ser Lys Asn Leu Met Ile Val His Ser Asp Leu<br>635                       640                     645 | 2274 |
| gct gtt cac ttc cct gcc att cag tat gct gtg ctc tac aca ttg tat<br>Ala Val His Phe Pro Ala Ile Gln Tyr Ala Val Leu Tyr Thr Leu Tyr<br>650                       655                     660                     665 | 2322 |
| tct cat tgt acc agg cat gat cac ttt atc tct agc agc ctc agt tct<br>Ser His Cys Thr Arg His Asp His Phe Ile Ser Ser Ser Leu Ser Ser<br>                   670                     675                     680 | 2370 |
| gcc tct cct tct ttg ttt gat gga gct gtg att agc act gta act acg<br>Ala Ser Pro Ser Leu Phe Asp Gly Ala Val Ile Ser Thr Val Thr Thr<br>685                       690                     695 | 2418 |
| gct aca aag aaa cat ttc tca att ata tta aat ctt ctg gga ata tta<br>Ala Thr Lys Lys His Phe Ser Ile Ile Leu Asn Leu Leu Gly Ile Leu<br>700                       705                     710 | 2466 |
| ctt aag aaa gat aac ctt aac cag gac acg agg aaa ctg tta atg act<br>Leu Lys Lys Asp Asn Leu Asn Gln Asp Thr Arg Lys Leu Leu Met Thr<br>715                       720                     725 | 2514 |
| tgg gct ttg gaa gca gct gtt tta atg agg aag tct gaa aca tac gca<br>Trp Ala Leu Glu Ala Ala Val Leu Met Arg Lys Ser Glu Thr Tyr Ala<br>730                       735                     740                     745 | 2562 |
| cct tta ttc tct ctt ccg tct ttc cat aaa ttt tgc aaa ggc ctt tta<br>Pro Leu Phe Ser Leu Pro Ser Phe His Lys Phe Cys Lys Gly Leu Leu<br>                   750                     755                     760 | 2610 |
| gcc aac act ctc gtt gaa gat gtg aat atc tgt ctg cag gca tgc agc<br>Ala Asn Thr Leu Val Glu Asp Val Asn Ile Cys Leu Gln Ala Cys Ser<br>765                       770                     775 | 2658 |
| agt cta cat gct ctg tcc tct tcc ttg cca gat gat ctt tta cag aga<br>Ser Leu His Ala Leu Ser Ser Ser Leu Pro Asp Asp Leu Leu Gln Arg<br>                   780                     785                     790 | 2706 |
| tgt gtc gat gtt tgc cgt gtt caa cta gtg cac agt gga act cgt att<br>Cys Val Asp Val Cys Arg Val Gln Leu Val His Ser Gly Thr Arg Ile<br>795                       800                     805 | 2754 |
| cga caa gca ttt gga aaa ctg ttg aaa tca att cct tta gat gtt gtc<br>Arg Gln Ala Phe Gly Lys Leu Leu Lys Ser Ile Pro Leu Asp Val Val<br>810                       815                     820                     825 | 2802 |
| cta agc aat aac aat cac aca gaa att caa gaa att tct tta gca tta<br>Leu Ser Asn Asn Asn His Thr Glu Ile Gln Glu Ile Ser Leu Ala Leu<br>                   830                     835                     840 | 2850 |
| aga agt cac atg agt aaa gca cca agt aat aca ttc cac ccc caa gat<br>Arg Ser His Met Ser Lys Ala Pro Ser Asn Thr Phe His Pro Gln Asp<br>845                       850                     855 | 2898 |
| ttc tct gat gtt att agt ttt att ttg tat ggg aac tct cat aga aca<br>Phe Ser Asp Val Ile Ser Phe Ile Leu Tyr Gly Asn Ser His Arg Thr<br>                   860                     865                     870 | 2946 |
| ggg aag gac aat tgg ttg gaa aga ctg ttc tat agc tgc cag aga ctg<br>Gly Lys Asp Asn Trp Leu Glu Arg Leu Phe Tyr Ser Cys Gln Arg Leu<br>875                       880                     885 | 2994 |
| gat aag cgt gac cag tca aca att cca cgc aat ctc ctg aag aca gat<br>Asp Lys Arg Asp Gln Ser Thr Ile Pro Arg Asn Leu Leu Lys Thr Asp<br>890                       895                     900                     905 | 3042 |
| gct gtc ctt tgg cag tgg gcc ata tgg gaa gct gca caa ttc act gtt<br>Ala Val Leu Trp Gln Trp Ala Ile Trp Glu Ala Ala Gln Phe Thr Val<br>                   910                     915                     920 | 3090 |
| ctt tct aag ctg aga acc cca ctg ggc aga gct caa gac acc ttc cag<br>Leu Ser Lys Leu Arg Thr Pro Leu Gly Arg Ala Gln Asp Thr Phe Gln<br>925                       930                     935 | 3138 |

```
aca att gaa ggt atc att cga agt ctc gca gct cac aca tta aac cct      3186
Thr Ile Glu Gly Ile Ile Arg Ser Leu Ala Ala His Thr Leu Asn Pro
            940                 945                 950 gat cag gat gtt agt cag tgg aca act gca gac aat gat gaa ggc cat      3234
Asp Gln Asp Val Ser Gln Trp Thr Thr Ala Asp Asn Asp Glu Gly His
    955                 960                 965 ggt aac aac caa ctt aga ctt gtt ctt ctt ctg cag tat ctg gaa aat      3282
Gly Asn Asn Gln Leu Arg Leu Val Leu Leu Leu Gln Tyr Leu Glu Asn
970                 975                 980                 985 ctg gag aaa tta atg tat aat gca tac gag gga tgt gct aat gca tta      3330
Leu Glu Lys Leu Met Tyr Asn Ala Tyr Glu Gly Cys Ala Asn Ala Leu
                990                 995                 1000 act tca cct ccc aag gtc att aga act ttt ttc tat acc aat cgc caa      3378
Thr Ser Pro Pro Lys Val Ile Arg Thr Phe Phe Tyr Thr Asn Arg Gln
            1005                1010                1015 act tgt cag gac tgg cta acg cgg att cga ctc tcc atc atg agg gta      3426
Thr Cys Gln Asp Trp Leu Thr Arg Ile Arg Leu Ser Ile Met Arg Val
        1020                1025                1030 gga ttg ttg gca ggc cag cct gca gtg aca gtg aga cat ggc ttt gac      3474
Gly Leu Leu Ala Gly Gln Pro Ala Val Thr Val Arg His Gly Phe Asp
    1035                1040                1045 ttg ctt aca gag atg aaa aca acc agc cta tct cag ggg aat gaa ttg      3522
Leu Leu Thr Glu Met Lys Thr Thr Ser Leu Ser Gln Gly Asn Glu Leu
1050                1055                1060                1065 gaa gta acc att atg atg gtg gta gaa gca tta tgt gaa ctt cat tgt      3570
Glu Val Thr Ile Met Met Val Val Glu Ala Leu Cys Glu Leu His Cys
                1070                1075                1080 cct gaa gct ata cag gga att gct gtc tgg tca tca tct att gtt gga      3618
Pro Glu Ala Ile Gln Gly Ile Ala Val Trp Ser Ser Ser Ile Val Gly
            1085                1090                1095 aaa aat ctt ctg tgg att aac tca gtg gct caa cag gct gaa ggg agg      3666
Lys Asn Leu Leu Trp Ile Asn Ser Val Ala Gln Gln Ala Glu Gly Arg
        1100                1105                1110 ttt gaa aag gcc tct gtg gag tac cag gaa cac ctg tgt gcc atg aca      3714
Phe Glu Lys Ala Ser Val Glu Tyr Gln Glu His Leu Cys Ala Met Thr
    1115                1120                1125 ggt gtt gat tgc tgc atc tcc agc ttt gac aaa tcg gtg ctc acc tta      3762
Gly Val Asp Cys Cys Ile Ser Ser Phe Asp Lys Ser Val Leu Thr Leu
1130                1135                1140                1145 gcc aat gct ggg cgt aac agt gcc agc ccg aaa cat tct ctg aat ggt      3810
Ala Asn Ala Gly Arg Asn Ser Ala Ser Pro Lys His Ser Leu Asn Gly
                1150                1155                1160 gaa tcc aga aaa act gtg ctg tcc aaa ccg act gac tct tcc cct gag      3858
Glu Ser Arg Lys Thr Val Leu Ser Lys Pro Thr Asp Ser Ser Pro Glu
            1165                1170                1175 gtt ata aat tat tta gga aat aaa gca tgt gag ttc tac atc tca att      3906
Val Ile Asn Tyr Leu Gly Asn Lys Ala Cys Glu Phe Tyr Ile Ser Ile
        1180                1185                1190 gcc gat tgg gct gct gtg cag gaa tgg cag aac gct atc cat gac ttg      3954
Ala Asp Trp Ala Ala Val Gln Glu Trp Gln Asn Ala Ile His Asp Leu
    1195                1200                1205 aaa aag agt acc agt agc act tcc ctc aac ctg aaa gct gac ttc aac      4002
Lys Lys Ser Thr Ser Ser Thr Ser Leu Asn Leu Lys Ala Asp Phe Asn
1210                1215                1220                1225 tat ata aaa tca tta agc agc ttt gag tct gga aaa ttt gtt gaa tgt      4050
Tyr Ile Lys Ser Leu Ser Ser Phe Glu Ser Gly Lys Phe Val Glu Cys
                1230                1235                1240 acc gag cag tta gaa ttg tta cca gga gaa aat atc aat cta ctt gct      4098
Thr Glu Gln Leu Glu Leu Leu Pro Gly Glu Asn Ile Asn Leu Leu Ala
            1245                1250                1255
```

```
gga gga tca aaa gaa aaa ata gac atg aaa aaa ctg ctt cct aac atg    4146
Gly Gly Ser Lys Glu Lys Ile Asp Met Lys Lys Leu Leu Pro Asn Met
        1260                1265                1270 tta agt ccg gat ccg agg gaa ctt cag aaa tcc att gaa gtt caa ttg    4194
Leu Ser Pro Asp Pro Arg Glu Leu Gln Lys Ser Ile Glu Val Gln Leu
    1275                1280                1285 tta aga agt tct gtt tgt ttg gca act gct tta aac ccg ata gaa caa    4242
Leu Arg Ser Ser Val Cys Leu Ala Thr Ala Leu Asn Pro Ile Glu Gln
1290                1295                1300                1305 gat cag aag tgg cag tct ata act gaa aat gtg gta aag tac ttg aag    4290
Asp Gln Lys Trp Gln Ser Ile Thr Glu Asn Val Val Lys Tyr Leu Lys
                1310                1315                1320 caa aca tcc cgc atc gct att gga cct ctg aga ctt tct act tta aca    4338
Gln Thr Ser Arg Ile Ala Ile Gly Pro Leu Arg Leu Ser Thr Leu Thr
            1325                1330                1335 gtt tca cag tct ttg cca gtt cta agt acc ttg cag ctg tat tgc tca    4386
Val Ser Gln Ser Leu Pro Val Leu Ser Thr Leu Gln Leu Tyr Cys Ser
        1340                1345                1350 tct gct ttg gag aac aca gtt tct aac aga ctt tca aca gag gac tgt    4434
Ser Ala Leu Glu Asn Thr Val Ser Asn Arg Leu Ser Thr Glu Asp Cys
    1355                1360                1365 ctt att cca ctc ttc agt gaa gct tta cgt tca tgt aaa cag cat gac    4482
Leu Ile Pro Leu Phe Ser Glu Ala Leu Arg Ser Cys Lys Gln His Asp
1370                1375                1380                1385 gtg agg cca tgg atg cag gca tta agg tat act atg tac cag aat cag    4530
Val Arg Pro Trp Met Gln Ala Leu Arg Tyr Thr Met Tyr Gln Asn Gln
                1390                1395                1400 ttg ttg gag aaa att aaa gaa caa aca gtc cca att aga agc cat ctc    4578
Leu Leu Glu Lys Ile Lys Glu Gln Thr Val Pro Ile Arg Ser His Leu
            1405                1410                1415 atg gaa tta ggt cta aca gca gca aaa ttt gct aga aaa cga ggg aat    4626
Met Glu Leu Gly Leu Thr Ala Ala Lys Phe Ala Arg Lys Arg Gly Asn
        1420                1425                1430 gtg tcc ctt gca aca aga ctg ctg gca cag tgc agt gaa gtt cag ctg    4674
Val Ser Leu Ala Thr Arg Leu Leu Ala Gln Cys Ser Glu Val Gln Leu
    1435                1440                1445 gga aag acc acc act gca cag gat tta gtc caa cat ttt aaa aaa cta    4722
Gly Lys Thr Thr Thr Ala Gln Asp Leu Val Gln His Phe Lys Lys Leu
1450                1455                1460                1465 tca acc caa ggt caa gtg gat gaa aaa tgg ggg ccc gaa ctt gat att    4770
Ser Thr Gln Gly Gln Val Asp Glu Lys Trp Gly Pro Glu Leu Asp Ile
                1470                1475                1480 gaa aaa acc aaa ttg ctt tat aca gca ggc cag tca aca cat gca atg    4818
Glu Lys Thr Lys Leu Leu Tyr Thr Ala Gly Gln Ser Thr His Ala Met
            1485                1490                1495 gaa atg ttg agt tct tgt gcc ata tct ttc tgc aag tct gtg aaa gct    4866
Glu Met Leu Ser Ser Cys Ala Ile Ser Phe Cys Lys Ser Val Lys Ala
        1500                1505                1510 gaa tat gca gtt gct aaa tca att ctg aca ctg gct aaa tgg atc cag    4914
Glu Tyr Ala Val Ala Lys Ser Ile Leu Thr Leu Ala Lys Trp Ile Gln
    1515                1520                1525 gca gaa tgg aaa gag att tca gga cag ctg aaa cag gtt tac aga gct    4962
Ala Glu Trp Lys Glu Ile Ser Gly Gln Leu Lys Gln Val Tyr Arg Ala
1530                1535                1540                1545 cag cac caa cag aac ttc aca ggt ctt tct act ttg tct aaa aac ata    5010
Gln His Gln Gln Asn Phe Thr Gly Leu Ser Thr Leu Ser Lys Asn Ile
                1550                1555                1560 ctc act cta ata gaa ctg cca tct gtt aat acg atg gaa gaa gag tat    5058
Leu Thr Leu Ile Glu Leu Pro Ser Val Asn Thr Met Glu Glu Glu Tyr
            1565                1570                1575
```

```
cct cgg atc gag agt gaa tct aca gtg cat att gga gtt gga gaa cct      5106
Pro Arg Ile Glu Ser Glu Ser Thr Val His Ile Gly Val Gly Glu Pro
            1580                1585                1590 gac ttc att ttg gga cag ttg tat cac ctg tct tca gta cag gca cct      5154
Asp Phe Ile Leu Gly Gln Leu Tyr His Leu Ser Ser Val Gln Ala Pro
1595                1600                1605 gaa gta gcc aaa tct tgg gca gcg ttg gcc agc tgg gct tat agg tgg      5202
Glu Val Ala Lys Ser Trp Ala Ala Leu Ala Ser Trp Ala Tyr Arg Trp
1610                1615                1620                1625 ggc aga aag gtg gtt gac aat gcc agt cag gga gaa ggt gtt cgt ctg      5250
Gly Arg Lys Val Val Asp Asn Ala Ser Gln Gly Glu Gly Val Arg Leu
                1630                1635                1640 ctg cct aga gaa aaa tct gaa gtt cag aat cta ctt cca gac act ata      5298
Leu Pro Arg Glu Lys Ser Glu Val Gln Asn Leu Leu Pro Asp Thr Ile
            1645                1650                1655 act gag gaa gag aaa gag aga ata tat ggt att ctt gga cag gct gtg      5346
Thr Glu Glu Glu Lys Glu Arg Ile Tyr Gly Ile Leu Gly Gln Ala Val
        1660                1665                1670 tgt cgg ccg gcg ggg att cag gat gaa gat ata aca ctt cag ata act      5394
Cys Arg Pro Ala Gly Ile Gln Asp Glu Asp Ile Thr Leu Gln Ile Thr
    1675                1680                1685 gag agt gaa gac aac gaa gaa gat gac atg gtt gat gtt atc tgg cgt      5442
Glu Ser Glu Asp Asn Glu Glu Asp Asp Met Val Asp Val Ile Trp Arg
1690                1695                1700                1705 cag ttg ata tca agc tgc cca tgg ctt tca gaa ctt gat gaa agt gca      5490
Gln Leu Ile Ser Ser Cys Pro Trp Leu Ser Glu Leu Asp Glu Ser Ala
                1710                1715                1720 act gaa gga gtt att aaa gtg tgg agg aaa gtt gta gat aga ata ttc      5538
Thr Glu Gly Val Ile Lys Val Trp Arg Lys Val Val Asp Arg Ile Phe
            1725                1730                1735 agc ctg tac aaa ctc tct tgc agt gca tac ttt act ttc ctt aaa ctc      5586
Ser Leu Tyr Lys Leu Ser Cys Ser Ala Tyr Phe Thr Phe Leu Lys Leu
        1740                1745                1750 aac gct ggt caa att cct tta gat gag gat gac cct agg ctg cat tta      5634
Asn Ala Gly Gln Ile Pro Leu Asp Glu Asp Asp Pro Arg Leu His Leu
    1755                1760                1765 agt cac aga gtg gaa cag agc act gat gac atg att gtg atg gcc aca      5682
Ser His Arg Val Glu Gln Ser Thr Asp Asp Met Ile Val Met Ala Thr
1770                1775                1780                1785 ttg cgc ctg ctg cgg ttg ctc gtg aag cat gct ggt gag ctt cgg cag      5730
Leu Arg Leu Leu Arg Leu Leu Val Lys His Ala Gly Glu Leu Arg Gln
                1790                1795                1800 tat ctg gag cac ggc ttg gag aca aca ccc act gca cca tgg agg gga      5778
Tyr Leu Glu His Gly Leu Glu Thr Thr Pro Thr Ala Pro Trp Arg Gly
            1805                1810                1815 att att ccg caa ctt ttc tca cgc tta aac cac cct gaa gtg tat gtg      5826
Ile Ile Pro Gln Leu Phe Ser Arg Leu Asn His Pro Glu Val Tyr Val
        1820                1825                1830 cgc caa agt att tgt aac ctt ctc tgc cgt gtg gct caa gat tcc cca      5874
Arg Gln Ser Ile Cys Asn Leu Leu Cys Arg Val Ala Gln Asp Ser Pro
    1835                1840                1845 cat ctc ata ttg tat cct gca ata gtg ggt acc ata tcg ctt agt agt      5922
His Leu Ile Leu Tyr Pro Ala Ile Val Gly Thr Ile Ser Leu Ser Ser
1850                1855                1860                1865 gaa tcc cag gct tca gga aat aaa ttt tcc act gca att cca act tta      5970
Glu Ser Gln Ala Ser Gly Asn Lys Phe Ser Thr Ala Ile Pro Thr Leu
                1870                1875                1880 ctt ggc aat att caa gga gaa gaa ttg ctg gtt tct gaa tgt gag gga      6018
Leu Gly Asn Ile Gln Gly Glu Glu Leu Leu Val Ser Glu Cys Glu Gly
            1885                1890                1895
```

```
gga agt cct cct gca tct cag gat agc aat aag gat gaa cct aaa agt    6066
Gly Ser Pro Pro Ala Ser Gln Asp Ser Asn Lys Asp Glu Pro Lys Ser
            1900                1905                1910 gga tta aat gaa gac caa gcc atg atg cag gat tgt tac agc aaa att    6114
Gly Leu Asn Glu Asp Gln Ala Met Met Gln Asp Cys Tyr Ser Lys Ile
1915                1920                1925 gta gat aag ctg tcc tct gca aac ccc acc atg gta tta cag gtt cag    6162
Val Asp Lys Leu Ser Ser Ala Asn Pro Thr Met Val Leu Gln Val Gln
1930                1935                1940                1945 atg ctc gtg gct gaa ctg cgc agg gtc act gtg ctc tgg gat gag ctc    6210
Met Leu Val Ala Glu Leu Arg Arg Val Thr Val Leu Trp Asp Glu Leu
            1950                1955                1960 tgg ctg gga gtt ttg ctg caa caa cac atg tat gtc ctg aga cga att    6258
Trp Leu Gly Val Leu Leu Gln Gln His Met Tyr Val Leu Arg Arg Ile
            1965                1970                1975 cag cag ctt gaa gat gag gtg aag aga gtc cag aac aac aac acc tta    6306
Gln Gln Leu Glu Asp Glu Val Lys Arg Val Gln Asn Asn Asn Thr Leu
        1980                1985                1990 cgc aaa gaa gag aaa att gca atc atg agg gag agg cac aca gct ttg    6354
Arg Lys Glu Glu Lys Ile Ala Ile Met Arg Glu Arg His Thr Ala Leu
1995                2000                2005 atg aag ccc atc gta ttt gct ttg gag cat gtg agg agt atc aca gcg    6402
Met Lys Pro Ile Val Phe Ala Leu Glu His Val Arg Ser Ile Thr Ala
2010                2015                2020                2025 gct cct gca gaa aca cct cat gaa aaa tgg ttt cag gat aac tat ggt    6450
Ala Pro Ala Glu Thr Pro His Glu Lys Trp Phe Gln Asp Asn Tyr Gly
            2030                2035                2040 gat gcc att gaa aat gcc cta gaa aaa ctg aag act cca ttg aac cct    6498
Asp Ala Ile Glu Asn Ala Leu Glu Lys Leu Lys Thr Pro Leu Asn Pro
            2045                2050                2055 gca aag cct ggg agc agc tgg att cca ttt aaa gag ata atg cta agt    6546
Ala Lys Pro Gly Ser Ser Trp Ile Pro Phe Lys Glu Ile Met Leu Ser
            2060                2065                2070 ttg caa cag aga gca cag aaa cgt gca agt tac atc ttg cgt ctt gaa    6594
Leu Gln Gln Arg Ala Gln Lys Arg Ala Ser Tyr Ile Leu Arg Leu Glu
        2075                2080                2085 gaa atc agt cca tgg ttg gct gcc atg act aac act gaa att gct ctt    6642
Glu Ile Ser Pro Trp Leu Ala Ala Met Thr Asn Thr Glu Ile Ala Leu
2090                2095                2100                2105 cct ggg gaa gtc tca gcc aga gac act gtc aca atc cat agt gtg ggc    6690
Pro Gly Glu Val Ser Ala Arg Asp Thr Val Thr Ile His Ser Val Gly
            2110                2115                2120 gga acc atc aca atc tta ccg act aaa acc aag cca aag aaa ctt ctc    6738
Gly Thr Ile Thr Ile Leu Pro Thr Lys Thr Lys Pro Lys Lys Leu Leu
            2125                2130                2135 ttt ctt gga tca gat ggg aag agc tat cct tat ctt ttc aaa gga ctg    6786
Phe Leu Gly Ser Asp Gly Lys Ser Tyr Pro Tyr Leu Phe Lys Gly Leu
            2140                2145                2150 gag gat tta cat ctg gat gag aga ata atg cag ttc cta tct att gtg    6834
Glu Asp Leu His Leu Asp Glu Arg Ile Met Gln Phe Leu Ser Ile Val
            2155                2160                2165 aat acc atg ttt gct aca att aat cgc caa gaa aca ccc cgg ttc cat    6882
Asn Thr Met Phe Ala Thr Ile Asn Arg Gln Glu Thr Pro Arg Phe His
2170                2175                2180                2185 gct cga cac tat tct gta aca cca cta gga aca aga tca gga cta atc    6930
Ala Arg His Tyr Ser Val Thr Pro Leu Gly Thr Arg Ser Gly Leu Ile
            2190                2195                2200 cag tgg gta gat gga gcc aca ccc tta ttt ggt ctt tac aaa cga tgg    6978
Gln Trp Val Asp Gly Ala Thr Pro Leu Phe Gly Leu Tyr Lys Arg Trp
        2205                2210                2215
```

```
caa caa cgg gaa gct gcc tta caa gca caa aag gcc caa gat tcc tac      7026
Gln Gln Arg Glu Ala Ala Leu Gln Ala Gln Lys Ala Gln Asp Ser Tyr
        2220                2225                2230 caa act cct cag aat cct gga att gta ccc cgt cct agt gaa ctt tat      7074
Gln Thr Pro Gln Asn Pro Gly Ile Val Pro Arg Pro Ser Glu Leu Tyr
    2235                2240                2245 tac agt aaa att ggc cct gct ttg aaa aca gtt ggg ctt agc ctg gat      7122
Tyr Ser Lys Ile Gly Pro Ala Leu Lys Thr Val Gly Leu Ser Leu Asp
2250                2255                2260                2265 gtg tcc cgt cgg gat tgg cct ctt cat gta atg aag gca gta ttg gaa      7170
Val Ser Arg Arg Asp Trp Pro Leu His Val Met Lys Ala Val Leu Glu
                2270                2275                2280 gag tta atg gag gcc aca ccc ccg aat ctc ctt gcc aaa gag ctc tgg      7218
Glu Leu Met Glu Ala Thr Pro Pro Asn Leu Leu Ala Lys Glu Leu Trp
            2285                2290                2295 tca tct tgc aca aca cct gat gaa tgg tgg aga gtt acg cag tct tat      7266
Ser Ser Cys Thr Thr Pro Asp Glu Trp Trp Arg Val Thr Gln Ser Tyr
        2300                2305                2310 gca aga tct act gca gtc atg tct atg gtt gga tac ata att ggc ctt      7314
Ala Arg Ser Thr Ala Val Met Ser Met Val Gly Tyr Ile Ile Gly Leu
    2315                2320                2325 gga gac aga cat ctg gat aat gtt ctt ata gat atg acg act gga gaa      7362
Gly Asp Arg His Leu Asp Asn Val Leu Ile Asp Met Thr Thr Gly Glu
2330                2335                2340                2345 gtt gtt cac ata gat tac aat gtt tgc ttt gaa aaa ggt aaa agc ctt      7410
Val Val His Ile Asp Tyr Asn Val Cys Phe Glu Lys Gly Lys Ser Leu
                2350                2355                2360 aga gtt cct gag aaa gta cct ttt cga atg aca caa aac att gaa aca      7458
Arg Val Pro Glu Lys Val Pro Phe Arg Met Thr Gln Asn Ile Glu Thr
            2365                2370                2375 gca ctg ggt gta act gga gta gaa ggt gta ttt agg ctt tca tgt gag      7506
Ala Leu Gly Val Thr Gly Val Glu Gly Val Phe Arg Leu Ser Cys Glu
        2380                2385                2390 cag gtt tta cac att atg cgg cgt ggc aga gag acc ctg ctg acg ctg      7554
Gln Val Leu His Ile Met Arg Arg Gly Arg Glu Thr Leu Leu Thr Leu
    2395                2400                2405 ctg gag gcc ttt gtg tac gac cct ctg gtg gac tgg aca gca gga ggc      7602
Leu Glu Ala Phe Val Tyr Asp Pro Leu Val Asp Trp Thr Ala Gly Gly
2410                2415                2420                2425 gag gct ggg ttt gct ggt gct gtc tat ggt gga ggt ggc cag cag gcc      7650
Glu Ala Gly Phe Ala Gly Ala Val Tyr Gly Gly Gly Gly Gln Gln Ala
                2430                2435                2440 gag agc aag cag agc aag aga gag atg gag cga gag atc acc cgc agc      7698
Glu Ser Lys Gln Ser Lys Arg Glu Met Glu Arg Glu Ile Thr Arg Ser
            2445                2450                2455 ctg ttt tct tct aga gta gct gag att aag gtg aac tgg ttt aag aat      7746
Leu Phe Ser Ser Arg Val Ala Glu Ile Lys Val Asn Trp Phe Lys Asn
        2460                2465                2470 aga gat gag atg ctg gtt gtg ctt ccc aag ttg gac ggt agc tta gat      7794
Arg Asp Glu Met Leu Val Val Leu Pro Lys Leu Asp Gly Ser Leu Asp
    2475                2480                2485 gaa tac cta agc ttg caa gag caa ctg aca gat gtg gaa aaa ctg cag      7842
Glu Tyr Leu Ser Leu Gln Glu Gln Leu Thr Asp Val Glu Lys Leu Gln
2490                2495                2500                2505 ggc aaa cta ctg gag gaa ata gag ttt cta gaa gga gct gaa ggg gtg      7890
Gly Lys Leu Leu Glu Glu Ile Glu Phe Leu Glu Gly Ala Glu Gly Val
                2510                2515                2520 gat cat cct tct cat act ctg caa cac agg tat tct gag cac acc caa      7938
Asp His Pro Ser His Thr Leu Gln His Arg Tyr Ser Glu His Thr Gln
            2525                2530                2535
```

```
cta cag act cag caa aga gct gtt cag gaa gca atc cag gtg aag ctg         7986
Leu Gln Thr Gln Gln Arg Ala Val Gln Glu Ala Ile Gln Val Lys Leu
        2540                2545                2550 aat gaa ttt gaa caa tgg ata aca cat tat cag gct gca ttc aat aat         8034
Asn Glu Phe Glu Gln Trp Ile Thr His Tyr Gln Ala Ala Phe Asn Asn
        2555                2560                2565 tta gaa gca aca cag ctt gca agc ttg ctt caa gag ata agc aca caa         8082
Leu Glu Ala Thr Gln Leu Ala Ser Leu Leu Gln Glu Ile Ser Thr Gln
2570                2575                2580                2585 atg gac ctt ggt cct cca agt tac gtg cca gca aca gcc ttt ctg cag         8130
Met Asp Leu Gly Pro Pro Ser Tyr Val Pro Ala Thr Ala Phe Leu Gln
                2590                2595                2600 aat gct ggt cag gcc cac ttg att agc cag tgc gag cag ctg gag ggg         8178
Asn Ala Gly Gln Ala His Leu Ile Ser Gln Cys Glu Gln Leu Glu Gly
                2605                2610                2615 gag gtt ggt gct ctc ctg cag cag agg cgc tcc gtg ctc cgt ggc tgt         8226
Glu Val Gly Ala Leu Leu Gln Gln Arg Arg Ser Val Leu Arg Gly Cys
                2620                2625                2630 ctg gag caa ctg cat cac tat gca acc gtg gcc ctg cag tat ccg aag         8274
Leu Glu Gln Leu His His Tyr Ala Thr Val Ala Leu Gln Tyr Pro Lys
                2635                2640                2645 gcc ata ttt cag aaa cat cga att gaa cag tgg aag acc tgg atg gaa         8322
Ala Ile Phe Gln Lys His Arg Ile Glu Gln Trp Lys Thr Trp Met Glu
2650                2655                2660                2665 gag ctc atc tgt aac acc aca gta gag cgt tgt caa gag ctc tat agg         8370
Glu Leu Ile Cys Asn Thr Thr Val Glu Arg Cys Gln Glu Leu Tyr Arg
                2670                2675                2680 aaa tat gaa atg caa tat gct ccc cag cca ccc cca aca gtg tgt cag         8418
Lys Tyr Glu Met Gln Tyr Ala Pro Gln Pro Pro Pro Thr Val Cys Gln
                2685                2690                2695 ttc atc act gcc act gaa atg acc ctg cag cga tac gca gca gac atc         8466
Phe Ile Thr Ala Thr Glu Met Thr Leu Gln Arg Tyr Ala Ala Asp Ile
                2700                2705                2710 aac agc aga ctt att aga caa gtg gaa cgc ttg aaa cag gaa gct gtc         8514
Asn Ser Arg Leu Ile Arg Gln Val Glu Arg Leu Lys Gln Glu Ala Val
                2715                2720                2725 act gtg cca gtt tgt gaa gat cag ttg aaa gaa att gaa cgt tgc att         8562
Thr Val Pro Val Cys Glu Asp Gln Leu Lys Glu Ile Glu Arg Cys Ile
2730                2735                2740                2745 aaa gtt ttc ctt cat gag aat gga gaa gaa gga tct ttg agt cta gca         8610
Lys Val Phe Leu His Glu Asn Gly Glu Glu Gly Ser Leu Ser Leu Ala
                2750                2755                2760 agt gtt att att tct gcc ctt tgt acc ctt aca agg cgt aac ctg atg         8658
Ser Val Ile Ile Ser Ala Leu Cys Thr Leu Thr Arg Arg Asn Leu Met
                2765                2770                2775 atg gaa ggt gca gcg tca agt gct gga gaa cag ctg gtt gat ctg act         8706
Met Glu Gly Ala Ala Ser Ser Ala Gly Glu Gln Leu Val Asp Leu Thr
                2780                2785                2790 tct cgg gat gga gcc tgg ttc ttg gag gaa ctc tgc agt atg agc gga         8754
Ser Arg Asp Gly Ala Trp Phe Leu Glu Glu Leu Cys Ser Met Ser Gly
        2795                2800                2805 aac gtc acc tgc ttg gtt cag tta ctg aag cag tgc cac ctg gtg cca         8802
Asn Val Thr Cys Leu Val Gln Leu Leu Lys Gln Cys His Leu Val Pro
2810                2815                2820                2825 cag gac tta gat atc ccg aac ccc atg gaa gcg tct gag aca gtt cac         8850
Gln Asp Leu Asp Ile Pro Asn Pro Met Glu Ala Ser Glu Thr Val His
                2830                2835                2840 tta gcc aat gga gtg tat acc tca ctt cag gaa ttg aat tcg aat ttc         8898
Leu Ala Asn Gly Val Tyr Thr Ser Leu Gln Glu Leu Asn Ser Asn Phe
        2845                2850                2855
```

```
                                                           -continued
cgg caa atc ata ttt cca gaa gca ctt cga tgt tta atg aaa ggg gaa       8946
Arg Gln Ile Ile Phe Pro Glu Ala Leu Arg Cys Leu Met Lys Gly Glu
        2860                2865                2870 tac acg tta gaa agt atg ctg cat gaa ctg gac ggt ctt att gag cag       8994
Tyr Thr Leu Glu Ser Met Leu His Glu Leu Asp Gly Leu Ile Glu Gln
    2875                2880                2885 acc acc gat ggc gtt ccc ctg cag act cta gtg gaa tct ctt cag gcc       9042
Thr Thr Asp Gly Val Pro Leu Gln Thr Leu Val Glu Ser Leu Gln Ala
2890                2895                2900                2905 tac tta aga aac gca gct atg gga ctg gaa gaa gaa aca cat gct cat       9090
Tyr Leu Arg Asn Ala Ala Met Gly Leu Glu Glu Glu Thr His Ala His
            2910                2915                2920 tac atc gat gtt gcc aga cta cta cat gct cag tac ggt gaa tta atc       9138
Tyr Ile Asp Val Ala Arg Leu Leu His Ala Gln Tyr Gly Glu Leu Ile
        2925                2930                2935 caa ccg aga aat ggt tca gtt gat gaa aca ccc aaa atg tca gct ggc       9186
Gln Pro Arg Asn Gly Ser Val Asp Glu Thr Pro Lys Met Ser Ala Gly
        2940                2945                2950 cag atg ctt ttg gta gca ttc gat ggc atg ttt gct caa gtt gaa act       9234
Gln Met Leu Leu Val Ala Phe Asp Gly Met Phe Ala Gln Val Glu Thr
    2955                2960                2965 gct ttc agc tta tta gtt gaa aag ttg aac aag atg gaa att ccc ata       9282
Ala Phe Ser Leu Leu Val Glu Lys Leu Asn Lys Met Glu Ile Pro Ile
2970                2975                2980                2985 gct tgg cga aag att gac atc ata agg gaa gcc agg agt act caa gtt       9330
Ala Trp Arg Lys Ile Asp Ile Ile Arg Glu Ala Arg Ser Thr Gln Val
            2990                2995                3000 aat ttt ttt gat gat gat aat cac cgg cag gtg cta gaa gag att ttc       9378
Asn Phe Phe Asp Asp Asp Asn His Arg Gln Val Leu Glu Glu Ile Phe
        3005                3010                3015 ttt cta aaa aga cta cag act att aag gag ttc ttc agg ctc tgt ggt       9426
Phe Leu Lys Arg Leu Gln Thr Ile Lys Glu Phe Phe Arg Leu Cys Gly
    3020                3025                3030 acc ttt tct aaa aca ttg tca gga tca agt tca ctt gaa gat cag aat       9474
Thr Phe Ser Lys Thr Leu Ser Gly Ser Ser Ser Leu Glu Asp Gln Asn
3035                3040                3045 act gtg aat ggg cct gta cag att gtc aat gtg aaa acc ctt ttt aga       9522
Thr Val Asn Gly Pro Val Gln Ile Val Asn Val Lys Thr Leu Phe Arg
3050                3055                3060                3065 aac tct tgt ttc agt gaa gac caa atg gcc aaa cct atc aag gca ttc       9570
Asn Ser Cys Phe Ser Glu Asp Gln Met Ala Lys Pro Ile Lys Ala Phe
            3070                3075                3080 aca gct gac ttt gtg agg cag ctc ttg ata ggg cta ccc aac caa gcc       9618
Thr Ala Asp Phe Val Arg Gln Leu Leu Ile Gly Leu Pro Asn Gln Ala
        3085                3090                3095 ctc gga ctc aca ctg tgc agt ttt atc agt gct ctg ggt gta gac atc       9666
Leu Gly Leu Thr Leu Cys Ser Phe Ile Ser Ala Leu Gly Val Asp Ile
    3100                3105                3110 att gct caa gta gag gca aag gac ttt ggt gcc gaa agc aaa gtt tct       9714
Ile Ala Gln Val Glu Ala Lys Asp Phe Gly Ala Glu Ser Lys Val Ser
3115                3120                3125 gtt gat gat ctc tgt aag aaa gcg gtg gaa cat aac atc cag ata ggg       9762
Val Asp Asp Leu Cys Lys Lys Ala Val Glu His Asn Ile Gln Ile Gly
3130                3135                3140                3145 aag ttc tct cag ctg gtt atg aac agg gca act gtg tta gca agt tct       9810
Lys Phe Ser Gln Leu Val Met Asn Arg Ala Thr Val Leu Ala Ser Ser
            3150                3155                3160 tac gac act gcc tgg aag aag cat gac ttg gtg cga agg cta gaa acc       9858
Tyr Asp Thr Ala Trp Lys Lys His Asp Leu Val Arg Arg Leu Glu Thr
        3165                3170                3175
```

```
agt att tct tct tgt aag aca agc ctg cag cgg gtt cag ctg cat att    9906
Ser Ile Ser Ser Cys Lys Thr Ser Leu Gln Arg Val Gln Leu His Ile
        3180                3185                3190 gcc atg ttt cag tgg caa cat gaa gat cta ctt atc aat aga cca caa    9954
Ala Met Phe Gln Trp Gln His Glu Asp Leu Leu Ile Asn Arg Pro Gln
3195                3200                3205 gcc atg tca gtc aca cct ccc cca cgg tct gct atc cta acc agc atg   10002
Ala Met Ser Val Thr Pro Pro Pro Arg Ser Ala Ile Leu Thr Ser Met
3210                3215                3220                3225 aaa aag aag ctg cat acc ctg agc cag att gaa act tct att gcg aca   10050
Lys Lys Lys Leu His Thr Leu Ser Gln Ile Glu Thr Ser Ile Ala Thr
                3230                3235                3240 gtt cag gag aag cta gct gca ctt gaa tca agt att gaa cag cga ctc   10098
Val Gln Glu Lys Leu Ala Ala Leu Glu Ser Ser Ile Glu Gln Arg Leu
        3245                3250                3255 aag tgg gca ggt ggt gcc aac cct gca ttg gcc cct gta cta caa gat   10146
Lys Trp Ala Gly Gly Ala Asn Pro Ala Leu Ala Pro Val Leu Gln Asp
        3260                3265                3270 ttt gaa gca acg ata gct gaa aga aga aat ctt gtc ctt aaa gag agc   10194
Phe Glu Ala Thr Ile Ala Glu Arg Arg Asn Leu Val Leu Lys Glu Ser
        3275                3280                3285 caa aga gca agt cag gtc aca ttt ctc tgc agc aat atc att cat ttt   10242
Gln Arg Ala Ser Gln Val Thr Phe Leu Cys Ser Asn Ile Ile His Phe
3290                3295                3300                3305 gaa agt tta cga aca aga act gca gaa gcc tta aac ctg gat gcg gcg   10290
Glu Ser Leu Arg Thr Arg Thr Ala Glu Ala Leu Asn Leu Asp Ala Ala
                3310                3315                3320 tta ttt gaa cta atc aag cga tgt cag cag atg tgt tcg ttt gca tca   10338
Leu Phe Glu Leu Ile Lys Arg Cys Gln Gln Met Cys Ser Phe Ala Ser
        3325                3330                3335 cag ttt aac agt tca gtg tct gag tta gag ctt cgt tta tta cag aga   10386
Gln Phe Asn Ser Ser Val Ser Glu Leu Glu Leu Arg Leu Leu Gln Arg
        3340                3345                3350 gtg gac act ggt ctt gaa cat cct att ggc agc tct gaa tgg ctt ttg   10434
Val Asp Thr Gly Leu Glu His Pro Ile Gly Ser Ser Glu Trp Leu Leu
        3355                3360                3365 tca gca cac aaa cag ttg acc cag gat atg tct act cag agg gca att   10482
Ser Ala His Lys Gln Leu Thr Gln Asp Met Ser Thr Gln Arg Ala Ile
3370                3375                3380                3385 cag aca gag aaa gag cag cag ata gaa acg gtc tgt gaa aca att cag   10530
Gln Thr Glu Lys Glu Gln Gln Ile Glu Thr Val Cys Glu Thr Ile Gln
                3390                3395                3400 aat ctg gtt gat aat ata aag act gtg ctc act ggt cat aac cga cag   10578
Asn Leu Val Asp Asn Ile Lys Thr Val Leu Thr Gly His Asn Arg Gln
        3405                3410                3415 ctt gga gat gtc aaa cat ctc ttg aaa gct atg gct aag gat gaa gaa   10626
Leu Gly Asp Val Lys His Leu Leu Lys Ala Met Ala Lys Asp Glu Glu
        3420                3425                3430 gct gct ctg gca gat ggt gaa gat gtt ccc tat gag aac agt gtt agg   10674
Ala Ala Leu Ala Asp Gly Glu Asp Val Pro Tyr Glu Asn Ser Val Arg
        3435                3440                3445 cag ttt ttg ggt gaa tat aaa tca tgg caa gac aac att caa aca gtt   10722
Gln Phe Leu Gly Glu Tyr Lys Ser Trp Gln Asp Asn Ile Gln Thr Val
3450                3455                3460                3465 cta ttt aca tta gtc cag gct atg ggt cag gtt cga agt caa gaa cac   10770
Leu Phe Thr Leu Val Gln Ala Met Gly Gln Val Arg Ser Gln Glu His
        3470                3475                3480 gtt gaa atg ctc cag gaa atc act ccc acc ttg aaa gaa ctg aaa aca   10818
Val Glu Met Leu Gln Glu Ile Thr Pro Thr Leu Lys Glu Leu Lys Thr
        3485                3490                3495
```

| | |
|---|---|
| caa agt cag agt atc tat aat aat tta gtg agt ttt gca tca ccc tta<br>Gln Ser Gln Ser Ile Tyr Asn Asn Leu Val Ser Phe Ala Ser Pro Leu<br>        3500                   3505                  3510 | 10866 |
| gtc acc gat gca aca aat gaa tgt tcg agt cca acg tca tct gct act<br>Val Thr Asp Ala Thr Asn Glu Cys Ser Ser Pro Thr Ser Ser Ala Thr<br>3515                   3520                   3525 | 10914 |
| tat cag cca tcc ttc gct gca gca gtc cgg agt aac act ggc cag aag<br>Tyr Gln Pro Ser Phe Ala Ala Ala Val Arg Ser Asn Thr Gly Gln Lys<br>3530                   3535                   3540                   3545 | 10962 |
| act cag cct gat gtc atg tca cag aat gct aga aag ctg atc cag aaa<br>Thr Gln Pro Asp Val Met Ser Gln Asn Ala Arg Lys Leu Ile Gln Lys<br>                   3550                   3555                   3560 | 11010 |
| aat ctt gct aca tca gct gat act cca cca agc acc gtt cca gga act<br>Asn Leu Ala Thr Ser Ala Asp Thr Pro Pro Ser Thr Val Pro Gly Thr<br>        3565                   3570                   3575 | 11058 |
| ggc aag agt gtt gct tgt agt cct aaa aag gca gtc aga gac cct aaa<br>Gly Lys Ser Val Ala Cys Ser Pro Lys Lys Ala Val Arg Asp Pro Lys<br>                   3580                   3585                   3590 | 11106 |
| act ggg aaa gcg gtg caa gag aga aac tcc tat gca gtg agt gtg tgg<br>Thr Gly Lys Ala Val Gln Glu Arg Asn Ser Tyr Ala Val Ser Val Trp<br>        3595                   3600                   3605 | 11154 |
| aag aga gtg aaa gcc aag tta gag ggc cga gat gtt gat ccg aat agg<br>Lys Arg Val Lys Ala Lys Leu Glu Gly Arg Asp Val Asp Pro Asn Arg<br>3610                   3615                   3620                   3625 | 11202 |
| agg atg tca gtt gct gaa cag gtt gac tat gtc att aag gaa gca act<br>Arg Met Ser Val Ala Glu Gln Val Asp Tyr Val Ile Lys Glu Ala Thr<br>                   3630                   3635                   3640 | 11250 |
| aat cta gat aac ttg gct cag ctg tat gaa ggt tgg aca gcc tgg gtg<br>Asn Leu Asp Asn Leu Ala Gln Leu Tyr Glu Gly Trp Thr Ala Trp Val<br>        3645                   3650                   3655 | 11298 |
| tgaatggcaa gacagtagat gagtctggtt aagcgaggtc agacatccac cagaatcaac | 11358 |
| tcagcctcag gcatccaaag ccacaccaca gtcggtggtg atgcaactgg gggcttactc | 11418 |
| tgaggaaacc taggaaatct cggtgcacta ggaagtgaat cccgcaggac agctgcactc | 11478 |
| agggatacgc ccaacaccat ggcctgcaac cccagggtca agggtgaagg aaagcaaagc | 11538 |
| tcaccgcctg aacacggaga ttgtctttct gccacagaac agcagcagac gtgtcgggag | 11598 |
| gttagctgcg gaaagaaatc gggatgccgc ggagcacaga gtgatttgga actccattcc | 11658 |
| acctgaccct gtgtgtacaa tccaggaaaa aaacaaaccc cactcagaaa cagagaaaac | 11718 |
| tggggtcgcg aagaaatcac agccaaggaa gatttgatgc attcagattc tcgtgtaaca | 11778 |
| cttgttgctt ggcaacagta ctggttgggt tgaccagtaa gtagaaaaag gctaaaggct | 11838 |
| atgcgatatg aatttcagaa atggactgaa aatggagagc tatgtaacag atacactaca | 11898 |
| gtagaagaac ttacttctga aatgaaggga aaaaaccac cccatcgttc cctactcctc | 11958 |
| cccaccactt acccgttccc cctttaccta atctagtaga ttagccatct ttcaaattca | 12018 |
| cttttatttc agtccttata tttcatatac ttccgtctcg atgctgttaa caacttctga | 12078 |
| taacatggaa aattcaagga ttgtttaaag gtctgatgat cacacacaaa atgtaattcc | 12138 |
| ggttatttaa gtcatttctg tgattctatc atgtacagtt tccagaattg tcactgtgca | 12198 |
| ttcaaaagta atgaatctaa cagacatttg atttaatgta cactcccttt gcttatagt | 12258 |
| gtgcattttt tttggaggtc attcaaattt tccctcttct gtgatagctg tagtttcttt | 12318 |
| catagaaagt agctaatcca gtgtaatctt ttacctttt aaaaaccaag atagagtatc | 12378 |
| tattagagtt ttacattgtt gatgatagat taacaataaa gtgatgttct ggtgaggta | 12438 |
| gactgaaatt tttttaattc atgtttttca tttgatactt ttaatttaca cttagtaaat | 12498 |

-continued

```
taaaagttgt ttaatttact tggcatttta ggacatgtac atgaaacagt gaaaatgaga    12558
tccaccaaca tcttttatta agttcagtta ttagtctgtg aagtgcttta cttttttgcac   12618 aattttaata gcttgctatt cagtaataca ttatagtgaa ttcatgatca aggtttcctt    12678
aaatttagca ttgcatttca gtactgactg tgtaagctaa attgctgatc caaaataaaa   12738
acccagacta gaatagggtt cttaaaatca agtatcaata caaaatagaa cacaattaaa    12798
atcttaattg ttggctgggc acagtggctc acgcctgtaa tcccagcact ttgggaggcc    12858
gaggcgggcg gatcatgagg ttaggagagc gagaccatcc tggctaacac ggtgaaaccc    12918
cgtctttact aaaatacaaa aaaattagc cgggtgtggt ggcgggcgcc tgtagtccca     12978
gctactcggg aggctgaggc aggagaatgg cgtgaaccca ggaggcggag cttgcagtga    13038
gccgagattg tgccactgca ctccagcctg ggcaacagag ctagactctg tgtcaaaaat    13098
aaatgactag at                                                        13110
```

<210> SEQ ID NO 10
<211> LENGTH: 3657
<212> TYPE: PRT
<213> ORGANISM: Homo sapiens

<400> SEQUENCE: 10

```
Met Ser Arg Arg Ala Pro Gly Ser Arg Leu Ser Ser Gly Gly Thr Asn
1               5                   10                  15

Tyr Ser Arg Ser Trp Asn Asp Trp Gln Pro Arg Thr Asp Ser Ala Ser
                20                  25                  30

Ala Asp Pro Gly Asn Leu Lys Tyr Ser Ser Arg Asp Arg Gly Gly
            35                  40                  45

Ser Ser Ser Tyr Gly Leu Gln Pro Ser Asn Ser Ala Val Val Ser Arg
        50                  55                  60

Gln Arg His Asp Asp Thr Arg Val His Ala Asp Ile Gln Asn Asp Glu
65                  70                  75                  80

Lys Gly Gly Tyr Ser Val Asn Gly Gly Ser Gly Glu Asn Thr Tyr Gly
                85                  90                  95

Arg Lys Ser Leu Gly Gln Glu Leu Arg Val Asn Asn Val Thr Ser Pro
            100                 105                 110

Glu Phe Thr Ser Val Gln His Gly Ser Arg Ala Leu Ala Thr Lys Asp
        115                 120                 125

Met Arg Lys Ser Gln Glu Arg Ser Met Ser Tyr Ser Asp Glu Ser Arg
    130                 135                 140

Leu Ser Asn Leu Leu Arg Arg Ile Thr Arg Glu Asp Asp Arg Asp Arg
145                 150                 155                 160

Arg Leu Ala Thr Val Lys Gln Leu Lys Glu Phe Ile Gln Gln Pro Glu
                165                 170                 175

Asn Lys Leu Val Leu Val Lys Gln Leu Asp Asn Ile Leu Ala Ala Val
            180                 185                 190

His Asp Val Leu Asn Glu Ser Ser Lys Leu Leu Gln Glu Leu Arg Gln
        195                 200                 205

Glu Gly Ala Cys Cys Leu Gly Leu Leu Cys Ala Ser Leu Ser Tyr Glu
    210                 215                 220

Ala Glu Lys Ile Phe Lys Trp Ile Phe Ser Lys Phe Ser Ser Ala
225                 230                 235                 240

Lys Asp Glu Val Lys Leu Leu Tyr Leu Cys Ala Thr Tyr Lys Ala Leu
                245                 250                 255
```

```
Glu Thr Val Gly Glu Lys Lys Ala Phe Ser Ser Val Met Gln Leu Val
            260                 265                 270

Met Thr Ser Leu Gln Ser Ile Leu Glu Asn Val Asp Thr Pro Glu Leu
        275                 280                 285

Leu Cys Lys Cys Val Lys Cys Ile Leu Leu Val Ala Arg Cys Tyr Pro
290                 295                 300

His Ile Phe Ser Thr Asn Phe Arg Asp Thr Val Asp Ile Leu Val Gly
305                 310                 315                 320

Trp His Ile Asp His Thr Gln Lys Pro Ser Leu Thr Gln Gln Val Ser
                325                 330                 335

Gly Trp Leu Gln Ser Leu Glu Pro Phe Trp Val Ala Asp Leu Ala Phe
            340                 345                 350

Ser Thr Thr Leu Leu Gly Gln Phe Leu Glu Asp Met Glu Ala Tyr Ala
        355                 360                 365

Glu Asp Leu Ser His Val Ala Ser Gly Glu Ser Val Asp Glu Asp Val
    370                 375                 380

Pro Pro Pro Ser Val Ser Leu Pro Lys Leu Ala Ala Leu Leu Arg Val
385                 390                 395                 400

Phe Ser Thr Val Val Arg Ser Ile Gly Glu Arg Phe Ser Pro Ile Arg
                405                 410                 415

Gly Pro Pro Ile Thr Glu Ala Tyr Val Thr Asp Val Leu Tyr Arg Val
            420                 425                 430

Met Arg Cys Val Thr Ala Ala Asn Gln Val Phe Phe Ser Glu Ala Val
        435                 440                 445

Leu Thr Ala Ala Asn Glu Cys Val Gly Val Leu Leu Gly Ser Leu Asp
    450                 455                 460

Pro Ser Met Thr Ile His Cys Asp Met Val Ile Thr Tyr Gly Leu Asp
465                 470                 475                 480

Gln Leu Glu Asn Cys Gln Thr Cys Gly Thr Asp Tyr Ile Ile Ser Val
                485                 490                 495

Leu Asn Leu Leu Thr Leu Ile Val Glu Gln Ile Asn Thr Lys Leu Pro
            500                 505                 510

Ser Ser Phe Val Glu Lys Leu Phe Ile Pro Ser Ser Lys Leu Leu Phe
        515                 520                 525

Leu Arg Tyr His Lys Glu Lys Glu Val Val Ala Val Ala His Ala Val
    530                 535                 540

Tyr Gln Ala Val Leu Ser Leu Lys Asn Ile Pro Val Leu Glu Thr Ala
545                 550                 555                 560

Tyr Lys Leu Ile Leu Gly Glu Met Thr Cys Ala Leu Asn Asn Leu Leu
                565                 570                 575

His Ser Leu Gln Leu Pro Glu Ala Cys Ser Glu Ile Lys His Glu Ala
            580                 585                 590

Phe Lys Asn His Val Phe Asn Val Asp Asn Ala Lys Phe Val Val Lys
        595                 600                 605

Phe Asp Leu Ser Ala Leu Thr Thr Ile Gly Asn Ala Lys Asn Ser Leu
    610                 615                 620

Ile Gly Met Trp Ala Leu Ser Pro Thr Val Phe Ala Leu Leu Ser Lys
625                 630                 635                 640

Asn Leu Met Ile Val His Ser Asp Leu Ala Val His Phe Pro Ala Ile
                645                 650                 655

Gln Tyr Ala Val Leu Tyr Thr Leu Tyr Ser His Cys Thr Arg His Asp
            660                 665                 670
```

```
His Phe Ile Ser Ser Ser Leu Ser Ser Ala Ser Pro Ser Leu Phe Asp
            675                 680                 685

Gly Ala Val Ile Ser Thr Val Thr Thr Ala Thr Lys Lys His Phe Ser
690                 695                 700

Ile Ile Leu Asn Leu Leu Gly Ile Leu Lys Lys Asp Asn Leu Asn
705                 710                 715                 720

Gln Asp Thr Arg Lys Leu Leu Met Thr Trp Ala Leu Glu Ala Ala Val
                725                 730                 735

Leu Met Arg Lys Ser Glu Thr Tyr Ala Pro Leu Phe Ser Leu Pro Ser
            740                 745                 750

Phe His Lys Phe Cys Lys Gly Leu Leu Ala Asn Thr Leu Val Glu Asp
            755                 760                 765

Val Asn Ile Cys Leu Gln Ala Cys Ser Ser Leu His Ala Leu Ser Ser
770                 775                 780

Ser Leu Pro Asp Asp Leu Leu Gln Arg Cys Val Asp Val Cys Arg Val
785                 790                 795                 800

Gln Leu Val His Ser Gly Thr Arg Ile Arg Gln Ala Phe Gly Lys Leu
                805                 810                 815

Leu Lys Ser Ile Pro Leu Asp Val Val Leu Ser Asn Asn Asn His Thr
            820                 825                 830

Glu Ile Gln Glu Ile Ser Leu Ala Leu Arg Ser His Met Ser Lys Ala
            835                 840                 845

Pro Ser Asn Thr Phe His Pro Gln Asp Phe Ser Asp Val Ile Ser Phe
            850                 855                 860

Ile Leu Tyr Gly Asn Ser His Arg Thr Gly Lys Asp Asn Trp Leu Glu
865                 870                 875                 880

Arg Leu Phe Tyr Ser Cys Gln Arg Leu Asp Lys Arg Asp Gln Ser Thr
                885                 890                 895

Ile Pro Arg Asn Leu Leu Lys Thr Asp Ala Val Leu Trp Gln Trp Ala
            900                 905                 910

Ile Trp Glu Ala Ala Gln Phe Thr Val Leu Ser Lys Leu Arg Thr Pro
            915                 920                 925

Leu Gly Arg Ala Gln Asp Thr Phe Gln Thr Ile Glu Gly Ile Ile Arg
            930                 935                 940

Ser Leu Ala Ala His Thr Leu Asn Pro Asp Gln Asp Val Ser Gln Trp
945                 950                 955                 960

Thr Thr Ala Asp Asn Asp Glu Gly His Gly Asn Asn Gln Leu Arg Leu
                965                 970                 975

Val Leu Leu Leu Gln Tyr Leu Glu Asn Leu Glu Lys Leu Met Tyr Asn
            980                 985                 990

Ala Tyr Glu Gly Cys Ala Asn Ala Leu Thr Ser Pro Pro Lys Val Ile
            995                 1000                1005

Arg Thr Phe Phe Tyr Thr Asn Arg Gln Thr Cys Gln Asp Trp Leu Thr
            1010                1015                1020

Arg Ile Arg Leu Ser Ile Met Arg Val Gly Leu Leu Ala Gly Gln Pro
1025                1030                1035                1040

Ala Val Thr Val Arg His Gly Phe Asp Leu Leu Thr Glu Met Lys Thr
                1045                1050                1055

Thr Ser Leu Ser Gln Gly Asn Glu Leu Glu Val Thr Ile Met Met Val
            1060                1065                1070

Val Glu Ala Leu Cys Glu Leu His Cys Pro Glu Ala Ile Gln Gly Ile
            1075                1080                1085
```

-continued

```
Ala Val Trp Ser Ser Ser Ile Val Gly Lys Asn Leu Leu Trp Ile Asn
        1090                1095                1100

Ser Val Ala Gln Gln Ala Glu Gly Arg Phe Glu Lys Ala Ser Val Glu
1105                1110                1115                1120

Tyr Gln Glu His Leu Cys Ala Met Thr Gly Val Asp Cys Cys Ile Ser
                1125                1130                1135

Ser Phe Asp Lys Ser Val Leu Thr Leu Ala Asn Ala Gly Arg Asn Ser
        1140                1145                1150

Ala Ser Pro Lys His Ser Leu Asn Gly Glu Ser Arg Lys Thr Val Leu
            1155                1160                1165

Ser Lys Pro Thr Asp Ser Ser Pro Glu Val Ile Asn Tyr Leu Gly Asn
        1170                1175                1180

Lys Ala Cys Glu Phe Tyr Ile Ser Ile Ala Asp Trp Ala Ala Val Gln
1185                1190                1195                1200

Glu Trp Gln Asn Ala Ile His Asp Leu Lys Lys Ser Thr Ser Ser Thr
                1205                1210                1215

Ser Leu Asn Leu Lys Ala Asp Phe Asn Tyr Ile Lys Ser Leu Ser Ser
        1220                1225                1230

Phe Glu Ser Gly Lys Phe Val Glu Cys Thr Glu Gln Leu Glu Leu Leu
        1235                1240                1245

Pro Gly Glu Asn Ile Asn Leu Leu Ala Gly Gly Ser Lys Glu Lys Ile
        1250                1255                1260

Asp Met Lys Lys Leu Leu Pro Asn Met Leu Ser Pro Asp Pro Arg Glu
1265                1270                1275                1280

Leu Gln Lys Ser Ile Glu Val Gln Leu Leu Arg Ser Ser Val Cys Leu
                1285                1290                1295

Ala Thr Ala Leu Asn Pro Ile Gln Asp Gln Lys Trp Gln Ser Ile
        1300                1305                1310

Thr Glu Asn Val Val Lys Tyr Leu Lys Gln Thr Ser Arg Ile Ala Ile
            1315                1320                1325

Gly Pro Leu Arg Leu Ser Thr Leu Thr Val Ser Gln Ser Leu Pro Val
        1330                1335                1340

Leu Ser Thr Leu Gln Leu Tyr Cys Ser Ser Ala Leu Glu Asn Thr Val
1345                1350                1355                1360

Ser Asn Arg Leu Ser Thr Glu Asp Cys Leu Ile Pro Leu Phe Ser Glu
                1365                1370                1375

Ala Leu Arg Ser Cys Lys Gln His Asp Val Arg Pro Trp Met Gln Ala
        1380                1385                1390

Leu Arg Tyr Thr Met Tyr Gln Asn Gln Leu Leu Glu Lys Ile Lys Glu
        1395                1400                1405

Gln Thr Val Pro Ile Arg Ser His Leu Met Glu Leu Gly Leu Thr Ala
        1410                1415                1420

Ala Lys Phe Ala Arg Lys Arg Gly Asn Val Ser Leu Ala Thr Arg Leu
1425                1430                1435                1440

Leu Ala Gln Cys Ser Glu Val Gln Leu Gly Lys Thr Thr Ala Gln
                1445                1450                1455

Asp Leu Val Gln His Phe Lys Leu Ser Thr Gln Gly Gln Val Asp
        1460                1465                1470

Glu Lys Trp Gly Pro Glu Leu Asp Ile Glu Lys Thr Lys Leu Leu Tyr
        1475                1480                1485

Thr Ala Gly Gln Ser Thr His Ala Met Glu Met Leu Ser Ser Cys Ala
        1490                1495                1500
```

```
Ile Ser Phe Cys Lys Ser Val Lys Ala Glu Tyr Ala Val Ala Lys Ser
1505                1510                1515                1520

Ile Leu Thr Leu Ala Lys Trp Ile Gln Ala Glu Trp Lys Glu Ile Ser
            1525                1530                1535

Gly Gln Leu Lys Gln Val Tyr Arg Ala Gln His Gln Asn Phe Thr
        1540                1545                1550

Gly Leu Ser Thr Leu Ser Lys Asn Ile Leu Thr Leu Ile Glu Leu Pro
        1555                1560                1565

Ser Val Asn Thr Met Glu Glu Glu Tyr Pro Arg Ile Glu Ser Glu Ser
    1570                1575                1580

Thr Val His Ile Gly Val Gly Glu Pro Asp Phe Ile Leu Gly Gln Leu
1585                1590                1595                1600

Tyr His Leu Ser Ser Val Gln Ala Pro Glu Val Ala Lys Ser Trp Ala
                1605                1610                1615

Ala Leu Ala Ser Trp Ala Tyr Arg Trp Gly Arg Lys Val Val Asp Asn
                1620                1625                1630

Ala Ser Gln Gly Glu Gly Val Arg Leu Leu Pro Arg Glu Lys Ser Glu
            1635                1640                1645

Val Gln Asn Leu Leu Pro Asp Thr Ile Thr Glu Glu Lys Glu Arg
    1650                1655                1660

Ile Tyr Gly Ile Leu Gly Gln Ala Val Cys Arg Pro Ala Gly Ile Gln
1665                1670                1675                1680

Asp Glu Asp Ile Thr Leu Gln Ile Thr Glu Ser Glu Asp Asn Glu Glu
                1685                1690                1695

Asp Asp Met Val Asp Val Ile Trp Arg Gln Leu Ile Ser Ser Cys Pro
                1700                1705                1710

Trp Leu Ser Glu Leu Asp Glu Ser Ala Thr Glu Gly Val Ile Lys Val
            1715                1720                1725

Trp Arg Lys Val Val Asp Arg Ile Phe Ser Leu Tyr Lys Leu Ser Cys
            1730                1735                1740

Ser Ala Tyr Phe Thr Phe Leu Lys Leu Asn Ala Gly Gln Ile Pro Leu
1745                1750                1755                1760

Asp Glu Asp Asp Pro Arg Leu His Leu Ser His Arg Val Glu Gln Ser
                1765                1770                1775

Thr Asp Asp Met Ile Val Met Ala Thr Leu Arg Leu Leu Arg Leu Leu
            1780                1785                1790

Val Lys His Ala Gly Glu Leu Arg Gln Tyr Leu Glu His Gly Leu Glu
        1795                1800                1805

Thr Thr Pro Thr Ala Pro Trp Arg Gly Ile Ile Pro Gln Leu Phe Ser
1810                1815                1820

Arg Leu Asn His Pro Glu Val Tyr Val Arg Gln Ser Ile Cys Asn Leu
1825                1830                1835                1840

Leu Cys Arg Val Ala Gln Asp Ser Pro His Leu Ile Leu Tyr Pro Ala
                1845                1850                1855

Ile Val Gly Thr Ile Ser Leu Ser Ser Glu Ser Gln Ala Ser Gly Asn
            1860                1865                1870

Lys Phe Ser Thr Ala Ile Pro Thr Leu Leu Gly Asn Ile Gln Gly Glu
        1875                1880                1885

Glu Leu Leu Val Ser Glu Cys Glu Gly Gly Ser Pro Pro Ala Ser Gln
        1890                1895                1900

Asp Ser Asn Lys Asp Glu Pro Lys Ser Gly Leu Asn Glu Asp Gln Ala
1905                1910                1915                1920
```

-continued

Met Met Gln Asp Cys Tyr Ser Lys Ile Val Asp Lys Leu Ser Ser Ala
            1925                1930                1935

Asn Pro Thr Met Val Leu Gln Val Gln Met Leu Val Ala Glu Leu Arg
            1940                1945                1950

Arg Val Thr Val Leu Trp Asp Glu Leu Trp Leu Gly Val Leu Leu Gln
            1955                1960                1965

Gln His Met Tyr Val Leu Arg Arg Ile Gln Gln Leu Glu Asp Glu Val
            1970                1975                1980

Lys Arg Val Gln Asn Asn Asn Thr Leu Arg Lys Glu Glu Lys Ile Ala
1985                1990                1995                2000

Ile Met Arg Glu Arg His Thr Ala Leu Met Lys Pro Ile Val Phe Ala
                    2005                2010                2015

Leu Glu His Val Arg Ser Ile Thr Ala Ala Pro Ala Gly Thr Pro His
                    2020                2025                2030

Glu Lys Trp Phe Gln Asp Asn Tyr Gly Asp Ala Ile Glu Asn Ala Leu
                    2035                2040                2045

Glu Lys Leu Lys Thr Pro Leu Asn Pro Ala Lys Pro Gly Ser Ser Trp
            2050                2055                2060

Ile Pro Phe Lys Glu Ile Met Leu Ser Leu Gln Gln Arg Ala Gln Lys
2065                2070                2075                2080

Arg Ala Ser Tyr Ile Leu Arg Leu Glu Glu Ile Ser Pro Trp Leu Ala
                    2085                2090                2095

Ala Met Thr Asn Thr Glu Ile Ala Leu Pro Gly Glu Val Ser Ala Arg
                    2100                2105                2110

Asp Thr Val Thr Ile His Ser Val Gly Gly Thr Ile Thr Ile Leu Pro
                    2115                2120                2125

Thr Lys Thr Lys Pro Lys Lys Leu Leu Phe Leu Gly Ser Asp Gly Lys
            2130                2135                2140

Ser Tyr Pro Tyr Leu Phe Lys Gly Leu Glu Asp Leu His Leu Asp Glu
2145                2150                2155                2160

Arg Ile Met Gln Phe Leu Ser Ile Val Asn Thr Met Phe Ala Thr Ile
                    2165                2170                2175

Asn Arg Gln Glu Thr Pro Arg Phe His Ala Arg His Tyr Ser Val Thr
                    2180                2185                2190

Pro Leu Gly Thr Arg Ser Gly Leu Ile Gln Trp Val Asp Gly Ala Thr
                    2195                2200                2205

Pro Leu Phe Gly Leu Tyr Lys Arg Trp Gln Gln Arg Glu Ala Ala Leu
            2210                2215                2220

Gln Ala Gln Lys Ala Gln Asp Ser Tyr Gln Thr Pro Gln Asn Pro Gly
2225                2230                2235                2240

Ile Val Pro Arg Pro Ser Glu Leu Tyr Tyr Ser Lys Ile Gly Pro Ala
                    2245                2250                2255

Leu Lys Thr Val Gly Leu Ser Leu Asp Val Ser Arg Arg Asp Trp Pro
                    2260                2265                2270

Leu His Val Met Lys Ala Val Leu Glu Glu Leu Met Glu Ala Thr Pro
            2275                2280                2285

Pro Asn Leu Leu Ala Lys Glu Leu Trp Ser Ser Cys Thr Thr Pro Asp
            2290                2295                2300

Glu Trp Trp Arg Val Thr Gln Ser Tyr Ala Arg Ser Thr Ala Val Met
2305                2310                2315                2320

Ser Met Val Gly Tyr Ile Ile Gly Leu Gly Asp Arg His Leu Asp Asn
                    2325                2330                2335

```
Val Leu Ile Asp Met Thr Thr Gly Glu Val Val His Ile Asp Tyr Asn
                2340                2345                2350

Val Cys Phe Glu Lys Gly Lys Ser Leu Arg Val Pro Glu Lys Val Pro
            2355                2360                2365

Phe Arg Met Thr Gln Asn Ile Glu Thr Ala Leu Gly Val Thr Gly Val
        2370                2375                2380

Glu Gly Val Phe Arg Leu Ser Cys Gln Val Leu His Ile Met Arg
2385            2390                2395                2400

Arg Gly Arg Glu Thr Leu Leu Thr Leu Leu Glu Ala Phe Val Tyr Asp
                2405                2410                2415

Pro Leu Val Asp Trp Thr Ala Gly Gly Glu Ala Gly Phe Ala Gly Ala
            2420                2425                2430

Val Tyr Gly Gly Gly Gln Gln Ala Glu Ser Lys Gln Ser Lys Arg
        2435                2440                2445

Glu Met Glu Arg Glu Ile Thr Arg Ser Leu Phe Ser Ser Arg Val Ala
        2450                2455                2460

Glu Ile Lys Val Asn Trp Phe Lys Asn Arg Asp Glu Met Leu Val Val
2465                2470                2475                2480

Leu Pro Lys Leu Asp Gly Ser Leu Asp Glu Tyr Leu Ser Leu Gln Glu
            2485                2490                2495

Gln Leu Thr Asp Val Glu Lys Leu Gln Gly Lys Leu Glu Glu Ile
            2500                2505                2510

Glu Phe Leu Glu Gly Ala Glu Gly Val Asp His Pro Ser His Thr Leu
        2515                2520                2525

Gln His Arg Tyr Ser Glu His Thr Gln Leu Gln Thr Gln Gln Arg Ala
        2530                2535                2540

Val Gln Glu Ala Ile Gln Val Lys Leu Asn Glu Phe Glu Gln Trp Ile
2545                2550                2555                2560

Thr His Tyr Gln Ala Ala Phe Asn Asn Leu Glu Ala Thr Gln Leu Ala
            2565                2570                2575

Ser Leu Leu Gln Glu Ile Ser Thr Gln Met Asp Leu Gly Pro Pro Ser
        2580                2585                2590

Tyr Val Pro Ala Thr Ala Phe Leu Gln Asn Ala Gly Gln Ala His Leu
        2595                2600                2605

Ile Ser Gln Cys Glu Gln Leu Glu Gly Glu Val Gly Ala Leu Leu Gln
    2610                2615                2620

Gln Arg Arg Ser Val Leu Arg Gly Cys Leu Glu Gln Leu His His Tyr
2625                2630                2635                2640

Ala Thr Val Ala Leu Gln Tyr Pro Lys Ala Ile Phe Gln Lys His Arg
            2645                2650                2655

Ile Glu Gln Trp Lys Thr Trp Met Glu Glu Leu Ile Cys Asn Thr Thr
        2660                2665                2670

Val Glu Arg Cys Gln Glu Leu Tyr Arg Lys Tyr Glu Met Gln Tyr Ala
            2675                2680                2685

Pro Gln Pro Pro Pro Thr Val Cys Gln Phe Ile Thr Ala Thr Glu Met
        2690                2695                2700

Thr Leu Gln Arg Tyr Ala Ala Asp Ile Asn Ser Arg Leu Ile Arg Gln
2705                2710                2715                2720

Val Glu Arg Leu Lys Gln Glu Ala Val Thr Val Pro Val Cys Glu Asp
            2725                2730                2735

Gln Leu Lys Glu Ile Glu Arg Cys Ile Lys Val Phe Leu His Glu Asn
            2740                2745                2750
```

```
Gly Glu Glu Gly Ser Leu Ser Leu Ala Ser Val Ile Ile Ser Ala Leu
            2755                2760                2765

Cys Thr Leu Thr Arg Arg Asn Leu Met Met Glu Gly Ala Ala Ser Ser
    2770                2775                2780

Ala Gly Glu Gln Leu Val Asp Leu Thr Ser Arg Asp Gly Ala Trp Phe
2785                2790                2795                2800

Leu Glu Glu Leu Cys Ser Met Ser Gly Asn Val Thr Cys Leu Val Gln
                2805                2810                2815

Leu Leu Lys Gln Cys His Leu Val Pro Gln Asp Leu Asp Ile Pro Asn
            2820                2825                2830

Pro Met Glu Ala Ser Glu Thr Val His Leu Ala Asn Gly Val Tyr Thr
        2835                2840                2845

Ser Leu Gln Glu Leu Asn Ser Asn Phe Arg Gln Ile Ile Phe Pro Glu
    2850                2855                2860

Ala Leu Arg Cys Leu Met Lys Gly Glu Tyr Thr Leu Glu Ser Met Leu
2865                2870                2875                2880

His Glu Leu Asp Gly Leu Ile Glu Gln Thr Thr Asp Gly Val Pro Leu
                2885                2890                2895

Gln Thr Leu Val Glu Ser Leu Gln Ala Tyr Leu Arg Asn Ala Ala Met
            2900                2905                2910

Gly Leu Glu Glu Glu Thr His Ala His Tyr Ile Asp Val Ala Arg Leu
        2915                2920                2925

Leu His Ala Gln Tyr Gly Glu Leu Ile Gln Pro Arg Asn Gly Ser Val
    2930                2935                2940

Asp Glu Thr Pro Lys Met Ser Ala Gly Gln Met Leu Leu Val Ala Phe
2945                2950                2955                2960

Asp Gly Met Phe Ala Gln Val Glu Thr Ala Phe Ser Leu Leu Val Glu
                2965                2970                2975

Lys Leu Asn Lys Met Glu Ile Pro Ile Ala Trp Arg Lys Ile Asp Ile
            2980                2985                2990

Ile Arg Glu Ala Arg Ser Thr Gln Val Asn Phe Phe Asp Asp Asp Asn
        2995                3000                3005

His Arg Gln Val Leu Glu Glu Ile Phe Phe Leu Lys Arg Leu Gln Thr
    3010                3015                3020

Ile Lys Glu Phe Phe Arg Leu Cys Gly Thr Phe Ser Lys Thr Leu Ser
3025                3030                3035                3040

Gly Ser Ser Ser Leu Glu Asp Gln Asn Thr Val Asn Gly Pro Val Gln
                3045                3050                3055

Ile Val Asn Val Lys Thr Leu Phe Arg Asn Ser Cys Phe Ser Glu Asp
            3060                3065                3070

Gln Met Ala Lys Pro Ile Lys Ala Phe Thr Ala Asp Phe Val Arg Gln
        3075                3080                3085

Leu Leu Ile Gly Leu Pro Asn Gln Ala Leu Gly Leu Thr Leu Cys Ser
    3090                3095                3100

Phe Ile Ser Ala Leu Gly Val Asp Ile Ile Ala Gln Val Glu Ala Lys
3105                3110                3115                3120

Asp Phe Gly Ala Glu Ser Lys Val Ser Val Asp Leu Cys Lys Lys
                3125                3130                3135

Ala Val Glu His Asn Ile Gln Ile Gly Lys Phe Ser Gln Leu Val Met
            3140                3145                3150

Asn Arg Ala Thr Val Leu Ala Ser Ser Tyr Asp Thr Ala Trp Lys Lys
        3155                3160                3165
```

```
His Asp Leu Val Arg Arg Leu Glu Thr Ser Ile Ser Ser Cys Lys Thr
    3170                3175                3180

Ser Leu Gln Arg Val Gln Leu His Ile Ala Met Phe Gln Trp Gln His
3185                3190                3195                3200

Glu Asp Leu Leu Ile Asn Arg Pro Gln Ala Met Ser Val Thr Pro Pro
                3205                3210                3215

Pro Arg Ser Ala Ile Leu Thr Ser Met Lys Lys Leu His Thr Leu
            3220                3225                3230

Ser Gln Ile Glu Thr Ser Ile Ala Thr Val Gln Glu Lys Leu Ala Ala
        3235                3240                3245

Leu Glu Ser Ser Ile Glu Gln Arg Leu Lys Trp Ala Gly Gly Ala Asn
            3250                3255                3260

Pro Ala Leu Ala Pro Val Leu Gln Asp Phe Glu Ala Thr Ile Ala Glu
3265                3270                3275                3280

Arg Arg Asn Leu Val Leu Lys Glu Ser Gln Arg Ala Ser Gln Val Thr
                3285                3290                3295

Phe Leu Cys Ser Asn Ile Ile His Phe Glu Ser Leu Arg Thr Arg Thr
                3300                3305                3310

Ala Glu Ala Leu Asn Leu Asp Ala Ala Leu Phe Glu Leu Ile Lys Arg
            3315                3320                3325

Cys Gln Gln Met Cys Ser Phe Ala Ser Gln Phe Asn Ser Ser Val Ser
            3330                3335                3340

Glu Leu Glu Leu Arg Leu Leu Gln Arg Val Asp Thr Gly Leu Glu His
3345                3350                3355                3360

Pro Ile Gly Ser Ser Glu Trp Leu Leu Ser Ala His Lys Gln Leu Thr
                3365                3370                3375

Gln Asp Met Ser Thr Gln Arg Ala Ile Gln Thr Glu Lys Glu Gln Gln
            3380                3385                3390

Ile Glu Thr Val Cys Glu Thr Ile Gln Asn Leu Val Asp Asn Ile Lys
            3395                3400                3405

Thr Val Leu Thr Gly His Asn Arg Gln Leu Gly Asp Val Lys His Leu
    3410                3415                3420

Leu Lys Ala Met Ala Lys Asp Glu Glu Ala Ala Leu Ala Asp Gly Glu
3425                3430                3435                3440

Asp Val Pro Tyr Glu Asn Ser Val Arg Gln Phe Leu Gly Glu Tyr Lys
                3445                3450                3455

Ser Trp Gln Asp Asn Ile Gln Thr Val Leu Phe Thr Leu Val Gln Ala
            3460                3465                3470

Met Gly Gln Val Arg Ser Gln Glu His Val Glu Met Leu Gln Glu Ile
            3475                3480                3485

Thr Pro Thr Leu Lys Glu Leu Lys Thr Gln Ser Gln Ser Ile Tyr Asn
    3490                3495                3500

Asn Leu Val Ser Phe Ala Ser Pro Leu Val Thr Asp Ala Thr Asn Glu
3505                3510                3515                3520

Cys Ser Ser Pro Thr Ser Ser Ala Thr Tyr Gln Pro Ser Phe Ala Ala
                3525                3530                3535

Ala Val Arg Ser Asn Thr Gly Gln Lys Thr Gln Pro Asp Val Met Ser
            3540                3545                3550

Gln Asn Ala Arg Lys Leu Ile Gln Lys Asn Leu Ala Thr Ser Ala Asp
        3555                3560                3565

Thr Pro Pro Ser Thr Val Pro Gly Thr Gly Lys Ser Val Ala Cys Ser
    3570                3575                3580
```

-continued

```
Pro Lys Lys Ala Val Arg Asp Pro Lys Thr Gly Lys Ala Val Gln Glu
3585                3590                3595                3600

Arg Asn Ser Tyr Ala Val Ser Val Trp Lys Arg Val Lys Ala Lys Leu
                3605                3610                3615

Glu Gly Arg Asp Val Asp Pro Asn Arg Arg Met Ser Val Ala Glu Gln
            3620                3625                3630

Val Asp Tyr Val Ile Lys Glu Ala Thr Asn Leu Asp Asn Leu Ala Gln
        3635                3640                3645

Leu Tyr Glu Gly Trp Thr Ala Trp Val
    3650                3655

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
agcaagctcc ctcctgtctc                                              20
```

ATM RELATED KINASE, ATX, NUCLEIC ACIDS ENCODING SAME AND METHODS OF USE

This application is a divisional of U.S. application Ser. No. 11/643,551 filed Dec. 20, 2006, now U.S. Pat. No. 7,217,551, which is a divisional of U.S. application Ser. No. 10/456,238 filed Jun. 6, 2003 now U.S. Pat. No. 7,166,716, which claims priority to U.S. Provisional Application No. 60/813,607 filed Jun. 6, 2002, each of which is incorporated by reference.

This invention was made with government support under grant number CA76193 awarded by the National Institutes of Health. The United States Government has certain rights in this invention.

BACKGROUND OF THE INVENTION

This invention relates generally to the fields of molecular biology and molecular medicine and more specifically to the identification of phosphoinositide 3-kinase related kinases (PIKKs) involved in cell cycle control and mRNA surveillance pathways.

The mitotic cell cycle is the process by which a cell creates an exact copy of its chromosomes and then segregates each copy into two cells. The sequence of events of the cell cycle is regulated such that cell division does not occur until the cell has completed accurate DNA replication. To ensure that cells pass accurate copies of their genomes on to the next generation, evolution has overlaid the core cell cycle machinery with a series of surveillance pathways termed cell cycle checkpoints. The overall function of these checkpoints is to detect damaged or abnormally structured DNA, and to coordinate cell cycle progression with DNA repair.

Members of the phosphoinositide 3-kinase related kinases (PIKK) family of kinases are involved in cell cycle checkpoints and DNA damage repair. The PIKK family members identified to date express a carboxylterminal domain that displays significant sequence homology to the catalytic domains of phosphoinositide (PI) 3-kinases. Indeed, many, but not all of the PIKKs have been shown to possess protein serine-threonine kinase activities (McMahon et al., *Cell* 94:363-374 (1998); Vassilev et al., *Cell* 2:869-875 (1998); Grant et al., *Cell* 2:863-867 (1998); Hunter, *Cell* 83:1-4 (1995); Tibbetts and Abraham, *Signaling Networks and Cell Cycle: Themolecular Basis of Cancer and Other Diseases* pp. 267-301 (2000)). In mammalian cells, three PIKK family members, ATM, ATR, and DNA-dependent protein kinase (DNA-PK), serve as proximal signal transducers in cell-cycle checkpoint and DNA repair pathways (Abraham, *Genes & Dev.* 15:2177-2196 (2001); Durocher and Jackson, *Curr. Opin. Cell Biol.* 13:2225-231 (2001)). The critical roles of ATM in orchestrating cellular responses to various forms of stress are underscored by the diverse pathologies associated with the hereditary disorder, ataxiatelangiectasia (A-T) (Crawford, *Seminarsin Ped. Neuro.* 5:287-294 (1998); Rotman and Shiloh, *Human Mol. Gen.* 7:1555-1563 (1998); Rotman and Shiloh, *Oncogene* 18:6135-6144 (1999)). A-T patients lack functional ATM and develop symptoms including extreme sensitivity to irradiation, cerebellar degeneration, oculocutaneous telangiectasias, gonadal deficiencies, immunodeficiencies, and increased risk of cancer (Lehman and Carr, *Trends in Genet.* 11:375-377 (1995)). Fibroblasts derived from these patients show defects in cell cycle checkpoints and are defective in their response to irradiation (Painter and Young, *Proc. Natl. Acad. Sci.* (USA) 77:7315-7317 (1980)).

In general, the proteins in the PIKK family of kinases play important roles in mRNA surveillance and cell cycle progression in order to insure genetic integrity from generation to generation. Compounds that modulate PIKK polypeptides can result in altered progression through the cell cycle leading to increased or decreased cell survival. For example, a PIKK-modulatory compound can make a cell more or less susceptible to cell death in the presence of radiation or a cytotoxic agent.

All cancer cells have a dysfunctional cell cycle and continue through the cell cycle in an inappropriate manner, either by failing to respond to negative growth signals or by failing to die in response to the appropriate signal. In addition, most cancer cells lack genomic integrity and often have an increased chromosome count compared to normal cells. Therefore, compounds that inhibit cell cycle checkpoints or DNA damage repair, in combination with the cytotoxic agents, can cause cancer cell death by forcing cancer cells to progress through the cell cycle in the presence of DNA damaging agents such that they undergo events that lead to cell death.

Thus, there exists a need to identify additional members of the PIKK family of kinases and compounds that modulate these kinases. The present invention satisfies this need and provides related advantages as well.

SUMMARY OF THE INVENTION

The invention provides an isolated nucleic acid molecule having substantially the same nucleotide sequence as SEQ ID NO:1. Also provided is an isolated oligonucleotide having at least 15 contiguous nucleotides of a nucleotide sequence referenced as SEQ ID NO:11. An isolated polypeptide having substantially the same amino acid sequence as SEQ ID NO:2 is further provided as well as an antibody, or antigen binding fragment thereof, which specifically binds to an ATX polypeptide and has an amino acid sequence as referenced in SEQ ID NO:2. A method for identifying an ATX-modulatory compound is additionally provided. The method consists of measuring the level of an ATX polypeptide in the presence of a test compound, wherein a difference in the level of said ATX polypeptide in the presence of said test compound compared to in the absence of said test compound indicating that said test compound is an ATX-modulatory compound, and wherein said ATX-modulatory compound is not caffeine or wortmannin.

DETAILED DESCRIPTION OF THE INVENTION

Figure 1:
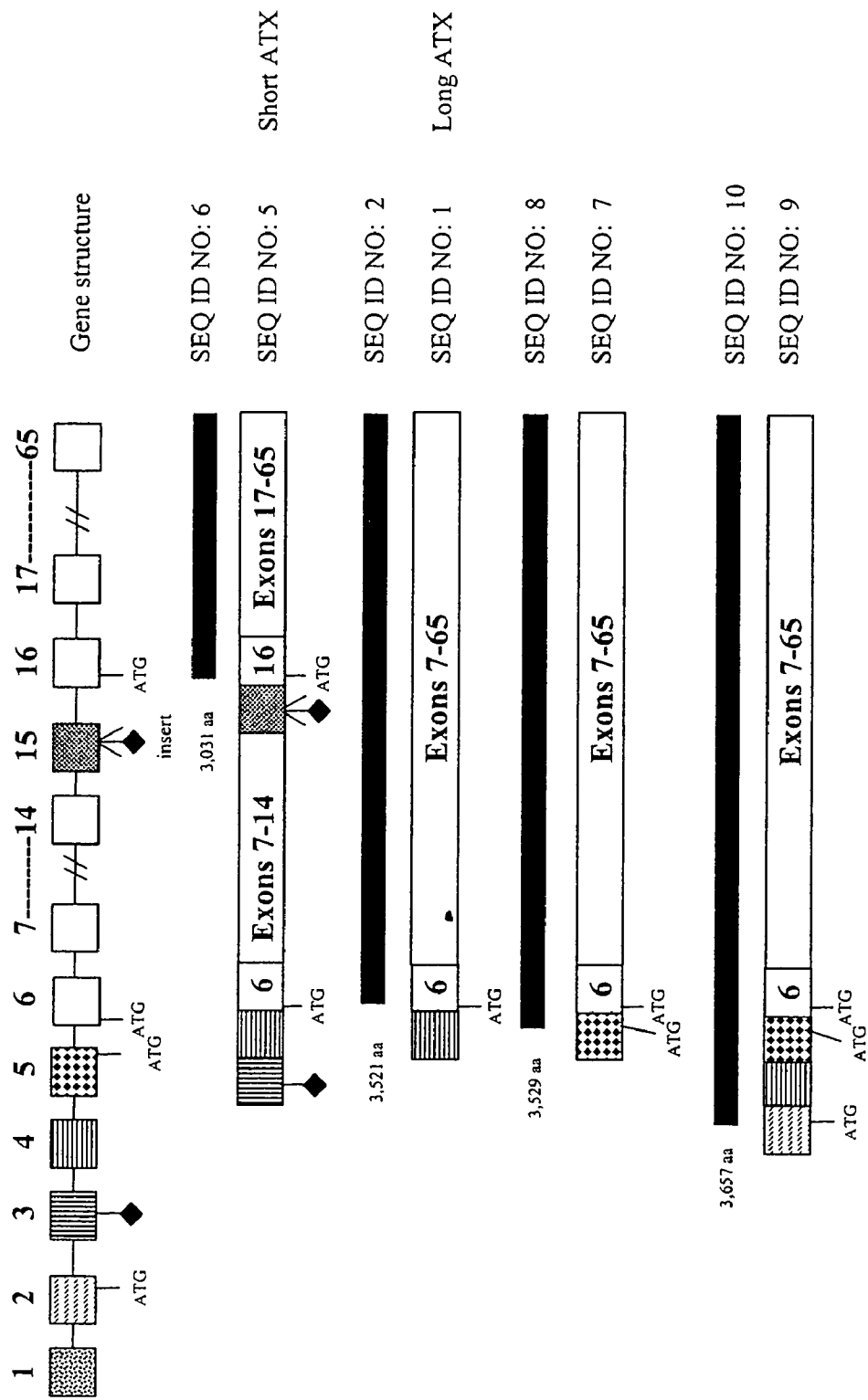
FIG. 1A shows the genomic structure of the ATX locus along with clones isolated to date. The black diamonds denote the locations of translational stop codons and black bars indicate open reading frames that give rise to various ATX polypeptides. The lines and symbols below exon 15 indicate an allelic variant that contains a 27 bp insertion having two in-frame stop codons.
FIG. 1B shows the location of N-terminal homology 1 (NH1), NH2, PI3-K catalytic (PI3-Kc), PKC-λ/ι-interacting protein (LIP), and FAT-C (C) domains. The numbers shown indicate % identity/similarity and shading highlights amino acid identity with ATX. A sequence alignment of the PI 3-Kc domains of ATX, CeSMG-1, mTOR, and ATM is shown.
FIG. 1C shows immune complex kinase assays with GST-p53$_{1-70}$, GST-p53$_{1-70}$ (S15A), or with GSThUpf1 1019-1118 as substrates. The reaction products were immunoblotted with α-HA (lower panel).
FIG. 1D shows immune complex assays with cells or α-HA-ATX immunoprecipitates treated with wortmannin.
Figure 1:
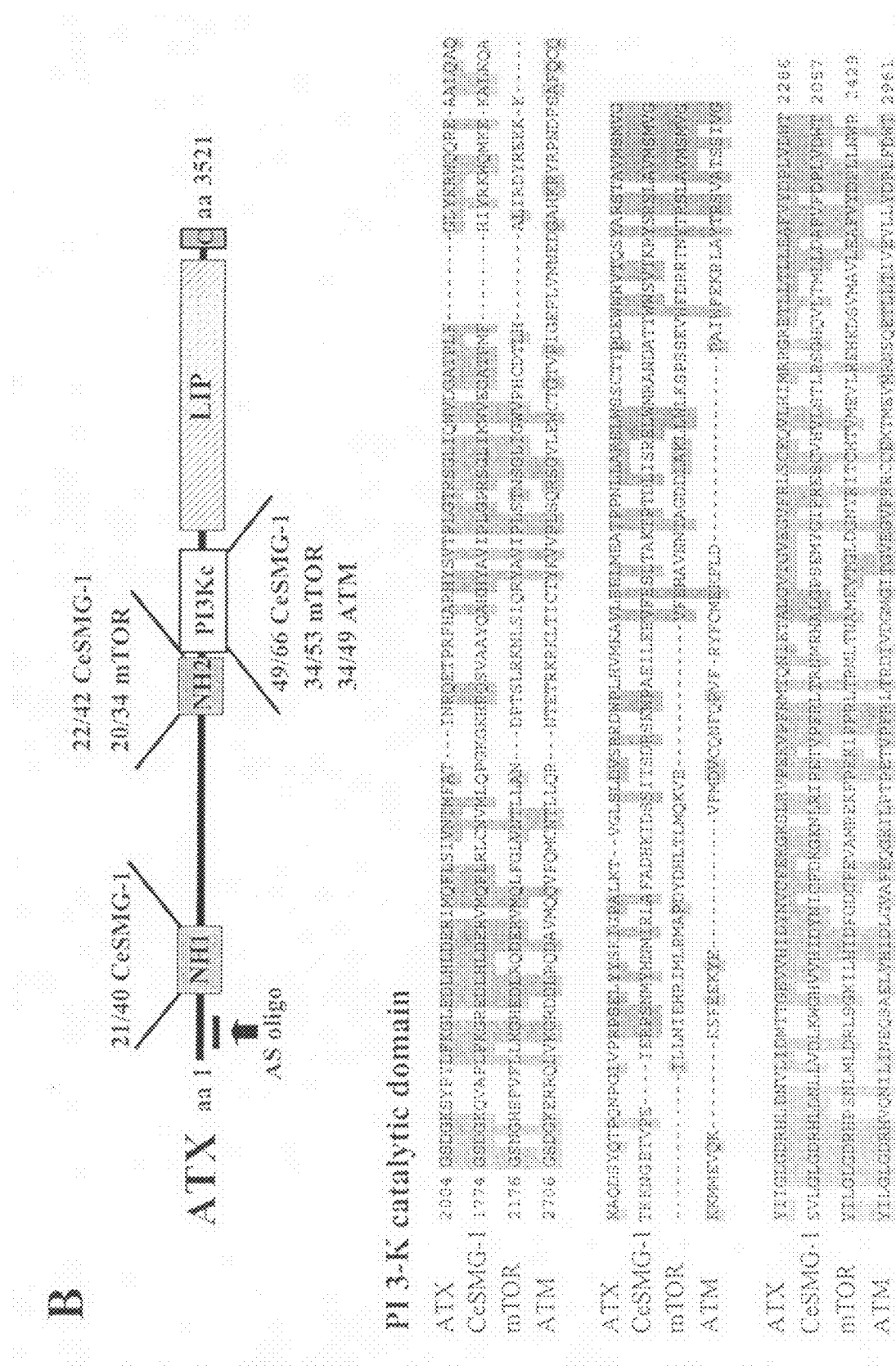
Figure 1:
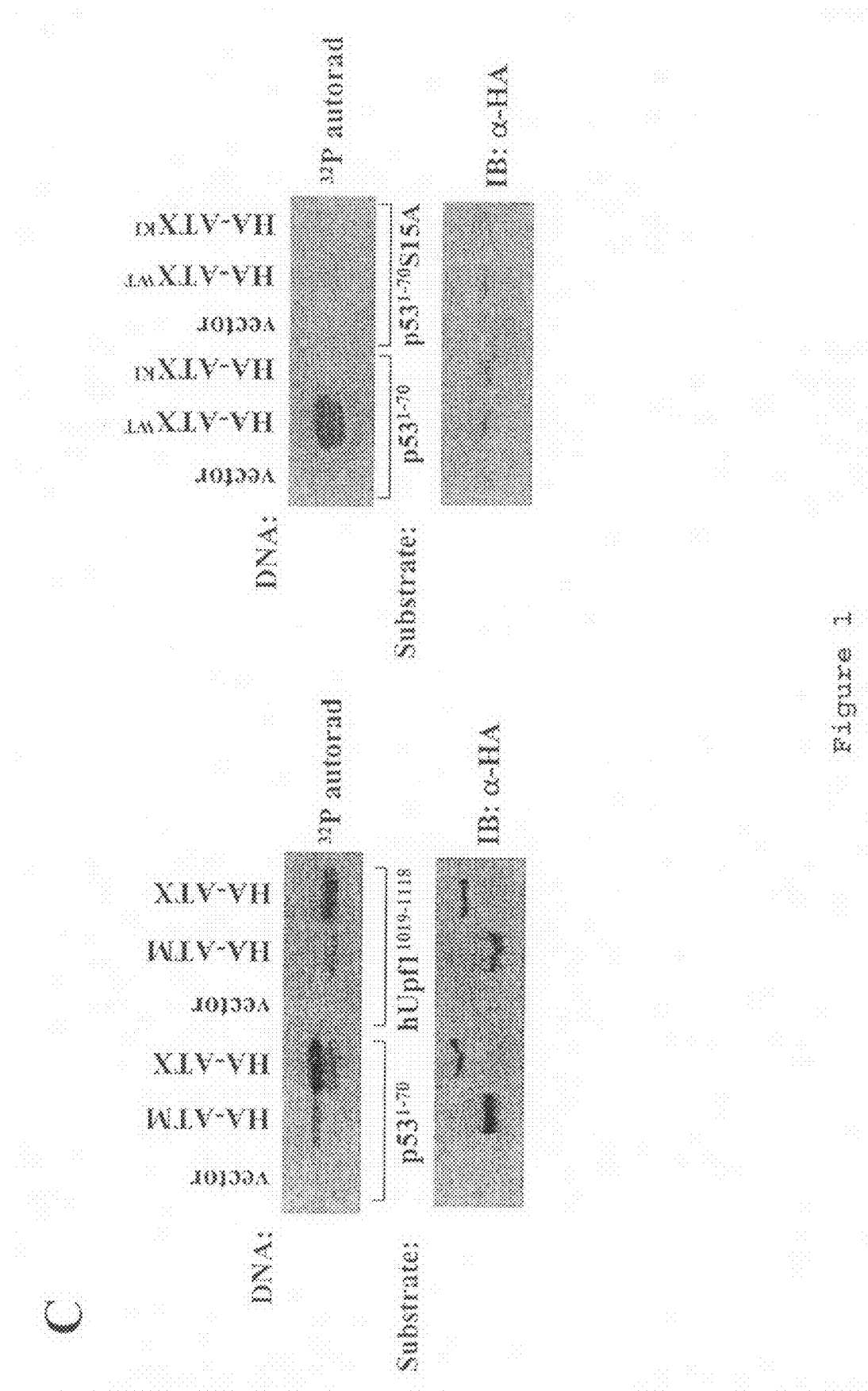
Figure 1:
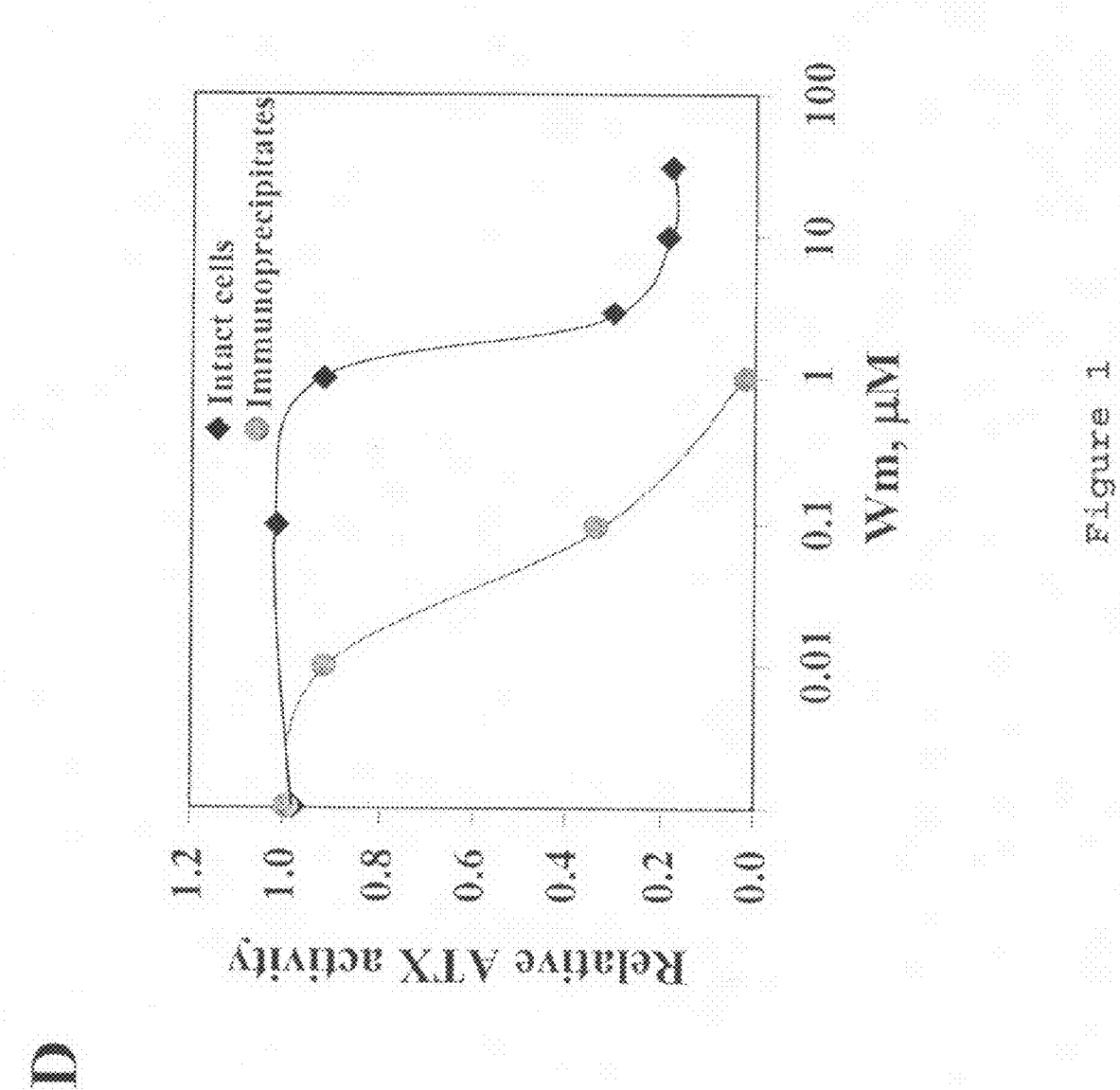

This invention is directed to isolated ATX nucleic acids and polypeptides. ATX is a novel PIKK kinase family member that participates in stress-induced p53 and cell cycle checkpoint activation in cells exposed to DNA damaging agents. In addition, ATX can activate the intrinsic non-sense mediated mRNA decay (NMD) pathway in these cells. The invention is also directed to methods of identifying ATX-modulatory compounds and using these compounds to modulate cell survival. Compounds that modulate cellular survival can be useful in the treatment of diseases characterized by excessive cell growth or excessive cell death.

In one embodiment, an expressed sequence tag (EST) with homology to a conserved region in the catalytic domains of PIKK family members was used to isolate a full-length cDNA encoding a novel member of the PIKK family, termed ATX. The ATX polypeptide was detected in both the nucleus and cytoplasm of human cells, and formed nuclear foci upon exposure to UV light. In addition, the cell cycle regulatory proteins p53 and hUpf1 were found to be phosphorylated by ATX. Furthermore, the reduction of endogenous ATX in a cell using anti-sense oligonucleotides resulted in decreased survival of cells, and decreased phosphorylation and stabilization of p53 in cells exposed to UV light. Similar to other PIKK family members, ATX activity was inhibited by wortmannin and caffeine.

As used herein, the term "ATX polypeptide" refers to a polypeptide with substantially the same amino acid sequence as that shown in SEQ ID NO:2 (human ATX). "Substantially the same amino acid sequence" is intended to mean an amino acid sequence contains a considerable degree of sequence identity or similarity, such as at least 70%, 80%, 90%, 95%, 98%, or 100% sequence identity or similarity, to a reference amino acid sequence. Substantially the same amino acid sequence includes conservative and non-conservative amino acid changes, gaps, and insertions to an amino acid sequence. Conservative and non-conservative amino acid changes, gaps, and insertions to an amino acid sequence can be compared to a reference sequence using available algorithms and programs such as the Smith-Waterman algorithm and the BLAST homology search program (Altschul et al., *J. Mol. Biol.* 215:403-410 (1990)).

It is understood that a fragment of ATX can be sufficient in order to produce an ATX activity. Activities associated with ATX include, for example, kinase activity, cell cycle checkpoint activity, and NMD activity. For example, fragments of ATX which retain substantially an activity of the entire polypeptide are included within the definition. Fragments can include, for example, amino terminal, carboxyl terminal, or internal deletions of a full length ATX polypeptide. In addition, fragments can include domains of a full length ATX polypeptide, such as for example, a kinase domain, NH1 domain, NH2 domain, or LIP domain. A fragment can contain, for example, at least about 10, 100, 500, 1,000, 1,500, 2,000, 2,500, 3,000, 3,500 or more contiguous or non-contiguous amino acid residues of a full-length ATX polypeptide. ATX polypeptide fragments include the fragments described above, but excludes fragments KIAA0421 (Accession number AB007881), KIAA0220 (Accession number D86974), and LIP (Accession number U32581), which are present in databases. Polypeptide fragments can be generated using a variety of methods. For example, polypeptide fragments can be generated using recombinant DNA methods, enzymatic cleavage, or chemical cleavage of larger polypeptides.

It is understood that limited modifications to the ATX polypeptide can be made without destroying an activity of ATX. For example, ATX is intended to include other ATX family members such as those polypeptides that are found to exhibit the above sequence homologies. Such members include, for example, homologs of ATX that can be cloned from other organisms such as monkeys, cows, rats, mice, chickens, frogs, flies or worms. The sequence of possible homologs of human ATX are available in nucleotide databases.

Various modifications of the ATX primary amino acid sequence can result in polypeptides having substantially equivalent, decreased, or enhanced function as compared to the sequence set forth as SEQ ID NO:2. Those skilled in the art recognize that such modifications can be desirable at times in order to enhance the bioactivity, bioavailability or stability of ATX, or to facilitate its synthesis or purification. Contemplated amino acid substitutions to the native sequence of ATX can include, for example, conservative changes, wherein a substituted amino acid has similar structural or chemical properties such as replacement of a polar amino acid with another polar amino acid or replacement of a charged amino acid with a similarly charged amino acid. Those skilled in the art also recognize that nonconservative changes such as replacement of an uncharged polar amino acid with an nonpolar amino acid or replacement of a charged amino acid with an uncharged polar amino acid, can also be made without affecting a function of ATX. In addition, a variety of polypeptide modifications are known in the art for constraining the structure of polypeptides to enhance stability or binding (Cabezas and Satterthwait, *J. Am. Chem. Soc.* 121:3862-3875 (1999); Stanfield et al., *Structure* 7:131-142 (1999)).

A polypeptide can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. Chemical modifications of the polypeptide such as, for example, alkylation, acylation, carbamylation, and iodination can also be used to modify an ATX polypeptide. In addition, various molecules, such as other polypeptides, carbohydrates, or lipids, or small molecules can be attached to ATX including fragments of ATX. For example, ATX can contain a label moiety, a sequence such as a FLAG epitope, or be fused to another polypeptide such as a DNA binding domain.

Those skilled in the art can determine which residues and which regions of a ATX sequence are likely to be tolerant of modification and still retain an activity associated with ATX. For example, amino acid substitutions or chemical or enzymatic modifications at residues that are less well conserved between species are more likely to be tolerated than substitutions at highly conserved residues. Accordingly, an alignment can be performed among ATX sequences of various species to determine residues and regions in which modifications are likely to be tolerated (FIG. 1B). Additional guidance for determining residues and regions of ATX likely to be tolerant of modification is provided by studies of ATX fragments and variants. In addition, it can be useful to modify ATX in a way that destroys an activity associated with ATX. For example, as disclosed herein, the mutation of an aspartic acid to an alanine at conserved residue Asp-2195 in the ATX kinase domain generates a kinase-inactive version of ATX.

As used herein, the term "level" in reference to a level of an ATX nucleic acid or polypeptide refers to the amount, accumulation, or rate of synthesis of a molecule or to the amount or rate of an activity associated with the molecule. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide or nucleic acid. In addition, a level can be represented, for example, by the extent of phosphorylation of a substrate molecule or by the amount of an activity such as cell cycle checkpoint activity, NMD activity or ability to induce cell death or cell survival. The term can be used to refer to an absolute amount of a molecule or activity in a sample or to a relative amount of the molecule or activity, including amounts and activities determined under steady-state or non-steady-state conditions. For example, the expression level of a molecule can be determined relative to a control component molecule in a sample.

As used herein, the term "p53" is intended to mean a polypeptide with substantially the same amino acid sequence as that shown in SEQ ID NO:4 (human p53). As described above for ATX, it is understood that p53 includes fragments of the full length p53 polypeptide. For example, the amino terminal 70 amino acids of p53 (p53 1-70) can be used in the methods of the invention as a substrate for ATX kinase activity. Also, for example, a fragment of p53 that includes the LSQE sequence located at amino acids 14 to 17 of p53 can be used as a substrate for ATX kinase activity. In addition, as described above for ATX, a p53 polypeptide includes p53 from species other than humans, and includes modifications to the p53 polypeptide including conservative and non-conservative amino acid changes, post-translational modifications and chemical modification. Also, as described for ATX, a p53 polypeptide can contain additional sequences such as a known epitope or a label moiety.

The term "specifically binds" is intended to mean the molecule will have an affinity for the target molecule that is measurably higher than its affinity for a non-specific interaction. For example, a nucleic acid can specifically bind to another nucleic acid by complementary base pairing between the nucleotides. In addition, a polypeptide such as an antibody that specifically binds another polypeptide will have an affinity for the target polypeptide or antigen that is measurably higher than its affinity for a non-specific interaction. Furthermore, a compound such as a small organic molecule can specifically bind to a target molecule with an affinity that is measurably higher than its affinity for a non-specific interaction. Binding affinity can be low or high affinity so long as the binding is sufficient to be detectable. For example, a compound can bind ATX with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less. Several methods for detecting or measuring nucleotide, polypeptide, and other compound binding are well known in the art and disclosed herein.

As used herein, the term "compound" is intended to mean an isolated macromolecule of natural or synthetic origin that can be assayed using the methods of the invention. A compound includes, for example, a polypeptide, peptidomimetic, non-peptidyl compound, carbohydrate, lipid, an antibody or antibody fragment, a small organic or inorganic molecule, or a nucleotide sequence including an aptamer, antisense oligonucleotide, interfering RNA or ribozyme. For example, a compound can be an isolated cDNA sequence. A compound can have a known or unknown structure. A compound can be isolated or be part of a population of compounds such as a library. For example, a compound can be a small organic compound obtained from a combinatorial chemical library. A library of compounds can be a random collection of compounds or can be rationally designed based on a physical characteristic. A compound which is assayed in the methods of the invention can be called a "test compound" and if the test compound has the ability to modulate the level of ATX it can be called an "ATX-modulatory compound." One compound or more than one compound can be used in the methods of the invention.

As used herein, a "stressor agent" is any agent that can induce a stress response pathway within a cell. Several stressor agents are known in the art such as UV light, ionizing radiation, reactive oxygen intermediates, cytotoxic agents, and replicational stress imposed by DNA replication inhibitors including, for example, hydroxyurea and aphidicolin. In addition, environmental conditions such as excessive heat can induce a stress response pathway within a cell resulting in, for example, the induction of heat shock proteins. Stress response pathways include DNA repair pathways, non-sense mediated mRNA decay (NMD), heat shock pathways, the induction of apoptosis, activation of the NFkB transcription factor, activation of the stress-activated MAP kinase pathways including, for example, JNK and p38 pathways, and activation of ubiquitin-dependent proteolysis.

As used herein, the term "non-sense mediated messenger RNA (mRNA) decay (NMD)" is intended to mean the surveillance mechanism within cells whereby imperfect mRNAs that contain premature translation termination codons are preferentially degraded. These imperfect mRNAs can result in polypeptides that are nonfunctional or have altered function such as gain-of function or dominant negative mutations.

As used herein, the term an "amount effective" or "effective amount" when used in reference to a compound that modulates cell survival or growth is intended to mean an amount of the compound or molecule sufficient to increase or decrease cell survival or growth. Modulation also includes induction of cell survival or growth or complete blockage of cell survival or growth. In addition, an effective amount of a compound is intended to mean an amount of the compound that is sufficient to treat or reduce the severity of a condition in an affected subject.

The invention provides an isolated nucleic acid molecule having substantially the same nucleotide sequence as SEQ ID NO:1. In addition, the invention provides an isolated nucleic acid molecule having substantially the same nucleotide sequence as SEQ ID NO:1 where the nucleic acid molecule encodes an ATX polypeptide containing an amino acid sequence shown in SEQ ID NO:2. For example, the invention provides an isolated nucleic acid molecule containing the sequence shown in SEQ ID NO:1.

Substantially the same nucleic acid sequence is intended to mean a nucleic acid sequence contains a considerable degree of sequence identity or similarity, such as at least 70%, 80%, 90%, 95%, 98%, or 100% sequence identity or similarity, to a reference nucleic acid sequence. Substantially the same nucleic acid sequence includes nucleic acid changes, gaps, and insertions to an nucleic sequence. Nucleic acid changes, gaps, and insertions to a nucleic acid sequence can be compared to a reference sequence using available algorithms and programs such as the Smith-Waterman algorithm and the BLAST homology search program (Altschul et al., *J. Mol. Biol.* 215:403-410 (1990)).

Isolated nucleic acid molecules include DNA sequences and RNA transcripts, both sense and complementary antisense strands, including splice variants thereof encoding ATX polypeptides. An isolated nucleic acid molecule can contain a double stranded molecules or single stranded molecules, including RNA as well as coding and noncoding DNA. DNA sequences of the invention include genomic and cDNA sequences as well as wholly or partially chemically synthesized DNA sequences. Genomic DNA of the invention comprises the protein coding region for a polypeptide of the invention and includes allelic variants of the preferred nucleic acid of the invention. Genomic DNA of the invention is distinguishable from genomic DNAs encoding polypeptides other than ATX in that it includes an ATX protein coding region found in ATX-encoding cDNA of the invention. Genomic DNA of the invention can be transcribed into RNA, and the resulting RNA transcript can undergo one or more splicing events wherein one or more introns of the transcript are removed, or "spliced out." Peptide nucleic acids (PNAs) encoding a polypeptide of the invention are also contemplated (Corey, TIBTech 15:224-229 (1997)). PNAs are DNA analogs containing neutral amide backbone linkages that are resistant to DNA degradation enzymes and which bind to complementary sequences at higher affinity than analogous DNA sequences as a result of the neutral charge on the backbone of the molecule.

RNA transcripts that can be spliced by alternative mechanisms, and therefore be subject to removal of different RNA sequences but still encode an ATX polypeptide, are referred to in the art as splice variants which are embraced by the invention. Splice variants comprehended by the invention therefore are encoded by the same DNA sequences but arise from distinct mRNA transcripts. Allelic variants are known in the art to be modified forms of a wild type gene sequence, the modification resulting from recombination during chromosomal segregation or exposure to conditions which give rise to genetic mutation. Allelic variants, like wild type genes, are inherently naturally occurring sequences (as opposed to non-naturally occurring variants which arise from in vitro manipulation).

An allelic variant of ATX is disclosed herein as SEQ ID NO:5. This form of ATX is produced as the result of allelic variation in exon 15 which leads to the insertion of 27 nucleotides beginning at nucleotide 1427 (FIG. 1A). This sequence alteration causes the insertion of two in-frame stop codons and the use of the next available ATG codon in exon 16 as the translational stat site, resulting in an amino-terminally truncated or short form of ATX. A form of ATX that is similar to the long form of ATX disclosed herein (SEQ ID NO:1) is referenced as SEQ ID NO:7. This form of ATX has exon 5 spliced to exon 6 which results in a different N-terminus and 8 additional amino acids in the resulting polypeptide (FIG. 1A). In the experiments disclosed herein clones that were isolated with exon 5 frequently contained exon 3 which place an in-frame stop codon at the 3' end of this DNA (Example 1). The longest form of ATX (SEQ ID NO:9) was isolated, however the exon 3 associated stop codon was present in this transcript as well.

In addition to genomic DNA, isolated nucleic acids include cDNA. cDNA can be obtained through reverse transcription of an RNA nucleic acid encoding ATX, followed by second strand synthesis of a complementary strand to provide a double stranded DNA. In addition, nucleic acid molecules can be chemically synthesized meaning produced by purely chemical, as opposed to enzymatic, methods. Wholly chemically synthesized DNA sequences are produced entirely by chemical means, and partially synthesized DNAs are those where only portions of the resulting DNA were produced by chemical means.

ATX nucleic acid molecules include homologs of the human ATX sequence. Species homologs in general share at least 50%, at least 60%, at least 70%, at least 80%, at least 90%, at least 95% or at least 99% homology with a human DNA of the invention. ATX nucleic acids include species homologs of the human ATX sequence, but exclude a mouse EST that contains a sequence homologous to the 3' part of ATX is (GenBank Accession Number BC024431) and a *Macaca fascicularis* brain cDNA clone Qf1A-15747 (accession number AB056380).

The invention also provides anti-sense oligonucleotides based on SEQ ID NO:1. For example, the invention provides an isolated oligonucleotide having at least 15 contiguous nucleotides of the nucleotide sequence 5'-AGCAAGCTC-CCTCCTGTCTC-3' (SEQ ID NO:11). The oligonucleotide shown in SEQ ID NO:11 is an ATX anti-sense oligonucleotide that has been shown herein to decrease the level of ATX in a cell (Example 5).

Nucleic acids of the invention also permit identification and isolation of nucleic acid encoding related ATX polypeptides by well known techniques including Southern hybridization, Northern hybridization, and polymerase chain reaction (PCR). Examples of related nucleic acids include human and non-human nucleic acid sequences, including allelic variants, as well as nucleic acids encoding polypeptides homologous to ATX and structurally related polypeptides sharing one or more biological, immunological, or physical properties of ATX.

The invention provides a method for detecting an ATX nucleic acid molecule in a sample, by contacting the sample with an ATX nucleic acid molecule under conditions that allow specific hybridization to ATX nucleic acid, and detecting the specific hybridization. In addition, the invention provides a method for detecting an ATX nucleic acid molecule in a sample, by contacting a nucleic acid fraction derived from the sample with a PCR primer pair set under conditions that allow amplification of an ATX nucleic acid, and detecting amplified ATX nucleic acid. Kits for detecting ATX nucleic acids based on these methods are provided as well.

Fragments of ATX nucleic acid molecules are useful in the invention, for example, as probes for detection of full length or other fragment ATX nucleic acids. A nucleic acid fragment can include for example 5', 3', or internal deletions of a full length ATX nucleic acid sequence. For example, the invention provides an isolated ATX nucleic acid molecule as referenced in SEQ ID NO:5. Alternatively, the invention provides ATX nucleic acid fragments other than the fragment as referenced in SEQ ID NO:5. For example, the invention provides ATX nucleic acid fragments that contain carboxyl terminal deletions of a full length ATX polypeptide. In addition, fragments can include domains of a full length ATX nucleic acid sequence, for example, a kinase domain, NH1 domain, NH2 domain, or LIP domain. A fragment can contain, for example, at least about 10, 100, 1,000, 2,500, 5,000, 7,500, 10,000, 12,500 or more contiguous or non-contiguous nucleic acid residues of a full-length ATX nucleic acid sequence. ATX nucleic acid fragments include the fragments described above, but excludes fragments KIAA0421 (Accession number AB007881), KIAA0220 (Accession number D86974), and LIP (Accession number U32581), which are present in databases. One or more fragment nucleic acids can be included in kits that are used to detect the presence of a nucleic acids encoding ATX, or used to detect variations in a nucleic acid sequence encoding ATX, including polymorphisms, for example, single nucleotide polymorphisms.

The nucleic acids of the invention can contain heterologous sequences that are not part of the ATX-encoding sequences in nature. The heterologous nucleic acid sequence can be separated from the ATX-coding sequence by an encoded cleavage site that will permit removal of non-ATX polypeptide sequences from the expressed fusion protein. Heterologous nucleic acids sequences can include sequences encoding epitopes, such as poly-histidine sequences, FLAG tags, glutathione-S-transferase, thioredoxin, and maltose binding protein domains, that facilitate purification of the fusion protein. In addition heterologous nucleic acids can encode domains, such as leucine zipper motifs, that promote multimer formation between the fusion protein and itself or other proteins or immunoglobulins or fragments thereof that can enhance circulatory half-life of the encoded protein.

The nucleic acid molecules of the invention also include DNA sequences encoding ATX species that hybridize under highly or moderately stringent conditions to the non-coding strand, or complement, of the nucleic acid in SEQ ID NO: 1. ATX-encoding nucleic acids of the invention include a) the nucleic acid sequence set out in SEQ ID NO: 1; b) nucleic acids encoding a polypeptide encoded by the nucleic acid of (a), and c) nucleic acids that hybridize to the complement of the nucleic acids of (a) or (b) under moderately or highly stringent conditions. Exemplary high stringency conditions include a final wash in 0.2×SSC/0.1% SDS at 65° C. to 75° C., and exemplary moderate stringency conditions include a final wash at 2× to 3×SSC/0.1% SDS at 65° C. to 75° C. It is understood in the art that conditions of equivalent stringency can be achieved through variation of temperature and buffer, or salt concentration as described in Ausubel, et al. (Eds.), Protocols in Molecular Biology, John Wiley & Sons (1994). Modifications in hybridization conditions can be empirically determined or precisely calculated based on the length and the percentage of guanosine/cytosine (GC) base pairing of the probe.

The invention also provides a vector containing the isolated ATX nucleic acid molecules described above. For example, the invention provides a vector containing an isolated nucleic acid molecule having substantially the same nucleotide sequence as SEQ ID NO:1.

Vectors include autonomously replicating recombinant expression constructs such as plasmid and viral DNA vectors. The invention includes vectors where ATX-encoding nucleic acids are operatively linked to an endogenous or exogenous promoter, enhancer, or operator sequence and a transcription terminator sequence. Promoter and enhancer sequences are generally selected for the ability to increase gene expression, while operator sequences are generally selected for the ability to regulate gene expression. It is understood in the art that the choice of host cell is relevant to selection of an appropriate regulatory sequence. Vectors used in the invention can also include sequences encoding one or more selectable markers that permit identification of host cells bearing the construct. Vectors can also include sequences that facilitate homologous recombination in a host cell.

Suitable vectors for expression in prokaryotic or eukaryotic cells are well known to those skilled in the art (see, for example, Ausubel et al., supra, 1999). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. A vector can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell. For example, as disclosed herein, the long form of ATX can be sub-cloned into pcDNA 3.1 with an HA tag and transfected using Fugene 6 into human embryonic kidney 293T cells (Example 2 and Example 5).

Vectors useful for expression of an ATX polypeptide can contain a regulatory element that provides tissue specific or inducible expression of an operatively linked nucleic acid. Such inducible systems, include, for example, tetracycline inducible system (Gossen & Bizard, *Proc. Natl. Acad. Sci. USA,* 89:5547-5551. (1992); Gossen et al., *Science,* 268: 1766-1769 (1995); Clontech, Palo Alto, Calif.)); metallothionein promoter induced by heavy metals; insect steroid hormone responsive to ecdysone or related steroids such as muristerone (No et al., *Proc. Natl. Acad. Sci. USA,* 93:3346-3351 (1996); Yao et al., *Nature,* 366:476-479 (1993); Invitrogen, Carlsbad, Calif.); mouse mammory tumor virus (MMTV) induced by steroids such as glucocortocoid and estrogen (Lee et al., *Nature,* 294:228-232 (1981); and heat shock promoters inducible by temperature changes.

In addition, viral vectors such as retroviral, adenovirus, adeno-associated virus, lentivirus, and herpesvirus vectors can be used to express ATX polypeptides into a cell. Viral based systems provide the advantage of being able to introduce relatively high levels of a heterologous nucleic acid into a variety of cells. Additionally, such viruses can introduce heterologous DNA into nondividing cells. Viral vectors include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

The invention further provides a host cell containing an ATX-encoding vector as described above. For example, the invention provides a host cell that contains a vector which contains an isolated nucleic acid molecule having substantially the same nucleotide sequence as SEQ ID NO:1. Host cells include prokaryotic and eukaryotic cells. Nucleic acids of the invention can be introduced into the host cell as part of a circular plasmid, or as linear DNA having an isolated protein coding region or a viral vector. Methods for introducing DNA into the host cell are well known in the art and include transformation, transfection, electroporation, nuclear injection, or fusion with carriers such as liposomes, micelles, ghost cells, protoplasts, and other transformed cells. Detailed procedures for these methods can be found in Sambrook et al., *Molecular Cloning: A Laboratory Manual* (Cold Spring Harbor Laboratory Press, 1989) and the references cited therein). Expression systems of the invention include bacterial, yeast, fungal, plant, insect, invertebrate, and mammalian cells systems.

Useful mammalian expression vectors and methods of introducing such vectors into mammalian cells either ex vivo or in vivo, for expression of the encoded polypeptide, are well known in the art. For example, a plasmid expression vector can be introduced into a cell by calcium-phosphate mediated transfection, DEAE-Dextran-mediated transfection, lipofection, polybrene- or polylysine-mediated transfection, electroporation, or by conjugation to an antibody, gramacidin S, artificial viral envelopes or other intracellular carriers. A viral expression vector can be introduced into a cell in an expressible form by infection or transduction, for example, or by encapsulation in a liposome.

The invention also provides a method of producing an ATX polypeptide by a) growing the host cell described above under conditions appropriate for expression of the ATX polypeptide, and b) isolating the ATX polypeptide from the host cell or host cell growth medium. This method can be used to produce ATX polypeptide, for example, as a source of immunogen for the development of antibodies specifically reactive with ATX.

ATX polypeptide isolated from the cells or from the medium in which the cells are grown by purification methods known in the art, for example, conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein.

The DNA sequence information provided by the present invention also makes possible the development through, for example, homologous recombination or "knock-out" strategies of animals that fail to express functional ATX or that express a variant of ATX (Capecchi, *Science* 244:1288-1292 (1989)). Such animals are useful as models for studying the in vivo activities of ATX and modulators of ATX.

The invention provides an isolated polypeptide containing substantially the same amino acid sequence as SEQ ID NO:2. For example, the invention provides a polypeptide containing an amino acid sequence as referenced in SEQ ID NO:2. The sequence shown in SEQ ID NO:2 corresponds to the "long form" of ATX (FIG. 1A).

As described further above, an isolated ATX polypeptide includes conservative and non-conservative amino acid changes to the sequence shown in SEQ ID NO:2. In addition, an isolated ATX polypeptide includes species homologs and fragments of ATX. For example, the invention provides an isolated ATX polypeptide fragment as referenced in SEQ ID NO:6. Alternatively, the invention provides ATX polypeptide fragments other than the fragment as referenced in SEQ ID NO:6. For example, the invention provides ATX polypeptide fragments that contain carboxyl terminal deletions of a full length ATX polypeptide. Furthermore, an ATX polypeptide can contain polypeptide modifications or heterologous sequences such as an epitope tag. Polypeptides of the invention can be isolated from natural cell sources, chemically synthesized, or produced by recombinant procedures involving the host cells of the invention.

The invention provides an antibody, or antigen binding fragment thereof, which specifically binds to an ATX polypeptide containing an amino acid sequence as referenced in SEQ ID NO:2. Antibodies include, for example, monoclonal and polyclonal antibodies, single chain antibodies, chimeric antibodies, bifunctional or bispecific antibodies, humanized antibodies, human antibodies, and complementary determining region (CDR)-grafted antibodies, including compounds which include CDR or antigen-binding sequences, which specifically bind to a polypeptide of the invention. Antibody fragments, including Fab, Fab', $F(ab')_2$, and Fv, are also provided by the invention. Screening assays to determine binding specificity or exclusivity of an antibody of the invention are well known in the art (see Harlow et al. (Eds), Antibodies A Laboratory Manual; Cold Spring Harbor Laboratory; Cold Spring Harbor, N.Y. (1988)).

Antibodies that recognize and bind fragments of the ATX polypeptides of the invention are also contemplated, provided that the antibodies specifically bind ATX polypeptides. As with antibodies that are specific for full length ATX polypeptides, antibodies of the invention that recognize ATX fragments are those which can distinguish ATX polypeptides from other PIKK polypeptides despite inherent sequence identity, homology, or similarity found in the family of proteins.

Antibodies of the invention can be produced using any method well known in the art, using any polypeptide, or immunogenic fragment thereof, of the invention. Immunogenic polypeptides can be isolated from natural sources, from recombinant host cells, or can be chemically synthesized. For example, as disclosed herein, antibodies specifically reactive with ATX were generated using glutathione S-transferase (GST) fusion proteins containing ATX amino acids 2281-2339 (anti-ATX-Ab-1) or amino acids 1691-1790 (anti-ATX-Ab-2) (Example 2). Polypeptide of the invention can also be conjugated to a hapten such as keyhole limpet hemocyanin (KLH) in order to increase immunogenicity. Methods for synthesizing such peptides are known in the art, for example, as in R. P. Merrifield, J. Amer. Chem. Soc. 85: 2149-2154 (1963); J. L. Krstenansky, et al., FEBS Lett. 211:10 (1987). Antibodies to a polypeptide of the invention can also be prepared through immunization using a nucleic acid of the invention, as described in Fan et al., Nat. Biotech. 17:870-872 (1999). DNA encoding a polypeptide can be used to generate antibodies against the encoded polypetide following topical administration of naked plasmid DNA or following injection, for example, intramuscular injection, of the DNA.

Non-human antibodies can be humanized by any methods known in the art. In one method, the non-human CDRs are inserted into a human antibody or consensus antibody framework sequence. Further changes can then be introduced into the antibody framework to modulate affinity or immunogenicity. Antibodies of the invention further include plastic antibodies or molecularly imprinted polymers (MIPs) (Haupt and Mosbauch, TIBTech 16:468-475 (1998)). Antibodies of this type can be useful in immunoaffinity separation, chromatography, solid phase extraction, immunoassays, for use as immunosensors, and for screening chemical or biological libraries. Advantages of antibodies of this type are that no animal immunization is required, the antibodies are relatively inexpensive to produce, they are resistant to organic solvents, and they are reusable over long period of time.

The invention provides a method for detecting ATX polypeptide in a sample by contacting the sample with an ATX antibody under conditions that allow specific binding of the antibody to the polypeptide add detecting the bound antibody. Antibodies of the invention can also include one or more labels that permit detection of the antibody and antibody binding. Labels can include, for example, radioactivity, fluorescence (or chemiluminescence), one of a high affinity binding pair (such as biotin/avidin), enzymes, or combinations of one or more of these labels. Antibodies of the invention are also useful, for example, for therapeutic purposes (by modulating activity of ATX), diagnostic purposes to detect or quantitate ATX, as well as purification of ATX. Kits containing an antibody or antibodies of the invention are also provided.

The DNA and amino acid sequence information provided by the present invention also makes possible the systematic analysis of the structure and function of ATX. DNA and amino acid sequence information for ATX also permits identification of compounds with which an ATX polypeptide or nucleic acid will interact. Methods to identify compounds that bind to ATX include solution assays, in vitro assays where ATX polypeptides are immobilized, and cell based assays. Identification of compounds that bind ATX polypeptides provides potential targets for therapeutic or prophylactic intervention in pathologies associated with ATX biological activity.

The invention provides a method for identifying a compound that specifically binds to an ATX polypeptide of the invention, by a) contacting the ATX polypeptide with a compound, and b) determining specific binding of the compound to said ATX polypeptide. As described further above, the term compound includes macromolecules of natural or synthetic origin including, for example, a polypeptide, peptidomimetic, non-peptidyl compound, carbohydrate, lipid, and antibody or antibody fragment, a small organic or inorganic molecule, or a nucleic acid including an aptamer.

Identification of compounds that bind the ATX polypeptide can be achieved by isolating the ATX polypeptide/binding complex, and separating the ATX polypeptide from the binding compound. An additional step of characterizing the physical, biological, or biochemical properties of the binding compound can also be performed. In one embodiment, the ATX polypeptide/binding complex can be isolated using a antibody immunospecific for either the ATX polypeptide or the candidate binding compound. In another embodiment, the complex can be isolated using a second binding compound that interacts with either the ATX polypeptide or the candidate binding compound. In still another embodiment, either the polypeptide ATX or the candidate binding compound comprises a label or tag that facilitates its isolation, and methods of the invention to identify binding compounds include a step of isolating the ATX polypeptide/binding complex through interaction with the label or tag. An exemplary tag of this type is a poly-histidine sequence, generally around six histidine residues, that permits isolation of a compound so labeled using nickel chelation. Other labels and tags, such as the FLAG tag, thioredoxin, and GST, each of which is well known in the art.

An in vitro assay can be performed where the ATX polypeptide can be immobilized and then contacted with a candidate binding compound. In an alternative embodiment, the candidate binding compound can be immobilized and binding of the ATX polypeptide is detected. Immobilization can be accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin or streptavidin moiety. Detection of binding can be accomplished, for example, (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known in the art.

A cell based assay that can be used in the method of the invention for detecting an ATX binding compound is a yeast or mammalian two-hybrid assay (Fields and Song, Nature 340:245-246 (1989); Fields, Methods: A Companion to Methods in Enzymology 5:116-124 (1993); U.S. Pat. No. 5,283, 173 issued Feb. 1, 1994 to Fields, et al.). Modifications and variations on the two-hybrid assay have previously been described (Colas and Brent, TIBTECH 16:355-363 (1998)).

The invention also provides a method for identifying an ATX-modulatory compound by measuring the level of an ATX polypeptide in the presence of a test compound, where a difference in the level of the ATX polypeptide in the presence of the test compound compared to in the absence of the test compound indicating that the test compound is an ATX-modulatory compound. In addition, the invention provides a method for identifying an ATX-modulatory compound by measuring the level of an ATX polypeptide in the presence of a test compound, where a difference in the level of the ATX polypeptide in the presence of the test compound compared to in the absence of the test compound indicating that the test compound is an ATX-modulatory compound, and where the ATX-modulatory compound is not caffeine or wortmannin. The ATX-modulatory compound can decrease or increase the level of ATX polypeptide.

Agents that modulate, for example, increase, decrease, or block the level of ATX can be identified by incubating a test compound with an ATX polypeptide or nucleic acid and determining the effect of the test compound on ATX activity or expression. The level of ATX can include the expression level of ATX or an activity level of ATX. The selectivity, or specificity, of an ATX-modulatory compound can be evaluated by comparing its effects on ATX or an ATX-encoding nucleic acids to its effect on other polypeptides or compounds. Cell based methods, such as two-hybrid assays to identify DNAs encoding binding compounds and split hybrid assays to identify inhibitors of ATX polypeptide interaction with a known binding polypeptide, as well as in vitro methods, including assays where an ATX polypeptide, ATX-encoding nucleic acid, or a binding compound are immobilized, and solution assays are included in this method of the invention.

As understood by those of skill in the art, assay methods for identifying compounds that modulate an activity generally require comparison to a "control." One type of a control is a reaction or cell that is treated substantially the same as the test reaction or cell exposed to the compound, with the distinction that the control reaction or cell is not exposed to the compound.

As disclosed herein, the compounds wortmannin and caffeine can modulate (inhibit) the level of ATX (Example 3 and Example 7). Wortmannin is known to inhibit ATM kinase and is an irreversible inhibitor of PIKKs. Caffeine is a known inhibitor of the G2 cell cycle checkpoint. As disclosed herein, caffeine reversed the accumulation of G2/M phase cells induced by ATX anti-sense treatment, indicating that ATX deficiency can trigger the activation of a caffeine-sensitive G2 checkpoint (Example 7).

The invention provides a method for identifying an ATX-modulatory compound where the level of ATX polypeptide is measured by determining the kinase activity of the ATX polypeptide. The kinase activity of ATX can be measured using methods well known in the art such as kinase assays and immune complex kinase assays as performed herein in Example 3. These assays contain ATX, a substrate, and a suitable buffer including [g-32 P]ATP and $Mn^{2+}$. Phosphorylated substrates can also be detected using phospho-specific antibodies.

In addition, the invention provides a method for identifying an ATX-modulatory compound where the level of ATX polypeptide is measured by determining the phosphorylation of a p53 polypeptide or fragment. For example, a GST fusion protein containing the first 70 amino acids of p53 (GST-$p53_{1-70}$) can be used as a substrate to measure the level of ATX polypeptide by its kinase activity (Example 3). In addition to p53, the phosphorylation of hUpf1; a helicase, can be used to measure the level of ATX polypeptide (Example 3).

The invention also provides a method for identifying an ATX-modulatory compound where the level of ATX polypeptide is measured by determining the level of p53 polypeptide accumulation. As shown herein, a decrease in ATX polypeptide, such as results from the use of an anti-sense oligonucleotide, leads to a reduction in p53 polypeptide accumulation (Example 6). Thus, the level of p53 can be used as a measure of ATX polypeptide level.

The invention further provides a method for identifying an ATX-modulatory compound where the level of ATX polypeptide is measured by determining the level of non-sense mediated messenger RNA (mRNA) decay (NMD). NMD is a surveillance mechanism within cells whereby imperfect mRNAs that contain premature translation termination codons are preferentially degraded. As disclosed herein, treatment of cells with an ATX anti-sense oligonucleotide, which reduced endogenous ATX expression, demonstrated that ATX expression is required for maximal NMD activity (Example 9). The level of NMD is correlated to the level of ATX in the cell and so the level of NMD can be used as a measure of ATX polypeptide level.

ATX-modulatory compounds can be identified that decrease or increase the level of ATX polypeptide or nucleic acid. A decrease in the level of ATX can be a partial reduction or a total blockage of the level of ATX, and an increase in the level of ATX can be a partial increase or an induction of the level of ATX from a previously undetectable level. For example, an ATX-modulatory compound can increase the level of NMD activity in a cell. It can be desirable to increase the level of NMD activity in a cell in order to protect the cell from deleterious gain-of-function mutations caused by truncated polypeptides resulting from the translation of imperfect mRNAs that contain premature translation termination. Alternatively, an ATX-modulatory compound can decrease the level of NMD activity in a cell. It can be desirable to decrease the level of NMD activity in a cell in some cases where the truncated polypeptide does not have a deleterious effect but instead retains some activity that can compensate for the normal gene function.

ATX-modulatory compounds can include, for example, antibodies and other proteins or peptides which specifically bind to an ATX polypeptide or an ATX-encoding nucleic acid, oligonucleotides which bind to an ATX polypeptide or an ATX gene sequence, and other non-peptide compounds, for example, isolated or synthetic organic and inorganic molecules, which specifically react with an ATX polypeptide or underlying nucleic acid. ATX-modulatory compounds of the invention can interact specifically or exclusively to an ATX polypeptide or ATX-encoding nucleic acid, however, modulators that interact with an ATX polypeptide or an ATX-encoding nucleic acid with higher affinity or avidity compared to other compounds are also included in the invention. Mutant ATX polypeptides which affect the enzymatic activity or cellular localization of the wild-type ATX polypeptides are also contemplated by the invention. Targets for the development of ATX-modulatory compounds can include, for example: (1) regions of an ATX polypeptide which contact other proteins, (2) regions that localize an ATX polypeptide within a cell, (3) regions of an ATX polypeptide which bind substrate, (4) allosteric regulatory binding site(s) of an ATX polypeptide, (5) phosphorylation site(s) of an ATX polypeptide as well as other regions of the protein where covalent modification regulates biological activity and (6) regions of an ATX polypeptide which are involved in multimerization of subunits. Still other ATX-modulatory compounds include those that recognize specific ATX-encoding and regulatory nucleic acid sequences. ATX-modulatory compounds that modulate the level of ATX can be therapeutically useful in treatment of diseases and physiological conditions in which ATX is known or suspected to be involved.

Methods of the invention to identify ATX-modulatory compounds include variations on any of the methods described above to identify ATX binding compounds, the variations including techniques where a binding compound has been identified and the binding assay is carried out in the presence and absence of a candidate ATX-modulatory compound. A modulatory compound is identified in those instances where the level of binding between an ATX polypeptide and a binding compound changes in the presence of the candidate modulatory compound compared to the level of binding in the absence of the candidate modulatory compound. An ATX-modulatory compound that increases binding between an ATX polypeptide and the binding compound is described as an enhancer or activator, and a modulatory compound that decreases binding between the ATX polypeptide and the binding compound is described as an inhibitor. In vitro methods of the invention are amenable to high throughput assays as described below.

In addition to the assays described above which can be modified to identify binding compounds, other methods are contemplated to identify modulatory compounds. In one embodiment, methods of the invention can include use of the split hybrid assay as generally described in WO98/13502 and variations on this method as described in WO95/20652.

The methods of the invention can also utilize high throughput screening (HTS) assays to identify compounds that interact with or inhibit biological activity of an ATX polypeptide. HTS assays permit screening of large numbers of compounds in an efficient manner. Cell-based HTS systems include melanophore assays, yeast-based assay systems, and mammalian cell expression systems (Jayawickreme and Kost, Curr. Opin. Biotechnol. 8:629-634 (1997)). Automated (robotic) and miniaturized HTS assays are also embraced (Houston and Banks, Curr. Opin. Biotechnol. 8:734-740 (1997)). HTS assays are designed to identify "hits" or "lead compounds" having the desired property, from which modifications can be designed to improve the desired property. Chemical modification of the "hit" or "lead compound" is often based on an identifiable structure/activity relationship (SAR) between the "hit" and the ATX polypeptide.

There are a number of different libraries used for the identification of small molecule modulators, including, (1) chemical libraries, (2) natural product libraries, and (3) combinatorial libraries comprised of random peptides, oligonucleotides or organic molecules.

Chemical libraries consist of structural analogs of known compounds or compounds that are identified as "hits" or "leads" via natural product screening. Natural product libraries are collections from microorganisms, animals, plants, or marine organisms which are used to create mixtures for screening by, for example, (1) fermentation and extraction of broths from soil, plant or marine microorganisms or (2) extraction of plants or marine organisms. Natural product libraries include polyketides, non-ribosomal peptides, and variants (non-naturally occurring) variants thereof. Combinatorial libraries are composed of large numbers of peptides, oligonucleotides or organic compounds as a mixture. They can be prepared by traditional automated synthesis methods, PCR, cloning or proprietary synthetic methods. Libraries that can be utilized by the invention include peptide and oligonucleotide combinatorial libraries. Still other libraries of interest include protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). Identification of modulators through use of the various libraries described herein permits modification of the candidate "hit" (or "lead") to optimize the capacity of the "hit" to modulate activity.

Anti-sense oligonucleotides which recognize and hybridize to nucleic acid encoding ATX can also be utilized by the methods of the invention. Full length and fragment anti-sense oligonucleotides are provided. One skilled in the art of will appreciate that fragment anti-sense molecules of the invention include (i) those which specifically or exclusively recognize and hybridize to ATX-encoding RNA (as determined by sequence comparison of DNA encoding ATX to DNA encoding other molecules) as well as (ii) those which recognize and hybridize to RNA encoding variants of the ATX family of proteins. Antisense oligonucleotides that hybridize to RNA encoding other members of the PIKK family of proteins are also identifiable through sequence comparison to identify characteristic, or signature, sequences for the family of molecules. Identification of sequences unique to ATX-encoding nucleic acids, as well as sequences common to the family of PIKK-encoding nucleic acids, can be deduced through use of any publicly available sequence database, or through use of commercially available sequence comparison programs. After identification of the desired sequences, isolation through restriction digestion or amplification using any of the various polymerase chain reaction techniques well known in the art can be performed. Anti-sense oligonucleotides can be used for regulating expression of ATX by those cells expressing ATX mRNA. Antisense molecules are generally from about 5 to about 100 nucleotide in length, and preferably are about 10 to 20 nucleotides in length. Antisense nucleic acids capable of specifically binding to ATX expression control sequences or ATX RNA are introduced into cells, for example, by a viral vector or colloidal dispersion system such as a liposome.

The anti-sense nucleic acid binds to the ATX-encoding target nucleotide sequence in the cell and prevents transcription or translation of the target sequence. Phosphorothioate and methylphosphonate anti-sense oligonucleotides are specifically contemplated for therapeutic use by the invention. The anti-sense oligonucleotides may be further modified by poly-L-lysine, transferrin polylysine, or cholesterol moieties at their 5' end.

The invention also provides methods to modulate ATX expression through the use of RNA interference. (RNAi) (Brummelkamp et al., Science 296:550-553 (2002); Elbashir et al., Nature 411:494-498 (2002)). RNAi is a process of sequence-specific gene silencing by post-transcriptional RNA degradation, which is initiated by double-stranded RNA (dsRNA) homologous in sequence to the silenced gene. A double-stranded RNA (dsRNA) that is used for RNAi is referred to herein as an "interfering RNA." For example, a suitable dsRNA for RNAi can contain sense and antisense strands of about 21 contiguous nucleotides corresponding to the gene to be targeted that form 19 RNA base pairs, leaving overhangs of two nucleotides at each 3' end (Elbashir et al., supra; Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. 98:7863-7868 (2001). dsRNA can be synthesized in vitro and introduced into a cell by methods known in the art. By using RNAi methods, the targeted RNA is degraded, and translation of the target polypeptide is decreased or abolished.

The invention further provides methods to modulate ATX expression through the use of ribozymes (Gibson and Shillitoe, Mol. Biotech. 7:125-137 (1997)). Ribozyme technology can be utilized to inhibit translation of ATX mRNA in a sequence specific manner through (i) the hybridization of a complementary RNA to a target mRNA and (ii) cleavage of the hybridized mRNA through nuclease activity inherent to the complementary strand. Ribozymes can be identified by empirical methods or be specifically designed based on accessible sites on the target mRNA (Bramlage, et al., *Trends in Biotech* 16:434-438 (1998)). Delivery of ribozymes to target cells can be accomplished using either exogenous or endogenous delivery techniques well known in the art. Exogenous delivery methods can include use of targeting liposomes or direct local injection. Endogenous methods include use of viral vectors and non-viral plasmids. Ribozymes can be ATX-modulatory compounds and specifically modulate expression of ATX when designed to be complementary to regions unique to a nucleic acid encoding ATX. Specifically modulate means that ribozymes of the invention exclusively recognize a nucleic acid encoding ATX.

The invention further provides methods to modulate transcription of ATX through use of oligonucleotide-directed triple helix formation (Lavrovsky, et al., *Biochem. Mol. Med.* 62:11-22 (1997)). Triple helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Target sequences for hybridization include promoter and enhancer regions to permit transcriptional regulation of ATX expression. In addition to use of oligonucleotides, triple helix formation techniques of the invention also include use of peptide nucleic acids as described in Corey, *TIBTECH* 15:224-229 (1997). Oligonucleotides which are capable of triple helix formation are also useful for site-specific covalent modification of target DNA sequences. Oligonucleotides useful for covalent modification can be coupled to various DNA damaging agents as described in Lavrovsky, et al. (supra).

Mutations in the ATX gene can result in loss of normal function of the ATX gene product and underlie ATX-related human disease states. The invention therefore provides gene therapy methods to restore ATX activity in treating those disease states described herein. Delivery of a functional ATX gene to appropriate cells is effected ex vivo, in situ, or in vivo by use of vectors, for example, viral vectors such as adenovirus, adeno-associated virus, or a retrovirus, or ex vivo by use of physical DNA transfer methods such as liposomes or chemical treatments (Anderson, *Nature.*, supplement to vol. 392, no. 6679, pp. 25-20 (1998)). Alternatively, in some human disease states, preventing the expression of, or inhibiting the activity of, ATX can be useful in treating the disease states. In this case, anti-sense therapy or gene therapy, for example, where a dominant negative ATX mutant is introduced into a target cell type, can be applied to negatively regulate the expression of ATX.

The invention provides a method for modulating cell survival by introducing an ATX-modulatory compound identified by the methods described above into a cell in an amount effective to modulate survival of the cell. For example, the ATX-modulatory compound can decrease or increase cell survival.

A level of cell death or cell survival can be measured by any of a variety of methods known to one skilled in the art. For example, trypan blue staining can be used to measure the level of cell death in a cell. In addition, clonogenic assays, as described herein, can be used (Example 5). Other staining methods, for example, propidium iodide and Alomar Blue, also can be used to measure cell death. The stained cells can be visualized in any way that is convenient, for example, by microscopy or flow cytometry (FACS). In addition, cell viability and cell proliferation assays such as the lactose dehydrogenase (LDH) assay and the MTT (3-(4,5-dimethylthiazolyl-2)-2,5-diphenyltetrazolium bromide) assay are commercially available and can be used to measure cell viability. In addition, the uptake of 3H thymidine can be used to access the viability of cells.

The invention further provides a method for modulating cell survival by introducing an ATX-modulatory compound into a cell where the cell is exposed to a stressor agent. As described further above, a stressor agent is any agent that can induce a stress response pathway within a cell. A stressor agent can include, for example, UV light, ionizing radiation, reactive oxygen intermediates, or a chemical agent such as a cytotoxic or chemotherapeutic agent. In addition, environmental conditions such as excessive heat can induce a stress response pathway within a cell resulting in, for example, the induction of heat shock proteins. Stress response pathways include DNA repair pathways, non-sense mediated mRNA decay (NMD), heat shock pathways, the induction of apoptosis, activation of the NFkB transcription factor, activation of the stress-activated MAP kinase pathways including, for example, JNK and p38 pathways, and activation of ubiquitin-dependent proteolysis.

An example of an ATX-modulatory compound of the invention is an antisense oligonucleotide. The invention provides a method for decreasing cell survival by introducing an antisense oligonucleotide, such as SEQ ID NO: 11 into a cell in an amount effective to decrease survival of the cell.

Association of ATX with cell cycle progression makes compositions of the invention, including for example an ATX polypeptide, an inhibitor thereof, an antibody, or other modulator of ATX expression or biological activity, useful for treating a number of conditions. For example, the invention provides a method for treating a condition characterized by excessive cell survival or cell growth by administering to a patient having such a condition an effective amount of an ATX-modulatory compound where the effective amount of the compound increases cell death. For example, an ATX-modultory compound can be given to a patient with a neoplastic condition.

An ATX-modulatory compound that decreases the level of ATX can enhance the radiosensitivity or chemosensitivity of neoplastic cells. Therefore, it is contemplated that an ATX-modulatory compound can be given alone or in combination with another agent such as a cytotoxic or chemotherapeutic agent. Several cytotoxic agents, such as radiation, and chemotherapeutic agents, such as cis-platin, are well known in the art. An appropriate agent can be chosen based on several factors, such as the particular type of neoplastic condition at issue or the ability of the patient to tolerate the agent. For example, focused radiation therapy, including brachytherapy, can be used in conjunction with an ATX inhibitory compound in order to induce tumor cell death while minimizing cytotoxic effects on normal tissue.

A "neoplastic condition," refers to a condition associated with hyperproliferation of cells and includes benign and malignant expanding lesions of proliferating cells. Neoplastic conditions include benign and malignant hyperproliferative disorders. A benign neoplasm grows in an expansile manner, displacing or compressing surrounding tissues rather than invading them. A malignant neoplasm refers to a large group of diseases characterized by uncontrolled growth and spread of abnormal cells. Cancer, for example, is a malignant neoplastic condition that encompasses many sub-conditions that are characterized by insufficient death of abnormal cells.

Tumors of the colon, prostate, lung, cervix, stomach, breast and skin are examples of neoplastic conditions.

Aberrant ATX activity can be associated with various forms of cancer in, for example, adult and pediatric oncology, including growth of solid tumors/malignancies, myxiod and round cell carcinoma, locally advanced tumors, metastatic cancer, human soft tissue sarcomas, cancer metastases, including lymphatic metastases, squamous cell carcinoma of the head and neck, esophageal squamous cell carcinoma, oral carcinoma, blood cell malignancies, including multiple myeloma, leukemias, effusion lymphomas (body cavity based lymphomas), thymic lymphoma lung cancer, including small cell carcinoma, non-small cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, and solid tumors in the ovarian follicle, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas, skin cancers, including malignant melanoma, tumor progression of human skin keratinocytes, and squamous cell cancer, hemangiopericytoma, and Kaposi's sarcoma.

Aberrant ATX activity also can be associated with other conditions which include aberrant apoptotic mechanisms, including abnormal caspase activity; aberrant enzyme activity associated with cell cycle progression, including for example cyclins A, B, D and E; alterations in viral (such as Epstein-Barr virus, papillomavirus) replication in latently infected cells; chromosome structure abnormalities, including genomic stability in general, unrepaired chromosome damage, telomere erosion (and telomerase activity), breakage syndromes including for example, Sjogren's syndrome and Nijimegen breakage syndrome; embryonic stem cell lethality; abnormal embyonic development; sensitivity to ionizing radiation; acute immune complex alveolitis; and Fanconi anemia. ATX-modulatory compounds can be used alone or in combination with another agent in the treatment of these conditions.

The invention also provides a method for treating a condition characterized by excessive cell death by administering to a patient having such a condition an effective amount of an ATX-modulatory compound where the effective amount of the compound increases cell survival. For example, an ATX-modulatory compound can be given to a patient with a neurodegenerative condition in order to increase neuronal cell survival. In addition the invention provides a method of prolonging the in vivo survival of transplanted cells for the treatment of a disease or pathological condition. Also, for example, a compound that increases the level of ATX can be given to a patient who is exposed to stressors such as UV light in order to protect against genetic mutations.

The effective compounds of the invention described herein can optionally be formulated together with a pharmaceutically acceptable carrier for delivery to a cultured cell or to a subject. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight polypeptide; or another stabilizer or excipient. Pharmaceutically acceptable carriers, including solvents, stabilizers, solubilizers and preservatives, are described, for example, in Martin, *Remington's Pharm. Sci.*, 15th Ed. (Mack Publ. Co., Easton, 1975).

Those skilled in the art can formulate the therapeutic molecules to ensure proper distribution in vivo. For example, the blood-brain barrier (BBB) excludes many highly hydrophilic compounds. To ensure that the effective compounds of the invention cross the BBB, if desired, they can be formulated, for example, in liposomes, or chemically derivatized. For a review of strategies for increasing bioavailability of polypeptide drugs in the brain, and of methods for determining the permeability of polypeptides through the BBB using in vitro and in vivo assays, see Engleton et al., *Peptides* 9:1431-1439 (1997). Strategies that have been successfully used to increase the permeability of other neuropeptides through the BBB are particularly contemplated. Modifications to a polypeptide of the invention that can increase its BBB penetration include conjugating the peptide to a lipophilic moiety, such as a lipophilic amino acid or methyldihydropyridine. Similar modifications to invention polypeptides or peptidomimetics are likewise expected to be advantageous.

Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include both biodegradable and non-degradable polymers and hydrogels. Those skilled in the art understand that the choice of the pharmaceutical formulation and the appropriate preparation of the composition will depend on the intended use and mode of administration.

The effective compounds of the invention can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously. The present invention also provides compounds containing an acceptable carrier such as any of the standard pharmaceutical carriers, including phosphate buffered saline solution, water and emulsions such as an oil and water emulsion, and various types of wetting agents.

An effective dose of an effective compound of the invention can be determined, for example, by extrapolation from the concentration required in the ATX binding or ATX activity assays described herein; or from the dose required to modulate cell proliferation. An effective dose of an effective compound of the invention for the treatment of a pathology can also be determined from appropriate animal models, such as transgenic mice. Animal models for pathologies such as tumors are well-known in the art. An effective dose for treating this disease is a dose that results in either partial or complete regression of the tumor, reduction in metastasis, reduced discomfort, or prolonged life span. The appropriate dose for treatment of a human subject with a therapeutic molecule of the invention can be determined by those skilled in the art, and is dependent on the nature and bioactivity of the particular compound, the desired route of administration, the gender, age and health of the individual, the number of doses and duration of treatment, and the particular condition being treated.

It is understood that modifications which do not substantially affect the activity of the various embodiments of this invention are also included within the definition of the invention provided herein. Accordingly, the following examples are intended to illustrate but not limit the present invention.

EXAMPLE 1

Molecular Cloning of ATX

This example shows the cloning of ATX nucleic acids. During a BLAST search for mTOR-related proteins, it was noted that an expressed sequence tag (EST) (KIAA0421) contained a 5'-terminus with an open reading frame (ORF) that bore clear homology to a conserved region in the catalytic domains of PIKK family members. To access the full-length cDNA, the EST was used to generate a primer for 5'-RACE with human brain cDNA as the template. The initial 5'-RACE product extended the region of homology with the PIKK catalytic domain. Sequential screens of human brain (Clontech #HL1128a) and Jurkat T cell cDNA libraries (Stratagene #936219), combined with 5'-RACE of brain and Jurkat cDNA, resulted in the isolation of several overlapping DNA fragments that were assembled into approximately 12 kb of contiguous nucleotide sequence. This cDNA contains an ORF of 10,563 nucleotides with an additional 1.8 kb of 3'-UTR, and encodes a 3,521 amino acid polypeptide with a deduced molecular mass of 395 kDa. The first nucleotide of the ATG translation initiation codon in exon 6 as has been designated as nucleotide "1", and nucleotides upstream of this ATG are identified in the 3' to 5' direction with negative numbers. The conclusion that this sequence was derived from a single mRNA transcript was confirmed by PCR with primers that were complementary to the extreme 5'-terminus (nucleotides −90 to −67) and 3'-terminus (nucleotides 10,553 to 10,570) of the corresponding cDNA. The cloned cDNA sequence is contained in a genomic BAC clone (AC020716), which allowed localization of the gene encoding this putative PIKK family member to human chromosome 16. Based on its functional overlap with ATM, this new PIKK family member was named "ATX".

The collective results of the 5'-RACE and RT-PCR assays of mRNA derived from Jurkat T cell, human brain, and other human cell lines indicated that the ATX locus gives rise to several mRNA transcripts (FIG. 1A). One repetitively isolated ATX cDNA clone contains exon 4 spliced directly to exon 6, and yields the 3,521 amino acid polypeptide described above. This mRNA transcript and encoded polypeptide has been designated "long ATX", to distinguish it from a "short ATX" polypeptide (3,031 amino acids) produced as a result of allelic variation in exon 15, which leads to the insertion of 27 nucleotides beginning at nucleotide 1427 (FIG. 1A). This sequence alteration causes the insertion of two in-frame stop codons, and use of the next available ATG codon (in exon 16) as the translational start site gives rise to the amino-terminally truncated, short form of ATX. The 5' end of the ATX allele that encodes short ATX is contained within a second genomic BAC clone (AC003007) derived from human chromosome 16. Yamashita et al. have identified two human cDNA clones, both designated hSMG-1, one of which (FIG. 1A, second from bottom, SEQ ID NO: 7) was similar to the long ATX cDNA clone (SEQ ID NO:1) (Yamashita et al., *Genes and Development* 15:2215-2228 (2001)). Exon 5 was not included in our long cDNA clone due to the infrequent appearance of this exon during our 5'-RACE and RT-PCR analyses of human cell line-derived mRNA. Furthermore, the minority of cDNAs that did include the exon 5 sequence frequently contained exon 3, which placed an in-frame stop codon at the 5'-end of this cDNA (FIG. 1A). The longest ATX cDNA clone (ORF beginning at exon 2, SEQ ID NO:9) identified by Yamashita et al. (Yamashita et al., supra, 2001) was also isolated in our screening procedure. However, it was repeatedly found that the exon 3-associated stop codon was present in this transcript.

EXAMPLE 2

Expression of Endogenous and Recombinant ATX

In order to examine the expression of ATX mRNA in various tissues, a multiple tissue Northern blot was hybridized with a 32P-labelled, ATX cDNA probe that spanned exons 38-39 (nucleotides 5,071-5,370). The ATX probe detected a major mRNA species that, based on its electrophoretic mobility, was significantly larger the 9.5 kb calibration marker, and could reasonably accommodate the predicted ORF (10.5 kb) of long ATX (data not shown). This ATX transcript was widely expressed in human tissues, with the highest levels observed in heart and skeletal muscle. These results are consistent with those obtained in immunoblot analyses with ATX-specific antibodies, which showed that ATX protein was uniformly expressed in hematopoietic, mesenchymal, and epithelial cell lines (data not shown). Database searches with the ATX amino acid sequence revealed the highest degree of homology to *C. elegans* SMG1, a protein required for NMD in the worm. Both ATX and CeSMG1 contain the PI 3-kinase related catalytic domain, which identifies these proteins as members of the PIKK family (FIG. 1B). Outside of the catalytic domain, the regional sequence homology between ATX and other PIKK family members was limited to the FKBP-12●rapamycin binding (FRB, designated NH2 in FIG. 1B) domain of mTOR, and to the NH1 and NH2 domains of CeSMG1. The FRB domain mediates the high-affinity interaction between mTOR and the antiproliferative FKBP12●rapamycin complex (Chen et al., *Proc. Natl. Acad. Sci. USA*, 92:4947-4951 (1995)). However, the FRB-related domain of ATX does not confer any detectable binding affinity for FKBP12●rapamycin (data not shown); hence, it is unlikely that ATX is a relevant target for rapamycin in intact cells. The expression of the short and long forms of ATX were compared after transient transfection of the respective cDNAs into human embryonic kidney 293T cells. The short ATX polypeptide was poorly expressed relative to long ATX (data not shown). However, these results do not exclude the possibility that the shorter form of ATX is expressed and contributes to the overall functions of ATX in mammalian cells.

In order to compare the translation product derived from the long ATX cDNA with the endogenously expressed ATX polypeptide, HEK 293T cells were transfected with HA-tagged expression plasmids encoding either wild-type ATX (HA-ATXWT) or a catalytically inactive ATX mutant (HA-ATXKI). The HA-ATXKI mutant contains an Asp>Ala substitution at a conserved residue (Asp-2195) in the ATX catalytic domain. Similar mutations in the catalytic domains of ATM, ATR, and DNA-PKCS have been shown to generate kinase-inactive (KI) versions of these PIKK family members (Canman et al., *Science*, 281:1677-1679 (1998); Cliby et al., *EMBO Journal*, 17:159-169 (1998); Hunter, supra, 1995).

For analyses of the endogenous ATX protein, two different rabbit polyclonal antibodies were prepared against GST fusion proteins containing peptide fragments derived from ATX. The first antibody (α-ATX Ab-1) was generated against a GST fusion protein containing amino acids 2281-2339 of ATX, while the second (α-ATX Ab-2) was obtained from immunizations with GST fused to amino acids 1691-1790 of ATX. The α-ATX Ab1 immunoblot analyses of whole cell extracts from non-transfected or HA-ATX-transfected HEK 293T cells revealed a single major immunoreactive band migrating at the predicted molecular mass of ~395 kDa (data not shown). An immunoreactive protein bearing a nearly identical electrophoretic mobility was detected in α-HA immunoprecipitates from transfected 293T cells. These results indicate that the molecular mass of the recombinant protein produced from the long ATX cDNA corresponds closely to that of the endogenous ATX protein. Consistent with the predicted size of ATX, the band recognized by the α-ATX antibodies migrated with a significantly lower electrophoretic mobility than either ATM (molecular mass, 370 kDa) or ATR (molecular mass, 305 kDa).

Methods:

Cloning

The longer ATX ORF was appended with an amino-terminal hemagglutinin (HA) epitope tag sequence (CYPYDVP-DYASL), and was subsequently amplified as two partially overlapping fragments from Jurkat cDNA. The nucleotide at position 4,620 was mutated in each of the two PCR products to create a SacII site that could be utilized to ligate the two ATX fragments, which were inserted into the XhoI and NotI sites of pcDNA3.1 (Invitrogen) (HA-ATX). The mutation used to generate the SacII did not alter the ATX polypeptide sequence. The expression vector encoding the catalytically inactive ATX mutant (HA-ATXKI) contains an Ala substitution at Asp-2195, which was generated by site-directed mutagenesis with the QuickChange kit (Stratagene). All plasmid constructs were sequenced to insure the fidelity of the PCR and cloning procedures.

Cell Lines

U2OS osterosarcoma and human embryonic kidney (HEK) 293T cells were cultured in low-glucose Dulbecco's Modified Eagle's Medium (DMEM), supplemented with 10% fetal bovine serum. The ATM-deficient human fibroblast line, AT4BI, was maintained in DMEM/F-12 medium supplemented with 10% fetal bovine serum. Where indicated, cells were γ-irradiated with a 137Cs source or UV irradiated with a UV-B source (λmax, 305 nm).

Antibodies

ATX-specific antibodies were raised by immunizing rabbits (Cocalico Biologicals, Inc.) with the indicated glutathione S-transferase (GST) fusion protein. Anti-ATX Ab-1 was raised against a GST fusion protein containing ATX amino acids 2281-2339, and α-ATX Ab-2 was raised against a GST fusion protein containing ATX amino acids 1691-1790. For purification of α-ATX Ab-2, GST-reactive antibodies were first absorbed on GSH-agarose. The flow-through fraction was then affinity purified over Affi-Gel 15 (BIO-RAD) coupled to the GST-ATX1691-1790 fusion protein. The α-PLC-γ1 antiserum was prepared as described (Secrist et al., *J. Biol. Chem.*, 268: 5886-5893 (1993)). The α-ATM (Ab-3), α-ATR (Ab-1), α-phospho-Ser15-p53, and α-p53 (Ab-6) reagents were obtained from Oncogene Science Research Products. Additional antibodies were obtained from (sources in parentheses): α-HA (clone 12CA5; BabCo), α-FLAG-M2 and α-tubulin (Sigma), α-Cds1/Chk2 (Upstate Biotechnology), and α-GAL4 (clone RK5C1; Santa Cruz Biotechnology).

Two-dimensional PAGE

HEK 293 cells were lysed and protein analyzed as described {Pal, 2001 #1360}, except that cellular extracts were incubated for 2 h with α-FLAG-M2 mAb, followed by 2 h with protein G agarose (Sigma) to immunoprecipitate the FLAG-hUpf1 protein. Prior to elution, the immunoprecipitates were washed in lysis buffer as described {Pal et al., *Rna* 7:5-15 (2001) #1360}.

Immunofluorescence

For immunofluorescence microscopy of endogenous ATX, $6 \times 10^4$ U2OS cells were plated onto 22-mm2 glass coverslips. After 40 h, cells were exposed to 400 J/m2 UV-B, then fixed 1, 4 or 8 hrs later in phosphate-buffered saline (PBS) containing 4% paraformaldehyde for 20 min, and incubated in methanol at −20° for 15 min. The coverslips were rehydrated in phosphate-buffered saline (PBS) and incubated overnight at 4° C. in blocking solution (PBS containing 3% BSA and 2% goat serum). Coverslips were subsequently overlayed for 1 h with affinity purified α-ATX Ab-2 (1 μg per ml) in blocking solution at room temperature. Coverslips were washed with PBS, 0.2% Tween-20, and overlayed for 45 min at room temperature with fluorescein isothiocyanate (FITC)-conjugated goat anti-rabbit IgG (Caltag) (1:2000 in blocking solution). Samples were then washed and incubated with 100 μg per ml RNaseA in PBS for 30 min, followed by 1 μg per ml propidium iodide for 5 min. After extensive washing in PBS containing 0.2% Tween-20, coverslips were mounted on slides with an aqueous anti-fade mounting reagent (Vectashield, Vector Laboratories). Immunofluorescence images were generated with a Carl Zeiss LSM410 scanning laser confocal microscope.

EXAMPLE 3

Characterization of ATX Kinase Activity

With the exception of the TOR proteins, the PIKK family members that bear functional catalytic domains phosphorylate substrates bearing the Ser/Thr-Gln motif (Tibbetts and Abraham, supra, 2000). To determine whether the ATX kinase domain displayed a similar phosphorylation site selectivity, HEK 293T cells were transfected with a plasmid vector encoding HA-tagged ATXWT, ATXKI, or, for comparative purposes, HA-ATMWT. Detergent extracts from the transfected cell populations were immunoprecipitated with α-HA antibody, and protein kinase assays were performed in buffer containing Mn2+, [γ-32P]ATP, and a GST fusion protein containing the first 70 amino acids of p53 (GST-p53$_{1-70}$) as the substrate (FIG. 1C). The GST-p53$_{1-70}$ protein was previously identified as a substrate for ATM and ATR in immune complex kinase assays (Tibbetts et al., *Genes and Development* 13:152-157 (1999)). Interestingly, the specific kinase activity of HA-ATXWT towards GST-p53$_{1-70}$ was significantly higher than that of HA-ATM (FIG. 1C, left panel). Based on the ratios of 32P incorporation into substrate to levels of HA-tagged protein kinase, it can be estimated that the specific kinase activity of ATXWT was approximately 3.5-fold higher than that of ATMWT. As observed with ATM as the test kinase (Banin et al., *Science* 281:1674-1677 (1998); Canman et al., *Science* 281:1677-1679 (1998); Tibbetts et al., supra, 1999), phosphorylation of GST-p53$_{1-70}$ by ATXWT was nearly abolished by substitution of the Ser-15 residue in p53 with Ala (FIG. 1C, right panel). Because Ser-15 resides in the optimal sequence (LSQE) for phosphorylation by ATM (O'Neill et al., *J. Biol. Chem.* 275:22719-22727 (2000)), this finding indicates that ATX is a Ser/Thr-Glndirected kinase, with the potential to phosphorylate a set of substrates that overlaps with those modified by ATM. In contrast to the amino-terminal fragment of p53, the PHAS-I/4E-BP1 protein, which is the prototypical substrate for mTOR, was poorly phosphorylated by HA-ATXWT in immune complex kinase assays (data not shown).

The amino acid sequences surrounding the four phosphorylation sites (LSQP, LSQD, LSQD, and LSQY) identified in this study resemble the consensus site for phosphorylation by ATM (O'Neill et al., supra, 2000). A GST fusion protein that contained the carboxyl-terminal region of hUpf1 (amino acids 1019-1118), including all four of the ATX phosphorylation sites was constructed. This GST-hUpf11019-1118 protein was tested as a substrate for HA-ATXWT versus HA-ATMWT in immune complex kinase assays. Once again, this substrate was phosphorylated by both ATM and ATX, with the latter protein kinase showing the higher specific catalytic activity under these in vitro assay conditions (FIG. 1C, left panel). Furthermore, the results of repeated assays indicated that GST-p53$_{1-70}$ was more avidly phosphorylated by ATX than was the GST-hUpf11019-1118 substrate.

The protein kinase activities of the mammalian PIKKs characteristically display a strong dependence on Mn2+ as a cofactor for the phosphotransferase reaction, and variable sensitivity to inhibition by wortmannin (Abraham, *Genes and Development* 15:2177-2196 (2001)). In our studies, the protein kinase activity of ATX was also dependent on the addition of Mn2+ to the kinase reaction buffer (data not shown). In addition, pretreatment of the immunoprecipitated HA-ATXWT protein with wortmannin resulted in a concentration-dependent inhibition of GST-p53$_{1-70}$ phosphorylation. The drug concentration required for 50% inhibition (IC50) of ATX activity in vitro was between 10 and 100 nM (FIG. 1D), which is comparable to the previously published IC50 (80 nM) for wortmannin as an ATM inhibitor (Sarkaria et al., *Cancer Res.* 58:4375-4382 (1998)). Wortmannin is an irreversible inhibitor of PIKKs (Walker et al., *Molecular Cells* 6:909-919 (2000)) and can be used to assess the potency of this drug as an ATX inhibitor in intact cells. To this end, U2OS osteosarcoma cells were pretreated for 30 min with the indicated concentrations of wortmannin, followed by the preparation of cellular extracts for immunoprecipitation of endogenous ATX with α-ATX Ab-2. Under these conditions, wortmannin inhibited ATX kinase activity with an IC50 of 1-3 μM, which is considerably higher than that observed following direct treatment of the immunoprecipitated protein kinase with this drug (FIG. 1D). A similarly dramatic decrease in the inhibitory potency of wortmannin was observed with ATM as the target enzyme in intact cells (Sarkaria et al., supra, 1998).

Immune Complex Kinase Assays

Native or recombinant ATX proteins were immunoprecipitated from cell extracts as described above, and the immunoprecipitates were washed twice in lysis buffer, once in high-salt buffer (100 mM Tris-HCl, pH 7.4, 500 mM LiCl) and once in kinase buffer (10 mM Hepes, pH 7.4, 50 mM NaCl, 50 mM β-glycerol phosphate). Forty μl kinase buffer (containing 10% glycerol, 1 mM DTT, 10 mM MnCl$_2$, 20 nM microcystin, protease inhibitors, 1 μg of the indicated substrate, 10 μM ATP, and 10 μCi [γ-32P]ATP (6000 Ci/mmole) (NEN)] was added to each sample, and kinase reactions were performed for 30 min at 30° C. Reactions were terminated by addition of 40 μl of 4X-SDS-PAGE sample buffer, and heating to 100° C.

EXAMPLE 4

Subcellular Localization of ATX

The subcellular localization of ATX was examined by biochemical fractionation of U2OS cells, followed by immunoprecipitation of crude nuclear and cytoplasmic fractions with α-ATX Ab-2. Comparable levels of ATX were found in the nuclear and cytoplasmic extracts from U2OS cells (data not shown). The integrity of these subcellular fractions was confirmed by immunoprecipitation and immunoblotting of parallel samples with antibodies specific for PLCγ1 and ATR, which are localized to the cytoplasm and nucleus, respectively. The presence of ATX in both the cytoplasmic and nuclear compartments was further documented by immunostaining of U2OS cells with affinity-purified α-ATX Ab-2. Exposure of cells to genotoxic agents triggers the appearance of DNA damage-induced nuclear foci containing either ATM or ATR (Andegeko et al., *J. Biol. Chem.* 276:38334-38230 (2001); Tibbetts et al., *Genes and Development* 14:2989-3002 (2000)). To determine whether ATX undergoes similar changes in subcellular localization in response to genotoxic stress, U2OS cells were treated with 400 J/m2 UV-B, and stained with α-ATX Ab-2. Exposure to UV triggered the appearance of ATX-containing nuclear foci. The ATX-positive foci were evident within 1 h after UV treatment, and continued to accumulate in the cells until at least 8 h post-treatment, at which time greater than 50% of the cells exhibited multiple ATX-containing foci. In contrast, the formation of ATX foci after treatment of U2OS cells with 20 Gy IR was not detected.

In addition, the effect of genotoxic stress on the protein kinase activity of ATX in immune complex assays was determined. Consistent with the results of the immunofluorescence staining experiments, treatment of the cells with IR failed to induce a reproducible increase in the protein kinase activity observed in α-ATX immunoprecipitates (data not shown). On the other hand, UV exposure caused a modest but consistent increase in ATX kinase activity that reached a maximal level at 4 h post-irradiation. Collectively, the results of the nuclear localization and protein kinase activity studies indicated that, like ATM and ATR, ATX participated in cellular responses to DNA damage or other forms of stress induced by UV irradiation.

Methods:

Cell Fractionation, Immunoprecipitation, and Immunoblotting

For subcellular fractionations, U2OS cells were resuspended in cold homogenization buffer (25 mM Hepes, pH 7.4, 250 mM sucrose, 1 mM EGTA, 5 mM MgCl2, 50 mM NaF, 1 mM DTT, plus protease inhibitors) and Dounce homogenized on ice with 40 strokes in a Tefloncoated homogenizer. The nuclei were pelleted at 500×g, and the supernatant was collected as the crude cytoplasmic fraction. Prior to immunoprecipitation, 150 mM NaCl and 1% (wt/vol) NP-40 (final concentration) were added to the crude cytoplasmic fractions. Nuclear extracts were prepared by suspending the nuclear pellets in extraction buffer (50 mM Tris-HCl, pH 7.4, 150 mM NaCl, 1% NP-40, 1 mM dithiothreitol), supplemented with protease inhibitors (10 μg per ml leupeptin, 10 μg per ml aprotinin, 1 μM pepstatin). After 15 min on ice, the samples were centrifuged, and the supernatant was collected for analysis. For immunoprecipitations, cell extracts were prepared by resuspending washed cell pellets in lysis buffer (50 nM Tris-HCl, pH 7.4, 150 mM NaCl, 1% NP-40, 1 mM dithiothreitol) plus protease inhibitors. When samples were prepared for immune complex kinase assays, the lysis buffer was modified to contain 1% Tween-20 detergent in place of NP-40, and additional phosphatase inhibitors (20 mM β-glycerol phosphate and 50 nM microcystin). Samples were incubated on ice for 15 min, and then clarified by centrifugation. HA-tagged recombinant proteins were immunoprecipitated from cell extracts with 4 µg of α-HA antibody. Endogenous ATX protein was immunoprecipitated with 8 µg of α-ATX Ab-2. After separation by SDS-PAGE, the proteins were detected by autoradiography (for kinase reaction products) or by immunoblotting. Proteins immunoblotted with rabbit and mouse antibodies were detected with protein A-horseradish peroxidase (HRP) (Amersham), and sheep anti-mouse IgG-HRP (Amersham), respectively. Immunoreactive proteins were illuminated with Renaissance chemiluminescence system (NEN).

EXAMPLE 5

Effect of Decreased ATX Function on Cellular Sensitivity to UV and IR

In order to gain further insights into the role of ATX in stress responses, U2OS cells were transfected with the kinase-inactive ATXKI mutant, and the UV- and IR-sensitivities of the transfected cells in clonogenic survival assays was examined. Control cell populations were transfected with either empty plasmid (pcDNA3.1) or with ATXWT-encoding plasmid. At 48 h post-transfection, the cells were treated with various doses of UV-B (FIG. 2A) or IR (FIG. 2B). The treated cells were then cultured in G418-containing medium in order to select for stably transfected cells. Cellular survival was determined after 10 days in culture by staining emergent colonies with Coomassie blue, followed by colorimetric quantitation of the amount of dye-bound protein present in each sample. Expression of ATXKI, but not ATXWT, reduced the basal survival of otherwise untreated U2OS cells (FIG. 2B, top panel). These results indicate that endogenous ATX function is required for the maintenance of normal cell viability or growth in culture. Furthermore, expression of ATXKI dramatically increased the sensitivity of U2OS cells to the cytostatic/cytotoxic effects of both UV and IR in these clonogenic survival assays.

Figure 2:
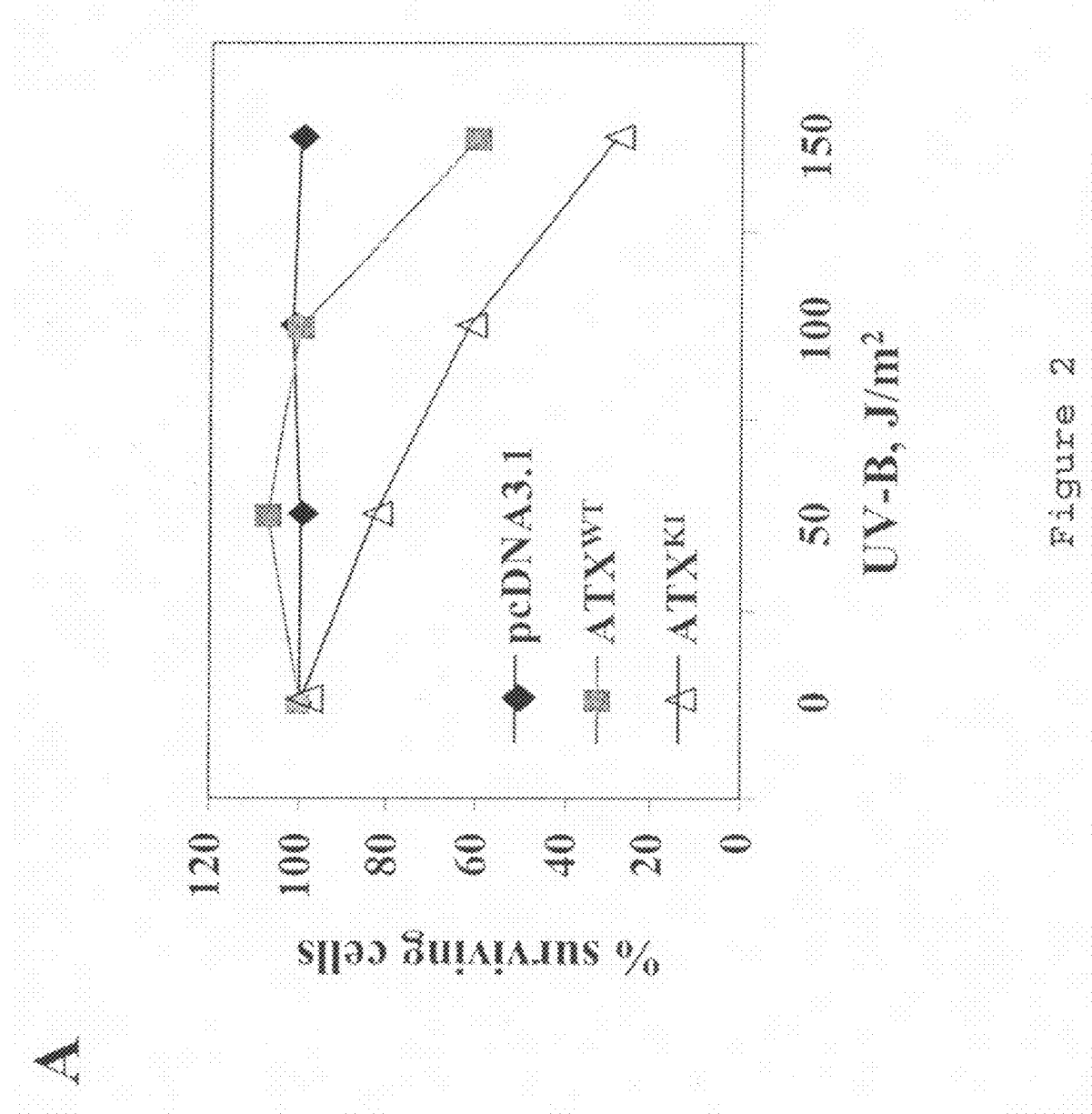
FIG. 2A shows clonogenic survival assays after UV exposure.
FIG. 2B shows clonogenic survival assays after IR exposure. The upper panel displays colony outgrowth results from cells transfected with the indicated plasmids, and not exposed to IR.
FIG. 2C shows clonogenic survival assays of cells treated with ATX-directed antisense oligonucleotides (AS). The right panel displays colony survival results from non-irradiated cells treated with the indicated oligonucleotides.
Figure 2:
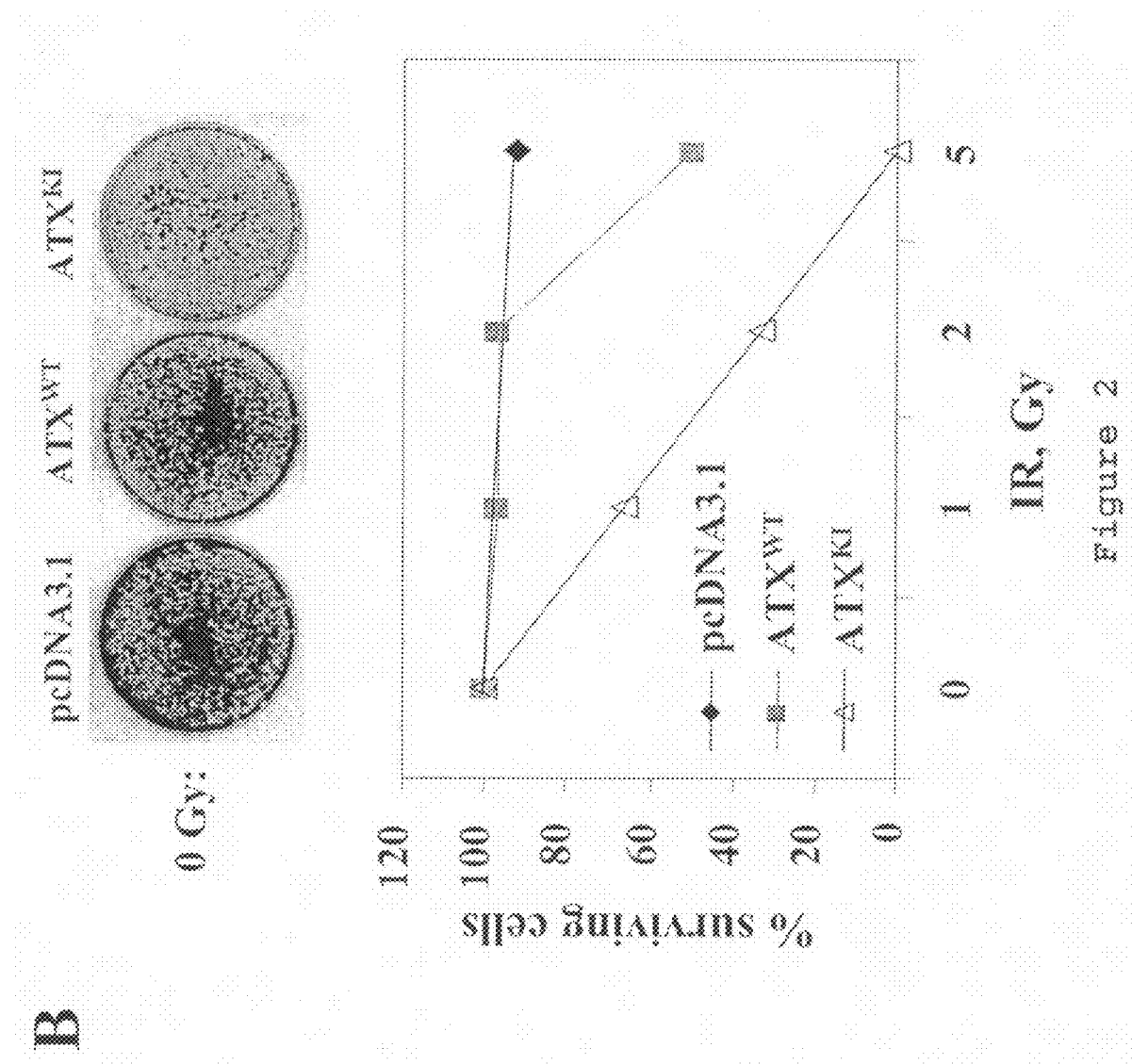
Figure 2:
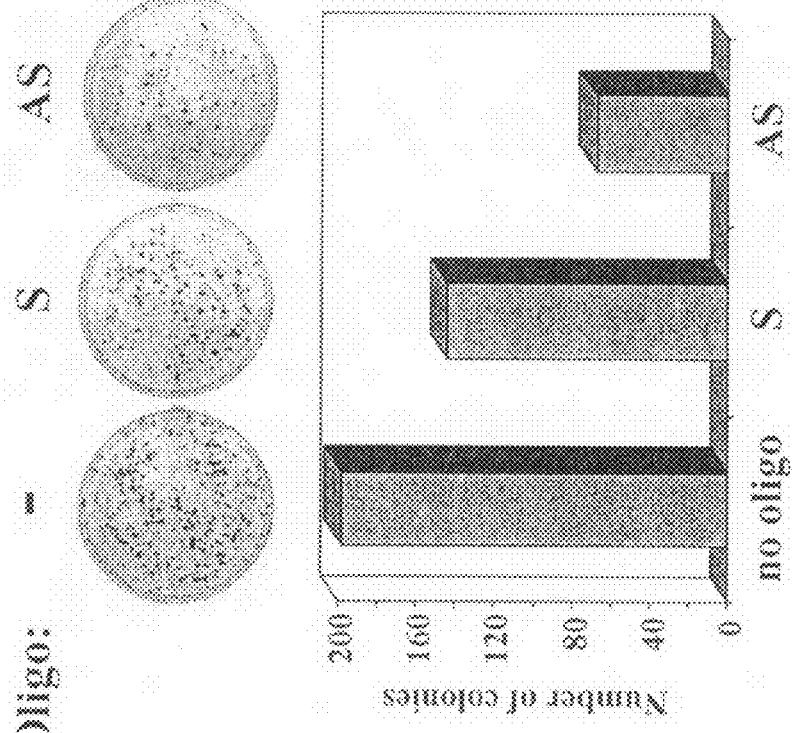
Figure 2:
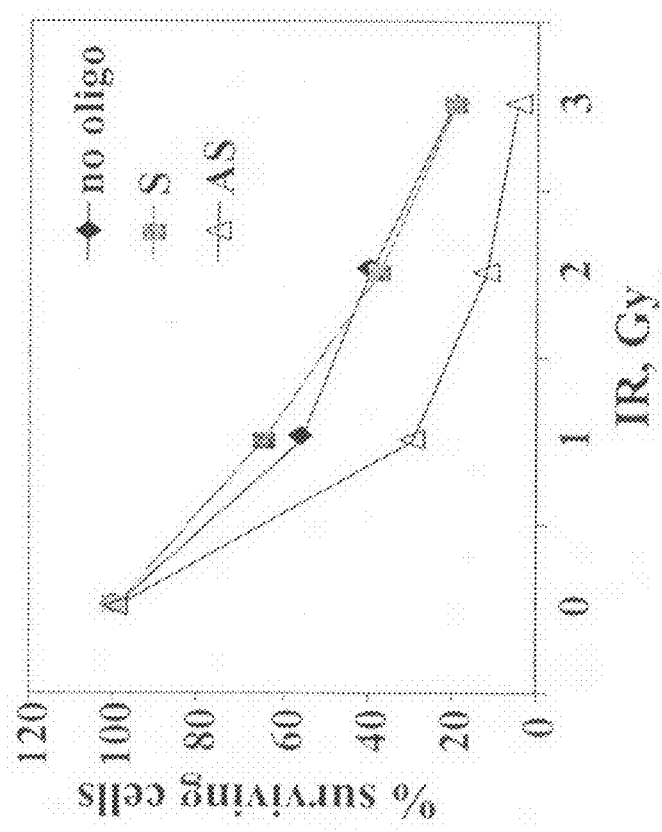

To address concerns related to potential non-specific effects of ATXKI expression on cellular functions, an antisense oligonucleotide-based approach to reduce the level of ATX expression in U2OS cells was developed. The cells were mock transfected, or transfected with sense (S) or antisense (AS) oligonucleotides, and then treated for 24 h with various genotoxic agents. The cells were then trypsinized and replated, and clonogenic survival was analyzed after 10 days in culture. The results obtained with AS-treated cells were strikingly similar to those obtained with the ATXKI-expressing cells (FIGS. 2 A-C). While transfection of U2OS cells with the S oligonucleotide reduced the basal level of colony outgrowth by 25%, treatment with the AS oligonucleotide decreased basal clonogenic activity by 75% (FIG. 2C, right panel). Hence, the AS-induced decrease in ATX protein expression was accompanied by a reduction in cell viability or proliferation in the absence of environmental stress. Furthermore, the AS-treated cells were significantly more sensitive to the suppressive effects of IR (FIG. 2C, left panel) and UV treatments (data not shown) on clonogenic survival. The reduction in ATX protein caused by AS treatment ranged from 50-90% in over 10 independent trials.

Methods:

Cell Transfections

To prepare recombinant HA-tagged ATX and ATM proteins, HEK 293T cells were plated onto 60-mm dishes (9×105 cells per dish), and were transfected with 5 µg pcDNA3.1 (empty vector), HA-ATXWT, HA-ATXKI, or HA-ATMWT-plasmid DNAs. Transfections were performed with the Fugene 6 transfection reagent (Roche), according to the manufacturer's instructions. For NMD assays (see Example 9, below), U2OS cells were seeded onto 100 mm dishes (1×106 cells per dish). After 20 h, cells were transfected with 1.5 µg of pmCMV-G1 test plasmid, either Norm or 39Ter (Ishigaki et al., 2001); 1.5 µg of phCMV-MUP reference plasmid (Ishigaki et al., Cell 106:607-617 (2001)); and 7 µg of empty plasmid (pcDNA 3.1), plasmids encoding HA-ATMWT, HA-ATMKI, HA-ATXWT or HA-ATXKI. For antisense transfection experiments, U2OS cells were seeded onto 60 mm dishes (1×105 cells per dish) in complete medium supplemented with penicillin/streptomycin. After 30 h, cells were either mock transfected or transfected with sense (S) or antisense (AS) phosphorothioate oligonucleotides (Genset Oligos, La Jolla, Calif.). The S oligonucleotide spans ATX nucleotides 210-229 (5'-GAGACAGGAGGGAGCTTGCT-3'), and the AS oligonucleotide is complementary to this sequence (5'-AGCAAGCTCCCTCCTGTCTC-3'). The cells were transfected with oligonucleotides at final concentrations of 8 µg/ml, with Fugene 6:DNA ratio of 1.6:1. Forty-eight hours after transfection, dishes were exposed to IR, UV-B, or 5-FU, and then harvested for immunoblotting, cell-cycle distribution, or cell survival assays. To examine ATX protein levels in oligonucleotide-treated cells, whole cell extracts were resolved by SDS-PAGE and immunoblotted with α-ATX Ab-1. When oligonucleotide-transfected cells were used for NMD assays, U2OS cells were seeded in culture dishes as described above. The cells were transfected using the Fugene reagent, with 1.5 µg of pmCMV-G1 test plasmid, 0.7 µg of phCMV-MUP reference plasmid, and 24 µg of S or AS oligonucleotide.

Clonogenic and G418 Survival Assays

U2OS cells were seeded into 60 mm dishes (1×105 cells per dish) in complete medium. After 48 h, cells were transfected as described above. Forty-eight hours after transfection, dishes were exposed to IR or UV-B, and G418 was added at 1 mg per ml in complete medium. G418-resistant cells were stained 10 days later with Coomassie Blue. To quantitate the outgrowth of drug-resistant cells, the Coomassie Blue-bound protein was solubilized at 37°C with 0.1 M NaOH, and the soluble material was analyzed by absorbance spectroscopy at a wavelength of 590 nm. For AT4BI cell survival assays, cells were transfected with pcDNA3.1, pcDNA3.1-FLAG-ATM, or HA-ATX. After 48 h, the transfected cells were exposed to the indicated doses of IR, and G418 was added at 8 hours post-irradiation. Drug-resistant colonies were stained with Coomassie Blue after 10 days in culture, and the samples were analyzed with Image Pro Plus software to quantitate cell density. For clonogenic assays where oligonucleotides were used, the cells were plated and transfected with S or AS oligonucleotides as described above. Forty-eight hours after transfection, cells were exposed to IR or UV. Twenty-four hours after exposure to damaging agents, cells were replated at 1000 cells per 60 mm dish and colonies allowed to form for 10 days. Dishes were stained with Coomassie Blue, and the number of colonies (minimum size, 50 cells per colony) was counted by visual examination.

EXAMPLE 6

Role of ATX in p53 Activation

Figure 3:
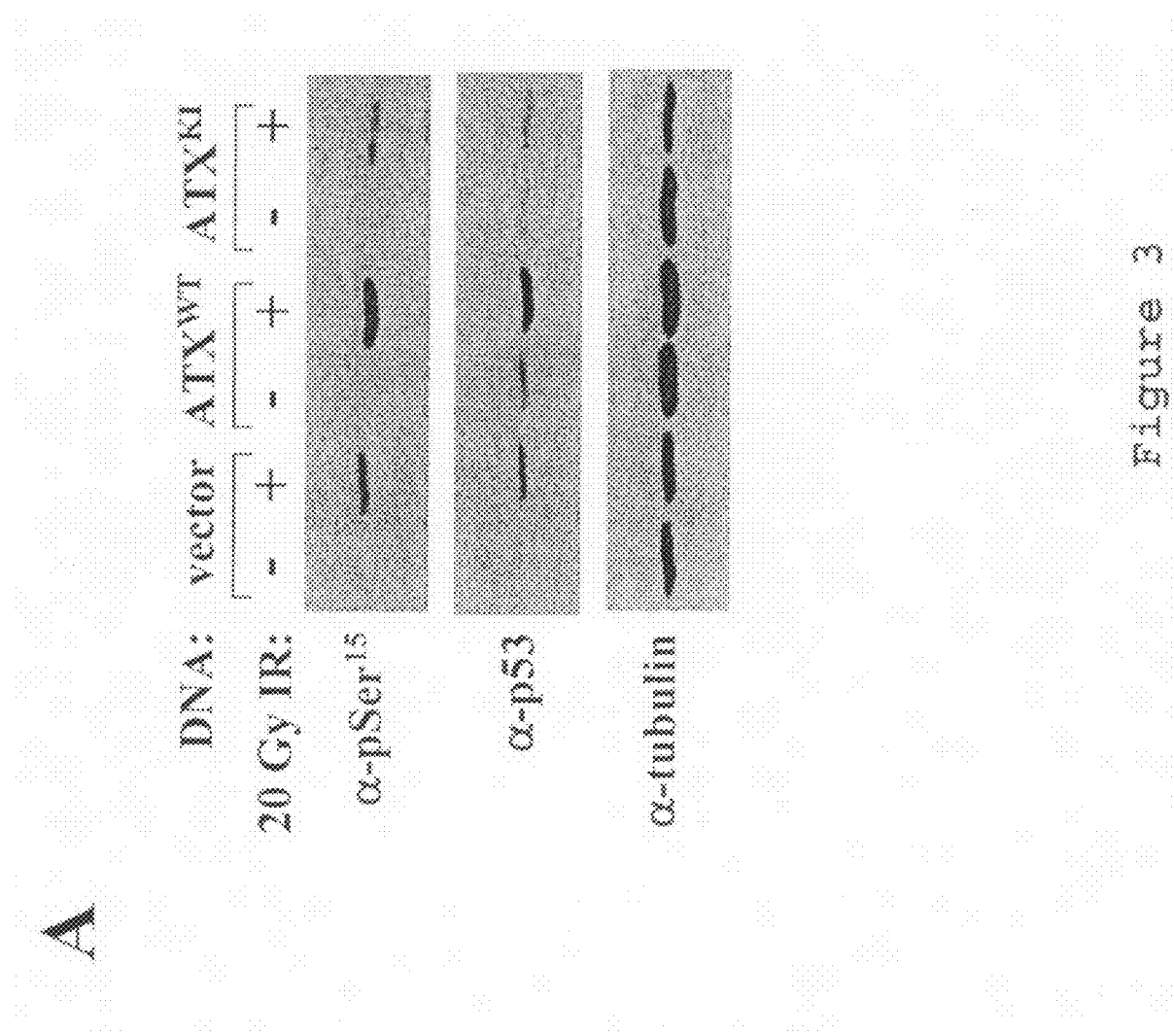
FIG. 3A shows whole cell extracts resolved by SDS-PAGE and sequentially immunblotted with the indicated antibodies.
FIG. 3B shows extracts of transfected cells separated by SDS-PAGE and sequentially immunoblotted with the indicated antibodies. The p53 phosphoserine-15 specific antibody is designated α-pSer15.
FIG. 3C shows extracts of cells treated with S or AS oligonucleotides and analyzed as described in panel A.
FIG. 3D shows cell cycle progression in AS-transfected cells examined by flow cytometry. The table shows the percentages of cells in each cell cycle phase. The right panel shows immunoblot analyses from the same cell population.
FIG. 3E shows an effect of caffeine on AS-induced cell cycle defects. The table shows percentages of cells in each cell-cycle phase, plus the ratio of G2/M to G1 cells for each sample. The right panel shows immunoblotting results from the same cell populations.
Figure 3:
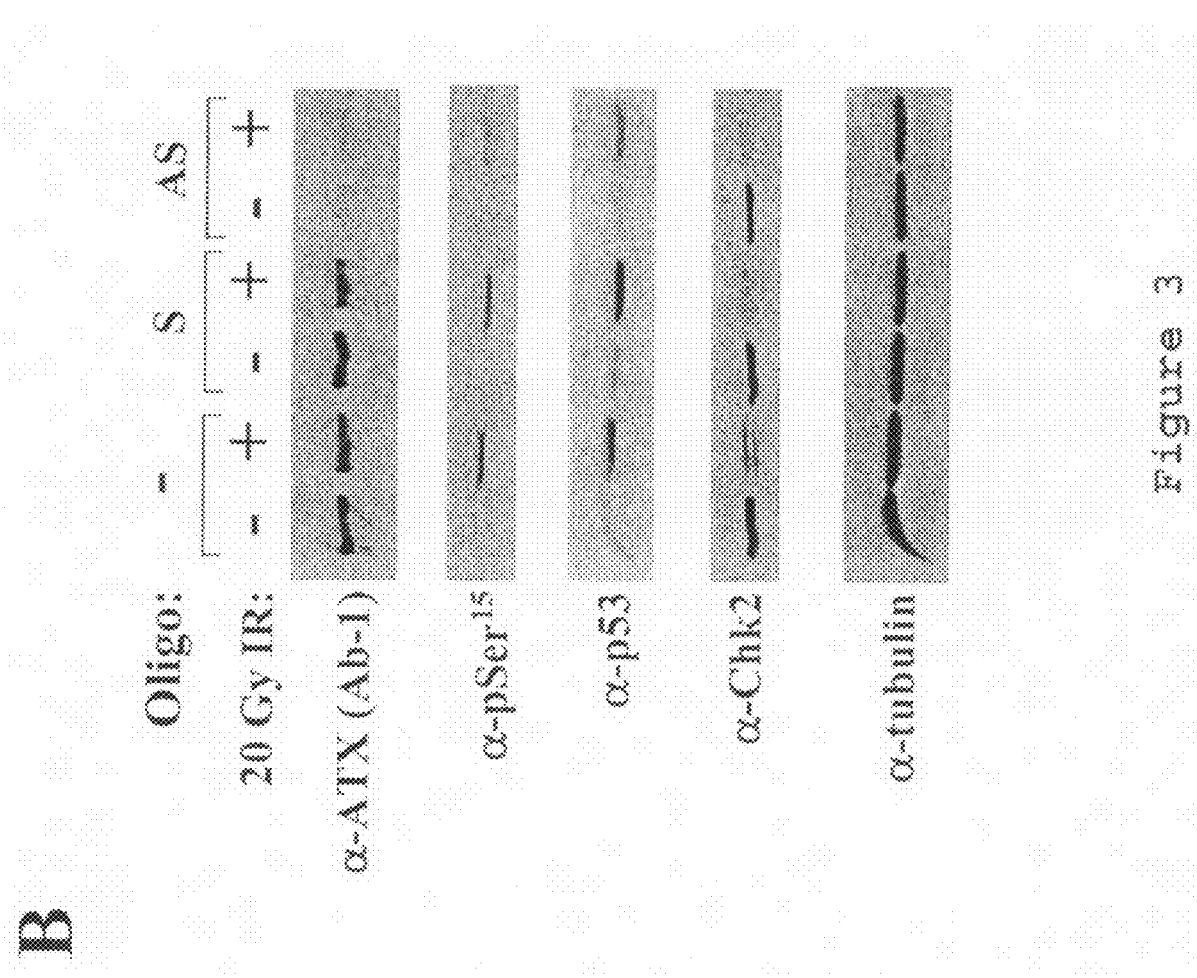
Figure 3:
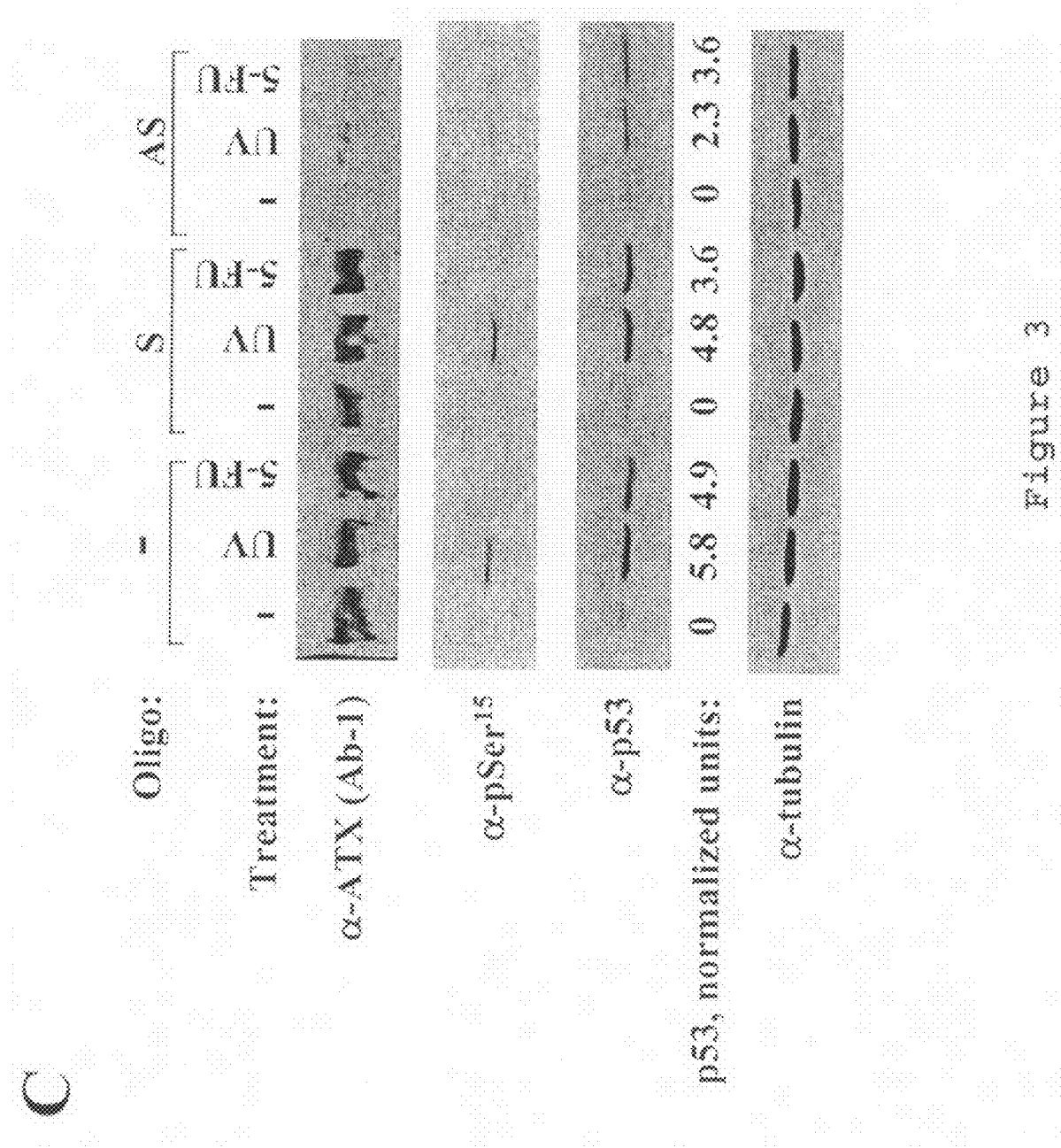
Figure 3:
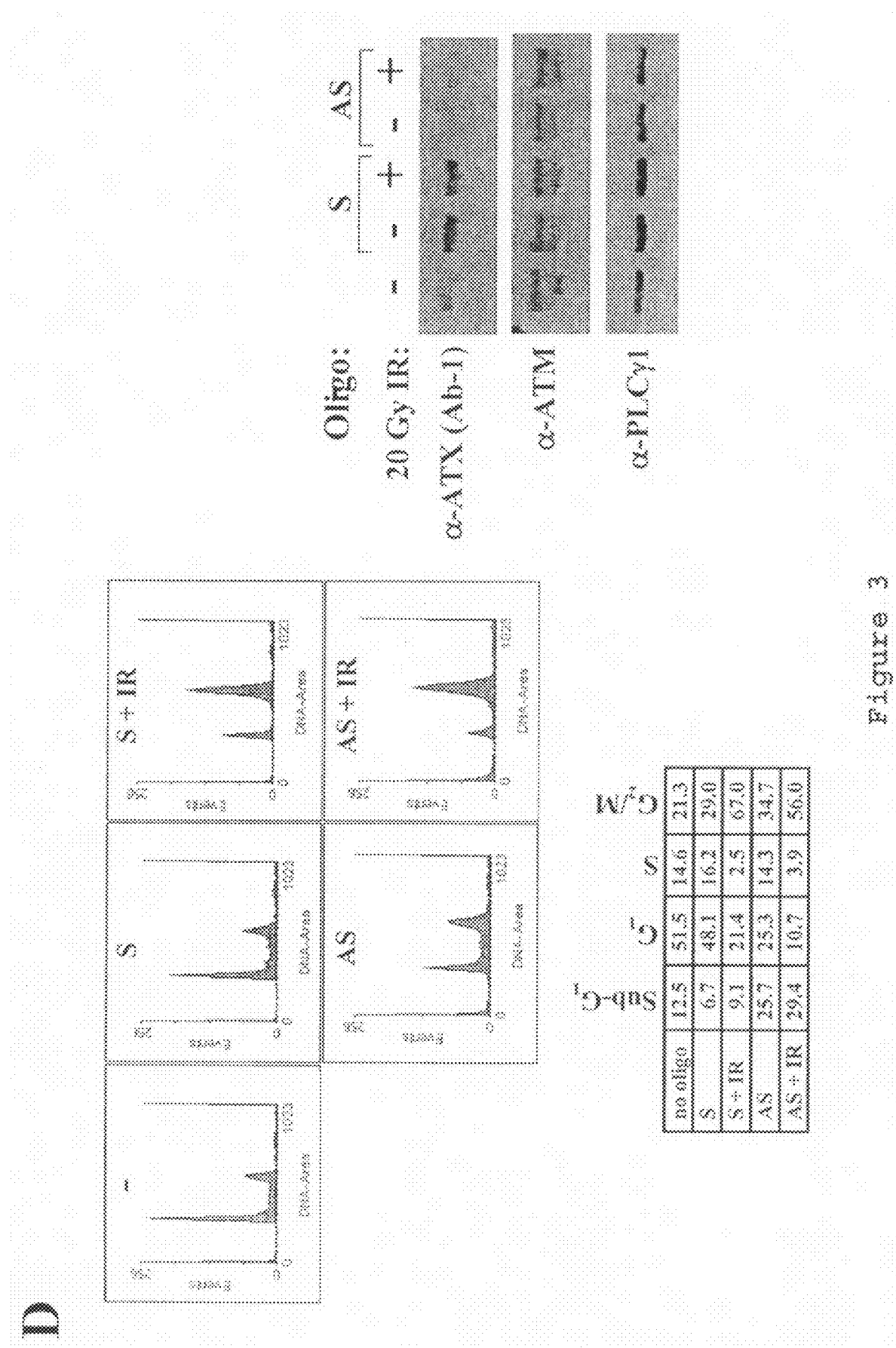
Figure 3:
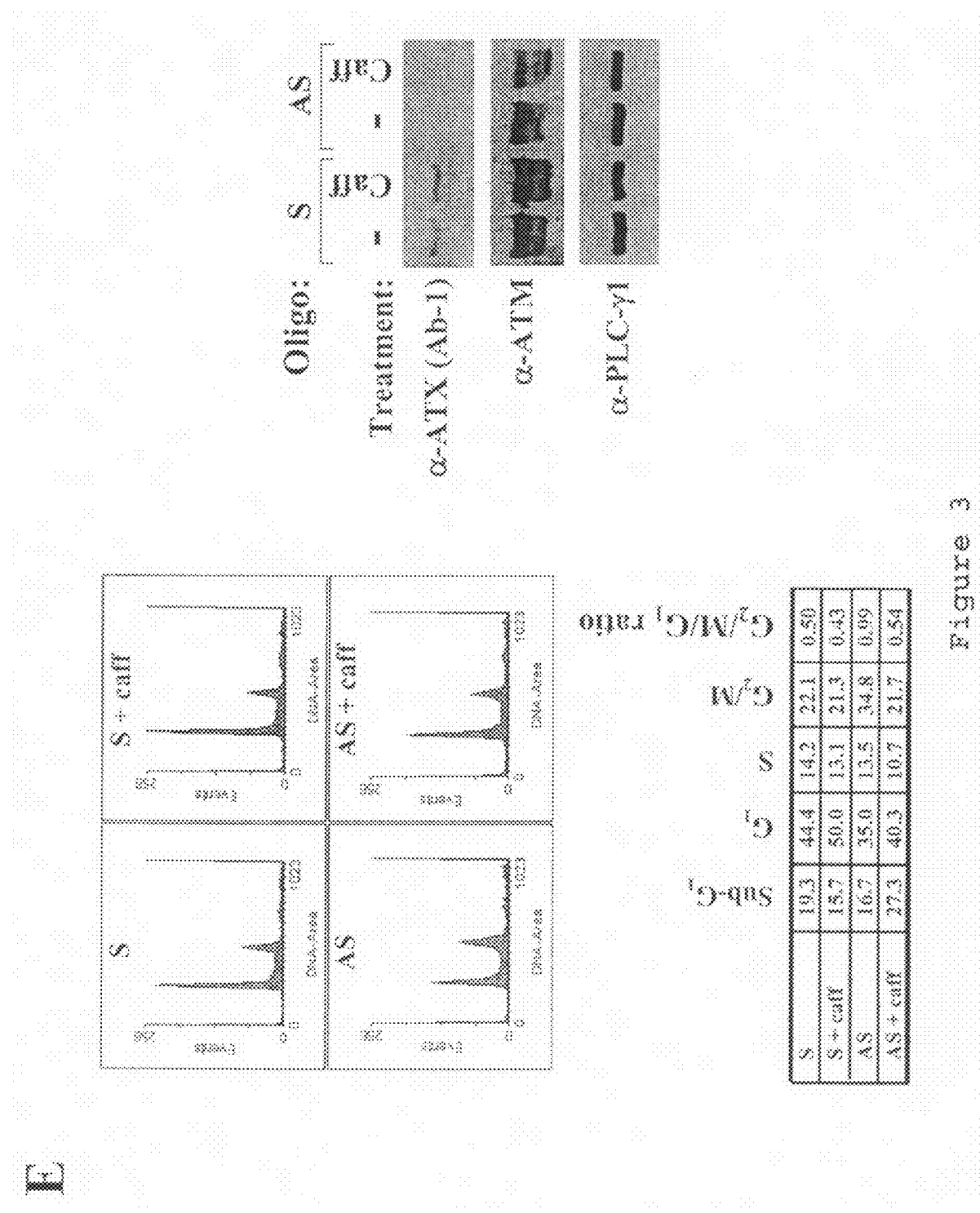

A major mediator of stress-induced signaling in mammalian cells is the tumor suppressor protein, p53 (Ko and Prives, *Genes and Development* 10:1054-1072, (1996); Ryan et al., *Curr. Opin. Cell Biol.* 13:332-337 (2001)). ATX phosphorylates p53 on Ser-15 (FIG. 1C), a site implicated in the regulation of p53 stability and transcriptional activity (Dumaz and Meek, *Curr. Opin. Cell Biol.* 13:225-231 (1999); Zhang and Xiong, *Science* 292:1910-1915 (2001)). Therefore, the possibility that these two proteins are functionally linked during cellular stress responses was investigated. U2OS cells were transiently transfected with a HA-ATXWT or HA-ATXKI expression plasmid, together with a GFP-encoding plasmid to allow for FACS-based enrichment of the transfected cells. The GFP+ cells were then examined for IR-induced stabilization of p53, as well as for specific phosphorylation of this protein on Ser-15. Expression of ATXKI strongly suppressed both the phosphorylation of Ser-15 and the overall accumulation of p53 in IR-treated cells (FIG. 3A). In contrast, overexpression of ATXWT enhanced both of these responses in cells exposed to IR. Consistent with findings presented above, treatment of U2OS cells with the AS oligonucleotide led to a decrease in endogenous ATX expression, and concomitantly reduced both the phosphorylation and stabilization of p53 induced by IR exposure (FIG. 3B). These results indicated that ATX exhibits functional overlap with ATM during IR-induced p53 activation.

Recent findings point toward ATM as a critical upstream regulator of the activity of the checkpoint kinase, hChk2, in IR-damaged cells (Ahn et al., *Cancer Res.* 60:5934-5936 (2000); Melchionna et al., *Nat. Cell Biol.* 2:762-765 (2000)). To determine whether ATX was also involved in hChk2 activation, the effect of AS oligonucleotide treatment on the IR-dependent phosphorylation of hChk2 was examined. In contrast to the p53 results, the AS-treated cells retained the ability to phosphorylate hChk2 in response to IR-induced stress (FIG. 3B). These results indicate that, while ATM and ATX serve as positive regulators of p53 function, ATX plays no identifiable role as an upstream activator of a distinct ATM target protein, the hChk2 kinase. Moreover, the differential effects of AS treatment on p53 expression versus hChk2 activation argue against the possibility that AS exposure leads to nonspecific inhibition of checkpoint signaling responses to IR-induced DNA damage.

Additional studies with AS oligonucleotide-treated cells demonstrated that, in contrast to ATM (Canman et al., *Science* 281, 1677-1679. 1998; Siliciano et al., *Genes Dev* 11, 3471-3481 (1997)), ATX plays a role in the phosphorylation and stabilization of p53 in cells exposed to UV light (FIG. 3C). As observed with IR as the stress-inducing agent, a reduction in ATX protein expression severely impaired both Ser-15 phosphorylation and p53 protein accumulation in UV-damaged cells. The recognition of UV light-induced DNA damage occurs primarily during S phase, when pyrimidine dimers and other bulky lesions interfere with replication fork progression (Friedberg, *DNA Repair and Mutagenesis* (Washington, D.C., ASM Press) (1995); Lindahl and Wood, *Cell* 103:1121-1131 (1999)).

In order to further define the potential linkage between DNA replicational stress and ATX, the response of AS-treated cells to 5-fluorouracil (5-FU), an S-phase specific cytotoxic agent was examined (Danenberg et al., *Seminars in Oncology.* 26:621-631 (1999); Grem, *Investigational New Drugs* 18:299-313 (2000)). Previous findings indicated that the cytotoxic effects of 5-FU are strongly p53-dependent (Bunz et al., *J. Clin. Invest.* 104:263-269 (1999)). Treatment of U2OS cells with 5-FU increased p53 expression to levels similar to those observed in UV-irradiated cells (FIG. 3C). However, the accumulation of p53 induced by 5-FU exposure was not accompanied by an increase in Ser-15 phosphorylation. These findings indicate that the mechanism of p53 stabilization triggered by 5-FU does not involve upstream protein kinases that modify the Ser-15 site. Consistent with this conclusion, the level of p53 induction by 5-FU in AS-treated cells was identical to that observed in their S-treated counterparts. These results indicate that the inhibitory effect of the AS treatment on p53 activation is selective for those forms of stress that induce the phosphorylation of p53 at Ser-15.

Changes in phosphorylation at Ser-15 are typically accompanied by alterations in the expression of the p53 protein, which complicates the interpretation of results obtained by immunoblotting of whole cell extracts with phospho-Ser-15-specific antibodies. In order to confirm that reduced ATX expression interferes with stress-induced Ser-15 phosphorylation, U2OS cells were transfected with either the S or AS oligonucleotide, and then were pretreated with the proteasome inhibitor, LLnV, to stabilize p53. In the presence of LLnV, the p53 level in each test population was relatively unaffected by UV exposure (data not shown). However, the ratio of phospho-Ser-15 to total p53 protein was increased by UV irradiation of both the mock-transfected and S oligonucleotide-treated cells. Although AS treatment partially interfered with the accumulation of p53 under these conditions, the reduction in ATX expression effectively blocked the stoichiometric increase in Ser-15 phosphorylation triggered by UV-induced stress.

EXAMPLE 7

Role of ATX in IR-induced Cell Cycle Arrest

Since p53 plays a central role in activation of the G1 checkpoint, and influences S, G2, and M checkpoints as well (Giaccia and Kastan, *Genes & Development* 12:2973-2983 (1998); Ko and Prives, supra, 1996), a functional deficiency of ATX might alter the cell-cycle arrest responses to IR and other genotoxic agents. To test this possibility, U2OS cells were pre-treated with S or AS oligonucleotides, exposed to IR, and cell-cycle distributions at 24 h post-irradiation were determined. In the absence of IR, AS treatment led to a reduction in the percentage of G1 phase cells, and a concomitant accumulation of G2/M phase cells, when compared to their S oligonucleotide-treated counterparts (FIG. 3D). The AS-treated cells also contained an increased subpopulation with <2N DNA content, which is indicative of apoptotic cells. After IR exposure, cells treated with the S oligonucleotide accumulated in both G1 and G2/M phases and were cleared out of S phase, a profile typical of p53-positive cells that retain G1 checkpoint function. In contrast, the AS-treated cells arrested primarily in G2/M phase after IR exposure. The cell-cycle distribution of the AS-treated cells was reminiscent of that observed in cells that have lost p53-dependent checkpoint function (North and Hainaut, *Pathol. Biol.* 48:255-270 (2000); Waldman et al., *Cancer Res.* 55:5187-5190 (1995)). Immunoblot analyses of the same cell populations confirmed that AS exposure led to a profound reduction in ATX protein levels in U2OS cells. In contrast, AS exposure caused no significant change in the expression levels of two control proteins, ATM and PLC-γ1.

The cell-cycle distribution results described in FIG. 3D demonstrated that ATX-deficient cells accumulate with 4N DNA content under both basal culture conditions and after IR-induced stress. This arrest state could reflect the activation of either a G2 or a mitotic checkpoint (or both checkpoints). To distinguish between these possibilities, the effects of caffeine, a known inhibitor of the G2 checkpoint (Powell et al., Cancer Res. 55:1643-1648 (1995); Russell et al., Cancer Res. 55:1639-1642 (1995); Yao et al., Nat, Med. 2:1140-1143 (1996)), on the cell cycle distribution of the AS-treated cells were examined. The G2 checkpoint inhibitor was added to the culture medium at 8 h prior to harvest for determination of cell-cycle distributions (FIG. 3E, left panel), and immunoblotting for ATX expression (right panel). Caffeine completely reversed the accumulation of G2/M phase cells induced by AS treatment, indicating that ATX deficiency triggered the activation of a caffeine-sensitive G2 checkpoint. The immunoblotting results confirmed that AS-treated cells displayed a marked, specific reduction in ATX protein expression. In addition, treatment of the AS cells with caffeine also resulted in an increase in the percentage of hypodiploid cells, which indicates that an intact G2 checkpoint partially protects the ATX-deficient cells from apoptotic death, for example, by preventing a catastrophic entry into M phase.

EXAMPLE 8

ATX Overexpression Complements IR Sensitivity in ATM-deficient Cells

Figure 4:
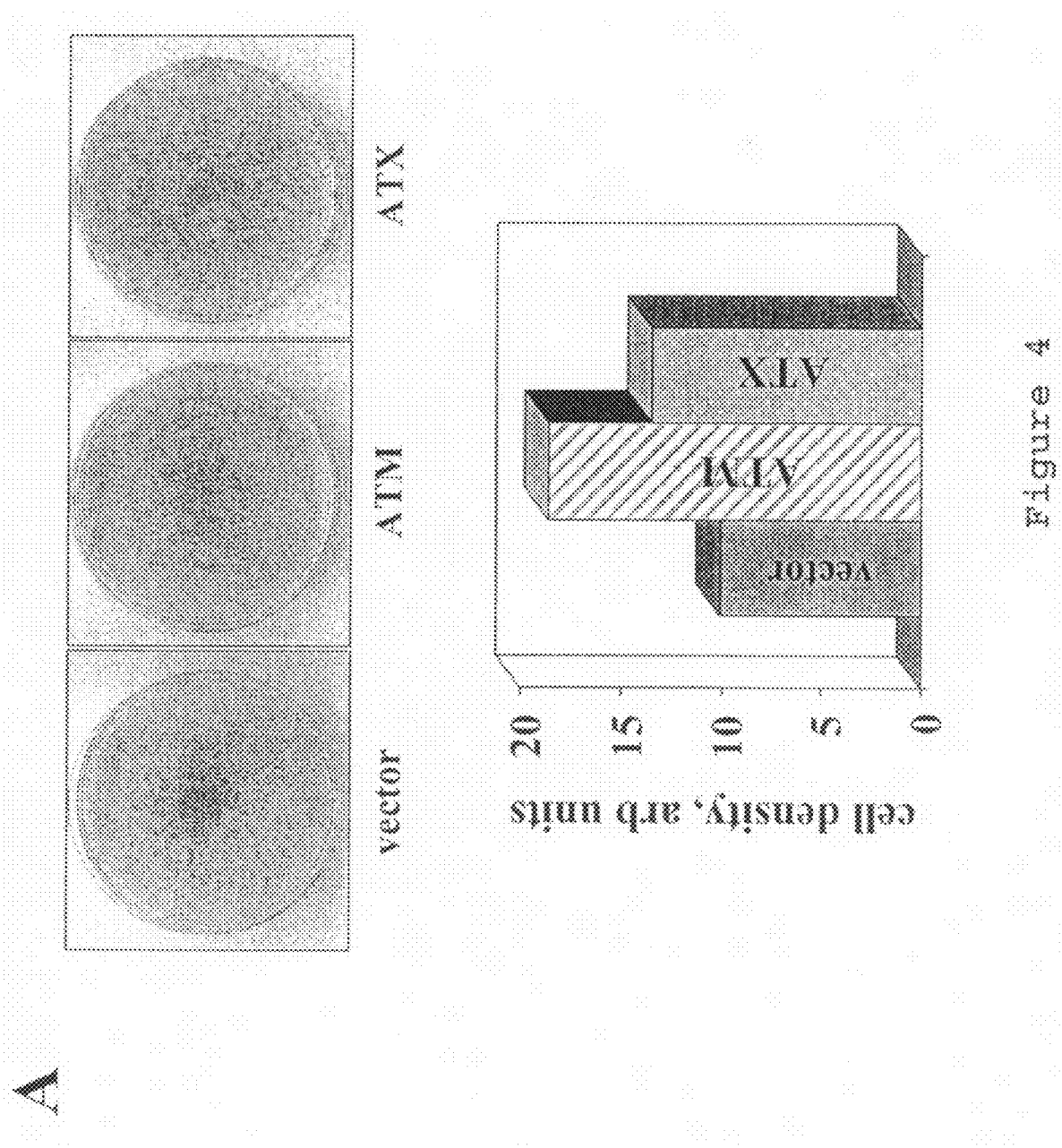
FIG. 4A shows an effect of ATX overexpression on basal viability. Cell densities of the scanned images from each sample were obtained with the ImagePro Plus software program.
FIG. 4B shows an effect of ATX overexpression on radiosensitivity. Surviving cells were quantitated as described in panel except that arbitrary unit values for each group were normalized to the corresponding nonirradiated control.
Figure 4:
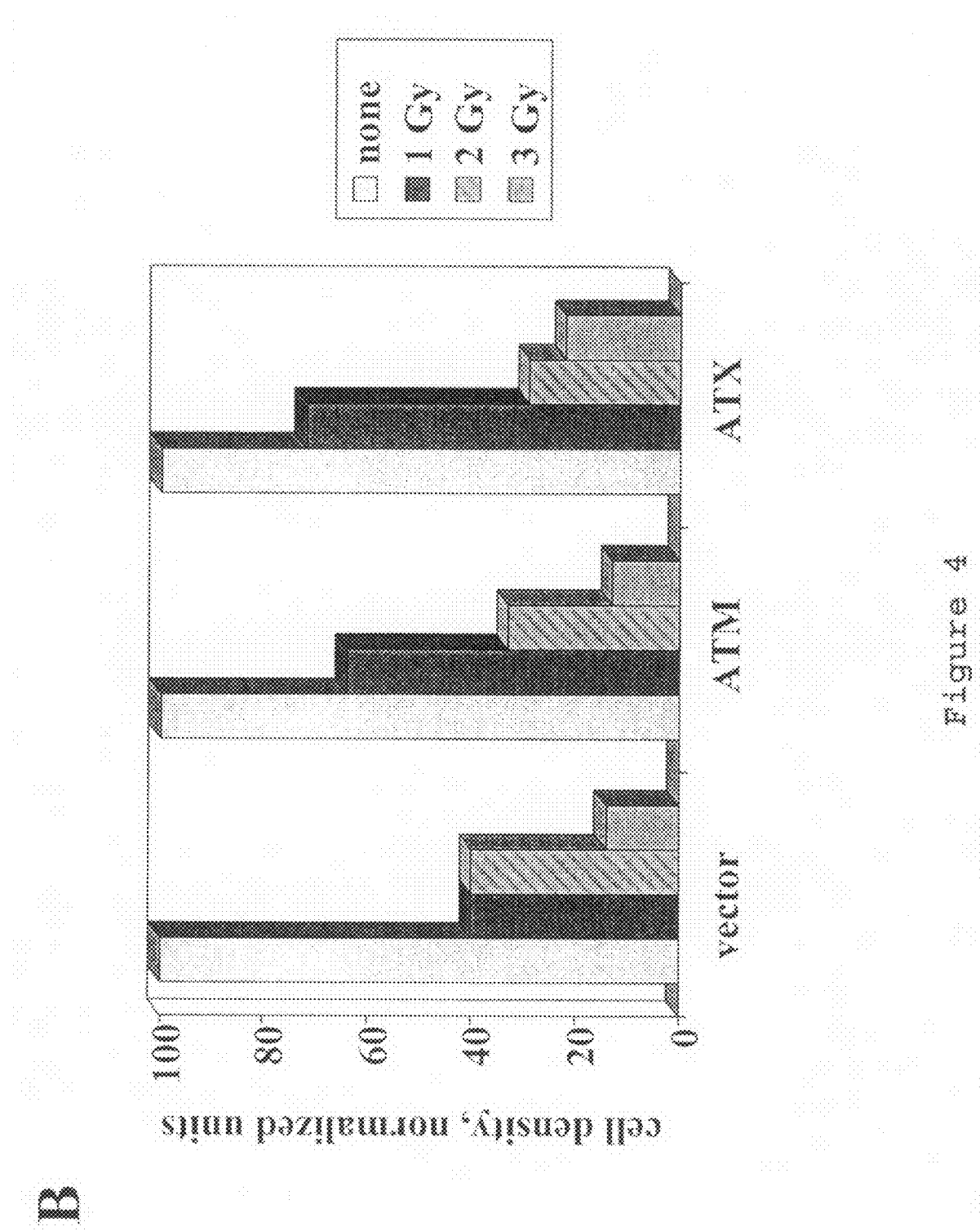

Based on the finding that ATM and ATX display overlapping functions as activators of p53, it was investigated whether ATX overexpression can complement the phenotypic defects found in cells from A-T patients. One characteristic defect of cells from A-T patients is reduced clonogenic survival in culture, even in the absence of DNA dsb-inducing agents (Rotman and Shiloh, Oncogene 18:6135-6144 (1998)). As shown in FIG. 4A, transient transfection of ATM-null AT4BI cells with an ATM expression plasmid increased the outgrowth of G418-resistant colonies by approximately 2-fold, relative to cells transfected with empty vector. The clonogenic defect of AT4BI cells was partially rescued (approximately 1.5-fold increase in colony survival) by transient expression of ATX. Thus, ATX overexpression partially complements the intrinsic clonogenic survival defect of ATM-null cells. Furthermore, low-dose (1 Gy) IR treatment sharply reduced the clonogenic survival of mock-transfected AT4BI cells, and this radiosensitive phenotype was rescued to equivalent degrees by transfection of the cells with ATM or ATX (FIG. 4B). Thus, overexpression of ATX complements, at least in part, the stress response defects observed in cells from A-T patients.

EXAMPLE 9

Roles of ATX and ATM in hUpf1 Phosphorylation and NMD

The Upf1 helicase undergoes serum-inducible phosphorylation in intact cells, as demonstrated by two-dimensional (2-D) gel electrophoresis (Pal et al., supra, 2001). Based on the evidence disclosed herein that ATX is a UV-responsive kinase, the possibility that UV light exposure triggers the phosphorylation of hUpf1 in ATXWT-transfected U2OS cells was investigated. Serum stimulation or UV treatment induced virtually identical shifts in the 2-D electrophoretic mobility of hUpf1, which indicates that these agents provoke the phosphorylation of this protein at similar sites (data not shown). In contrast, expression of the catalytically-inactive ATXKI protein blocked the appearance of the most highly shifted form of hUpf1, and caused the accumulation of a broad band with intermediate electrophoretic mobility. The latter hUpf1 species can be less phosphorylated forms of the protein. Thus, overexpression of ATXKI interferes with both the serum- and UV-induced phosphorylation of hUpf1; however, these results also indicate that the hUpf1 is targeted by at least one additional protein kinase in these cells.

Figure 5:
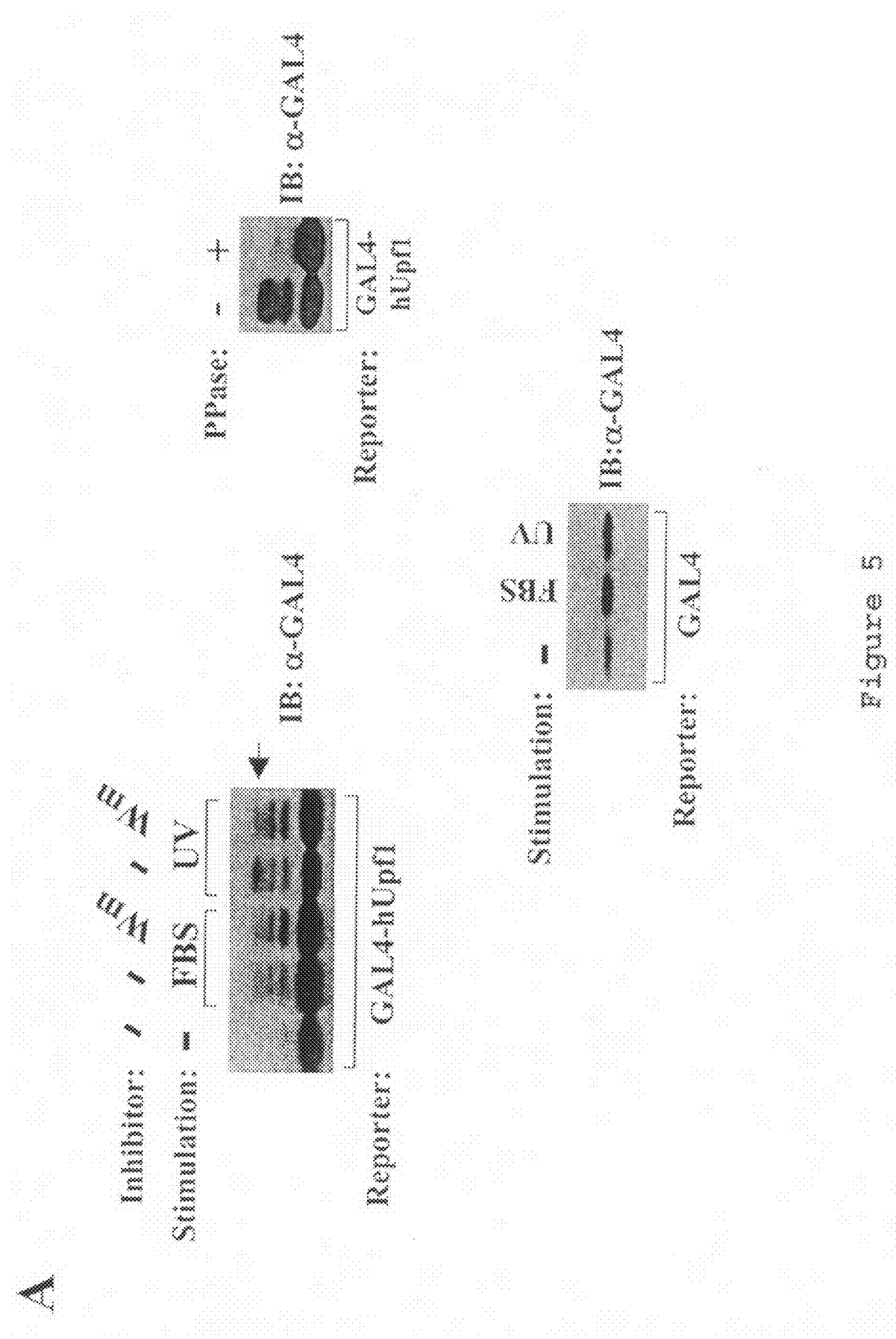
FIG. 5A shows cells transfected with GAL4 or GAL4-hUpf1 1019-1118 expression constructs with the indicated samples treated with wortmannin. The right panel shows phosphatase treatment. The soluble proteins were separated by SDS-PAGE and immunoblotted with α-GAL4 mAb. The arrow indicates the uppermost band of the phosphorylated GAL4-hUpf1 1019-1118 reporter protein.
FIG. 5B shows an effect of ATMKI or ATXKI expression on UV stimulation of GAL4-hUpf1 phosphorylation.

Based on the functional overlap between ATM and ATX during stress-induced p53 activation, it was possible that these PIKKs might also share the ability to regulate the RNA surveillance pathway leading to NMD. To focus our studies of hUpf1 phosphorylation on the Ser-Gln-rich region, a mammalian expression vector encoding GAL4 fused to the carboxyl terminus (amino acids 1019-1118) of hUpf1 (GAL4-hUpf11019-1118) was generated. Expression of GAL4-hUpf11019-1118 in U2OS cells generates a major immunoreactive band that migrates with a molecular mass of ~35 kDa in serum-starved cells. Stimulation of the transfected cells with 10% fetal bovine serum or UV light leads to the increased expression of forms of GAL4-hUpf11019-1118 that display reduced electrophoretic mobility (FIG. 5A, left panel). In this experiment, cells were harvested at 6 h after serum or UV exposure; however, the GAL4-hUpf11019-1118 mobility shifts could be detected as early as 2 h after cellular stimulation with either agent. The appearance of these shifted GAL4-hUpf11019-1118 bands is due to phosphorylation, as treatment of the cell extracts with λ phosphatase collapses the complex pattern of α-Gal4-reactive species into the major ~35 kDa band, which represents non-phosphorylated GAL4-hUpf11019-1118 (FIG. 5A, right panel). Moreover, the observed GAL4-hUpf11019-1118 mobility shifts were due to phosphorylation of the hUpf1 fragment, as the electrophoretic mobility GAL4 alone was not altered by cellular exposure to serum or UV (FIG. 5A, lower panel). In the experiment shown in FIG. 5A (left panel), selected samples were pretreated with 20 µM wortmannin in order to inhibit endogenous ATX and ATM kinase activities (Sarkaria et al., supra, 1998)). In the wortmannin-treated cells, the FBS- or UV-induced generation of the most slowly migrating form of GAL4-hUpf11019-1118 (indicated with an arrow) was preferentially inhibited. This drug effect was accompanied by an increase in the abundance of the less shifted bands, which can represent less phosphorylated forms of GAL4-hUpf11019-1118. These results indicate that, although a wortmannin-sensitive protein kinase(s) contributes to the inducible phosphorylation of the GAL4-hUpf11019-1118 reporter protein, the hUpf1 carboxyl-terminal region is also targeted for modification by at least one additional, wortmannin-resistant protein kinase.

To further examine the contributions of ATM and ATX to the phosphorylation of GAL4-hUpf11019-1118, U2OS cells were cotransfected with wild-type (WT) or kinase-inactive (KI) versions of HA-ATM or HA-ATX. Expression of either HA-ATMKI or HA-ATXKI strongly suppressed the phosphorylation of GAL4-hUpf11019-1118 in cells treated with UV light (FIG. 5B) or serum (data not shown). Expression of the catalytically active HA-ATMWT or HA-ATXWT proteins enhanced the phosphorylation of GAL4-hUpf11019-1118 in both unstimulated and stimulated cells. The latter results add further support to the notion that ATX and ATM are capable of phosphorylating hUpf1 carboxyl-terminal region in intact cells. In these experiments, the HA-tagged ATM and ATX proteins were overexpressed by approximately 2- and 1.5-fold, respectively, when compared to their endogenous counterparts (data not shown).

Figure 6:
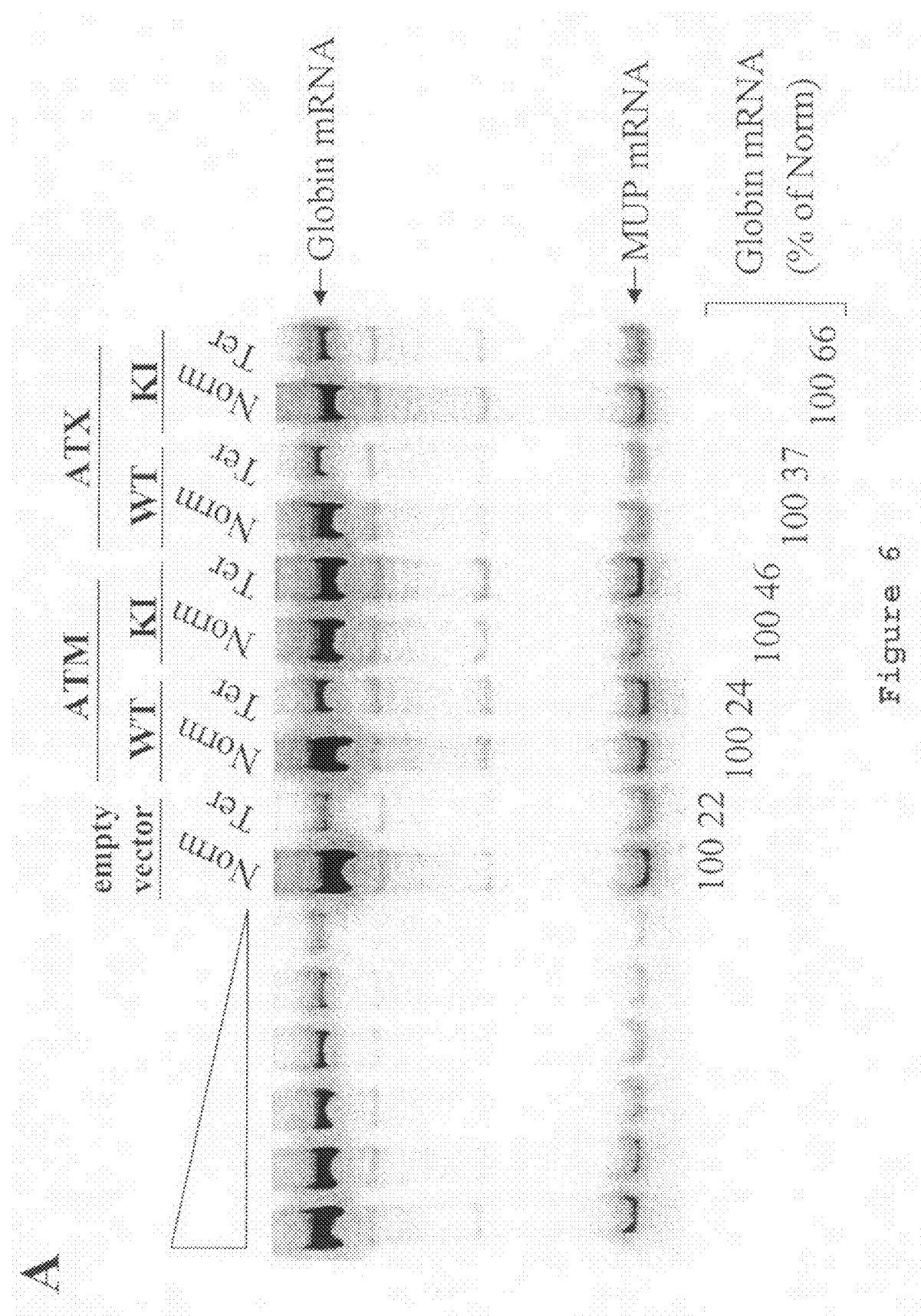
FIG. 6A shows an effect of HA-ATXKI or HAATMKI expression on NMD. Nuclear RNA was isolated from transfected cells and β-globin and MUP mRNAs were quantitated by RT-PCR and PhosphorImaging. For each pair of transfections, the level of Globin mRNA was normalized to the level of MUP mRNA and expressed below each lane as a percentage of the normalized level of Globin Norm mRNA, which was defined as 100.
FIG. 6B shows an effect of ATX AS oligonucleotide on NMD.
Figure 6:
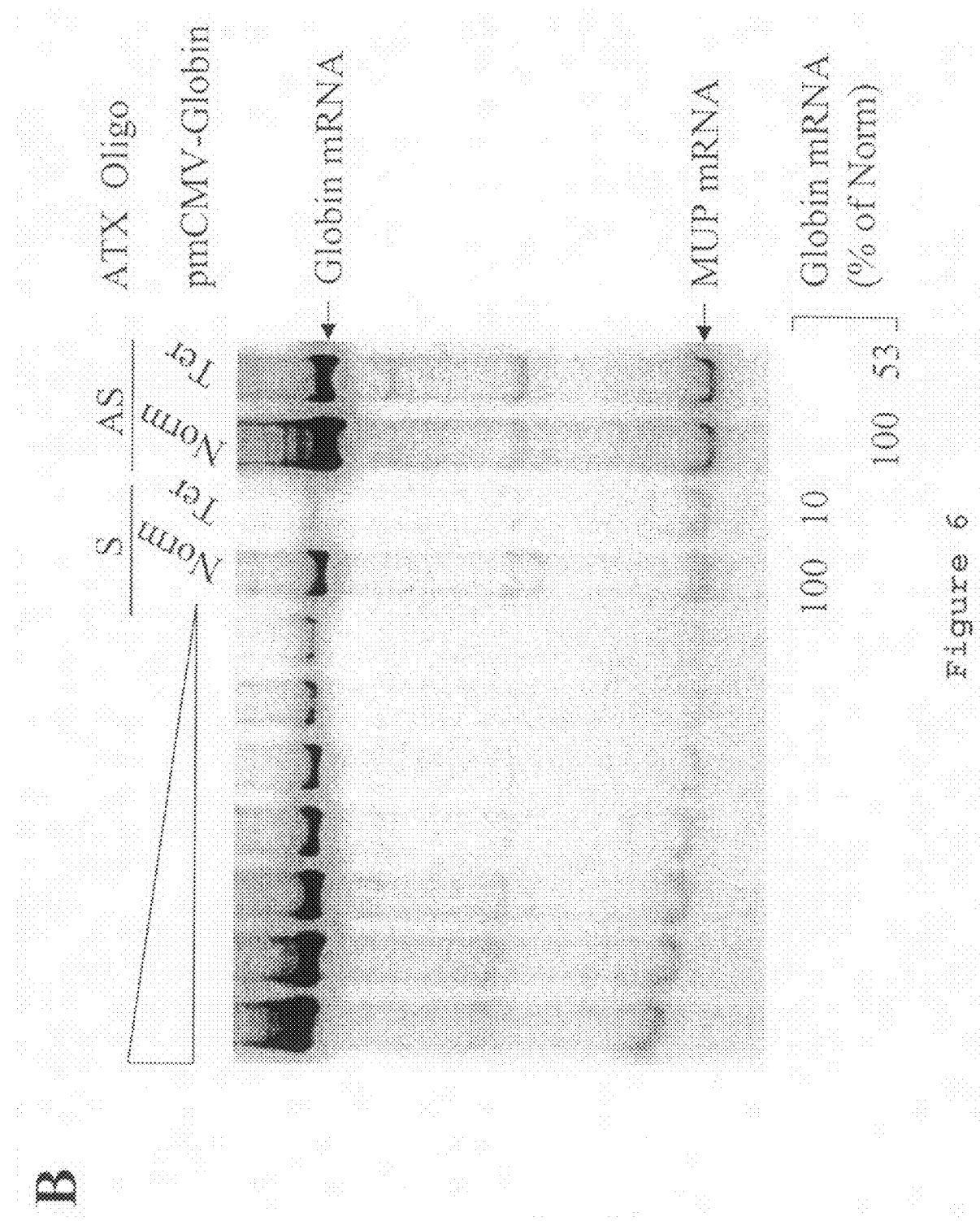

In addition, the effects of HA-ATXKI and HA-ATMKI overexpression on NMD were comparatively examined using an established assay (Sun et al., *Proc. Natl. Acad. Sci. USA* 95:10009-1998). U2OS cells were transfected with a plasmid encoding either the normal human β-globin gene (Norm) or a mutated β-globin gene bearing a premature termination codon (Ter), together with a reference plasmid encoding the mouse urinary protein (MUP). Where indicated, the cells were co-transfected with empty vector, or expression vectors encoding wild-type or kinase-inactive versions of ATM (HA-ATMWT, HA-ATMKI) or ATX (HA-ATXWT, HA-ATXKI) (FIG. 6A). Expression of the kinase-inactive HA-ATMKI or HA-ATXKI proteins abrogated NMD of the Ter-containing β-globin mRNA. Furthermore, treatment of the cells with the AS oligonucleotide to reduce endogenous ATX expression confirmed that ATX expression is required for maximal NMD activity under these assay conditions (FIG. 6B). Collectively, these results indicate that ATM and ATX function as shared components of the pathways leading to both NMD and p53 activation during UV- and IR-induced stress.

Methods:

Construction of GST and GAL4-hUpf1 Fusion Proteins

The hUpf11019-1118-BamHI fragment was generated by PCR amplification of full-length hUpf1 using the following primers: 5'-AGGAGGGGATCCGGACGCCAGAAGAAC-CGCTTTGGG-3', 5'-AGGAGGGGATCCATACTGGGA-CAGCCCCGTCAC-3'. This fragment was subcloned into the BamHI site of pGEX-2T and pCMX-GAL4 (N) to generate the GSThUpf11019-1118 and GAL4-hUpf11019-1118 fusion proteins, respectively.

GAL4-hUpf1 Mobility Shift Assays

U2OS cells were plated in 60 mm dishes (4×105 cells per dish), and then transfected with 0.5 µg pCMX-GAL4 or pCMX-GAL4-hUpf11019-1118, together with 4.5 µg pcDNA3.1-HA-ATXWT, HA-ATXKI, HA-ATMWT, or HA-ATMKI plasmid DNAs. The HA-ATMKI protein contains an Asp-2870>Ala mutation that inactivates the kinase domain. Twenty hours after transfection, serum was removed from the medium, and the cells were cultured for an additional 24 h. The cells were then treated with 10% fetal bovine serum or 100 J/m2 UV-B. Where indicated, the serum-starved cells were pretreated for 30 min with 20 µM wortmannin prior to treatment with serum or UV. Cells were harvested in lysis buffer containing 25 mM Hepes, pH 7.4, 300 mM NaCl, 1.5 mM MgCl2, 1 mM EGTA, 1% Triton X-100, 20 mM β-glycerophosphate, 20 nM microcystin, 0.1 mM sodium orthovanadate, 1 mM DTT, plus protease inhibitors. For phosphatase treatment, 600 U λ phosphatase was added to cellular extracts (New England Biolabs). Cell extracts were resolved on by SDS-PAGE, and were immunoblotted with α-GAL4 antibody.

RNA Isolation and Assays of NM

Total or nuclear RNA was isolated using Trizol (Invitrogen) or the NE-PER kit (Pierce), respectively. The extent of NMD was determined by using RT-PCR to quantitate the levels of Globin and MUP mRNA as described previously (Ishigaki et al., *Cell* 83: 1-4 (2001)), except that 21 cycles of PCR were used when analyzing the effects of ATX-specific S and AS oligonucleotides.

EXAMPLE 10

Decreased Expression of ATX Results in Spontaneously Increased DNA Damage

Figure 7:
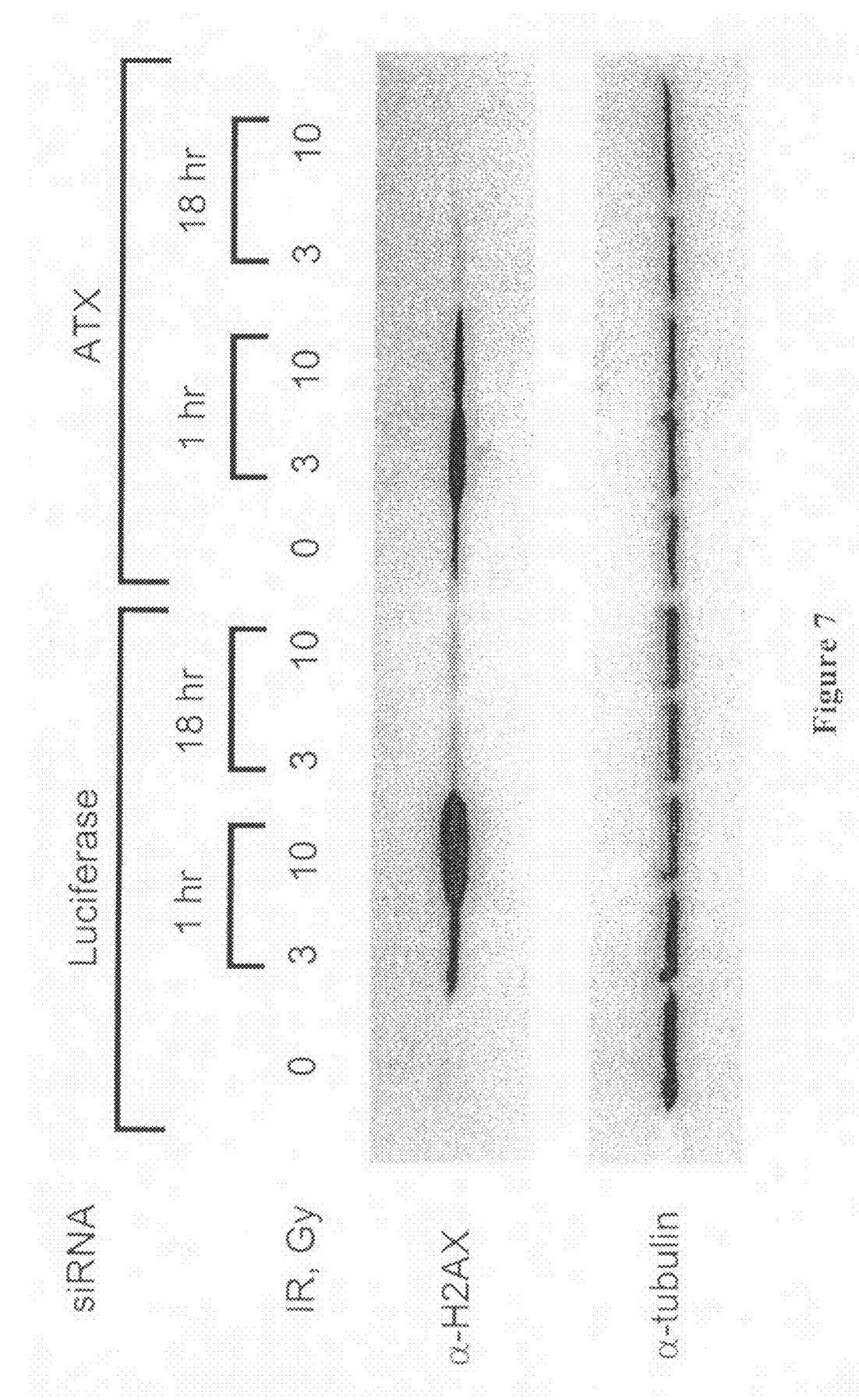
FIG. 7 shows the effect of small-interfering (si) RNA reduction of ATX on response to ionizing radiation (IR). U20S cells transfected with si RNA directed against luciferase (control) or ATX were treated with different doses of ionizing radiation and lysed after 1 hour or 18 hours. Cellular extracts were separated by SDS-PAGE and immunoblotted with an anti-phospho-Histone H2AX antibody. The level of a control polypeptide, α-tubulin, is shown in the lower panel for comparison.

U2OS osteosarcoma cells were treated with small-interfering (si) RNA directed against luciferase (control) or ATX. The siRNA consistently induces a >80% decrease in the expression of ATX protein at day 3 post-transfection. The transfected cells were treated with 0, 3, or 10 Gy ionizing radiation (IR), and then lysed after either 1 hour or 18 hours. The cell extracts were separated by SDS-PAGE and immunoblotted with an anti-phospho-Histone H2AX antibody. A significant increase in phospho-Histone H2AX immunoreactivity in 0 Gy IR-treated cells exposed to the ATX siRNA relative to the corresponding luciferase siRNA-transfected control cells was detected (see FIG. 7). The level of a control polypeptide, α-tubulin, was also determined to show equal loading of each lane.

The appearance of phospho-Histone H2AX marks DNA double-strand breaks or other forms of DNA damage, as indicated by the strong induction of immunoreactivity in IR-treated cells. These results indicate that ATX-deficient cells can spontaneously develop DNA damage. Furthermore, the compromised phosphorylation of Histone H2AX observed in IR-treated, ATX-deficient cells indicates that loss of ATX function can also compromise DNA damage recognition and/or repair in mammalian cells.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method for identifying an ATX-modulatory compound, comprising measuring the level of an ATX polypeptide comprising the amino acid sequence as SEQ ID NO:2 in the presence of a test compound, wherein a difference in the level of that said ATX polypeptide in the presence of said test compound compared to in the absence of that said test compound indicating that said test compound is an ATX-modulatory compound, and wherein said ATX-modulatory compound is not caffeine or wortmannin.

2. The method of claim 1, wherein said ATX-modulatory compound decreases the level of ATX polypeptide.

3. The method of claim 1, wherein said ATX-modulatory compound increases the level of ATX polypeptide.

4. The method of claim 1, wherein said level of ATX polypeptide is measured by determining the kinase activity of said ATX polypeptide.

5. The method of claim 1, wherein said level of ATX polypeptide is measured by determining the phosphorylation of a mammalian p53 polypeptide or a fragment thereof, comprising a phosphporylation site for the kinase activity of said ATX polypeptide.

6. The method of claim 1, wherein said level of ATX polypeptide is measured by determining the level of p53 polypeptide accumulation.

* * * * *